United States Patent
Torp et al.

(10) Patent No.: US 12,226,253 B2
(45) Date of Patent: Feb. 18, 2025

(54) ULTRASOUND BLOOD-FLOW MONITORING

(71) Applicant: CIMON MEDICAL AS, Trondheim (NO)

(72) Inventors: Hans Torp, Trondheim (NO); Torbjørn Hergum, Os (NO)

(73) Assignee: CIMON MEDICAL AS, Trondheim (NO)

( * ) Notice: Subject to any disclaimer, the term of this patent is extended or adjusted under 35 U.S.C. 154(b) by 0 days.

(21) Appl. No.: 16/967,929

(22) PCT Filed: Feb. 7, 2019

(86) PCT No.: PCT/GB2019/050344
§ 371 (c)(1),
(2) Date: Aug. 6, 2020

(87) PCT Pub. No.: WO2019/155226
PCT Pub. Date: Aug. 15, 2019

(65) Prior Publication Data
US 2021/0251599 A1    Aug. 19, 2021

(30) Foreign Application Priority Data
Feb. 7, 2018   (GB) ...................................... 1802007
Oct. 19, 2018  (GB) ...................................... 1817102

(51) Int. Cl.
*A61B 8/00*   (2006.01)
*A61B 8/06*   (2006.01)
*A61B 8/08*   (2006.01)

(52) U.S. Cl.
CPC .............. *A61B 8/06* (2013.01); *A61B 8/0866* (2013.01); *A61B 8/0883* (2013.01);
(Continued)

(58) Field of Classification Search
CPC ......... A61B 8/06; A61B 8/4227; A61B 8/461; A61B 8/488; A61B 8/5207; A61B 8/4483; A61B 8/0866; A61B 8/0883
See application file for complete search history.

(56) References Cited

U.S. PATENT DOCUMENTS 3,554,030 A    1/1971   Peronneau
4,067,236 A    1/1978   Hottinger
(Continued)

FOREIGN PATENT DOCUMENTS

CN    1189217 A    7/1998
CN    2933323 Y    8/2007
(Continued)

OTHER PUBLICATIONS

Seternes, A.; "Early bird: A newly developed ultrasound probe for measuring peripheral microcirculation"; NTNU Lecture delivered Sep. 22, 2017; 2017; 105 pages.
(Continued)

*Primary Examiner* — Joel Lamprecht
*Assistant Examiner* — James F McDonald, III
(74) *Attorney, Agent, or Firm* — CANTOR COLBURN LLP

(57) ABSTRACT

The invention provides a method of monitoring blood flow in a vertebrate animal subject. Unfocussed plane-wave ultrasound pulses are transmitted into the subject, along a transmission axis, from a single-element ultrasound transducer (2) fastened to the subject (5). Reflections of the ultrasound pulses are received, generating a succession of pulse-Doppler response signals over time. Each pulse-Doppler response signal is processed to determine a first respective spatial-maximum velocity value for blood flowing towards the single transducer element (2), and a second respective spatial-maximum velocity value for blood flowing away.
(Continued)

Heartbeats are identified from said spatial-maximum velocity values and a quality metric is assigned to each identified heartbeat. A subset of the spatial-maximum velocity values is identified for which the assigned quality metric exceeds a threshold level. The values from the subset are monitored, and, when a set of values from the subset satisfies a predetermined alert criterion an audible or visual alert is signalled.

17 Claims, 67 Drawing Sheets

(52) U.S. Cl.
CPC .......... *A61B 8/4227* (2013.01); *A61B 8/4483* (2013.01); *A61B 8/461* (2013.01); *A61B 8/488* (2013.01); *A61B 8/5207* (2013.01)

(56) References Cited

U.S. PATENT DOCUMENTS

| | | | |
|---|---|---|---|
| 4,431,936 | A | 2/1984 | Fu et al. |
| 4,509,526 | A | 4/1985 | Barnes et al. |
| 4,757,823 | A | 7/1988 | Hofmeister et al. |
| 5,329,194 | A | 7/1994 | Dow et al. |
| 5,402,789 | A | 4/1995 | Dow et al. |
| 5,560,363 | A | 10/1996 | Torp et al. |
| 6,017,307 | A | 1/2000 | Raines |
| 6,176,143 | B1 | 1/2001 | Mo et al. |
| 6,423,006 | B1 | 7/2002 | Banjanin |
| 8,617,076 | B2* | 12/2013 | Kabakov ............ A61B 8/5276 600/453 |
| 8,622,913 | B2 | 1/2014 | Dentinger et al. |
| 8,727,991 | B2 | 5/2014 | Hasegawa-Johnson |
| 9,597,055 | B2 | 3/2017 | Kabakov |
| 10,610,193 | B2 | 4/2020 | Bar-Zion et al. |
| 10,914,826 | B2 | 2/2021 | Daigle et al. |
| 2002/0055680 | A1* | 5/2002 | Miele ............... A61B 8/04 600/450 |
| 2003/0013947 | A1 | 1/2003 | Frattarola |
| 2006/0100530 | A1* | 5/2006 | Kliot ............... A61B 5/681 600/483 |
| 2006/0111633 | A1 | 5/2006 | McMorrow et al. |
| 2006/0122513 | A1 | 6/2006 | Taylor |
| 2008/0015439 | A1 | 1/2008 | Raju et al. |
| 2009/0105594 | A1 | 4/2009 | Reynolds et al. |
| 2009/0264760 | A1 | 10/2009 | Lazebnik et al. |
| 2009/0326379 | A1 | 12/2009 | Daigle et al. |
| 2010/0210947 | A1 | 8/2010 | Burcher et al. |
| 2011/0082373 | A1 | 4/2011 | Gurley et al. |
| 2013/0158407 | A1* | 6/2013 | Kabakov ............ A61B 8/0866 600/453 |
| 2013/0281877 | A1 | 10/2013 | Hsu et al. |
| 2015/0073271 | A1 | 3/2015 | Lee et al. |
| 2015/0374540 | A1 | 12/2015 | Lopath et al. |
| 2016/0030001 | A1 | 2/2016 | Stein et al. |
| 2016/0278736 | A1 | 9/2016 | Hamilton et al. |
| 2017/0172424 | A1* | 6/2017 | Eggers ............... A61B 8/488 |
| 2017/0360415 | A1* | 12/2017 | Rothberg ............ A61B 8/465 |
| 2018/0021021 | A1 | 1/2018 | Zwierstra et al. |
| 2019/0175138 | A1 | 6/2019 | Torp et al. |
| 2019/0353764 | A1 | 11/2019 | Vignon et al. |
| 2019/0388056 | A1 | 12/2019 | Rodriguez |
| 2022/0151586 | A1 | 5/2022 | Torp et al. |
| 2022/0151587 | A1 | 5/2022 | Torp et al. |

FOREIGN PATENT DOCUMENTS

| | | |
|---|---|---|
| CN | 102123668 A | 7/2011 |
| CN | 102440002 A | 5/2012 |
| CN | 103284753 A | 9/2013 |
| CN | 104011559 A | 8/2014 |
| CN | 104706382 A | 6/2015 |
| CN | 106037800 A | 10/2016 |
| CN | 107296628 A | 10/2017 |
| EP | 0014793 A1 | 9/1980 |
| EP | 2918232 A1 | 9/2015 |
| EP | 2940487 A1 | 11/2015 |
| GB | 2047404 A | 11/1980 |
| GB | 2237877 A | 5/1991 |
| JP | H02182246 A | 7/1990 |
| JP | 10328189 A | 12/1998 |
| JP | 2011526181 A | 10/2011 |
| JP | 2012170748 A | 9/2012 |
| JP | 2013223728 A | 10/2013 |
| JP | 2015150366 A | 8/2015 |
| JP | 6443237 B2 | 12/2018 |
| RU | 2686418 C2 | 4/2019 |
| WO | 9208408 A1 | 5/1992 |
| WO | 9502361 A1 | 1/1995 |
| WO | 9724986 A2 | 7/1997 |
| WO | 0072756 A1 | 12/2000 |
| WO | 2007057826 A1 | 5/2007 |
| WO | 2008060422 A2 | 5/2008 |
| WO | 2009158399 A1 | 12/2009 |
| WO | 2013014647 A1 | 7/2012 |
| WO | 2013059659 A1 | 4/2013 |
| WO | 2013088314 A1 | 6/2013 |
| WO | 2013154229 A1 | 10/2013 |
| WO | 2014107769 A1 | 7/2014 |
| WO | 2016113687 A1 | 7/2016 |
| WO | 2017109080 A1 | 6/2017 |
| WO | 2018025050 A1 | 2/2018 |

OTHER PUBLICATIONS

Torp, H. et al.; "Produktark NeoDoppler"; NTNU website; published Nov. 30, 2016; No longer available online; 1 page.

Atkinson, P. et al.; "Pulse-Doppler Ultrasound and Its Clinical Application"; The Yale Journal of Biology and Medicine, vol. 50, Issue No. 4; 1977; pp. 367-373.

Basu, S. et al.; "Cerebral blood flow velocity in early-onset neonatal sepsis and its clinical significance"; European Journal of Pediatrics, vol. 171, Issue No. 6; 2012; pp. 901-909.

Burns, S. et al.; "Design for an Ultrasound-Based Instrument for Measurement of Tissue Blood Flow"; Biomaterials, Artificial Cells, and Artificial Organs, vol. 17, Issue No. 1; 1989; pp. 61-68.

Charlton, M. et al.; "The microcirculation and its measurement in sepsis"; Journal of Intensive Care Society, vol. 18, Issue No. 3; 2017; pp. 221-227.

International Search Report and Written Opinion for International Application PCT/GB2019/050341; International Filing Date: Feb. 7, 2019; Date of Mailing: May 21, 2019; 17 pages.

International Search Report and Written Opinion for International Application PCT/GB2019/050342; International Filing Date: Feb. 7, 2019; Date of Mailing: May 31, 2019; 13 pages.

International Search Report and Written Opinion for International Application PCT/GB2019/050343; International Filing Date: Feb. 7, 2019; Date of Mailing: May 24, 2019; 13 pages.

International Search Report and Written Opinion for International Application PCT/GB2019/050344; International Filing Date: Feb. 7, 2019; Date of Mailing: May 21, 2019; 14 pages.

IPO UK Search Report for Application GB1802005.7; Patents Act 1977; Search Report under Section 17(5); Date Mailed: Jul. 23, 2018; 8 pages.

IPO UK Search Report for Application GB1802007.3; Patents Act 1977; Search Report under Section 17(5); Date Mailed: Aug. 3, 2018; 9 pages.

IPO UK Search Report for Application GB1802009.9; Patents Act 1977; Search Report under Section 17(5); Date Mailed: Aug. 8, 2018; 5 pages.

IPO UK Search Report for Application GB1802010.7; Patents Act 1977; Search Report under Section 17(5); Date Mailed: Jul. 31, 2018; 6 pages.

Kasai, C. et al.; "Real-Time Two-Dimensional Blood Flow Imaging Using an Autocorrelation Technique"; IEEE Transactions on Sonics and Ultrasonics, vol. SU-32, Issue No. 3; 1985; pp. 458-464.

(56) References Cited

OTHER PUBLICATIONS

Laerdal Medical AS; Moyo Fetal Heart Rate Monitor User Guide; 2015; 56 pages.
NTNU Discovery Website article, "Better conditions for premature infants"; Retrieved Jun. 30, 2017 from NTNU Discovery website at https://ntnudiscovery.no/en/portfolio/better-conditions-for-premature-infants/; 6 pages.
O'Brien, W.; "AAPM Tutorial: Single-Element Transducers"; Radiographics, vol. 13; 1993; pp. 947-957.
Spectromed JSC, Sonomed-300M Transcranial Doppler System User's Manual; 2011; 95 pages.
Torp, H. et al.; "Doppler Ultrasound"; Comprehensive Biomedical Physics, vol. 2; 2014; pp. 343-360.
Torp, H.; "NeoDoppler"; Retrieved Jun. 30, 2017 from the internet at http://conference.technoport.no/speaker/neodoppler/.
Youtube Screenshot (still image from web video) "NTNU Technology Transfer—Vi hjelper de gode ideene frem"; NTNU TTO; Retrieved Nov. 6, 2017 from the internet at https://www.youtube.com/watch?v=aXRPxcJ9wTA.
Alvisi, C. et al.; "Evaluation of cerebral blood flow changes by transfontanelle Doppler ultrasound in infantile hydrocephalus"; Child's Nervous System, vol. 1; 1985; pp. 244-247.
Japanese Office Action; Issued: Dec. 27, 2022; Application No. 2020-542817; 6 pages.
Anthony, M. et al.; "Neonatal cerebral blood flow velocity responses to changes in posture"; Archives of Disease in Childhood, vol. 69; 1993; pp. 304-308.
Coughtrey, H. et al.; "Postnatal evolution of slow variability in cerebral blood flow velocity"; Archives of Disease in Childhood, vol. 67; 1992; pp. 412-415.
Evans, D. et al.; "An automatic system for capturing and processing ultrasonic Doppler signals and blood pressure signals"; Physiological Measurement, vol. 10, Issue No. 3; 1989; pp. 241-251.
Fenton, A. et al.; "On line cerebral blood flow velocity and blood pressure measurement in neonates: a new method"; Archives of Disease in Childhood, vol. 65; 1990; pp. 11-14.
Ferrarri, F. et al.; "The Relationship between Cerebral Blood Flow Velocity Fluctuations and Sleep State in Normal Newborns"; Pediatric Research, vol. 35, Issue No. 1; 1994; pp. 50-54.
Kato, I. et al.; "Extrauterine environment influences spontaneous low-frequency oscillations in the preterm brain"; Brain & Development, vol. 35; 2013; pp. 17-25.
Livera, L. et al.; "Cyclical fluctuations in cerebral blood volume"; Archives of Disease in Childhood, vol. 67; 1992; pp. 62-63.
Menke, J. et al.; "Cross-Spectral Analysis of Cerebral Autoregulation Dynamics in High Risk Preterm Infants during the Perinatal Period"; Pediatric Research, vol. 42; 1997; pp. 690-699.
Michel, E. et al.; "Cyclic variation pattern of cerebral blood flow velocity and postconceptional age"; European Journal of Pediatrics, vol. 153; 1994; pp. 751-755.
Taga, G. et al.; "Spontaneous oscillation of oxy- and deoxy-hemoglobin changes with a phase difference throughout the occipital cortex of newborn infants observed using non-invasive optical topography"; Neuroscience Letters, vol. 282; 2000; pp. 101-104.
Von Siebenthal, K. et al.; "Cyclical fluctuations in blood pressure, heart rate and cerebral blood volume in preterm infants"; Brain & Development, vol. 21; 1999; pp. 529-534.
Zernikow, B. et al.; "Cerebral autoregulation of preterm neonates—a non-linear control system?"; Archives of Disease in Childhood, vol. 70; 1994; pp. F166-F173.
Chinese Office Action issued in Chinese Application No. 201780049048.3 dated Jun. 2, 2021.
Chinese Office Action issued in Chinese Application No. 202111294244.1 dated Feb. 7, 2024.
International Search Report issued in European Application No. 21201302.3 dated Jan. 14, 2022.
Notice of Reason for Refusal issued in Japanese Application No. 2019-506365 dated Jul. 2, 2021.

\* cited by examiner

Term baby on day 3 of life, clinical stable, BW 3600gram

GA 31+6, on day 6 of life, clinical stable, no respiratory support

GA 24+6, BW 615gram, 18 hours of life, non-invasive NAVA

GA 24+6, BW 615gram, 36 days of life, CPAP

GA 41+3, BW 4340gram, 32 hours of life, clinical stable

GA 39+4, BW 4040gram, 4 days of life, sepsis, (CRP159 on day2), clinical better

GA 36+0, BW 2400gram, Gastroschisis, on day one after surgery, mechanical ventilation GA 29+6, BW 1560gram, 25 hours of life, on CPAP, suspected sepsis

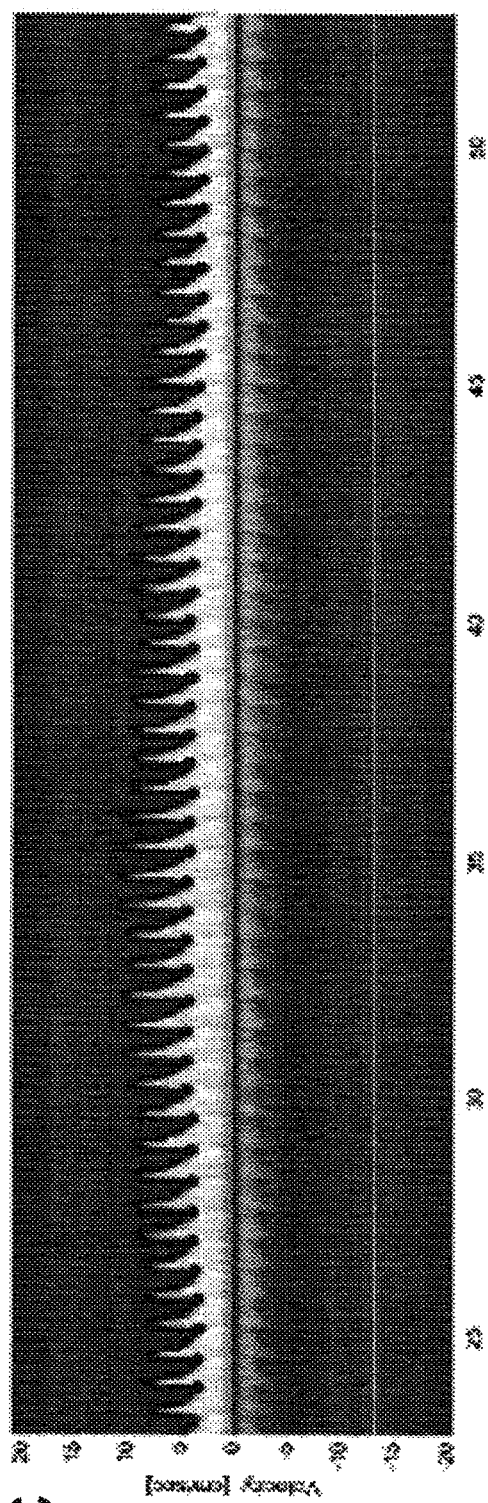
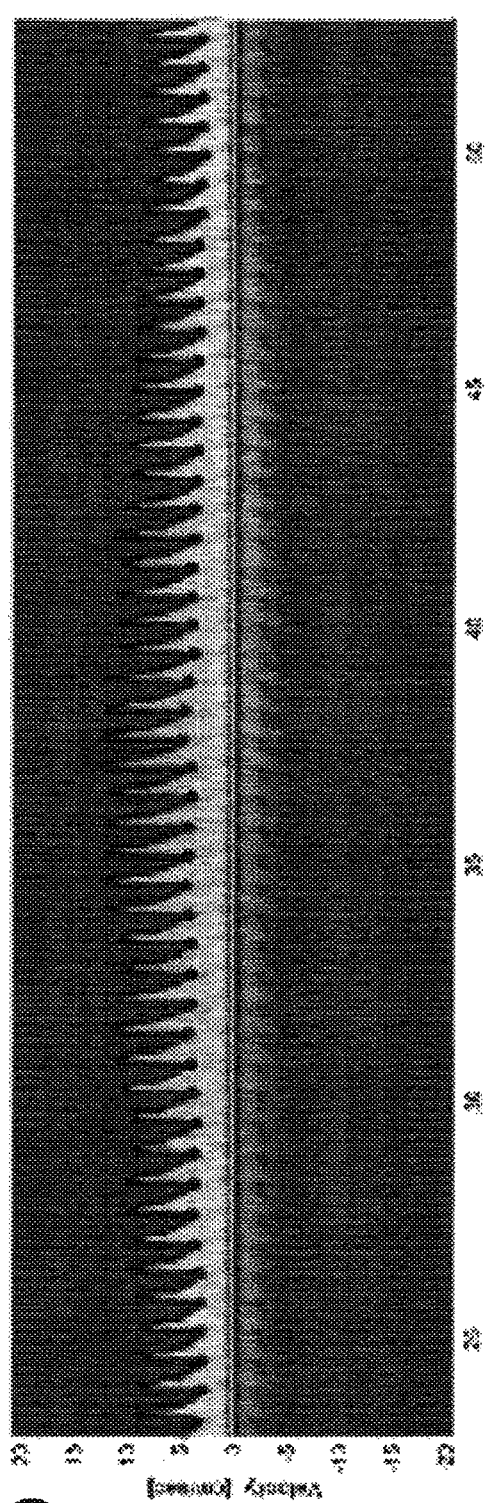
Fig. 38C
Fig. 38D

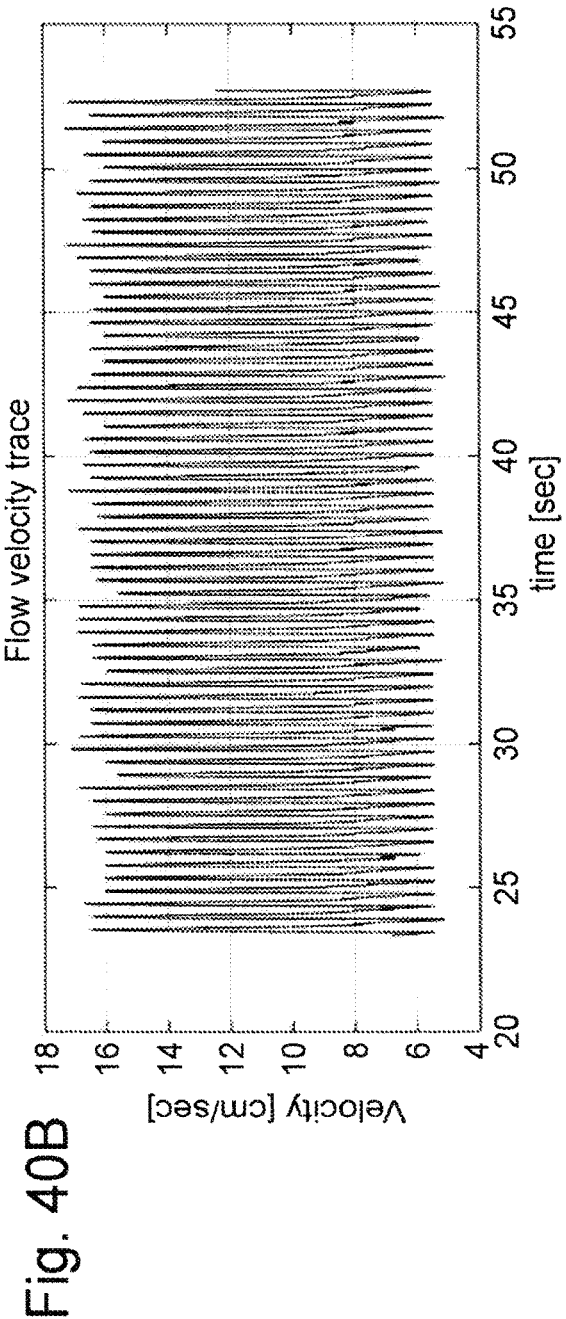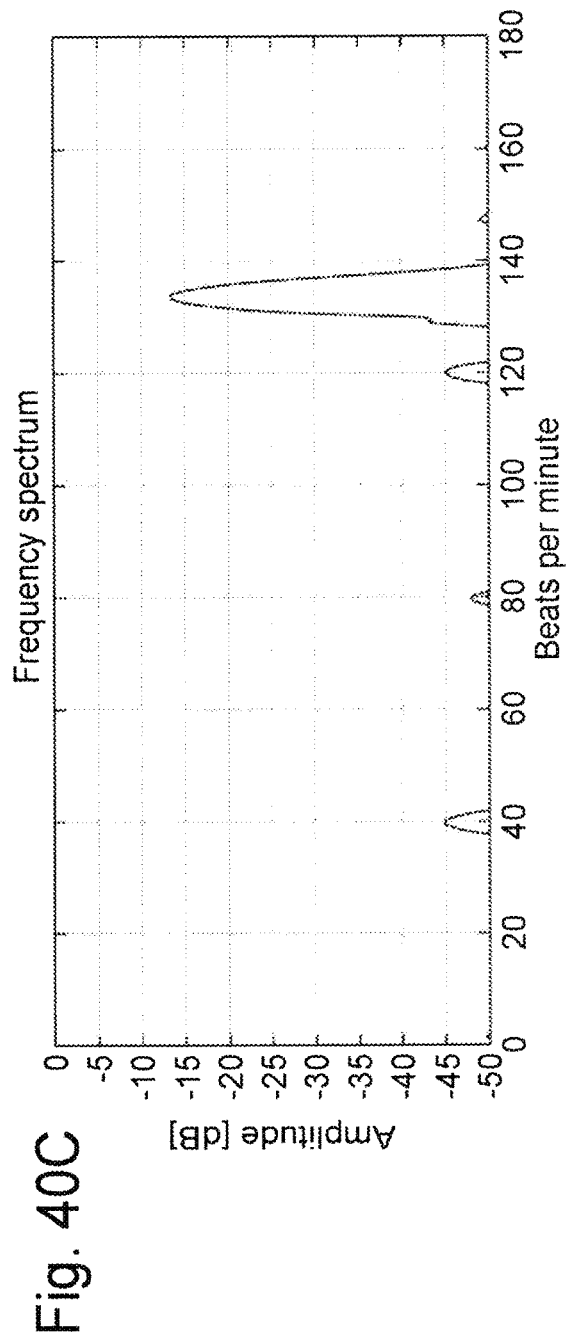

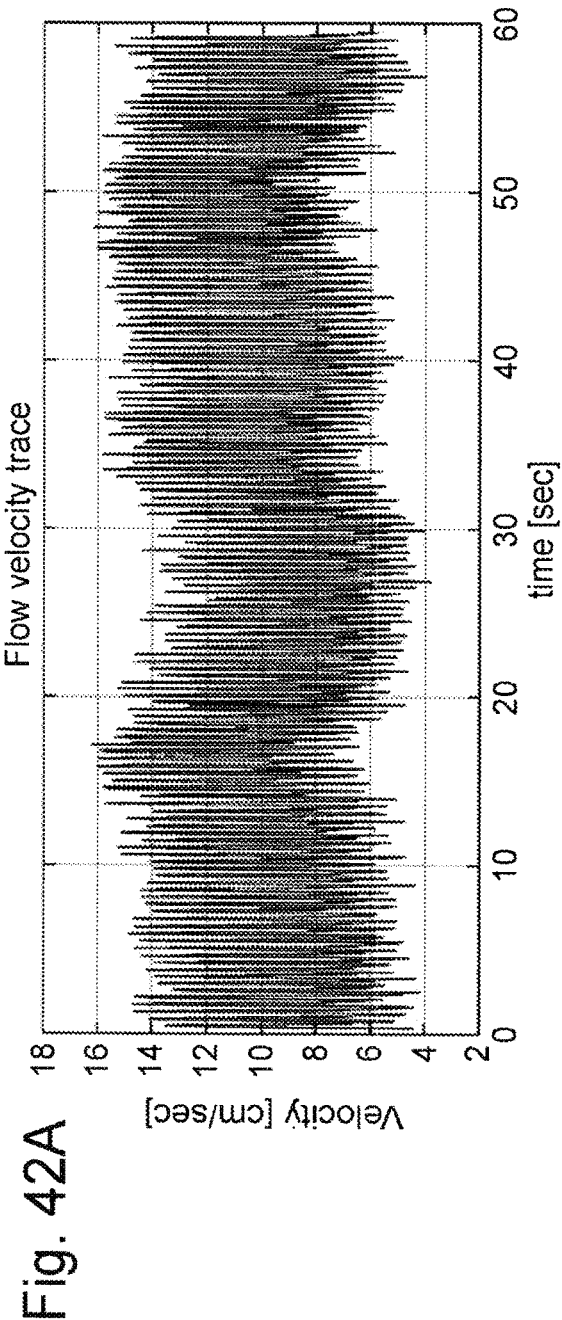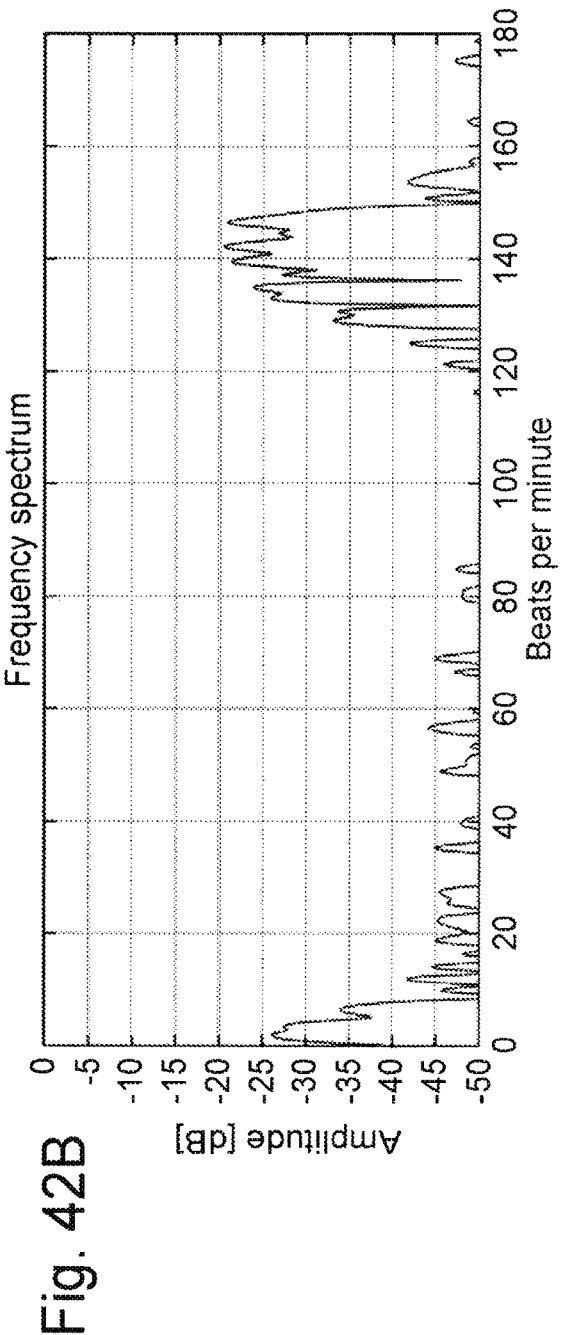
Fig. 42A
Fig. 42B

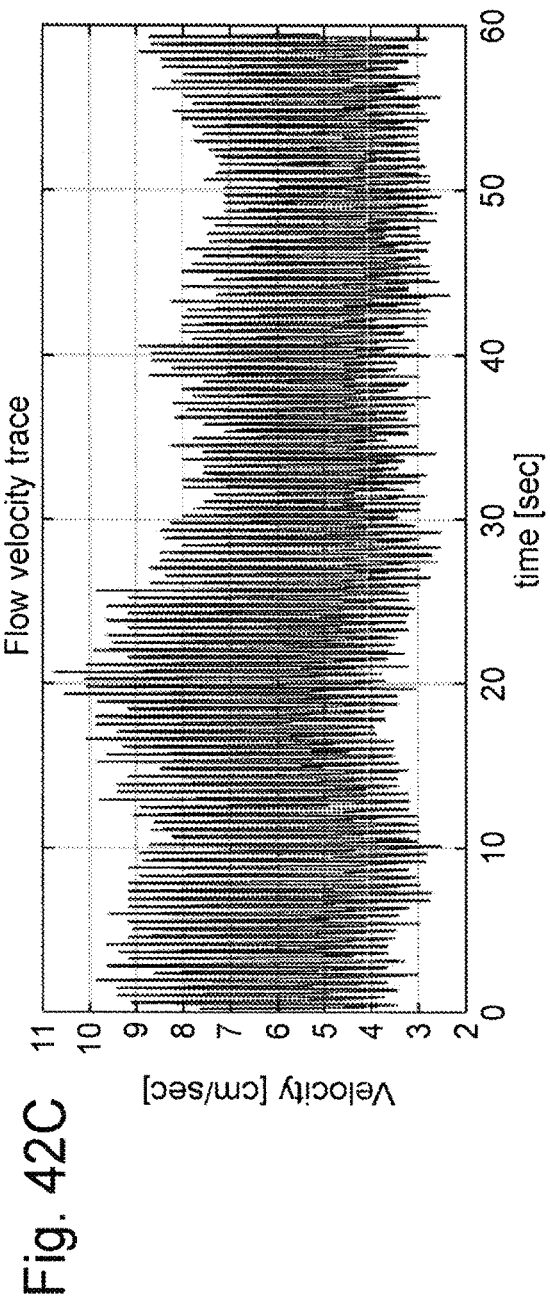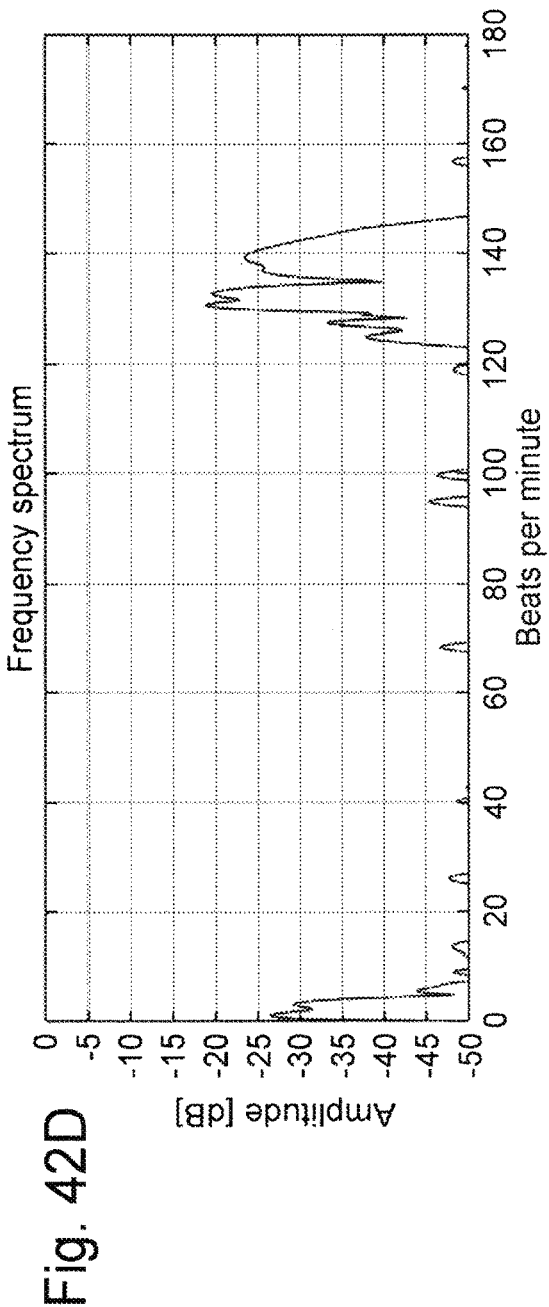

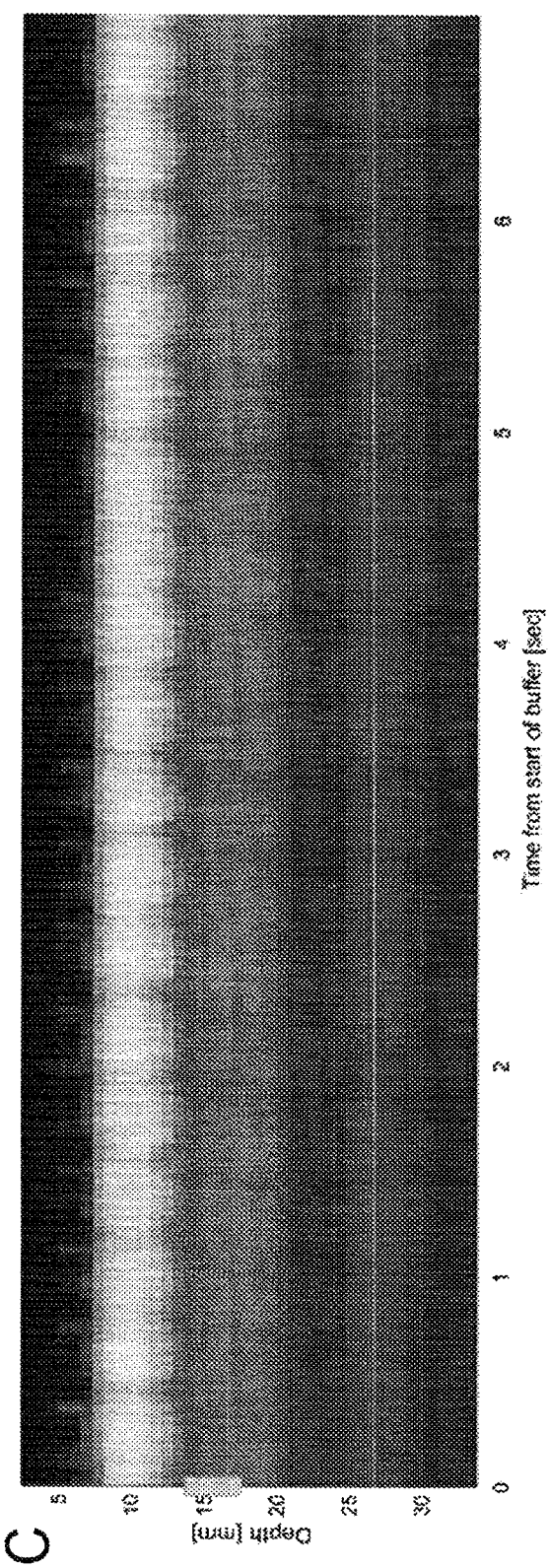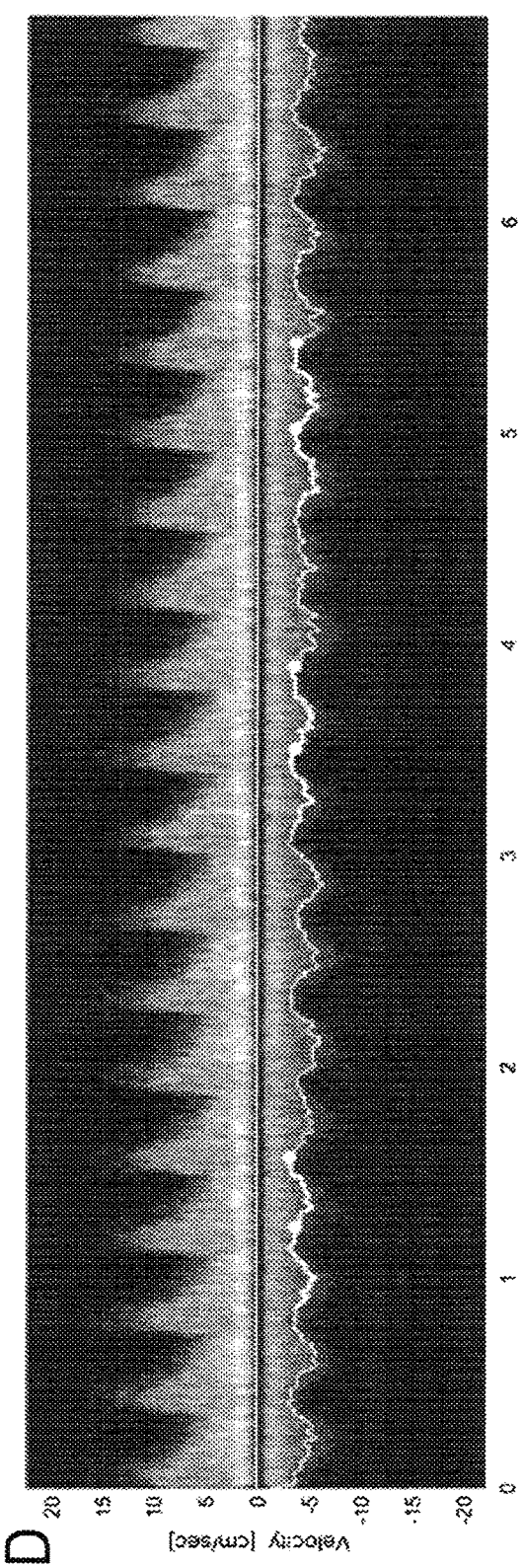
Fig. 44C
Fig. 44D

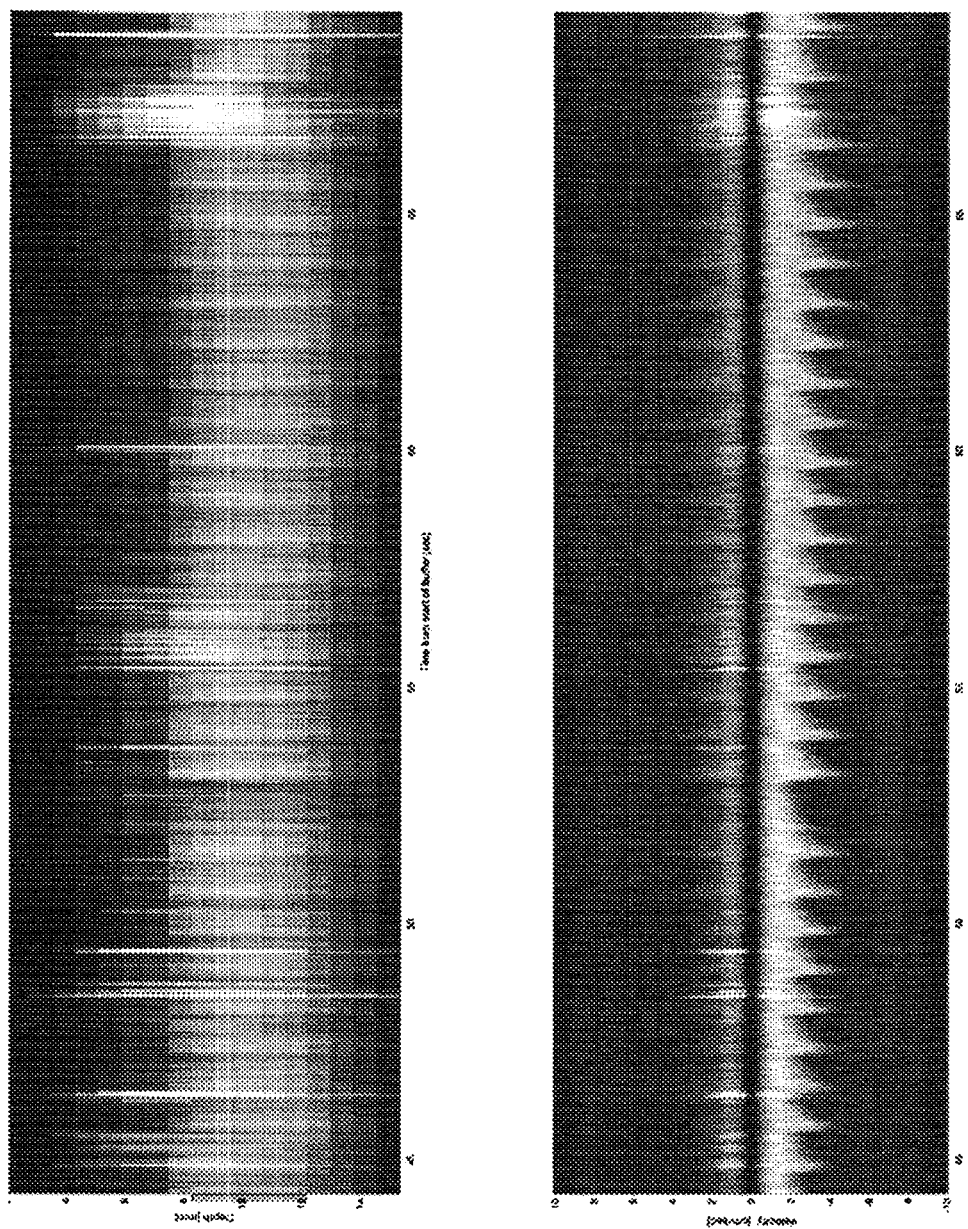
Fig. 46B
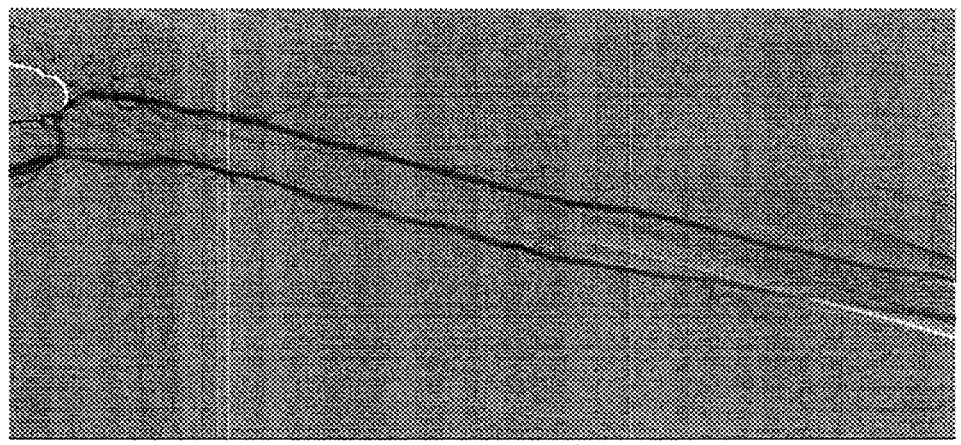

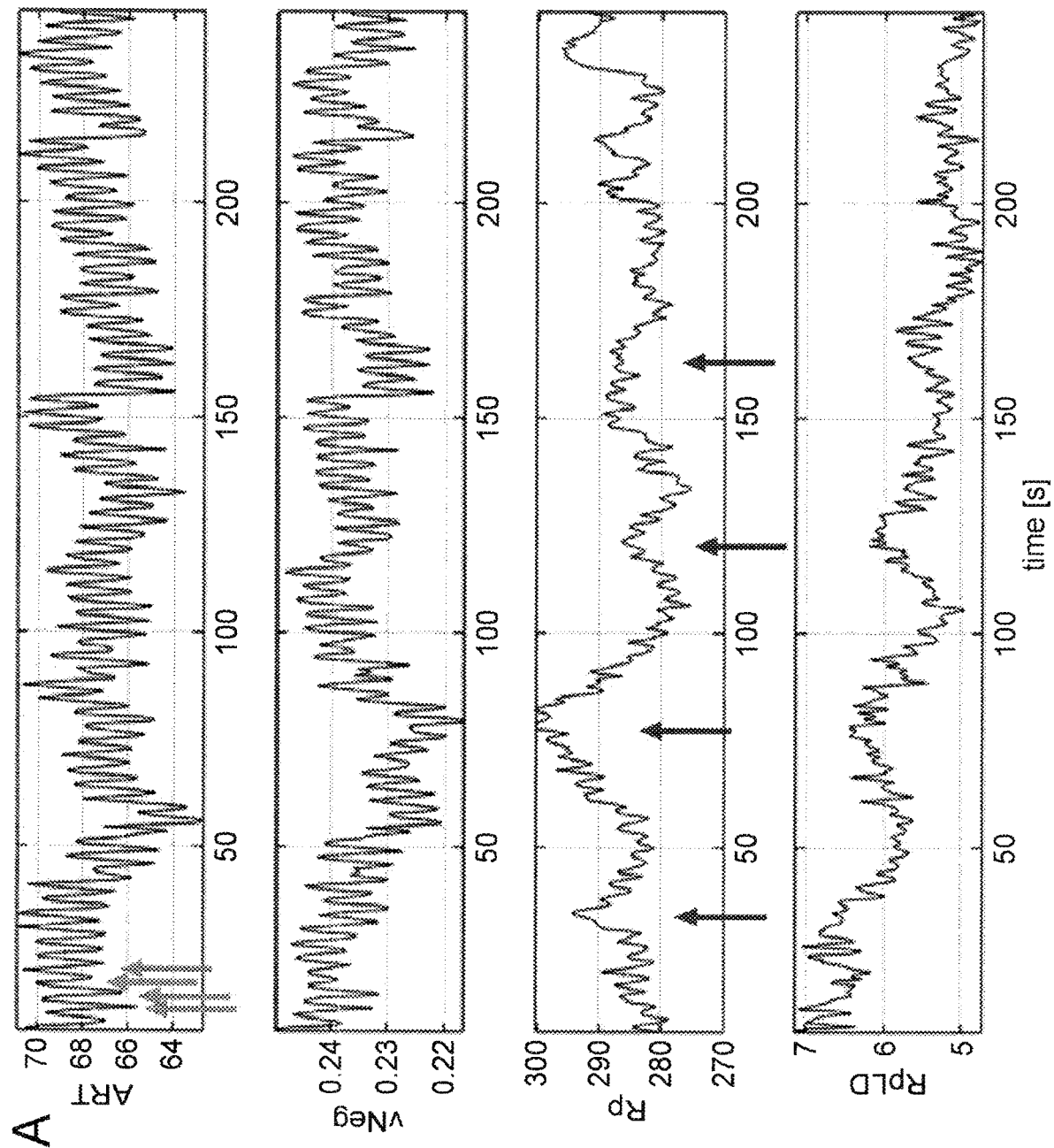

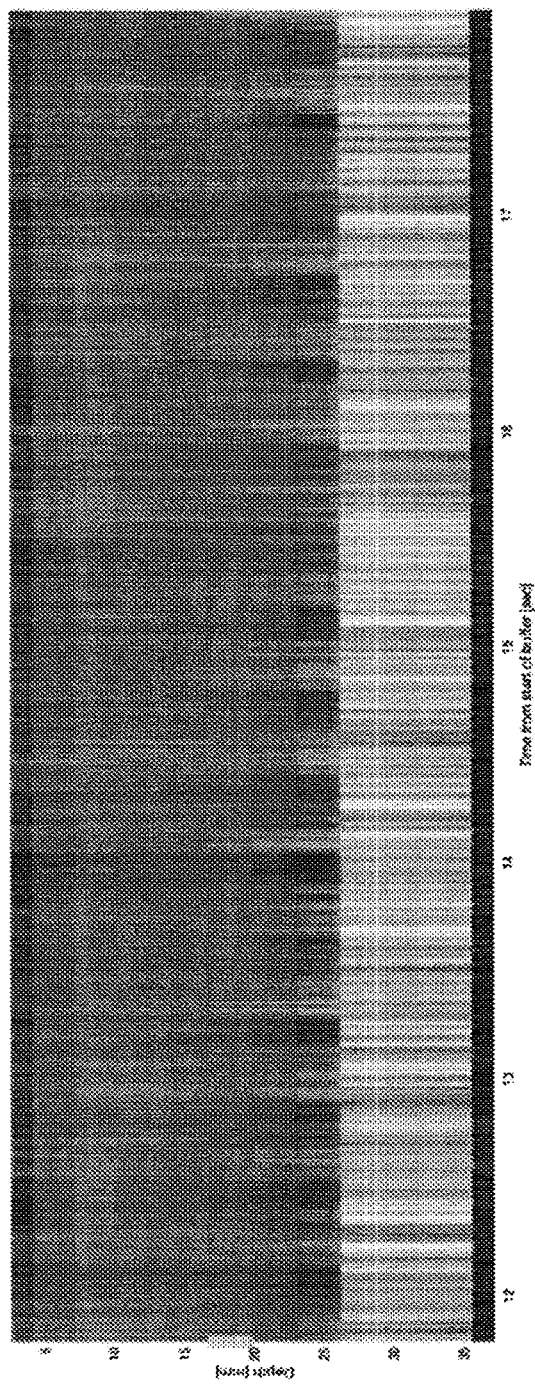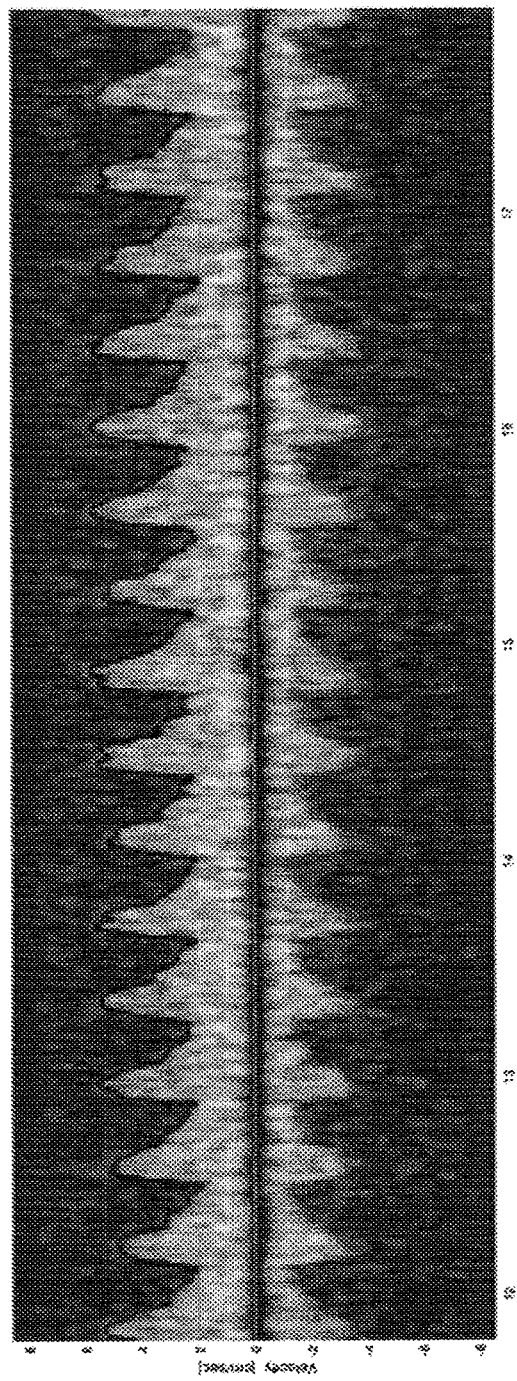
Fig. 49A
Fig. 49B

ULTRASOUND BLOOD-FLOW MONITORING

CROSS REFERENCE TO RELATED APPLICATIONS

This application is a National Stage application of PCT/GB2019/050344, filed Feb. 7, 2019, which claims the benefit of British Patent Application No. 1817102.5, filed Oct. 19, 2018 and British Patent Application No. 1802007.3, filed Feb. 7, 2018, all of which are incorporated by reference in their entirety herein.

BACKGROUND OF THE INVENTION

This invention relates to apparatus and methods for characterising or monitoring blood flow using ultrasound.

Various techniques have been used to analyse blood flow in human or animal subjects. These include laser Doppler scanning, near-infrared spectroscopy, and Doppler ultrasound imaging. However, such analyses must typically be performed by a skilled technician, who must be present with the patient throughout. The equipment for carrying out such analyses can also be very expensive (e.g., over one million U.S. dollars for a 3D ultrasound imaging system). Such techniques are therefore not well suited to the unattended monitoring of patients in settings such as hospital wards or at home.

The present invention seeks to provide a better approach.

SUMMARY OF THE INVENTION

From a first aspect, the invention provides a method for determining a characteristic of blood flow in a vertebrate animal subject, the method comprising:
  transmitting ultrasound pulses into the subject from an ultrasound transducer that is fastened to the subject;
  receiving reflections of the ultrasound pulses at the ultrasound transducer;
  generating pulse-Doppler response signals from the reflections; and
  processing the pulse-Doppler response signals to determine a characteristic of blood flow within the subject.

From a second aspect, the invention provides a system for determining a characteristic of blood flow in a vertebrate animal subject, the system comprising:
  an ultrasound transducer;
  a fastener or an adhesive layer for fastening the ultrasound transducer to the subject; and
  a controller,
wherein the controller is configured to:
  control the ultrasound transducer to transmit ultrasound pulses into the subject;
  sample reflections of the ultrasound pulses received at the ultrasound transducer;
  generate pulse-Doppler response signals from the reflections; and
  process the pulse-Doppler response signals to determine a characteristic of blood flow within the subject.

Thus it will be seen that, in accordance with these aspects, rather than a skilled operator having to manually hold an ultrasound transducer against the subject, an ultrasound transducer is fastened to the subject. This can facilitate the monitoring of blood flow over an extended period of time, without requiring the expense of a human operator attending the subject continually during the data collection process. Preferably the ultrasound transducer will be fastened to the subject on an external surface of the subject and thus will be non-invasive (i.e. fastening will preferably not involve a surgical procedure).

The ultrasound transducer may be fastened to the subject by chemical and/or mechanical means.

In one set of embodiments, the ultrasound transducer is bonded to the subject using an adhesive layer. This adhesive layer may be applied to a transducer element of the ultrasound transducer such that it lies between the transducer element and the subject. The ultrasound pulses may travel through the adhesive layer. In this case, the use of separate ultrasound gel may be unnecessary. Alternatively, the adhesive layer may bond a housing of the ultrasound transducer to the subject. Ultrasound gel may then be applied separately to eliminate any air gap between a transducer element and the subject. The adhesive layer may be able to bond the ultrasound transducer to the subject with a force that is greater than the weight of the ultrasound transducer.

In some embodiments, the system comprises a fastener for fastening the ultrasound transducer to the subject, such as the skin of the subject. The ultrasound transducer is preferably designed for external use. The fastener is preferably non-invasive. The fastener may comprise one or more straps, which may be of fabric, plastic, or any other flexible material. One or more straps of the fastener may be sized for securing, alone or in combination, around a limb, head, digit or other body part of the subject. The fastener may comprise an elasticated portion or a spring or other means for applying a compressive force to part of the subject's body. The fastener may have a surface for contacting the skin of the subject. The fastener may be configured to use friction, alone or in conjunction with other means such as an adhesive, to secure the ultrasound transducer resiliently in place against the subject. The fastener may comprise a clip. The fastener may comprise a mount for receiving the ultrasound transducer. The fastener may be bonded or secured to the ultrasound transducer—e.g., such that a tool is required to separate the ultrasound transducer from the fastener non-destructively. In other embodiments, the ultrasound transducer may be releasably secured to the fastener—e.g., retained only by friction.

The ultrasound transducer may be configured to transmit unfocused ultrasound pulses. The ultrasound pulses may be plane-wave pulses. (The skilled person will appreciate that, in practice, the wavefront may not be exactly planar—e.g., due to imperfections in the transducer, or due to interference (e.g., refraction and diffraction) as the waves travel, or due to the finite extent of the wavefront, and the expression "plane-wave" should be understood accordingly.) The transducer preferably has no acoustical lens.

The controller may be configured to generate a pulse-Doppler response signal from one or more transmitted ultrasound pulses wherein the pulse-Doppler response signal aggregates reflections from across a region in the subject that has substantially the same width as the transmitted pulse received at the region. The system may have a receive beam, or spatial sensitivity region, that is coincident with a transmit beam. The receive beam may have a width or diameter that is substantially equal to, or at least half, a width or diameter of the transmit beam, at a depth at which the characteristic of blood flow is determined. The transmit beam and receive beam may both be unfocused. The characteristic of blood flow may be determined for an aggregate blood flow through a plurality of blood vessels. This contrasts with conventional array-based Doppler blood-flow imaging systems that use a focused receive beam (e.g., using delay-and-sum beamforming techniques) to analyse blood flow within a very small region, typically lying within the width of a single artery (e.g., having a beam width of under 0.5 mm at the focal point).

The ultrasound transducer may comprise a plurality of transducer elements—e.g., arranged in a linear or rectangular array. Signals received at the plurality of transducer elements may be summed without any delay (in contrast with conventional delay-and-sum beamforming), and the pulse-Doppler response signals may be generated from the summation of the signals received at each respective transducer elements.

However, in one set of embodiments the ultrasound transducer is a single-element transducer. The (single) transducer element may be a piezoelectric element. The same element in the ultrasound transducer may transmit and receive ultrasound. This enables the cost of the transducer to be kept low. The transducer may emit ultrasound from a planar face. The planar face may have a width (e.g., a maximum, minimum or mean width) that is large compared with each transducer element in traditional array-based ultrasound transducers—for example, having a width of at least 2 mm, 5 mm, 10 mm, 20 mm or more. Compared with a wavelength of the ultrasound pulses transmitted from the transducer, the width of this transmitting surface may be 10 wavelengths, 50 wavelengths, or even 100 wavelengths or more. (Wavelengths, as referred to herein, may be understood as relating to waves travelling in soft human tissue—e.g. waves travelling at 1540 m/s.) A ratio of width to wavelength of ten, twenty, fifty times or more can help to provide a more uniform beam, which is desirable for providing responses from different depth regions that are comparable in volume. The transducer may transmit ultrasound energy in a substantially uniform beam—i.e., having a constant or near-constant cross-section in the propagation (depth) direction, at least up until a maximum depth at which reflections are processed to determine the characteristic of blood flow. The transducer (or a transmitting face thereof) may have any shape, but in one set of embodiments it is circular or rectangular. It may therefore transmit a circular or rectangular cylindrical beam into the organism—e.g., a circular beam having a diameter of approximately 5 mm or approximately 10 mm.

The characteristic of blood flow may be determined from reflections received from a region within the subject.

By not focusing the transmit beam, and by using a transducer much larger than a transmitted wavelength (e.g., ten times or more), the intensity of the ultrasound pulses may be substantially uniform across this region. This would not typically be possible with a focused transmit beam, the intensity of which would vary across the region, and across individual blood vessels. Similarly, by not focusing the receive beam, the reflections may be aggregated substantially uniformly from across the whole region. This would not typically be possible with a focused receive beam, which has only a small spatial sensitivity region.

A lateral extent of the region within the subject may be determined by the shape of the transducer or a transmitting face thereof. An axial position or extent of the region (i.e., in the propagation direction, also referred to herein as the depth direction) may be determined by the duration of each pulse (e.g., being at least half the pulse duration) and by a time delay at which the reflections are sampled, after the transmission of each pulse. As explained in more detail below, reflections from a plurality of different (e.g., non-overlapping) regions may be sampled and processed to generate separate respective Doppler signals; these reflections may be received from one or more common transmitted pulses—i.e., they may all cover substantially the same time period. Range-gating may be used to control the axial extent of the (or each) region. In some embodiments, the region has a depth of between 0.15 mm to 1 mm. The region may have a diameter or minimum width of approximately 5 mm, 10 mm or 20 mm.

The system is particularly well suited to determining a characteristic of blood flow close to the transducer. This is because a broad, unfocused beam means that the reflection from each blood cell is relatively weak. The region may therefore have a maximum distance from the transducer, in the propagation direction, that is less than a width (e.g., a maximum, minimum or mean width) of the transducer or transducer element, or that is no more than two, three, five or ten times this width.

The ultrasound transducer may comprise a housing—e.g., of plastic or metal. The ultrasound transducer may be substantially cuboid or substantially a circular cylinder. It may be disc-shaped. It may have a minimum, maximum or average diameter or width that is between 5 mm and 50 mm, or between 10 mm and 20 mm.

The housing may comprise an electromagnetic shielding layer, e.g., a metal layer, which may partially or wholly surround one or more electronic components or conductors in the transducer. The shielding may provide a Faraday cage for the transducer. The ultrasound transducer may be connected to the controller by an electrical or fibre-optic cable. The cable may be electromagnetically shielded—e.g., being a tri-axial cable. The use of electromagnetic shielding for the transducer has been found to be particularly important in some embodiments because the signal-to-noise ratio from a broad, unfocused beam can be much lower than in traditional medical ultrasonography.

The pulses may have a wavelength that is smaller than a diameter or width of the ultrasound transducer. In order to transmit plane waves with a uniform intensity, a wavelength of the pulses may be at least ten times smaller than a minimum, maximum or average diameter or width of the transducer or a transmitting face of the transducer. The pulses may have a frequency, or include a frequency component, in the range 5 MHz to 20 MHz—for example, around 8 MHz or 16 MHz. A balance may need be struck between the greater penetration depth of a longer wavelength (e.g., approximately 40 mm at 8 MHz, compared with 20 mm at 16 MHZ) and the greater resolution of a shorter wavelength. Similarly, a balance may need to be struck in the diameter of the transducer whereby it supports transmit and receive beams that are broad enough to capture all the blood vessels across a region of interest while being sufficiently small to fasten conveniently to the subject.

The ultrasound transducer may be flat—i.e., shallower in height than its maximum diameter or width. In particular, the ultrasound transducer may comprise a housing for an ultrasound transducer element, wherein the housing comprises or defines a planar window for passing ultrasound signals from the transducer element to outside the housing. An average (mean) height or a maximum height of the housing, perpendicular to said window, integrated over the area of the window, may be less than a maximum diameter or width of the window. The housing may be rigid. The housing may be a single piece of metal or plastics material. The housing may wholly or partially surround the transducer element. The ultrasound transducer may have additional components, such as lead and a flexible strain relief for the lead, which may be distinct from the housing and which may extend beyond a height equal to the maximum diameter or width.

From a further aspect, the invention provides a medical ultrasound transducer comprising:
- an ultrasound transducer element, for transmitting ultrasound signals; and
- a housing for the transducer element, wherein:
- the housing comprises or defines a planar window for passing ultrasound signals from the transducer element; and
- the housing has an average height, perpendicular to said window, over the area of the window, that is less than a maximum diameter or maximum width of the window.

Features of any other aspect may be features of this aspect also. In particular, the ultrasound transducer may have only a single transducer element. The ultrasound transducer may comprise a fastener or an adhesive layer for fastening the ultrasound transducer to the subject.

The ultrasound transducer unit may be used in a monitoring system as disclosed herein.

In one set of embodiments, the ultrasound transducer of this aspect or earlier aspects may define a rectangular window of approximately 5 mm×16 mm. The average height of the ultrasound transducer may be approximately 8 mm. In another set of embodiments, the ultrasound transducer may define a circular window of approximately 10 mm diameter. The average height of the ultrasound transducer may again be approximately 8 mm.

The transducer may be configured to be fastened to a subject with the planar window substantially parallel to the subject's skin. A transmitting face of the transducer element may be parallel to the planar window defined by the housing. In this way, the ultrasound pulses may be transmitted substantially perpendicularly to the subject's skin. However, in other embodiments, a transmitting face of the transducer element may be inclined to the planar window—for example, at an angle of between 5 and 45 degrees, such as at approximately 30 degrees or 45 degrees. This can facilitate the determining of a characteristic of blood where the blood is flowing broadly parallel to the planar window. This is because the pulse-Doppler response signals represent only those components of velocity that are perpendicular to the face of the transducer element, so flow parallel to the face does not give rise to any Doppler shift.

The ultrasound transducer may comprise one or more piezoelectric elements. The element may comprise a polymer or a ceramic or a polymer-ceramic composite. It may comprise lead zirconate titanate (PZT). In a preferred set of embodiments, the element comprises a ceramic (e.g., $PbZr_xTi_{1-x}O_3$ for x having a value between 0 and 1) that is doped with ions. It is preferably doped with acceptor ions (e.g., $K^+$, $Na^+$, $Fe^{+3}$, $Al^{+3}$ or $Mn^{+3}$)—i.e., a so-called "hard" piezoelectric ceramic. It may comprise Pz26 (Navy Type I PZT-4), Pz28 (Navy Type III PZT-8) or Pz24 from FerroPerm™ (Meggitt™). In some embodiments, the element has a clamped dielectric constant that is less than 500 or less than 250—e.g., around 240 or less.

The applicant has found that a PZT material having a lower dielectric constant than "soft" PZT materials, doped with donor ions, such as Pz27 and PZ29 from FerroPerm™ (Meggitt™) can advantageously be employed in certain embodiments of the present invention to provide an ultrasound transducer that is easier to drive electrically for a given thickness and area of the transducer. In particular, a hard ceramic transducer has been found to be particularly well suited for use in a single-element Doppler transducer; this is because the typically larger aperture area of such a transducer, compared with the transducer elements in conventional array-based medical ultrasound transducers, results in a lower electrical impedance, for a given choice of piezoelectric material. This reduced impedance (which can make the transducer more complex to drive) can be mitigated by using a harder material.

In some embodiments, the ultrasound transducer may comprise impedance tuning circuitry. However, by using a hard ceramic transducer, some embodiments may avoid the need for impedance tuning circuitry in the ultrasound transducer. Thus, in some embodiments, the ultrasound transducer does not contain any tuning transformer.

The characteristic of blood flow may relate to the velocity of the blood flow. It may relate to a component of velocity parallel to a transmission axis of the ultrasound transducer, or perpendicular to a transmission face of the ultrasound transducer. The characteristic may be any statistical measure derived from a set of velocity measurements over space and/or over time. It will be appreciated that any reference to "velocity" herein may refer to a component of velocity along a transmission or reception axis of the ultrasound transducer, and may therefore, in some cases, be represented by a scalar value (which may be signed or unsigned, depending on context).

The characteristic of blood flow may relate to the total blood flow within a region, which may be a cylindrical region, such as a circular or rectangular cylinder. The region may span the transmit beam and/or receive beam of the system. (It will be appreciated that references to cylinders and other shapes represent an idealised situation, and, in reality, the nature of ultrasound propagation in the animal medium means these shapes are only approximate, and may have soft, rather than hard, boundaries).

The characteristic may be a spatial-maximum velocity (parallel to the transmission axis) within a region. This may be determined, for example, by determining the maximum frequency-shift over all frequency shifts (or just positive or negative shifts) within a time-gated depth range that are above a minimum frequency-signal strength threshold. The characteristic may instead be derived from a set of spatial-maximum velocities determined at a succession of times. This set may represent a velocity trace of a spectrogram. The characteristic may be a time-maximum (VMax), time-minimum (VMin), or time-averaged mean (VMean) of the spatial-maximum velocity over a period of time; the period of time may be fixed or variable; it may be shorter or longer than one heartbeat—for example, between 5 and 30 seconds, such as 7 or 8 seconds, or it may be equal to one heartbeat. The characteristic may be a pulsatile index (PI), a resistivity index (RI), velocity area under the curve, an end diastolic velocity (VED), heart rate, blood flow volume through a region, or any other measure derived from the pulse-Doppler response signals. The characteristic may be a first or second order statistic of any of these parameters.

The characteristic may be evaluated repeatedly at intervals, which may be regular or irregular intervals. In some embodiments, one value of the characteristic may be estimated every time a new pulse-Doppler response signal is generated, or every 5 milliseconds, or every 10 milliseconds, (e.g., when the characteristic is a spatial-maximum), or every heartbeat or every 1, 5, 10 or 60 seconds (e.g., where the characteristic is VMax). A set of one or more heartbeats may be identified that satisfy a quality criterion—e.g., that the gradient of the positive and/or negative velocity traces satisfies a predetermined condition-thereby defining a set of valid heartbeats. The characteristic may be time-averaged over this set of valid heartbeats, or the characteristic may be such a time-average.

A value (e.g., a current value) of the characteristic may be displayed on a display device—e.g., as a number—or a set of historic values may be displayed. A plot over time may be generated from a series of values, and may be displayed on a display device. The plot may be superimposed with a spectrogram.

The controller may be configured to apply a noise filter or clutter filter to the pulse-Doppler response signals, to reduce contributions from stationary or slow-moving tissue, or from thermal noise. In some embodiments, the pulse-Doppler response signals are complex-demodulated. The response signals are preferably shifted to baseband.

Removing clutter signals with a clutter filter helps to detect where blood is present. Tissue Doppler, for example, is a conventional approach to imaging tissue velocity (e.g., of heart muscle), but since the signal from non-blood tissue is typically thousands of times stronger than signals from blood, moving blood will not be visible in a tissue Doppler display. The clutter filter enables blood flow to be detected. In some embodiments, a combination of signal power and a frequency characteristic (after clutter filtering) may be used to determine if there is blood present, as well as the direction and velocity of the blood.

Data representing a Doppler frequency spectrum, or a velocity spectrum, may be generated from a set of one or more of the pulse-Doppler response signals. The frequency or velocity spectrum may represent all blood flow through a region, as described herein—optionally all blood flow above a lower velocity bound and/or below an upper velocity bound. A succession of spectra may be calculated over time.

In some embodiments, the controller may process positive Doppler shifts from one or more of pulse-Doppler response signals separately from negative Doppler shifts. The controller may calculate, from one or more pulse-Doppler response signals, a first envelope from positive Doppler shifts, and a second envelope from negative Doppler shifts, corresponding to blood flow towards or away from the ultrasound transducer, respectively, within a region of the subject. The controller may use an autocorrelation operation to identify heartbeats from the pulse-Doppler response signals. It may assign a quality metric to each heartbeat. The quality metric may depend on a similarity of the pulse-Doppler response signal or signals, or data derived therefrom, such as a frequency or velocity spectrum, for a respective heartbeat to the pulse-Doppler response signal or signals, or data derived therefrom, for a preceding heartbeat—e.g., the immediately preceding heartbeat. Where two heartbeats are similar, the quality metric may be high, indicating that the heartbeats have been correctly identified with high confidence. The controller may evaluate the characteristic of blood flow only over those heartbeats that satisfy a quality criterion—e.g., for the quality metric exceeds a threshold level. Periods of time covering signals that are not identified as heartbeats with sufficiently high confidence may be excluded from a time window over which the characteristic of blood flow is determined. This can improve the reliability of the determined value or values.

In one set of embodiments, the characteristic may be determined over a set of frequencies that includes only positive frequencies (corresponding to frequencies higher than those of the transmitted pulses before demodulation), so that only flow in a direction having a component towards the transducer is included. In another set of embodiments, the characteristic may be determined over a set of frequencies that includes only negative frequencies (corresponding to frequencies lower than those of the transmitted pulses before demodulation), so that only flow in a direction having a component away from the transducer is included. The system may calculate two sets of values of the characteristic of blood flow, one for positive frequency shifts and another for negative frequency shifts, for blood flow within the same region. The system may comprise a display and may be configured to display one or more values of the characteristic for positive frequency shifts and one or more values of the characteristic for negative frequency shifts, for blood flow within the same region. These values may be displayed simultaneously—e.g., on different parts of the display. In this way, a physician can choose to monitor flow in just one direction, by looking at the relevant values on the display—this may be useful if, for example, one particular major artery is of interest in a region. In some embodiments, a maximum or mean speed towards the transducer and a maximum or mean speed away from the transducer, over a common time period, and within a common region, may be displayed, or may be displayable in response to an input from a user.

The idea of determining a characteristic of blood flow through a region respectively for two different directions at the same time is believed to be novel. In particular, conventional colour Doppler imagery does not allow such a distinction to be made, as it typically represents only an average velocity (averaged over the whole frequency spectrum) at a particular point.

From a further aspect, the invention provides a method for determining a characteristic of blood flow in a vertebrate animal subject, the method comprising:
 transmitting ultrasound pulses into the subject from an ultrasound transducer;
 receiving reflections of the ultrasound pulses at the ultrasound transducer from a region in the subject;
 generating pulse-Doppler response signals from the reflections; and
 processing the pulse-Doppler response signals to determine a first value of a characteristic of blood flow within the region for blood flowing towards the ultrasound transducer over a time period, and to determine a second value of the characteristic for blood flowing away from the ultrasound transducer over said time period.

From another aspect, the invention provides a system for determining a characteristic of blood flow in a vertebrate animal subject, the system comprising:
 an ultrasound transducer;
 a controller,
wherein the controller is configured to:
 control the ultrasound transducer to transmit ultrasound pulses into the subject;
 sample reflections of the ultrasound pulses received at the ultrasound transducer;
 generate pulse-Doppler response signals from the reflections; and
 process the pulse-Doppler response signals to determine a first value of a characteristic of blood flow within the region for blood flowing towards the ultrasound transducer over a time period, and to determine a second value of the characteristic for blood flowing away from the ultrasound transducer over said time period.

Each pulse-Doppler response signal may be processed to determine a respective first value and a respective second value from the same pulse-Doppler response signal.

The first value and/or the second value may be stored in memory, or output over a network interface, or displayed on a display device—e.g., numerically or graphically.

A first sequence of such first values and a second sequence of such second values may be determined over time. The first and second sequences may comprise values of the characteristic at common time periods across the sequences.

Features of other aspects and embodiments disclosed herein may be combined with these aspects. In particular, the ultrasound transducer may be fastened to the subject. It may be a single-element ultrasound transducer.

From another aspect, the invention provides a method of monitoring blood flow in a vertebrate animal subject, the method comprising:
  transmitting unfocussed plane-wave ultrasound pulses into the subject, along a transmission axis, from a single transducer element of a single-element ultrasound transducer that is fastened to the subject;
  receiving reflections of the ultrasound pulses at the single transducer element from a region in the subject;
  generating a succession of pulse-Doppler response signals from the reflections over time;
  processing each pulse-Doppler response signal to determine a first respective spatial-maximum velocity value for blood flowing through the region towards the single transducer element, and to determine a second respective spatial-maximum velocity value for blood flowing through the region away from the single transducer element;
  identifying heartbeats from said spatial-maximum velocity values;
  assigning a quality metric to each identified heartbeat;
  identifying a subset of the spatial-maximum velocity values for which the assigned quality metric exceeds a threshold level;
  monitoring values from the subset of spatial-maximum velocity values over time; and
  determining when a set of one or more values from the subset of spatial-maximum velocity values satisfies a predetermined alert criterion, and, in response to said determining, signalling an audible or visual alert.

From a further aspect, the invention provides a system for monitoring blood flow in a vertebrate animal subject, the system comprising:
  a single-element ultrasound transducer, having a single transducer element, for fastening to the subject;
  a controller,
wherein the controller is configured to:
  control the ultrasound transducer to transmit unfocussed plane-wave ultrasound pulses, along a transmission axis, from the single transducer element into the subject when the ultrasound transducer is fastened to the subject;
  sample reflections of the ultrasound pulses received at the single transducer element from a region in the subject;
  generate a succession of pulse-Doppler response signals from the reflections over time;
  process each pulse-Doppler response signal to determine a first respective spatial-maximum velocity value for blood flowing through the region towards the single transducer element, and to determine a second respective spatial-maximum velocity value for blood flowing through the region away from the single transducer element over said time period;
  identify heartbeats from said spatial-maximum velocity values;
  assign a quality metric to each identified heartbeat;
  identify a subset of the spatial-maximum velocity values for which the assigned quality metric exceeds a threshold level;
  monitor values from the subset of spatial-maximum velocity values over time; and
  determine when a set of one or more values from the subset of spatial-maximum velocity values satisfies a predetermined alert criterion, and, in response to said determining, signal an audible or visual alert.

A first amplitude envelope representing blood flow towards the transducer may be determined, and second amplitude envelope of blood flow away from the transducer may be determined. The first and second envelopes may be displayed on a display—e.g., as respective graphs over time. They may be overlaid on a display of a spectrogram, which may show positive and negative frequencies.

The first and second values may be determined for all blood flow with the region over the time period (within the limits of the detection capability of the system), or only for all blood flow above a respective lower velocity limit and/or below a respective upper velocity limit.

In some embodiments, the characteristic may be determined over a set of frequencies that excludes frequencies in a band around zero (corresponding to frequencies close to the carrier frequency of the transmitted pulses before demodulation). This may be achieved by applying a high-pass filter (e.g., with a cut-off frequency of between around 50 Hz to around 500 Hz) to the pulse Doppler response signals, shifted to baseband. In this way, reflections from stationary or slow-moving "clutter" can be rejected.

In general, it is expected that at least some embodiments of the invention may be able to reliably monitor blood flows having velocity components (parallel to an axis of the ultrasound beam) of around 1 cm/second or higher—e.g., flows in a range of around 3, 4 or 5 cm/s to 20 cm/sec or higher.

Data representing the characteristic may be stored in a storage medium and/or displayed on a display device and/or output over a network or other data connection. The system may comprise a memory for storing data representing the determined characteristic—e.g., for storing a series of values over time. The system may comprise a display device, such as a monitor, for displaying one or more values of the characteristic, such as a live display of the maximum velocity (VMax) over a time window.

A plurality of characteristics may be determined, and may be displayed, for blood flow within a single region—optionally separately for positive and negative frequency shifts.

The system may comprise a monitoring subsystem and may monitor the characteristic of blood flow over time. It may determine a series of values, each relating to blood flow through a region at a different point in time—e.g., velocity values. These points in time may span an interval longer than a minute, or longer than 30, 60, 120 or 240 minutes or more. The series of values may be monitored by the monitoring subsystem.

A signal may be generated if a set of one or more of the values satisfies a predetermined criterion. The criterion may include one or more conditions. The system may be configured so that all of which must be met for the signal to be generated, or so that the signal is generated when any one or more of the conditions is met. A condition may be that a value of the series of values drops below a threshold amount (which may be fixed or determined relative to one or more earlier values). A condition may be that a value of the series of values exceeds a threshold amount (which may be fixed or determined relative to one or more earlier values). A condition may be that the series of values drops or rises faster than a threshold rate. A condition may relate to a frequency component of the series of values. A condition may be that a frequency component, lying within a predetermined frequency range, is present in the series of value, or is not present in the series of value, or has an amplitude over time that rises or falls past a threshold level or that has a gradient exceeding a threshold gradient. In some embodiments, the predetermined frequency range may encompass a pulse (heartbeat) frequency of the subject. However, in other embodiments, the pulse (heartbeat) frequency of the subject may always or at times lie outside the predetermined frequency range. It may be a frequency range whose upper frequency is half, or a quarter, or less, of the pulse rate of the subject—for example, the frequency range may be 3-7 Hz, whereas the subject's pulse rate may be in the range 60 to 100 bpm, or 40 to 150 bpm, for example, depending on age, species and physical condition). As explained below, such a monitoring system may be useful for monitoring oscillations in blood flow measurements that don't correspond directly to the subject's heartrate.

The signal may cause an alarm to be raised—e.g., by sounding an audible or visual alert (a flashing light, a message on a display screen, etc.) or by sending a message over a network connection. The system may be a patient monitoring system—e.g., for bedside use in hospital, in an operating theatre, a general-practitioner (GP)'s office, or in a patient's home. The series of values may be monitored for a period of time longer than a minute, or longer than 30, 60, 120 or 240 minutes or more.

In other embodiments the characteristic of blood flow in the subject is monitored discontinuously, although preferably at a frequency which provides clinically useful information. For instance, the characteristic of blood flow in the subject may be actively monitored (i.e. ultrasound pulses are transmitted into the subject) for a 5, 10, 15, 30, 45, 60, 120 or 240 second period and these monitoring periods may be interspaced by a non-monitoring period of 1, 2, 3, 4, 5, 10, 15, 30, 45 or 60 minutes. During the non-monitoring period it may be preferable if ultrasound pulses are not transmitted into the subject. The duration of the periods of monitoring and/or the periods of non-monitoring may be adjusted to account for changes in the subject's medical status. For instance, subjects in a critical or deteriorating condition may have longer and/or more frequent monitoring, whereas non-critical, stable or improving subjects may have shorter and/or less frequent monitoring. Such adjustments may be made by a clinician or may be made automatically based on the output from the ultrasound monitoring itself or other medical data collection devices and systems which are assessing the subject's condition concurrently. In this way total ultrasound exposure for the subject may be minimised and/or the amount of data produced may be kept manageable.

In some embodiments, reflections of the ultrasound pulses are sampled from each of a plurality of regions within the subject. Respective values, or series of values, of the characteristic of blood flow in the respective region may be determined for each of the regions. Each characteristic may represent reflections from all the blood flow within the region, optionally between lower and/or upper velocity limits.

These regions may be at a plurality of different distances from the transducer—e.g., from a plurality of pairwise-abutting or pairwise-overlapping or spaced-apart regions. Each region may have a substantially uniform thickness in the depth direction, which may be between 0.15 mm and 1 mm or 2 mm—for example, around 0.8 mm. The thickness will equal $N \cdot \lambda/2$, where N is the number of periods (cycles) in the transmitted pulse; in some embodiments, the value of N may be in the range 2 to 10. In some embodiments, the wavelength of the transmitted pulses may be in the range 0.1-0.5 mm—for example, 0.3 mm. The regions may all have the same thickness. Each region may be a circular or rectangular cylinder. The regions may span different respective depths or depth ranges. The regions may be arranged coaxially along a transmission axis of the ultrasound transducer. Each region may cover one continuous depth range. In one set of embodiments, the plurality of regions are contiguous, and together cover one aggregate depth range—e.g., from 0 or 5 mm to 30 or 40 mm.

A furthest region from the transducer may be at a maximum distance from the transducer, in the propagation direction, that is less than a maximum, minimum or mean diameter or width of the transducer, or that is no more than two, three, five or ten times this diameter width. The maximum distance could be 5 mm, 10 mm, 20 mm or 40 mm. The maximum distance may depend on the clinical application of interest; for monitoring cerebral circulation, it might be 40 mm, whereas for monitoring peripheral circulation in a digit it might be 10 mm.

Respective values of the characteristic may be determined for each of a plurality of regions from reflections of the same ultrasound pulses. In other words, a single pulse may contribute to the determining of a characteristic of blood flow at a first depth range and of the same characteristic of blood flow at a second depth range which may be distinct from (i.e. not overlap) the first depth range. This is not done in conventional pulsed-wave Doppler systems.

Values of the characteristic at two or more different depths may be compared; for example, a ratio, or other comparison operation, may be calculated. Outputs of this comparison operation may be displayed or monitored. They may provide a clinically-significant indicator which may be used for generating alerts by a monitoring system. In some embodiments, an aggregated value (e.g., mean or sum) from a plurality of depths may be generated, and may be output.

In some embodiments, the pulse-Doppler response signals may be processed to determine, for each of a plurality of depths or depth ranges, a respective sequence of values, over time, of a measure representative of blood flow relative to the ultrasound transducer, within the subject at the respective depth or depth range. Each depth or depth range may correspond to a different respective region, as described above. This measure may, for example, be a power-weighted average (e.g., mean) frequency shift or velocity, or a frequency shift (or velocity) of maximum amplitude over one or more pulse-Doppler response signals. The measure may be evaluated at regular intervals—e.g., every 5 milliseconds. A graphical representation of the sequences of values may be displayed to a human operator. This can allow a human operator to identify one or more depths or depth ranges of interest from the plurality of depths or depth ranges. Values may be displayed for each of a set of depths or depth ranges that divides a viewing range into regular intervals—e.g., for every 1 mm interval from 5 mm to 35 mm. The values may be displayed as respective pixel intensities. A first axis may represent depth. A second axis may represent time.

The display may be similar to a conventional colour M-mode plot, but representing flow velocities at common time periods at multiple depths (i.e., generated from reflections of the very same Doppler pulse or pulses at multiple depths), rather than conventional approaches which use different pulses to acquire information at different respective depths. Moreover, the present approach does not require an array transducer, but can, at least in some embodiments, be generated with a single-element transducer.

It will be appreciated that the measure representative of blood flow may have a zero value or a low value at depths where no blood flow is present.

The operator may provide, as input, an indication of these one or more depths or depth ranges of interest to the controller. The controller may then process the pulse-Doppler response signals, or data derived therefrom, to determine respective values of one or more characteristics of blood flow for the indicated one or more depths or depth ranges. The characteristic(s) may be as described elsewhere herein—e.g., maximum velocity over a time window. The size of the depth range may be variable, and may be received as an input from the operator, in addition to the location of the depth range. For example, an operator may move a cursor to input upper and lower depth markers so as to select the range 20 mm-25 mm for further processing, or to select the range 10 mm-30 mm.

Embodiments of the system disclosed herein may have no conventional two-dimensional or three-dimensional imaging capability (e.g., no B-mode imaging). This graphical display provides a mechanism by which an operator can nevertheless view a "one-dimensional image", even from a single-element transducer, which can allow the operator to identify a depth of interest. For example, a depth that exhibits strong blood flow in the displayed values of the measure may be indicative of the presence of an artery at that depth.

From another aspect, the invention provides a method for determining and representing blood flow in a vertebrate animal subject, the method comprising:
  transmitting ultrasound pulses into the subject from an ultrasound transducer;
  receiving reflections of the ultrasound pulses at the ultrasound transducer;
  generating pulse-Doppler response signals from the reflections;
  processing the pulse-Doppler response signals to determine, for each of a plurality of depths or depth ranges, a respective sequence of values over time, of a measure that is representative of blood flow within the subject, relative to the ultrasound transducer at the respective depth or depth range, wherein the sequences comprise values representative of blood flow at common time periods across the plurality of depths or depth ranges; and
  displaying a graphical representation of the sequences of values to a human operator.

From a further aspect, the invention provides a system for determining and representing blood flow in a vertebrate animal subject, the system comprising:
  an ultrasound transducer;
  a controller; and
  a display,
  wherein the controller is configured to:
    control the ultrasound transducer to transmit ultrasound pulses into the subject;
    sample reflections of the ultrasound pulses received at the ultrasound transducer;
    generate pulse-Doppler response signals from the reflections;
    process the pulse-Doppler response signals to determine, for each of a plurality of depths or depth ranges, a respective sequence of values over time, of a measure that is representative of blood flow within the subject, relative to the ultrasound transducer at the respective depth or depth range, wherein the sequences comprise values representative of blood flow at common time periods across the plurality of depths or depth ranges; and
    control the display to display a graphical representation of the sequences of values to a human operator.

Features of other aspects disclosed herein may be features of embodiments of these aspects also.

It will be seen that this enables an operator to visualise simultaneous blood flow (i.e., flow within one time period) at multiple depths at once. This can allow for easy identification of a region or regions of interest. The nature of these regions may depend on the clinical context—e.g., being a depth range that contains a significant artery, or being a superficial depth range that is deeper than the capillaries (where flow will typically be too low to detect) but higher than any major arteries.

In some embodiments, the method may further comprise receiving, from the human operator, an input identifying a depth or depth range of interest. It may further comprise monitoring a characteristic of blood flow at said depth or depth range of interest. The characteristic may be a characteristic as described elsewhere herein. In some embodiments, the system may be configured to receive inputs identifying a plurality of depths or depth ranges of interest, and may be configured to determine a characteristic of blood flow at each depth or depth range of interest.

The plurality of depth ranges may be contiguous; they may span a range—e.g., from 0 mm to 40 mm. They may each have a depth of 1 mm, 2 mm or less, thereby providing a resolution of 1 mm, 2 mm or finer.

At each depth, two sequences of values may be determined—a first sequence relating to positive frequency shifts, and a second sequence relating to negative frequency shifts. Values from the two sequences may be represented independently on the graphical display. For example, for a particular time period and depth, if the value of the second sequence is zero, or below a threshold, a first colour (e.g., red) may be used to represent the value from the first sequence. If the value of the first sequence is zero, or below a threshold, a second colour (e.g., blue) may be used to represent the value from the second sequence. If both values are non-zero, or above a respective threshold, a third colour (e.g., white) may be used to represent both values. If both values are zero, or below respective thresholds, a fourth colour (e.g. black) may be displayed. Such an approach allows an operator to distinguish between a region with zero flow and a region with equal flow in both directions. Conventional colour Doppler imagery does not allow such a distinction to be made, as it typically represents only the average velocity (averaged over the frequency spectrum) at a point.

In some embodiments, the common time periods may be between 1 and 100 milliseconds—e.g., around 5 milliseconds. The time periods may be uniform and contiguous, such that new values for the sequences are determined at regular intervals.

The values may be displayed in a rolling time window, with older values (e.g., more than 7 seconds old) being removed from the display as new values are displayed.

The operator may use this display when positioning and/or fastening the ultrasound transducer. Thereafter, the system may automatically monitor the characteristic of blood flow at the selected depth range or ranges, without the need for further human intervention. In some embodiments, the system may monitor, over time, the respective sequence of values of the measure that is representative of blood flow, and may detect any displacement of the transducer relative to the subject from these values. This may be done using pattern matching or other appropriate image processing techniques. The system may compensate for such displacement by adjusting the depth(s) or depth range(s) of interest by a corresponding amount.

In any of the aspects disclosed herein, the controller may store data representative of, or derived from, the pulse-Doppler response signals over a period of time, which may span minutes, hours or days. This can allow a physician to view a graphical representation of the data and/or select a depth range and/or view a representation of the characteristic of blood flow, all using historic data, rather than live data.

In some embodiments, the controller may calculate a quality value for each of a plurality of depths or depth ranges. This may be based on comparing heartbeat waveforms (e.g., from a velocity envelope) as described above, or any other appropriate way. The controller may select a depth or depth range at which to determine the characteristic of blood flow based on the quality value—e.g., selecting a depth that gives the highest quality signal.

In some embodiments, the controller may be configured to monitor blood flow at a first depth to display or monitor information relating to flow at the first depth, and to monitor blood flow at a second depth, different from the first depth, as a reference to detect a fault condition. The second depth may contain a blood vessel (e.g., an artery) that is larger than any blood vessel that is present at the first depth, within the ultrasound receive beam, or that contains faster-flowing blood than any blood vessel that is present in the beam at the first depth. This can be useful, as it can be expected that blood flow should be possible at the second depth throughout a monitoring period, whereas the blood flow at the first depth may vary and may sometimes drop below the noise floor due to physiological changes such as vasoconstriction. Loss of signal at the second depth may then be used to detect a fault condition, such as the transducer having been knocked out of the position; an alarm may be signalled in response. The use of the reference signal can prevent false alarms that might otherwise occur if only the first depth were monitored for a fault condition.

In general, the pulses are preferably transmitted at intervals—preferably at regular intervals. A pulse repetition frequency of around 10 KHz may be used. The transmitted pulses are preferably sine-wave pulses having a common carrier frequency. A pulse-Doppler response signal may be generated from the reflections of just one pulse (e.g., a long pulse). However, in order to provide useful depth resolution, each pulse needs to be brief, and will therefore typically be too short to allow Doppler frequency shifts to be measured from the reflection of just a single pulse. (The bandwidth of a single pulse might typically be around 1 MHZ, whereas the Doppler shift from a blood cell in the region could be around 1 kHz.) Therefore, each value of the characteristic of blood flow is preferably determined from the reflections of a plurality of pulses (for example, around fifty pulses). A respective set of one or more samples may be obtained from each of a plurality of pulses, and this plurality of samples may then be used to generate a pulse-Doppler response signal, or a frequency or velocity spectrum, or other derived data, which may be processed to estimate a value of the characteristic.

The system, and its controller, may comprise one or more processors, DSPs, ASICs, volatile memory, non-volatile memory, inputs, outputs, etc. as will be appreciated by one skilled in the art. Some or all of the operations described herein may be carried out by, or under the control of, software stored in a memory and executing on one or more processors in the controller or monitoring system. The system may be a single unit or it may be distributed—e.g. with one or more operations being performed remotely from the living organism, such as on a remote server. A sampling module in the controller may comprise an amplifier and/or an ADC and/or one or more filters and/or demodulators.

In particular, in some embodiments, the controller may comprise two separate units—i.e. a first unit and a second unit. The first unit may control the transducer and sample the reflections. The second unit may determine the characteristic of blood flow from the pulse-Doppler response signals. The first unit or the second unit may sample the reflections of the pulses. The two units may communicate over a wired link, such as a USB cable, or a wireless link, such as a Bluetooth™ connection. In particular, the first unit may send data representing the pulse-Doppler response signals (preferably after bandpass filtering and complex demodulation) to the second unit, preferably wirelessly. The first unit may comprise a power supply, such as a battery. The first unit may comprise the ultrasound transducer, e.g., within a common housing—preferably a solid housing such as a box. The first unit may comprise means for fastening the first unit to a patient, such as a strap or an adhesive pad or region, or any other suitable fastener. The second unit may comprise a display. The second unit may be a mobile telephone (cell phone) or a tablet computer or other portable device. By dividing the system in this way, the first unit can be a portable sensor unit, which can easily be attached to a patient without the inconvenience of wired leads, and can be relatively low-cost, because it need only comprise a relatively basic microcontroller, while the more-complex processing of the response signals can be carried out on a more powerful device.

The operations described herein need not necessarily be performed close in time to one another. In particular, the reflected ultrasound signals may be acquired at a first period in time, and then processed at a later period of time, which may be hours or days apart.

The present system has many applications—e.g., neonatal monitoring, operative and post-operative care, monitoring cerebral circulation, monitoring peripheral circulation, monitoring microcirculation, monitoring for sudden blood loss in an emergency setting, etc.

The blood circulatory system of vertebrate animals is a closed system of conduits (blood vessels) and a pump (the heart) which circulate blood around the body as a means to deliver oxygen and nutrients to the tissues and remove carbon dioxide and the waste products of metabolism from the tissues. Functionally, the system may be considered to have two parts—the pulmonary circulation (which supplies blood to the lungs) and the systemic circulation (which supplies blood to all parts of the body except the lungs). As used herein, the parts of the systemic circulation outside of the torso may be termed the peripheral circulation. Anatomically, blood is pumped by the heart through arteries, then arterioles and, in mesenteric beds, metarterioles, to the capillaries where its soluble and/or gaseous contents equilibrate with the interstitial fluids of the tissues. Blood exits the capillaries into venules and then flows into the veins which lead back to the heart.

The larger arteries closest to the heart are elastic as a consequence of collagen and elastin filaments in the tunica media interspacing layers of smooth muscle cells. In contrast, smaller arteries, which draw blood from the elastic arteries and ultimately feed the arterioles (distributing arteries) are predominantly muscular in structure and do not have multiple layers of elastic tissue. Instead, the muscular arteries have a single prominent elastic layer, the internal elastic lamina, that forms the outermost part of the tunica intima of such vessels and which separates the tunica intima from the tunica media. Elastic arteries, the larger muscular arteries and the larger veins are of a size which requires a dedicated blood supply. This supply is provided by the vaso vasorum.

The term "minor vasculature", as used herein, encompasses the distributing arteries (muscular arteries), veins of equivalent size in the subject of interest, arterioles, metarterioles, capillaries, and venules. The term "major vasculature" encompasses the blood vessels larger than the distributing arteries, veins of equivalent size in the subject of interest, arterioles, metarterioles, capillaries, and venules. The minor vasculature may be divided into smaller vessels which are not supplied by the vaso vasorum and larger vessels which are.

For the present purposes, blood flow within the small arteries feeding directly into the arterioles, the arterioles, metarterioles, capillaries, venules, and small veins fed directly by the venules is considered to be the "microcirculation" and these vessels may therefore be termed "microvessels" or the "microvasculature". The microvasculature is not supplied by the vaso vasorum. Blood flow in the larger vessels (arteries and veins) is in contrast termed the "macrocirculation".

"Arterial microcirculation" may be considered to be blood flow in the small arteries feeding directly into the arterioles and the arterioles. "Venous microcirculation" may be considered to be blood flow in the venules and the small veins fed directly by the venules. "Arterial microvasculature", "arterial microvessels", "venous microvasculature" and "venous microvessels" should be interpreted accordingly.

Features of other aspects disclosed herein may be features of embodiments of these aspects also.

Characteristics of blood flow have been used to monitor and/or analyse the physiology of healthy vertebrate animals and to diagnose, monitor or predict the progression of disease and pathological conditions and/or treatment responses in such subjects. The methods, systems and apparatus described herein may be applied to such contexts.

The inventors have further recognised that the characteristics of blood flow in the peripheral circulation/vasculature (e.g. circulation in/vasculature of the head, limbs (legs, shoulders, arms, feet, hands, fingers and toes) may be determined in accordance with at least some methods of the invention and/or using at least some of the systems and apparatus of the invention and such information may contribute advantageously to the monitoring and/or analysis of the physiology of healthy vertebrate animals and to the diagnosis, monitoring or prediction of the progression of disease and pathological conditions and/or treatment responses in such subjects. Any of the above defined groups of blood vessels may be investigated in such embodiments.

The inventors have further recognised that the characteristics of blood flow in the superficial circulation/vasculature (circulation/vasculature in proximity to the skin's surface, e.g. less than about 20 mm, 15 mm, 10 mm, 9 mm, 8 mm, 7 mm, 6 mm, 5 mm, 4 mm, 3 mm, 2 mm or 1 mm from the epidermis) may be determined in accordance with at least some methods of the invention and/or using at least some of the apparatus of the invention and such information may contribute advantageously to the monitoring and/or analysis of the physiology of healthy vertebrate animals and to the diagnosis, monitoring or prediction of the progression of disease and pathological conditions and/or treatment responses in such subjects. Any of the above defined groups of blood vessels may be investigated in such embodiments.

Thus, in certain embodiments at least some of the methods of the invention are for determining a characteristic of blood flow in the peripheral circulation (e.g. in the superficial peripheral circulation, the peripheral minor vasculature, the peripheral arterial microvasculature, the superficial peripheral minor vasculature, or the superficial peripheral arterial microvasculature) of a vertebrate animal subject. In these embodiments the ultrasound transducer is fastened to the surface (e.g. skin) of the subject at a site which is not on the torso of the subject, e.g. a site on a limb (e.g. shoulder, arm, leg, hand, foot, toe, finger, paw, wing, fin, tail), neck or head (e.g. ear, nose, tongue, cheek, scalp, forehead). Some aspects of the invention provide suitable fastening means.

The inventors have further recognised that by determining the characteristics of blood flow in multiple blood vessels simultaneously the information obtained may contribute advantageously to the monitoring and/or analysis of the physiology of healthy vertebrate animals and to the diagnosis, monitoring or prediction of the progression of disease and pathological conditions and/or treatment responses in such subjects. A plurality of vessels of one or more of the above defined groups of blood vessels may be investigated in such embodiments. It may, in certain embodiments, be particularly advantageous to determine blood flow in a plurality of vessels of the minor vasculature, e.g. arterial microvessels simultaneously. The minor vasculature and/or microvessels, in particular the arterial microvessels, of the peripheral circulation may be targeted in these embodiments. More specifically, in these embodiments superficial vessels may be targeted.

In these embodiments references to determining the characteristics of blood flow in multiple blood vessels simultaneously includes determining the characteristics of blood flow in a plurality of vessels within a region at a certain depth/depth range and/or determining the characteristics of blood flow in one or more vessels within a plurality of depths/depth ranges within the region. This is discussed in more detail above.

In further embodiments the characteristics of blood flow in multiple blood vessels may be determined simultaneously from anatomically distant sites, e.g. the shoulder/upper arm and the hand or the head and the foot. A comparison of blood flow characteristics at each site may offer further insights into the diagnosis, monitoring or prediction of the progression of disease and pathological conditions and/or treatment response.

Thus, in certain embodiments at least some of the methods of the invention are for determining a characteristic of blood flow in multiple vessels, e.g. multiple vessels of the minor vasculature or multiple arterial microvessels or one or more of both, simultaneously. In these embodiments the ultrasound transducer is fastened to the surface (e.g. skin) of the subject at a site which contains a plurality of blood vessels, e.g. a plurality of vessels of the minor vasculature or a plurality of arterial microvessels or one or more of both, within range of the transducer. Some aspects of the invention provide suitable fastening means.

Thus, from a further aspect, the invention provides a method for determining a characteristic of blood flow in a vertebrate animal subject, the method comprising:
  transmitting ultrasound pulses into the subject from an ultrasound transducer that is applied to an external surface of the subject;

receiving reflections of the ultrasound pulses at the ultrasound transducer from at least one region within the subject, said at least one region containing a plurality of blood vessels;

generating pulse-Doppler response signals from the reflections; and processing the pulse-Doppler response signals to determine a characteristic of the blood flow through the plurality of vessels in said at least one region.

The invention extends to a system configured to implement such a method.

In one embodiment said method is a method for determining a characteristic of blood flow in the minor vasculature of a vertebrate animal subject, the method comprising:

transmitting ultrasound pulses into the subject from an ultrasound transducer that is applied to an external surface of the subject;

receiving reflections of the ultrasound pulses at the ultrasound transducer from at least one region within the subject, said at least one region containing a plurality of vessels of the minor vasculature;

generating pulse-Doppler response signals from the reflections; and processing the pulse-Doppler response signals to determine a characteristic of the blood flow through the plurality of vessels of the minor vasculature in said at least one region.

In one embodiment the method is a method for determining a characteristic of blood flow in the arterial microvasculature of a vertebrate animal subject, the method comprising:

transmitting ultrasound pulses into the subject from an ultrasound transducer that is applied to an external surface of the subject;

receiving reflections of the ultrasound pulses at the ultrasound transducer from at least one region within the subject, said at least one region containing a plurality of arterial microvessels;

generating pulse-Doppler response signals from the reflections; and processing the pulse-Doppler response signals to determine a characteristic of the blood flow through the plurality of arterial microvessels in said at least region.

The ultrasound transducer may be applied to the external surface manually (e.g., being held in place by a human operator), but preferably it is fastened to the external surface.

In any embodiment of this aspect plurality of vessels contained within said region(s) may be within the peripheral circulation and/or the superficial circulation and said methods determine a characteristic of the blood flow through said plurality of vessels.

In certain specific embodiments the region(s) containing a plurality of blood vessels does not contain an artery and/or a vein of the major vasculature. In other specific embodiments the region(s) containing a plurality of blood vessels does not contain an artery and/or a vein whose walls are supplied by a vaso vasorum.

The vessels targeted by at least some of the methods of the invention will be vessels having a flow which may provide clinically useful information, e.g. in the specific clinical contexts described herein. This is typically blood vessels having a flow rate sufficient to be detectable in the pulse-Doppler response signals, e.g. a flow rate of greater than 1 cm/s, e.g. greater than 3-4 cm/s. In certain embodiments vessels targeted will be those with a flow rate of less than 60 cm/s, e.g. less than 50 cm/s, 45 cm/s, 40 cm/s, 35 cm/s or 30 cm/s. Due to the differing sizes of the subjects to which at least some of the methods of the invention may be applied, different vessels may be targeted in order to obtain clinically useful information, but in certain embodiments this will not be arteries and/or a veins of the major vasculature, in particular arteries and/or a veins whose walls are supplied by a vaso vasorum. In adult human subjects, the vessels targeted are typically the muscular arteries, in particular those directly feeding the arterioles, and the arterioles.

It should further be noted that characteristics of blood flow determined in certain areas of the vasculature may provide insight into the characteristics of blood flow in other areas of the vasculature. The inventors have, in particular, recognised that characteristics of blood flow in the arterial microvasculature (especially the peripheral arterial microvasculature) can provide information on the characteristics of blood flow in the microcirculation (especially the peripheral microcirculation) more generally, and especially in the context of microvascular dysfunction (e.g. as observed in subjects with sepsis and associated with diabetes mellitus types 1 and 2, Raynaud's phenomenon, systemic sclerosis, hypertension, peripheral artery disease, chronic renal failure, hypercholesterolemia, hyperlipidaemia, obesity and hypertension).

Features of other aspects disclosed herein may be features of embodiments of these aspects also.

The inventors have recognised that at least some aspects of the invention have particular utility in the clinical care of sick infant subjects (in particular new-born infants), e.g. those infants which were born prematurely, those with cardiac abnormalities, those with infections and those which experienced oxygen deprivation around the time of delivery. More specifically, the inventors have further recognised that at least some aspects of the invention have particular utility in the clinical care of infant subjects undergoing surgical procedures as a means to monitor the subject for expected response to the procedure and for signs of adverse effects from the procedure.

Infants, in particular unborn or new-born infants, have less developed ability to autoregulate the brain blood flow than older children and adults. New-born infants which have been born prematurely have even less control of brain blood flow than full-term new-born infants and this control is inversely proportional to the degree of prematurity and severity of any associated diseases or conditions. This means that blood flow to and in the infant brain is more variable than blood flow to and in the adult brain. Significant fluctuations in cerebral blood flow in infant subjects can lead to brain injury, e.g. by causing haemorrhage and/or oxygen deprivation. Variations in systemic blood pressure and fluctuations in blood carbon dioxide ($CO_2$) levels are factors known to cause variations in cerebral blood flow and so are important mechanisms behind brain injury. As such, stability in physiological parameters in infants contributes to less fluctuation in cerebral blood flow and thus may help prevent brain injury. Cerebral blood flow in infant subjects may also be affected by, or a direct marker of, a wide variety of other conditions including, but not limited to, haemodynamic instability, patent ductus arterious (PDA), congenital heart defects, vasomotor dysfunction, brain vascular malformations, neonatal abstinence syndrome, seizures, persistent pulmonary hypertension of the newborn (PPHN), cerebral infarction and intracranial haemorrhage.

There remains a need for a practical non-invasive technique to monitor cerebral blood flow in infant vertebrate animal subjects for extended periods of time so as to provide information to the clinician which allows the clinician to diagnose or predict the onset of diseases and conditions caused or characterised by cerebral blood flow patterns, or which allows the clinician to treat the infant (e.g. pharmacologically or surgically) in a manner which minimises fluctuations in blood flow and, thereby, minimises risk of brain injury. A continuous monitoring system would give early warning signs of dysfunction in cerebral haemodynamic autoregulation and/or abnormalities in brain blood flow and allow the clinician to intervene rapidly and effectively to restore physiological homeostasis and reduce the risk of brain injury.

Today cerebral blood flow is estimated indirectly with invasive and/or manual systemic blood pressure measurements. The inventors have recognised that for unborn or new-born infant subjects, in particular sick neonates with increased risk of brain injury, systemic blood pressure gives only limited amounts of useful information about brain blood flow. Moreover, such measurements are prone to errors caused by movements and crying. The invasive nature of today's techniques for arterial blood pressure measurement are inherently painful and uncomfortable to the subject and may themselves lead to deleterious blood flow abnormalities. A reliable non-invasive means to continuously monitor cerebral blood flow in infants could supplement or even replace these unsatisfactory means to measure systemic blood pressure in such subjects.

The inventors have recognised that at least some of the methods, systems and apparatus of the invention are suited to meet these particular needs.

From a further aspect, the invention provides a method for monitoring or predicting the onset or progression of a disease or pathological condition and/or a response to treatment in an infant vertebrate animal subject, said method comprising
  transmitting ultrasound pulses into the subject via a fontanelle or a suture in the subject's skull or via an area of the subject's skull which has an average thickness of less than about 2 mm from an ultrasound transducer that is fastened to an external surface of the subject's skull;
  receiving reflections of the ultrasound pulses at the ultrasound transducer;
  generating pulse-Doppler response signals from the reflections; and
  processing the pulse-Doppler response signals to determine a characteristic of blood flow within the subject;
  monitoring the characteristic of blood flow over time; and optionally
  establishing a profile of said characteristic over time;
wherein the characteristic or the profile of said characteristic over time is indicative or predictive of the disease or pathological condition or response to treatment, or variation in said characteristic or the profile of said characteristic over time is indicative or predictive of the disease or pathological condition, or indicative or predictive of a change in the disease or pathological condition or response to treatment.

The invention extends to a system configured to implement such a method. In particular, the system is configured to transmit unfocused ultrasound pulses. The ultrasound pulses may be plane-wave pulses.

In certain embodiments the characteristic of blood flow in the subject is monitored over time continuously. In other embodiments the monitoring over time takes place repeatedly at a frequency which provides clinically useful information, e.g. as described above. In this embodiment the monitoring phases are interspaced with periods were monitoring does not take place. Preferably, ultrasound is not transmitted into the subject during the non-monitoring phases.

The method may also be considered a method for obtaining information relevant to monitoring or predicting the onset or progression of a disease or pathological condition and/or a response to treatment in an infant vertebrate animal subject. The methods described herein may be used alone as an alternative to other investigative techniques or in addition to such techniques in order to provide information relevant to monitoring or predicting the onset or progression of a disease or pathological condition and/or a response to treatment in an infant vertebrate animal subject.

In certain embodiments the method further comprises a step in which the characteristic or the profile of said characteristic over time or the variation in said characteristic or the profile of said characteristic over time is used, alone or together with additional clinical information (e.g. from other methods), to diagnose the disease or pathological condition or the extent or severity thereof or to provide a prognosis for the disease or pathological condition or to determine a response to treatment.

In these embodiments the characteristic or the profile of said characteristic over time or the variation in said characteristic or the profile of said characteristic over time may be compared to reference data previously obtained from the same subject, e.g. reference data obtained prior to the commencement of a treatment or treatment cycle or from a time earlier in said treatment. Divergence between the data sets may be indicative of a change in the disease or pathological condition or response to treatment. Thus, the steps of comparing the test and reference data and determining whether or not they diverge (or correspond) may be performed using mathematical, or statistical techniques, and generally this will be implemented by software (i.e. it will be performed using a computer). Statistical or mathematical methods for performing such a comparison and determination of correspondence are well known and widely available in the art. In other embodiments correspondence (or divergence) may be assessed or estimated visually by the skilled person.

In other embodiments the characteristic or the profile of said characteristic over time or the variation in said characteristic or the profile of said characteristic over time may be compared to reference data previously obtained from a cohort of analogous subjects undergoing analogous clinical care and/or a cohort of healthy subjects (subjects not displaying or at risk of the disease or pathological condition), i.e. a predetermined standard. In these embodiments correspondence (or divergence) between test data and reference data may be analysed as described above or by applying said test data to a mathematical model generated using the reference data. Such a mathematical model may be used to determine whether test data fits, or matches, a negative standard and/or a positive standard, e.g. whether it best fits, or best matches a negative and/or a positive standard. Mathematical methods for generating such models are well known. In other embodiments correspondence (or divergence) may be assessed or estimated visually by the skilled person.

In more specific embodiments the method may involve an alarm or indicator, in particular an automated alarm or indicator, occurring when the characteristic or the profile of said characteristic over time or the variation in said characteristic or the profile of said characteristic over time passes a certain threshold value, e.g. a value which may be indicative or predictive of the disease or pathological condition or response to treatment.

In certain embodiments the pathological condition is brain injury. The term "brain injury" is used in a broad sense to refer to acute non-specific destruction of, or physical/structural damage to, a part of a brain or the structures thereof, including non-specific neuronal death. It is not intended to cover the chronic structural changes induced by neurodegenerative diseases or tumours.

The injury may be a primary injury or a secondary injury. As a primary injury, this may include, but is not limited to, the immediate results of physical trauma (external physical forces have caused the damage), acute hypoxic/ischemic brain injury (lack of oxygen and/or blood flow) and/or acute haemorrhagic brain injury (bleeding within the cranial vault has caused the damage) and brain injury caused by hydrocephalus, chemical agents or a pathogenic microorganism (including a virus). Such insults cause some or all of contusion, laceration, axonal shearing and damage to the meninges and the blood brain barrier, in particular, intracerebral haemorrhage, subdural haemorrhage, subarachnoid haemorrhage, epidural haemorrhage, cerebral contusion, cerebral laceration, axonal stretch injury.

As a secondary injury this may include, but is not limited to, delayed hypoxic brain injury, delayed haemorrhagic brain injury, thrombotic brain injury, inflammatory brain injury, brain injury caused by cerebral oedema, brain injury caused by acidosis, brain injury caused by excess free radicals, and brain injury caused by excitotoxicity.

In more specific embodiments said brain injury may be a brain injury caused by preterm birth. Premature infants (infants born before 37 weeks of pregnancy) and, in particular, extremely premature infants (infants born before 28 weeks of pregnancy) during the first 3 days after birth have immature cardiovascular, respiratory, hormonal, vasomotor, cerebral haemodynamic autoregulation and renal systems. In addition to pathological conditions which are characteristic complications of premature infants (including, but not limited to, patent ductus arteriosus, infant respiratory distress syndrome), premature infants are subjected to numerous invasive and non-invasive procedures causing pain and discomfort. With their poor ability to control peripheral circulation and to autoregulate cerebral blood flow, these complications and pain, discomfort and physiological stress may lead to large variations in cerebral blood flow which can cause injury. This may be because the large variations in cerebral blood flow cause intracerebral/intraventricular haemorrhage and this results in brain injury. Monitoring a characteristic of cerebral blood flow in accordance with these aspects of the invention (e.g. end diastolic velocity, Vmean, PI, the ratio of average diastolic flow/peak systolic flow, venous flow and fluctuations therein may be used) can provide information to a clinician on which procedures and interventions to use to treat the complications of preterm birth, how such procedures and interventions are affecting cerebral blood flow and the likelihood that such procedures or interventions will cause deleterious effects. This in turn allows the clinician to select or adjust these procedures and interventions so that stress, pain and discomfort can be minimised or avoided, to position the infant's head to optimize cerebral flow and/or to adopt appropriate calming/soothing strategies.

In more specific embodiments said brain injury may be a brain injury caused by an intracranial haemorrhage, e.g. a (intra)cerebral haemorrhage, including intraventricular haemorrhage. Such haemorrhages may be induced by large variations in brain blood flow. Premature neonatal subjects may be especially at risk due to their inability to autoregulate brain blood flow. Monitoring a characteristic of cerebral blood flow in accordance with these aspects of the invention (e.g. end diastolic velocity, Vmean, PI, the ratio of average diastolic flow/peak systolic flow, venous flow and fluctuations therein may be used) can provide information to a clinician about the likelihood of intracranial haemorrhage, e.g. a (intra)cerebral haemorrhage, and/or the blood flow in the brain following cerebral haemorrhage. This allows the clinician to undertake suitable interventions, both preventative and reactionary, and to monitor the effects of those interventions. These interventions may be, for instance, establishing appropriate blood oxygenation levels, appropriate ventilation and/or fluid management, or appropriate pharmacological management of systemic blood pressure or hypothermic therapy.

In this and other contexts described herein, the method of the invention may provide an indication of when appropriate blood oxygenation levels, appropriate ventilation and/or fluid management, or appropriate pharmacological management of systemic blood pressure have been reached. For instance, the readings of the characteristic of blood flow being monitored may improve and preferably normalise or will at least stabilise and not worsen.

In more specific embodiments said brain injury may be periventricular leukomalacia. Periventricular leukomalacia is an injury to the brain white matter partly caused by decreased blood or oxygen supply to the periventricular region and glial cells. Resulting necrosis/apoptosis and subsequent resorption in these areas leads to the formation of gliosis scars or cysts which affect white matter function. Premature neonatal subjects may be especially at risk. Monitoring a characteristic of cerebral blood flow in accordance with these aspects of the invention can provide information to a clinician about the likelihood of a subject developing periventricular leukomalacia. This allows the clinician to undertake suitable interventions, both preventative and reactionary, and to monitor the effects of those interventions.

In more specific embodiments said brain injury may be caused by infection, e.g. cerebral infection and sepsis (including septic shock). Severe infection in infants can lead to circulatory (haemodynamic) instability, including low blood pressure and abnormal cerebral blood flow (particularly in sepsis), which in turn can lead to cyst formation or diffuse white matter injury which can affect brain function. Monitoring a characteristic of cerebral blood flow in accordance with these aspects of the invention can provide information to a clinician on the impact the infection is having on the subject's brain or to predict the onset of deleterious effects (injury) and this allows the clinician to undertake suitable interventions (e.g. antibiotic therapy, pressor therapy, inotrope therapy and fluid supply) and to monitor the effects of those interventions. Suitable characteristics or profiles thereof which may be monitored in this context may be Vmean measurements and/or the profile of low frequency (as compared to heart rate) oscillations in blood flow measurements (e.g. blood flow velocity). Such oscillation may be at a frequency of about 0.08 Hz, e.g. 0.01 to 0.2 Hz. A lack of such oscillations, e.g. in arterial flow velocity, may be indicative of sepsis and may in turn be correlated with poor outcome. An increase in cerebral blood flow may indicate onset of sepsis and likelihood of brain injury and may in turn be correlated with poor outcome.

In more specific embodiments said brain injury is a hypoxic/ischemic brain injury, e.g. caused by asphyxia before, during or after birth or during subsequent clinical care or due to persistent pulmonary hypertension of the newborn (PPHN) or a thrombotic or embolic occlusion. The brain injury may be hypoxic ischemic encephalopathy or a cerebral infarction. Hypoxic/ischemic brain injury in infants can also lead to circulatory (haemodynamic) instability. Restoration of normal blood flow to the brain following suspected asphyxia is essential to reduce the risk of permanent brain injury. Similarly, subjects with suspected (moderate to severe) hypoxic ischemic encephalopathy or cerebral infarction require careful treatment to reduce the risk of further injury and associated complications. These ends may be achieved, for instance, by providing treatment for low blood pressure with medications and/or fluids, by establishing appropriate oxygenation and/or glucose levels, by establishing appropriate ventilation and/or fluid management, or hypothermic therapy.

Monitoring a characteristic of cerebral blood flow in accordance with these aspects of the invention allows the clinician to gauge the need for intervention, undertake suitable interventions and to monitor the effects of those interventions. Suitable characteristics or profiles thereof which may be monitored in this context may be velocity, Vmean or PI measurements and/or the ratio of average diastolic flow/peak systolic flow. The blood flow velocity profile over a cardiac cycle may also be used. An irregular shape to this profile or evidence of backflow may be indicative of poor outcome. The profile of low frequency (as compared to heart rate) oscillations in blood flow measurements (e.g. blood flow velocity) may also be a suitable marker. Such oscillations may be at a frequency of about 0.08 Hz, e.g. 0.01 to 0.2 Hz. A lack of such oscillations, e.g. in arterial flow velocity, may be indicative of hypoxic/ischemic brain injury and may in turn be correlated with poor outcome.

In more specific embodiments said brain injury is a brain injury caused by hyperoxia during clinical care. Restoration of normal blood flow to the brain following suspected hyperoxia is essential to reduce the risk of permanent brain injury. This may be achieved, for instance, by establishing appropriate blood oxygenation levels or by establishing appropriate ventilation and/or fluid management, or hypothermic therapy. Monitoring cerebral blood flow in accordance with these aspects of the invention allows the clinician to gauge the need for intervention, undertake suitable interventions and to monitor the effects of those interventions.

In more specific embodiments said brain injury is a brain injury, e.g. hypoxic/ischemic brain injury, caused by reduced or unstable cerebral blood flow during clinical intervention (including, but not limited to intubation, anaesthesia, surgery, ventilation support (in particular invasive or non-invasive positive pressure ventilation), pressor therapy, inotrope therapy, fluid supply, catheterisation, extracorporeal membrane oxygenation). Such interventions can lead to fluctuations in blood $CO_2$ levels, fluctuations in blood pressure, low blood volume and/or release of cytotoxic substances which can injure the brain. Microembolization and air embolization are further risks for such interventions and can lead to unstable and/or insufficient cerebral blood flow and cause brain injury, e.g. by causing an infarction or a plurality thereof. Monitoring a characteristic of cerebral blood flow in accordance with these aspects of the invention in these contexts can provide information to a clinician which is useful to guide the use of such interventions on the subject, e.g. the type of intervention to use, the timing of that intervention and the response thereto. Monitoring a characteristic of cerebral blood flow in accordance with these aspects of the invention can also indicate further interventions to rectify or offset deleterious effects of earlier interventions or the cessation of earlier interventions.

In these contexts, increased cerebral blood flow from baseline (e.g. as measured by Vmean) may indicate high blood $CO_2$ levels or vasodilation. Decreased cerebral blood flow from baseline (e.g. as measured by Vmean) may indicate low blood $CO_2$ levels or vasoconstriction. Changes in PI or an irregular shape to the blood flow velocity profile over a cardiac cycle or evidence of backflow may be indicative of hypovolemia, hypotension and/or abnormalities in cerebral haemodynamics caused by invasive or non-invasive positive pressure ventilation.

In more specific embodiments said brain injury is brain injury caused by patent ductus arteriosus. In patent ductus arteriosus the vessel between the aorta and pulmonary artery, which has to be there in foetal life, fails to close and leads to increased blood flow through the lungs and reduced blood flow to the kidney, bowel and brain. Reduced cerebral blood flow may lead to brain injury, e.g. hypoxic/ischemic brain injury. Monitoring cerebral blood flow in accordance with these aspects of the invention may indicate intervention (e.g. surgical closure or pharmaceutical support, including but not limited to prostaglandin inhibitors), guide the timing thereof and/or provide information on the response to such intervention. More specifically, diastolic blood flow (e.g. the velocity thereof) or the profile thereof may be monitored in accordance with these aspects of the invention. The profile of diastolic flow, or a change in that profile, e.g. a decrease in that flow, the loss of that flow or a reversal in that flow over time may indicate the need for intervention, the timing thereof and/or the type thereof. In other embodiments PI or the ratio of average diastolic flow/peak systolic flow may be monitored. An increase in PI may indicate the need for intervention, the timing thereof and/or the type thereof. In other embodiments, the characteristic/profile may be compared with reference data from healthy subjects and differences between the test and reference data may indicate intervention, the timing thereof and/or the type thereof. The same assessments can be applied to monitoring the subject's response to said interventions.

In more specific embodiments said brain injury is brain injury caused by a congenital heart defect, e.g. a ductus dependent congenital cardiac lesion, which affects cerebral blood flow. Reduced cerebral blood flow may lead to brain injury, e.g. hypoxic/ischemic brain injury. Monitoring cerebral blood flow in accordance with these aspects of the invention may indicate intervention (e.g. surgical correction, pharmaceutical support, catheterisation and pressor, inotrope and fluid supply), guide the timing thereof and/or provide information on the response to such intervention.

In more specific embodiments said brain injury may be caused by hydrocephalus, e.g. post-haemorrhagic or congenital. Monitoring cerebral blood flow in accordance with these aspects of the invention may indicate intervention (e.g. shunting), guide the timing thereof and/or provide information on the response to such intervention. In this context peak systolic velocity, end diastolic velocity or PI may be monitored. An increase in peak systolic velocity or a reduction in end diastolic velocity may indicate a need for intervention.

In more specific embodiments said brain injury is caused by prolonged hypoglycaemia. The effects of treatments to restore glucose levels on cerebral blood flow may be monitored in accordance with these aspects of the invention and more generally the subject may be monitored to ensure pathological variations in glucose levels are reduced or prevented.

In more specific embodiments said brain injury is a brain injury arising from (caused by) fluctuations in blood $CO_2$ levels, infant respiratory distress syndrome, hypovolemia, and/or hypotension. Monitoring cerebral blood flow in accordance with these aspects of the invention allows the clinician to gauge the need for intervention to address these complications and/or to protect the subject's brain from damage, to undertake suitable interventions and to monitor the effects of those interventions. These complications may be managed, for instance, by providing treatment for low blood pressure with medications (e.g. pressors or inotropes) and/or fluids, by establishing appropriate oxygenation, or by establishing appropriate ventilation and/or fluid management.

In these contexts, increased cerebral blood flow from baseline (e.g. as measured by Vmean) may indicate high blood $CO_2$ levels or vasodilation. Decreased cerebral blood flow from baseline (e.g. as measured by Vmean) may indicate low blood $CO_2$ levels or vasoconstriction. Changes in PI or an irregular shape to the blood flow velocity profile over a cardiac cycle or evidence of backflow may be indicative of infant respiratory distress syndrome, hypovolemia and/or hypotension.

In more specific embodiments said brain injury is caused by hyperbilirubinemia (e.g. acute bilirubin encephalopathy (ABE), chronic bilirubin encephalopathy (CBE) or subtle bilirubin encephalopathy (SBE)). Bilirubin is known to accumulate in the grey matter of neurological tissue where it exerts direct neurotoxic effects leading to widespread apoptosis and necrosis of neurons. New-born subjects with hyperbilirubinemia have an increased cerebral blood flow velocity as compared with new-born subjects without hyperbilirubinemia. This increased velocity may be associated with decreased RI and PI, increased peak systolic velocity and vasodilation. Monitoring cerebral blood flow in accordance with these aspects of the invention, e.g. for these indicators, may indicate the risk of brain injury caused by hyperbilirubinemia and need for intervention (e.g. phototherapy or exchange transfusion), guide the timing thereof and/or provide information on the response to such intervention. In certain embodiments, the characteristic may be compared with reference data from healthy subjects and differences between the test and reference data may indicate intervention, the timing thereof and/or the type thereof. The same assessments can be applied to monitoring the subject's response to said interventions.

In certain embodiments the pathological condition is haemodynamic instability, e.g. arising from (caused by) infant respiratory distress syndrome, hypovolemia, hypotension, invasive or non-invasive positive pressure ventilation, asphyxia, hypoxic/ischemic brain injury and/or sepsis. Other serious or critical illnesses may result in haemodynamic instability. Monitoring cerebral blood flow in accordance with these aspects of the invention allows the clinician to gauge the need for intervention, to undertake suitable interventions and to monitor the effects of those interventions. In these contexts, increased or decreased cerebral blood flow from baseline (e.g. measured by Vmean), changes in PI or an irregular shape to the blood flow velocity profile over a cardiac cycle or evidence of backflow may be indicative of haemodynamic instability in the subject. The profile of low frequency oscillations in blood flow measurements (e.g. blood flow velocity) may also be used. Such oscillations may be at a frequency of about 0.08 Hz, e.g. 0.01 to 0.2 Hz. A lack of such oscillations, e.g. in arterial flow velocity, may be indicative of haemodynamic instability. Today haemodynamic instability is estimated indirectly with invasive and/or manual systemic blood pressure measurements, it is believed that the above described low frequency oscillations in blood flow measurements may, in particular, be a more effective marker (e.g. more sensitive, more reliable and/or more accurate).

Haemodynamic instability and its complications may be managed, for instance, by providing antibiotic therapy (if sepsis is suspected), treatment for low blood pressure with medications and/or fluids, by establishing appropriate oxygenation levels, or by establishing appropriate ventilation, and/or fluid management.

In certain embodiments the pathological condition is dysfunctional cerebral haemodynamic autoregulation. This condition is commonly seen in sick infant subjects and is particularly common in premature infants. It is associated with a high risk of complications, e.g. those described herein, and in particular those arising from or associated with heamodynamic instability and brain injury. The above discussion regarding these complications applies mutate mutandis. Monitoring cerebral blood flow in accordance with these aspects of the invention allows the clinician to gauge the need for intervention, to undertake suitable interventions and to monitor the effects of those interventions. In these contexts, the profile of low frequency oscillations in blood flow measurements (e.g. blood flow velocity) may be used. Such oscillation may be at a frequency of about 0.08 Hz, e.g. 0.01 to 0.2 Hz. A lack of such oscillations, e.g. in arterial flow velocity, may be indicative of dysfunctional cerebral haemodynamic autoregulation. Interventions may be those which are preventive for the complications of haemodynamic instability in infant subjects, e.g. those described herein.

In certain embodiments the pathological condition is a brain injury caused by haemodynamic instability and/or dysfunctional cerebral haemodynamic autoregulation. The above discussion of the monitoring of and interventions for haemodynamic instability and/or dysfunctional cerebral haemodynamic autoregulation applies mutatis mutandis to this embodiment.

In certain embodiments the pathological condition is hydrocephalus, e.g. posthaemmoragic or congenital. The above discussion in the context of brain injury caused by hydrocephalus applies mutatis mutandis.

In certain embodiments the pathological condition is patent ductus arteriosus. The above discussion in the context of brain injury caused by patent ductus arteriosus applies mutatis mutandis. PDA may lead to necrotising enterocolitis, intraventricular haemorrhage and/or bronchopulmonary dysplasia. Thus, the methods of the invention may be further considered to be methods for monitoring or predicting the onset or progression of such conditions in subjects with PDA.

In certain embodiments the pathological condition is a congenital heart defect, e.g. a ductus dependent congenital cardiac lesion, which affects cerebral blood flow. The above discussion in the context of brain injury caused by a congenital heart defect applies mutatis mutandis.

In certain embodiments the pathological condition is a cerebral infection and/or sepsis. The above discussion in the context of brain injury caused by cerebral infection or sepsis applies mutatis mutandis. In particular, monitoring a characteristic of cerebral blood flow in accordance with these aspects of the invention can provide information to a clinician on the extent of the infection and its progression and this allows the clinician to undertake suitable interventions (e.g. antibiotic therapy, pressor therapy, inotrope therapy and fluid supply) and to monitor the effects of those interventions. Suitable characteristics or profiles thereof which may be monitored in this context may be Vmean measurements and/or the profile of low frequency oscillations in blood flow (e.g. blood flow velocity) measurements. Such oscillations may be at a frequency of about 0.08 Hz, e.g. 0.01 to 0.2 Hz. A lack of such oscillations, e.g. in arterial flow velocity, may be indicative of sepsis. An increased cerebral blood flow may also indicate onset of sepsis.

In certain embodiments the pathological condition is persistent pulmonary hypertension of the newborn (PPHN). The above discussion in the context of brain injury caused by PPHN applies mutatis mutandis. In particular, monitoring a characteristic of cerebral blood flow in accordance with these aspects of the invention can provide information to a clinician on the extent of the condition and its progression and this allows the clinician to undertake suitable interventions (e.g. pressor therapy, inotrope therapy, nitric oxide therapy and establishing appropriate blood oxygenation levels or establishing appropriate ventilation and/or fluid management) and to monitor the effects of those interventions. Suitable characteristics or profiles thereof which may be monitored in this context may be velocity, Vmean or PI measurements and/or the ratio of average diastolic flow/peak systolic flow. The blood flow velocity profile over a cardiac cycle may also be used. An irregular shape to this profile or evidence of backflow may be indicative of PPHN.

In certain embodiments the pathological condition is infant respiratory distress syndrome, hypovolemia, and/or hypotension. The above discussion in the contexts of haemodynamic instability, e.g. arising from (caused by) these conditions and in the context of brain injury arising from (caused by) these conditions applies mutatis mutandis. In particular, monitoring cerebral blood flow in accordance with these aspects of the invention allows the clinician to gauge the need for intervention to address these complications, to undertake suitable interventions and to monitor the effects of those interventions. These complications may be managed, for instance, by providing treatment for low blood pressure with medications and/or fluids, by establishing appropriate oxygenation, or by establishing appropriate ventilation and/or fluid management.

In certain embodiments the pathological condition is an intracranial haemorrhage, e.g. a (intra)cerebral haemorrhage, including intraventricular haemorrhage. The above discussion in the context of brain injury caused by an intracranial haemorrhage applies mutatis mutandis.

In certain embodiments the pathological condition is cerebral infarction. Monitoring cerebral blood flow in accordance with these aspects of the invention (including venous flow) can provide information to a clinician about the likelihood of cerebral infarction occurring and/or the blood flow in the brain following cerebral infarction. This allows the clinician to undertake suitable interventions, both preventative and reactionary, and to monitor the effects of those interventions. These interventions may be, for instance, antithrombotic or anticoagulation therapy, surgical (e.g. thrombectomy), establishing appropriate blood oxygenation levels or establishing appropriate ventilation and/or fluid management, or hypothermic therapy.

In certain embodiments the pathological condition is a seizure. Monitoring cerebral blood flow in accordance with these aspects of the invention can provide information to a clinician about the likelihood of a seizure and/or the blood flow in the brain during and following a seizure. This allows the clinician to undertake suitable interventions, both preventative and reactionary, and to monitor the effects of those interventions. These interventions may be, for instance, anti-seizure medication, establishing appropriate blood oxygenation levels or establishing appropriate ventilation and/or fluid management, or hypothermic therapy.

In certain embodiments the pathological condition is neonatal abstinence syndrome. Cerebral blood flow in infants undergoing drug withdrawal may be abnormal. Monitoring cerebral blood flow in accordance with these aspects of the invention can provide information to a clinician about the progression of the withdrawal progress and the effects of any interventions. These interventions may be, for instance, control of body temperature, establishing appropriate ventilation and/or fluid management, anti-seizure medication and tapering doses of the drug on which the infant is dependent.

In certain embodiments the pathological condition is a vascular malformation of the brain, e.g. an arteriovenous malformation (AVM), a cavernous malformation (CM), a venous angioma (VA), a telangiectasia (TA), a vein of Galen malformation (VGM), or a combination of two or more of the foregoing. Monitoring cerebral blood flow in accordance with these aspects of the invention (including venous flow) can provide information to a clinician about the extent and location of the malformation and response to any interventions. These interventions may be, for instance, surgical removal (resection), endovascular embolization or stereotactic radiosurgery.

In certain embodiments the pathological condition is vasomotor dysfunction. This condition affects the subject's ability to regulate body temperature and a lack of such control is associated with intraventricular haemorrhage. Monitoring cerebral blood flow in accordance with these aspects of the invention can provide information to a clinician about the likelihood of vasomotor dysfunction in the subject and allows the clinician to undertake suitable interventions, both preventative and reactionary, and to monitor the effects of those interventions. These interventions may be, for instance, control of body temperature and establishing appropriate blood oxygenation levels or establishing appropriate ventilation and/or fluid management. In these contexts, end-diastolic velocity, specifically increased end-diastolic velocity, or PI may be indicative of vasomotor dysfunction in the subject. The profile of low frequency oscillations in blood flow measurements (e.g. blood flow velocity) may also be used. Such oscillation may be at a frequency of about 0.08 Hz, e.g. 0.01 to 0.2 Hz. A lack of such oscillations, e.g. in arterial flow velocity, may be indicative of vasomotor dysfunction.

In certain embodiments the pathological condition is preterm birth and the complications associated therewith or arising therefrom. The above discussion setting out in detail the complications which face premature infants applies mutatis mutandis to this embodiment. In particular, monitoring a characteristic of cerebral blood flow in accordance with these aspects of the invention can provide information to a clinician on the likelihood of such complications arising, the extent of any such complications which have arisen and their progression and this allows the clinician to undertake suitable interventions and to monitor the effects of those interventions.

As discussed above an infant's inability or reduced ability to autoregulate brain blood flow means that any clinical intervention has the potential to have an adverse effect in the infant brain and lead to injury. As such the methods of the invention may also be used broadly to monitor response to any clinical treatment applied to an infant subject (including, but not limited to, pharmaceutical, surgical, occupational or physiological therapies), e.g. to ensure detrimental variations in cerebral flow do not occur or to guide further intervention should variations occur. More specifically the treatment being monitored for response may include any and all of the above discussed treatments, e.g. as used in the context of the treatment of the pathological conditions described above, but also as they may be used in the treatment of other diseases or conditions. In these embodiments effects on cerebral blood flow may be expected and may represent a positive response in certain contexts (e.g. in sepsis a treatment may be intended to reduce dangerously elevated blood flow). Conversely a lack of change may represent a lack of response.

In more general terms the method of the invention is able to monitor or predict the onset or progression of a disease or pathological condition and/or a response to treatment in an infant vertebrate animal subject by providing a general indication of the health of the subject. It has been found that the profile of low frequency (as compared to heart rate) oscillations in blood flow measurements (e.g. blood flow velocity) may be indicative of the general health of a subject. Such oscillation may be at a frequency of about 0.08 Hz, e.g. 0.01 to 0.2 Hz. A lack of such oscillations, e.g. in arterial flow velocity, may be indicative of a serious or critical pathological state or illness. By serving as a general indication of the medical status of a subject, the method can provide an indication that more specific investigations are warranted.

Thus, in a further embodiment the invention provides a method for monitoring or predicting the onset or progression of a disease or pathological condition and/or a response to treatment in an infant vertebrate animal subject, wherein said method provides an indication of the health of said subject, said method comprising
  transmitting unfocused ultrasound pulses into the subject via a fontanelle or a suture in the subject's skull or via an area of the subject's skull which has an average thickness of less than about 2 mm from an ultrasound transducer that is fastened to an external surface of the subject's skull;
  receiving reflections of the ultrasound pulses at the ultrasound transducer;
  generating pulse-Doppler response signals from the reflections; and
  processing the pulse-Doppler response signals to determine a characteristic of cerebral blood flow within the subject;
  monitoring the characteristic of blood flow over time; and
  establishing a profile of said characteristic over time;
wherein low frequency oscillations in said characteristic over time are indicative of the health of said subject.

More specially, absence of low frequency oscillations in said characteristic over time are indicative of a critical pathological state and/or the presence of low frequency oscillations in said characteristic over time are indicative of a non-critical, e.g. non-pathological state. Such oscillations have a frequency which is lower than that of the heart rate of the subject. For instance, about 0.08 Hz, e.g. 0.01 to 0.2 Hz. In these embodiments the characteristic may be arterial blood flow velocity.

References herein to methods of the invention guiding intervention encompass situations in which a delay in intervention is indicated, for example a delay taking a blood sample may be indicated if the circulation is critical just at that moment.

The fontanelle may be the anterior fontanelle, the posterior fontanelle, the sphenoidal (anterolateral) fontanelle or the mastoid (posterolateral) fontanelle The suture may be the coronal suture, lambdoid suture, occipitomastoid suture, sphenofrontal suture, sphenoparietal suture, sphenosquamosal suture, sphenozygomatic suture, squamosal suture, zygomaticotemporal suture, zygomaticofrontal suture, frontal suture (Metopic suture), or sagittal suture.

Transmitting through a suture or fontanelle, rather than through the skull, can facilitate the use of higher-frequency ultrasound than would otherwise be possible—e.g., having a frequency of 8 or 16 MHz or even higher. This enables finer depth resolution than would otherwise be possible. It also allows unfocused plane-wave pulses to be used. This contrasts with ultrasonography performed through the skull (e.g. transcranial Doppler ultrasound), in which a focused transmit and/or receive beam path is required in order for sufficient energy to pass through the skull to obtain a useful signal.

The area of the subject's skull which has an average thickness of less than about 2 mm, e.g. less than 1.5 mm or 1 mm, may be found by adjusting the position of the ultrasound probe of the invention in relation to the subject's skull until a robust pulse Doppler signal is detected. Alternatively, areas may be found by any convenient monitoring means, e.g. CT scan. MRI or X-ray, but this may be less preferred for practical reasons. Suitable areas may be in the mastoid or temporal areas of the skull.

In this aspect the infant subject is a subject in which at least one fontanelle or suture is open (effectively transparent to ultrasound). In human subjects, closure of all fontanelles and sutures is typically complete by about 24 months of age. Thus, a human infant may be considered to be a subject less than about 24 months old, e.g. less than 22, 20, 18, 16, 14 or 12 months old. The term "infant" is considered to extend to intrapartum infant subjects, i.e. infants in the process of being born (the time period from onset of labour to delivery). The infant subject may be a subject that was (or is being) born preterm (premature). In other embodiments the subject, e.g. subject which was born preterm, may be a neonatal subject. In human subjects, neonatal subjects are considered to be less than 6 months old (postpartum), e.g. less than 4, 3, 2 or 1 month old. These aspects of the invention may be especially effective in human subjects which are born more than 1 week, e.g. more than 2, 3, 4, 5, 6, 7, or 8, 10, 12, 14 or 16 weeks prematurely. Expressed differently a preterm human infant is an infant which has been born at a gestational age of less than 37 weeks, e.g. less than 36, 34, 32, 30, 28 or 26 weeks. Severely premature human infants are considered to be those born at a gestational age of less than 28 weeks, e.g. less than 27 or 26 weeks.

The methods of the invention may be performed at any time during the clinician care of the subject. In certain embodiments it may be advantageous to perform the methods of the invention, or at least begin such methods, at the time of birth during the first 1, 2, 3, 4, 5, 10, 15 or 20 days following birth. In other embodiments the it may be advantageous to perform the methods of the invention, or at least begin such methods, at the time a subject is admitted to a health care facility for treatment, at the start of said treatment, at the start of a new treatment is started, or during the first 1, 2, 3, 4, 5, 10, 15 or 20 days following the admission of the start of the treatment.

The subject may be a subject at risk of the disease or pathological condition, e.g. brain injury.

In accordance with these aspects of the invention the characteristic of blood flow may be determined from any blood vessel, or vessels, in or region of the cerebral circulatory system of the subject within range of the ultrasound transducer having a flow rate sufficient to be detectable in the pulse-Doppler response signals. Thus, it is a characteristic of cerebral blood flow which is determined. In certain embodiments the characteristic is determined from blood flow in the minor vasculature or the microvasculature, e.g. the arterial microvasculature, but this is by no means essential and blood flow may, in other embodiments, be determined, alternatively or additionally, in any artery or vein, e.g. of the macrovasculature, present in the cerebral circulatory system of the subject (e.g. the central cerebral circulation). Thus, any vessel or plurality thereof, or any region comprising any cerebral blood vessel or plurality thereof within about 40 mm of the fontanelle or suture or area of the subject's skull which has an average thickness of less than about 2 mm which is used as the window through which the ultrasound pulses are transmitted in accordance with the invention may be the vessel or vessels or region from which the characteristic of blood flow is determined. In certain embodiments the vessel or part thereof or region from which a characteristic of blood flow may be determined is not at the surface of the brain. Such vessels or parts thereof or regions at the brain surface may be considered those which are located at no more than 5 mm from the surface of the brain, e.g. no more than 4, 3, 2, 1, 0.9, 0.8, 0.7, 0.6, 0.5 mm from the surface of the brain. In other embodiments such vessels or parts thereof or regions may be considered those which are located at no more than 5 mm from the internal surface of the fontanelle or suture or area of the subject's skull which has an average thickness of less than about 2 mm which is used as the window through which the ultrasound pulses are transmitted in accordance with the invention e.g. no more than 4, 3, 2, 1, 0.9, 0.8, 0.7, 0.6, 0.5 mm from the internal surface of said structures.

The vessel, or plurality thereof, or those which are contained within a region from which a characteristic of blood flow may be determined in accordance with the invention, may be one or more of the following cerebral blood vessels: internal carotid artery, anterior communicating artery, anterior cerebral artery, middle cerebral artery, posterior cerebral artery, pericallosal artery, ophthalmic artery, anterior choroidal artery, superior cerebellar artery, basilar artery, anterior inferior cerebellar artery, vertebral artery, posterior inferior cerebellar artery, anterior spinal artery, pontine artery, posterior communicating artery, superior sagittal sinus, basal vein of Rosenthal, internal cerebral vein, superior petrosal sinus, cavernous sinus, ophthalmic vein, inferior petrosal sinus, sigmoid sinus, transverse sinus, confluens of sinuses, great vein of Galen, straight sinus, and inferior sagittal sinus. Blood flow in the anterior cerebral artery, middle cerebral artery, posterior cerebral artery, pericallosal artery and superior sagittal sinus may be monitored alone or in combination in accordance with certain embodiments of the invention.

As can be seen, in certain embodiments the identity of the blood vessel(s) from which blood flow characteristics are determined in accordance with the invention is not critical and equally useful information may be obtained from measurements from a variety of regions within the subject's brain. This suggests that the ultrasound system of the invention has advantages over conventional Doppler monitoring techniques because it means that it may be possible for clinically useful readings to be obtained from a comparatively wide range of target regions (i.e. any region containing one or more of various cerebral blood vessels, in particular central vessels) rather than requiring a specific vessel to be accurately located and analysed. This in turn may mean that the ultrasound system of the invention may be used by operators which are not as highly trained as those required to operate conventional Doppler ultrasound and/or makes the system of the invention more amenable to automation.

In certain embodiments the characteristic of blood flow may be determined from one or more vessels at different depths/depth ranges and said characteristic at said different depths/depth ranges may be determined in parallel over time. In certain embodiments a depth which allows a characteristic of arterial flow to be determined will be selected together with a depth which allows a characteristic of venous flow to be determined. The method of the invention may involve comparing the characteristics of venous and arterial flows and the result of that comparison may be the characteristic or profile thereof which is monitored in accordance with the invention.

In certain embodiments the method of the invention comprises transmitting ultrasound pulses into the subject via no more than one fontanelle or suture at any one time. Expressed differently, the method of the invention does not comprise transmitting ultrasound pulses into the subject via a plurality of fontanelles or sutures at the same time or substantially the same time. In other embodiments the method of the invention comprises transmitting ultrasound pulses into the subject via no more than one fontanelle or suture. In other embodiments no more than one ultrasound transducer is used, e.g. at said no more than one fontanelle or suture. Expressed differently, the method of the invention does not comprise the use of a plurality of ultrasound transducers at a plurality of fontanelles or sutures.

In a further aspect the invention provides a method for treating or preventing a disease or pathological condition in an infant vertebrate animal subject, wherein said disease or pathological condition is selected from
 (a) brain injury;
 (b) patent ductus arteriosus;
 (c) a congenital heart defect;
 (d) sepsis;
 (e) cerebral infection;
 (f) haemodynamic instability;
 (g) hydrocephalus;
 (h) persistant pulmonary hypertension of the newborn;
 (i) infant respiratory distress syndrome;
 (j) hypovolemia;
 (k) hypotension;
 (l) intracranial haemorrhage;
 (m) cerebral infarction;
 (n) seizure;
 (o) neonatal abstinence syndrome;
 (p) vascular malformations of the brain; or
 (q) vasomotor dysfunction
 (r) dysfunctional cerebral haemodynamic autoregulation
 (s) preterm birth or a complication thereof
said method comprising
 transmitting ultrasound pulses into the subject via a fontanelle or a suture in the subject's skull or via an area of the subject's skull which has an average thickness of less than about 2 mm from an ultrasound transducer that is fastened to an external surface of the subject's skull;
 receiving reflections of the ultrasound pulses at the ultrasound transducer;
 generating pulse-Doppler response signals from the reflections; and processing the pulse-Doppler response signals to determine a characteristic of blood flow within the subject;
monitoring the characteristic of blood flow over time; and optionally
establishing a profile of said characteristic over time wherein the characteristic or the profile of said characteristic over time is indicative or predictive of said disease or pathological condition, or variation in said characteristic or the profile of said characteristic over time is indicative or predictive of said disease or pathological condition or is indicative or predictive of a change in the subject's disease or pathological condition; and
determining the presence or absence of said disease or pathological condition in said subject, or the likelihood of said disease or pathological condition occurring in said subject or progressing in said subject and treating said subject with a clinical intervention suitable for reducing or preventing said disease or pathological condition or reducing the likelihood of said disease or pathological condition occurring.

The features described above in connection with the methods for monitoring or predicting the onset or progression of said diseases or pathological conditions apply mutatis mutandis to this aspect.

In a specific embodiment the invention provides a method for reducing or preventing brain injury in an infant vertebrate animal subject, said method comprising
transmitting ultrasound pulses into the subject via a fontanelle or a suture in the subject's skull or via an area of the subject's skull which has an average thickness of less than about 2 mm from an ultrasound transducer that is fastened to an external surface of the subject's skull;
receiving reflections of the ultrasound pulses at the ultrasound transducer;
generating pulse-Doppler response signals from the reflections; and
processing the pulse-Doppler response signals to determine a characteristic of blood flow within the subject;
monitoring the characteristic of blood flow over time; and optionally
establishing a profile of said characteristic over time wherein the characteristic or the profile of said characteristic over time is indicative or predictive of a brain injury, or variation in said characteristic or the profile of said characteristic over time is indicative or predictive of a brain injury or is indicative or predictive of a change in the subject's brain injury; and
determining the likelihood of a brain injury occurring in said subject or progressing in said subject and treating said subject with a clinical intervention suitable for reducing or preventing said brain injury or reducing the likelihood of said brain injury.

The features described above in connection with the methods for monitoring or predicting the onset or progression of brain injury apply mutatis mutandis to this aspect.

In a further specific embodiment the invention provides a method for treating patent ductus arteriosus in an infant vertebrate animal subject, said method comprising
transmitting ultrasound pulses into the subject via a fontanelle or a suture in the subject's skull or via an area of the subject's skull which has an average thickness of less than about 2 mm from an ultrasound transducer that is fastened to an external surface of the subject's skull;
receiving reflections of the ultrasound pulses at the ultrasound transducer;
generating pulse-Doppler response signals from the reflections; and
processing the pulse-Doppler response signals to determine a characteristic of blood flow within the subject;
monitoring the characteristic of blood flow over time; and optionally
establishing a profile of said characteristic over time wherein the characteristic or the profile of said characteristic over time is indicative or predictive of patent ductus arteriosus, or variation in said characteristic or the profile of said characteristic over time is indicative or predictive of patent ductus arteriosus or is indicative or predictive of a change in the subject's patent ductus arteriosus; and
determining an appropriate time to intervene and/or an appropriate intervention and intervening accordingly to treat said patent ductus arteriosus.

The features described above in connection with the methods for monitoring or predicting patent ductus arteriosus apply mutatis mutandis to this aspect.

Features of other aspects disclosed herein may be features of embodiments of these aspects also.

Some embodiments may comprise a fastener for positioning the transducer over a fontanelle (e.g., anterior, posterior/lambdoid/occipital, sphenoidal/anterolateral, or mastoid/posterolateral) or a suture of an infant skull.

From a further aspect, the invention provides a fastener for fastening an ultrasound transducer over a fontanelle or suture in an infant skull, the fastener comprising:
a tensioning portion sized to encompass an infant skull while applying pressure to the infant skull so as to resist movement of the tensioning portion relative to the infant skull; and
a mount coupled to the tensioning portion and arranged to receive and hold an ultrasound transducer adjacent a fontanelle or suture of the infant skull.

In one set of embodiments, the fastener comprises a tube, which may be made from an elastic material, such a woven nylon. The tube may be open at a proximal end and at a distal end, or it may closed or closable at a distal end. It may comprise a drawstring for closing the distal end. The tensioning portion may form a part or all of this tube.

In another set of embodiments, the fastener comprises one or more straps for circling the infant's skull. The straps may comprise a securing mechanism, such as hook-and-loop tape or a buckle, for applying the fastener. The straps, when joined, may define the tensioning portion.

The mount may define a circular or rectangular opening, through which the ultrasound transducer can transmit ultrasound pulses. The mount may comprise a cylinder or spherical segment, which may be arranged to retain the ultrasound transducer by a friction fit.

The inventors have recognised that some aspects of the invention have particular utility in the clinical treatment of sepsis and septic shock, more specifically in the early and accurate of detection of subjects with or at significant risk of sepsis and septic shock and in the monitoring of these conditions as they progress and respond to treatment.

Sepsis, including its more serious complication septic shock, is one of the most frequent causes of death in hospitals. Sepsis may develop from apparently trivial infections, e.g. those in the skin, urinary tract, upper and lower airways, gastro-intestinal tract, but also those acquired following surgical interventions. In immune-depressed patients the development of sepsis from apparently trivial infections or even the natural microbial fauna is a significant risk. Despite intense efforts, sepsis remains a serious clinical problem globally, affecting 30 million and accounting for potentially six million deaths each year.

Sepsis is considered as a clinical syndrome characterized by "life-threatening organ dysfunction as a response to an overwhelming or dysregulated host response to infection" (Singer, M, et al (2016), The Third International Consensus Definitions for Sepsis and Septic Shock (Sepsis-3), JAMA, 315 (8): 801-10; incorporated herein in its entirety). A positive diagnosis relies on there being 1) a suspected infection, and 2) an acute change in the 'Sequential (Sepsis-Related) Organ Failure Assessment' score (SOFA) of two or more points (Singer, supra). The SOFA score ranges from zero to maximum 24 points depending on the degree of organ failures, secondary to the development of the syndrome; oxygen exchange capability, blood platelet count, blood bilirubin concentration, degree of hypotension, degree of impaired consciousness and renal function. Diagnosis is therefore inherently reliant on substantial progress of the disease.

Another important mechanism, occurring early in the septic course, is peripheral vasomotor dysfunction, i.e. the regulation of the tone, or suspense, of the vessel walls of the microvasculature. Blood flow and nutrient distribution throughout the body depends on strictly controlled and orchestrated constriction and dilatation of small flow-regulatory arteries. The sum of resistance against flow, generated by these vasomotor vessels, is an essential regulator of the blood pressure, which in turn is a guarantee for the perfusion of the vital organs. Sepsis induced vasomotor dysfunction leads to microvasculature dilatation, thereby resulting in reduced blood pressure and maldistribution of blood flow in the body. This may also be generally referred to herein as haemodynamic instability.

Septic shock is defined as critical subset of sepsis in which patients display profound profound cellular and metabolic abnormalities and in which circulatory conditions are further compromised leading to increased mortality. Patients with septic shock have high levels of serum-lactate acid (>2 mmol/L (18 mg/dL) in humans) and require vasopressors to maintain mean arterial blood pressure (MAP) at above about two thirds of normal (above about 65 mmHg in humans), despite adequate fluid resuscitation (Singer, supra).

The success of treatment in patients with or at risk of sepsis relies on early recognition and detection of sepsis in patients and the identification of patients at significant risk thereof. Early and accurate detection allows early antibiotic treatment and optimization of supportive care like fluids and pressor therapy. However, using today's methods an accurate diagnosis is inherently retrospective as it relies on the condition having progressed sufficiently to register changes on the SOFA score.

A recent survey of hospitals performed in Norway found that the early signs of sepsis are frequently not recognized in general practice or in the emergency room in hospitals, leading to a delay in initiation of lifesaving treatment. Currently, there is no objective validated diagnostic test to identify or to support the clinical diagnosis of sepsis at an early stage, in particular at the level of the microcirculation where the critical dysregulation (instability) arises. Analogously, there is no validated monitoring system available to guide therapy and evaluate the effects of sepsis treatments at the microcirculatory level or the level of the minor vasculature.

Accordingly, there is an urgent need to improve the early identification of sepsis in subjects at significant risk of sepsis, in particular those which are essentially asymptomatic (most general clinical parameters appear normal), and an urgent need to improve the on-going monitoring of the severity or progress of the condition in subjects undergoing treatment.

The inventors have recognised that at least some of the methods, systems and apparatus of the invention are suited to meet these particular needs.

From a further aspect, the invention provides a method for monitoring or predicting the onset of and/or progression of sepsis and/or a response to treatment thereof in a vertebrate animal subject, said method comprising:
    transmitting ultrasound pulses into the subject from an ultrasound transducer that is applied to an external surface of the peripheral anatomy of the subject;
    receiving reflections of the ultrasound pulses at the ultrasound transducer from at least one region containing at least one blood vessel of the peripheral vasculature, preferably a plurality thereof;
    generating pulse-Doppler response signals from the reflections; and
    processing the pulse-Doppler response signals to determine a characteristic of blood flow in the peripheral vasculature of the subject;
    monitoring the characteristic of blood flow over time; and optionally
    establishing a profile of said characteristic over time;
wherein the characteristic or the profile of said characteristic over time is indicative or predictive of sepsis in the subject or a response to the treatment thereof, or variation in said characteristic or a profile of said characteristic over time is indicative or predictive of sepsis in the subject or indicative or predictive of a change in the subject's sepsis or response to the treatment thereof.

The invention extends to a system configured to implement such a method. In particular, the system is configured to transmit unfocused ultrasound pulses. The ultrasound pulses may be plane-wave pulses.

In certain embodiments the characteristic of blood flow in the subject is monitored over time continuously. In other embodiments the monitoring over time takes place repeatedly at a frequency which provides clinically useful information, e.g. as described above. In this embodiment the monitoring phases are interspaced with periods were monitoring does not take place. Preferably, ultrasound is not transmitted into the subject during the non-monitoring phases.

The ultrasound transducer may be applied to the external surface manually (e.g., being held in place by a human operator), but preferably it is fastened to the external surface.

In accordance with these aspects of the invention the characteristic of blood flow may be monitored in any blood vessel, or vessels, in the peripheral vasculature of the subject having a flow rate sufficient to be detectable in the pulse-Doppler response signals. Thus in certain embodiments the blood vessel, or vessels, are those at a site on a limb (e.g. arm, shoulder, leg, hand (e.g. inside or back or between thumb and forefinger), foot, toe, finger, paw, wing, fin, tail), neck or head (e.g. ear, nose, tongue, cheek, scalp, forehead).

In other embodiments the characteristic of blood flow may be monitored in any blood vessel, or vessels, in the minor peripheral vasculature of the subject having a flow rate sufficient to be detectable in the pulse-Doppler response signals. In other embodiments the characteristic of blood flow may be monitored in any blood vessel, or vessels, in the peripheral microvasculature of the subject having sufficient flow to reflect ultrasound pulses.

It may be advantageous in certain embodiments to monitor the arterial microvasculature. In this regard the inventors have recognised that characteristics of blood flow in the arterial microvasculature (especially the peripheral arterial microvasculature), which is the vasculature slightly upstream of the capillary beds, can provide information on the characteristics of blood flow in the microcirculation (especially the peripheral microcirculation) more generally, and especially in the context of the circulatory dysfunction observed in subjects with haemodynamically unstable sepsis.

In any of these embodiments said vessels may be superficial vessels.

As used herein the terms "sepsis" and "septic shock" should be interpreted consistent with the guidance provided in Singer (supra). Thus, unless indicated otherwise, a reference sepsis includes extends to septic shock. Nevertheless, in certain embodiments the methods of the invention specifically exclude application in the context of septic shock.

The subject may be a subject at risk of sepsis. A subject at risk of sepsis is typically a subject with an assumed infection, in particular an assumed blood stream infection. In certain embodiments the subject at risk sepsis is also at risk of haemodynamic instability associated with sepsis and/or vasomotor dysfunction associated with sepsis. Such complications are considered to be distinct from microvascular dysfunction (in particular peripheral microvascular dysfunction), e.g. as defined described herein.

In certain embodiments the subject is not an infant subject as defined herein.

The method may also be considered a method for obtaining information relevant to monitoring or predicting the onset of and/or progression of sepsis and/or a response to treatment thereof in a vertebrate animal subject. The methods described herein may be used alone as an alternative to other investigative techniques or in addition to such techniques in order to provide information relevant to monitoring or predicting the onset of and/or progression of sepsis and/or a response to treatment thereof in a vertebrate animal subject.

In certain embodiments the method further comprises a step in which the characteristic or the profile of said characteristic over time or the variation in said characteristic or the profile of said characteristic over time is used, alone or together with additional clinical information (e.g. from other methods), to diagnose sepsis or the extent or severity thereof, or to provide a prognosis for the onset of and/or progression of sepsis in the subject, or to determine a response to the treatment of sepsis in the subject.

In these embodiments the characteristic or the profile of said characteristic over time or the variation in said characteristic or the profile of said characteristic over time may be compared to reference data previously obtained from the same subject, e.g. reference data obtained prior to the onset of sepsis, or the commencement of a treatment or treatment cycle or from a time earlier in said treatment. Divergence between the data sets may be indicative of a change in the disease or response to treatment. Thus, the steps of comparing the test and reference data and determining whether or not they diverge (or correspond) may be performed using mathematical, or statistical techniques, and generally this will be implemented by software (i.e. it will be performed using a computer). Statistical or mathematical methods for performing such a comparison and determination of correspondence are well known and widely available in the art. In other embodiments correspondence (or divergence) may be assessed or estimated visually by the skilled person.

In other embodiments the characteristic or the profile of said characteristic over time or the variation in said characteristic or the profile of said characteristic over time may be compared to reference data previously obtained from a cohort of analogous subjects, e.g. a cohort which developed sepsis or which were previously determined as being at risk of sepsis or which were undergoing analogous clinical care for sepsis and/or a cohort of healthy subjects (subjects not displaying or at risk of the disease or pathological condition), i.e. a predetermined standard. In these embodiments correspondence (or divergence) between test data and reference data may be analysed as described above or by applying said test data to a mathematical model generated using the reference data. Such a mathematical model may be used to determine whether test data fits, or matches, a negative standard and/or a positive standard, e.g. whether it best fits, or best matches a negative and/or a positive standard. Mathematical methods for generating such models are well known. In other embodiments correspondence (or divergence) may be assessed or estimated visually by the skilled person.

In more specific embodiments the method may involve an alarm or indicator, in particular an automated alarm or indicator, occurring when the characteristic or the profile of said characteristic over time or the variation in said characteristic or the profile of said characteristic over time passes a certain threshold value, e.g. a value which may be indicative or predictive of the onset or progression of sepsis or response to the treatment thereof.

In a further aspect the invention provides a method for treating or preventing sepsis in a vertebrate animal subject, said method comprising transmitting ultrasound pulses into the subject from an ultrasound transducer that is applied to an external surface of the peripheral anatomy of the subject;

receiving reflections of the ultrasound pulses at the ultrasound transducer from at least one region containing at least one blood vessel of the peripheral vasculature, preferably a plurality thereof;

generating pulse-Doppler response signals from the reflections; and processing the pulse-Doppler response signals to determine a characteristic of blood flow in the peripheral vasculature of the subject;

monitoring the characteristic of blood flow over time; and optionally establishing a profile of said characteristic over time;

wherein the characteristic or the profile of said characteristic over time is indicative or predictive of sepsis in the subject or variation in said characteristic or a profile of said characteristic over time is indicative or predictive of sepsis in the subject or is indicative or predictive of a change in the subject's sepsis diagnosing sepsis or determining the likelihood of sepsis occurring in said subject or progressing in said subject and treating said subject with a clinical intervention suitable for treating or preventing sepsis or reducing the likelihood of sepsis occurring.

Clinical intervention suitable for treating or preventing sepsis may include antibiotic therapy, pressor therapy, fluid replacement and/or emergency surgery, e.g. to address the underlying cause of the infection (e.g. intestine perforation, abscess).

The features described above in connection with the methods for monitoring or predicting the onset of and/or progression of sepsis and/or a response to treatment thereof injury apply mutatis mutandis to this aspect.

Features of other aspects disclosed herein may be features of embodiments of these aspects also.

In healthy tissues the microvasculature of the tissue is able to control blood flow within it sufficiently to meet the tissue's needs for oxygen and nutrients and the removal of waste products and $CO_2$. In certain diseases and conditions the microvasculature becomes dysfunctional and can no longer meet those needs adequately. Diseases and pathological conditions which are associated with microvasculature dysfunction include, but are not limited to, diabetes mellitus types 1 and 2, Raynaud's phenomenon, systemic sclerosis, hypertension, peripheral artery disease, chronic renal failure, hypercholesterolemia, hyperlipidemia, obesity and hypertension. Thus dysfunction may arise from a restriction in blood flow upstream of the area of dysfunction (e.g. due to a stenosis) which cannot be compensated by regulation of the tone of the vessels of the microvasculature and/or because of an inability of the microvasculature to regulate the tone (peripheral resistance) of its vessels in response to increased or decreased tissue demands. Microvascular dysfunction, e.g. peripheral microvasculature dysfunction, is considered to be distinct from vasomotor dysfunction and/or haemodynamic instability associated with sepsis or septic shock, e.g. as defined herein.

The inventors have recognised that some aspects of the invention have particular utility in the clinical treatment of dysfunction of the microvasculature, more specifically in the early and accurate of detection of subjects with or at significant risk of dysfunction of the microvasculature and in the monitoring of this dysfunction as it progresses and/or responds to treatment (e.g. surgical and/or pharmaceutical intervention). More specifically the inventors have recognised that characteristics of blood flow in the minor vasculature, e.g. the arterial microvasculature (especially the peripheral minor vasculature, e.g. peripheral arterial microvasculature) can provide information on the characteristics of blood flow in the microcirculation (especially the peripheral microcirculation) in the context of microvascular dysfunction (especially peripheral microvasculature dysfunction), e.g. associated with diabetes mellitus types 1 and 2, Raynaud's phenomenon, systemic sclerosis, hypertension, peripheral artery disease, chronic renal failure, hypercholesterolemia, hyperlipidemia, obesity and hypertension.

Thus, from a further aspect, the invention provides a method for monitoring or predicting the onset of and/or progression of dysfunction of the microvasculature and/or a response to treatment thereof in a vertebrate animal subject, said method comprising transmitting ultrasound pulses into the subject from an ultrasound transducer that is applied to an external surface of the peripheral anatomy of the subject;

receiving reflections of the ultrasound pulses at the ultrasound transducer from at least one region containing at least one blood vessel of the minor peripheral vasculature, preferably a plurality thereof;

generating pulse-Doppler response signals from the reflections; and processing the pulse-Doppler response signals to determine a characteristic of blood flow in the minor peripheral vasculature of the subject;

monitoring the characteristic of blood flow over time; and optionally establishing a profile of said characteristic over time;

wherein the characteristic or the profile of said characteristic over time is indicative or predictive of dysfunction of the microvasculature or response to treatment thereof or variation in said characteristic or a profile of said characteristic over time is indicative or predictive of dysfunction of the microvasculature or is indicative or predictive of a change in the dysfunction of the microvasculature or response to treatment thereof The invention extends to a system configured to implement such a method. In particular, the system is configured to transmit unfocused ultrasound pulses. The ultrasound pulses may be plane-wave pulses.

In certain embodiments the characteristic of blood flow in the subject is monitored over time continuously. In other embodiments the monitoring over time takes place repeatedly at a frequency which provides clinically useful information, e.g. as described above. In this embodiment the monitoring phases are interspaced with periods were monitoring does not take place. Preferably, ultrasound is not transmitted into the subject during the non-monitoring phases.

In accordance with these aspects of the invention the characteristic of blood flow may be monitored in any blood vessel, or vessels, in the minor peripheral vasculature of the subject having a flow rate sufficient to be detectable in the pulse-Doppler response signals.

In certain embodiments the blood vessel, or vessels, are those at a site on a limb (e.g. arm, shoulder, leg, hand (e.g. inside or back or between thumb and forefinger), foot, toe, finger, paw, wing, fin, tail), neck or head (e.g. ear, nose, tongue, cheek, scalp, forehead).

In other embodiments the characteristic of blood flow may be monitored in any blood vessel, or vessels, in the peripheral microvasculature of the subject having a flow rate sufficient to be detectable in the pulse-Doppler response signals.

It may be advantageous in certain embodiments to monitor a characteristic of blood flow in the arterial microvasculature. In this regard the inventors have recognised that characteristics of blood flow in the arterial microvasculature (especially the peripheral arterial microvasculature), the vasculature slightly upstream of the capillary beds, can provide information on the characteristics of blood flow in the microcirculation (especially the peripheral microcirculation) more generally, and especially in the context of the microvascular dysfunction.

In any of these embodiments said vessels may be superficial vessels.

The blood vessel, or vessels, may be within a region of the subject displaying signs of microvascular dysfunction, e.g. regions of, or in proximity to, skin ulcers, gangrene, tissue necrosis, cyanosis, numbness and coldness.

The dysfunction of the minor vasculature may be dysfunction associated with diabetes mellitus types 1 and 2, Raynaud's phenomenon, systemic sclerosis, hypertension, peripheral artery disease, chronic renal failure, hypercholesterolemia, hyperlipidemia, obesity and hypertension.

The subject may be at risk of microvascular dysfunction, e.g. may be a subject which has diabetes mellitus types 1 and 2, Raynaud's phenomenon, systemic sclerosis, hypertension, peripheral artery disease, chronic renal failure, hypercholesterolemia, hyperlipidemia, obesity and/or hypertension.

In certain embodiments the subject does not have and/or is not at risk of sepsis or septic shock, e.g. as defined herein. In certain embodiments the subject is not an infant subject as defined herein.

Treatment of microvasculature dysfunction may include treatments for the underlying causes, e.g. anti-diabetic, antihypertensive, cholesterol lowering and lipid lowering pharmaceutical treatments, angioplasty or bypass surgery and lifestyle changes (e.g. smoking cessation, calorie restricted diets and increased exercise).

The method may also be considered a method for obtaining information relevant to monitoring or predicting the onset of and/or progression of microvasculature dysfunction and/or a response to treatment thereof in a vertebrate animal subject. The methods described herein may be used alone as an alternative to other investigative techniques or in addition to such techniques in order to provide information relevant to monitoring or predicting the onset of and/or progression of microvasculature dysfunction and/or a response to treatment thereof in a vertebrate animal subject.

In certain embodiments the method further comprises a step in which the characteristic or the profile of said characteristic over time or the variation in said characteristic or the profile of said characteristic over time is used, alone or together with additional clinical information (e.g. from other methods), to diagnose microvasculature dysfunction or the extent or severity thereof, or to provide a prognosis for the onset of and/or progression of minor vasculature dysfunction in the subject, or to determine a response to the treatment of microvasculature dysfunction in the subject.

In these embodiments the characteristic or the profile of said characteristic over time or the variation in said characteristic or the profile of said characteristic over time may be compared to reference data previously obtained from the same subject, e.g. reference data obtained prior to the onset of microvasculature dysfunction, or the commencement of a treatment or treatment cycle or from a time earlier in said treatment. Divergence between the data sets may be indicative of a change in the dysfunction or response to treatment. Thus, the steps of comparing the test and reference data and determining whether or not they diverge (or correspond) may be performed using mathematical, or statistical techniques, and generally this will be implemented by software (i.e. it will be performed using a computer). Statistical or mathematical methods for performing such a comparison and determination of correspondence are well known and widely available in the art. In other embodiments correspondence (or divergence) may be assessed or estimated visually by the skilled person.

In other embodiments the characteristic or the profile of said characteristic over time or the variation in said characteristic or the profile of said characteristic over time may be compared to reference data previously obtained from a cohort of analogous subjects, e.g. a cohort which developed microvasculature dysfunction or which were previously determined as being at risk of microvasculature dysfunction or which were undergoing analogous clinical care for microvasculature dysfunction and/or a cohort of healthy subjects (subjects not displaying or at risk of the disease or pathological condition), i.e. a predetermined standard. In these embodiments correspondence (or divergence) between test data and reference data may be analysed as described above or by applying said test data to a mathematical model generated using the reference data. Such a mathematical model may be used to determine whether test data fits, or matches, a negative standard and/or a positive standard, e.g. whether it best fits, or best matches a negative and/or a positive standard. Mathematical methods for generating such models are well known. In other embodiments correspondence (or divergence) may be assessed or estimated visually by the skilled person.

The inventors have recognised that some aspects of the invention have particular utility in the monitoring of peripheral microvasculature function (circulation) during or following surgery, in particular vascular surgery. All surgical procedures carry a risk of damage, inadvertent or unavoidable, to the subject's vascular system. This can lead to microvascular dysfunction downstream of the damage. Monitoring characteristics of blood flow in the minor vasculature in certain areas (or area) on the subject allows clinicians to detect such dysfunction in the microvasculature and make suitable interventions to avoid or mitigate any compromise to the blood flow in the subject's microvasculature. In the specific context of vascular surgery, e.g. endovascular surgery, the outcome is typically to restore blood flow to an area of the body which is experiencing a reduced or interrupted supply, e.g. because of stenosis or traumatic damage. Monitoring characteristics of blood flow in the minor vasculature in certain areas (or area) on the subject allows clinicians to confirm that blood flow in the microvasculature has been restored or has not been further compromised.

From a further aspect, the invention provides a method for monitoring peripheral microcirculation in a vertebrate animal subject undergoing or recovering from surgery, said method comprising transmitting ultrasound pulses into the subject from an ultrasound transducer that is applied to an external surface of the subject;

receiving reflections of the ultrasound pulses at the ultrasound transducer from at least one region containing at least one blood vessel of the minor peripheral vasculature, preferably a plurality thereof;

generating pulse-Doppler response signals from the reflections; and processing the pulse-Doppler response signals to determine a characteristic of blood flow in the minor peripheral vasculature of the subject;

monitoring the characteristic of blood flow over time; and optionally establishing a profile of said characteristic over time;

wherein variation in said characteristic or the profile of said characteristic over time is indicative or predictive of a change in the peripheral microcirculation of the subject.

The invention extends to a system configured to implement such a method. In particular, the system is configured to transmit unfocused ultrasound pulses. The ultrasound pulses may be plane-wave pulses.

In certain embodiments the characteristic of blood flow in the subject is monitored over time continuously. In other embodiments the monitoring over time takes place repeatedly at a frequency which provides clinically useful information, e.g. as described above. In this embodiment the monitoring phases are interspaced with periods were monitoring does not take place. Preferably, ultrasound is not transmitted into the subject during the non-monitoring phases.

In certain embodiments the surgery is vascular surgery, e.g. endovascular and open vascular surgery. More specifically the surgery may be angioplasty or bypass surgery. In these embodiments the area of microcirculation to be monitored may be downstream of the artery undergoing surgical intervention. It may be advantageous to monitor an area previously determined to have microvasculature dysfunction as a consequence of the vascular defect being addressed by the surgical intervention in question (e.g. an area in vicinity of a skin ulcer which has been attributed to a defect in an upstream artery). In this way revascularisation of the dysfunctional area may be confirmed. In these embodiments the characteristic of blood flow to be determined may be determined in an area of the minor vasculature which comprises the target area of microcirculation or which is upstream of the target area of microcirculation and downstream of the artery undergoing surgical intervention.

During advanced endovascular or open vascular surgery, it may be advantageous to monitor circulation in the microvasculature of the lower limb musculature. This kind of surgery involves major arteries in the pelvis becoming blocked with endovascular or other surgical equipment and can lead to compromised circulation in the lower limb musculature with development of necrosis in the musculature and in some instances the need for major limb amputation. This could be reduced or prevented with constant/intermittent monitoring of the circulation in the microvasculature of the lower limbs by following a characteristic of the blood flow in the minor vasculature.

The method may also be considered a method for obtaining information relevant to monitoring microcirculation in a vertebrate animal subject undergoing or recovering from surgery. The methods described herein may be used alone as an alternative to other investigative techniques or in addition to such techniques in order to provide information relevant monitoring microcirculation in a vertebrate animal subject undergoing or recovering from surgery.

In certain embodiments the method further comprises a step in which the variation in said characteristic or the profile of said characteristic over time is used, alone or together with additional clinical information (e.g. from other methods), to diagnose microvasculature dysfunction in a vertebrate animal subject undergoing or recovering from surgery or the extent or severity thereof, or to provide a prognosis for the onset of and/or progression of microvasculature dysfunction in the subject.

In these embodiments the characteristic or the variation in said characteristic or the profile of said characteristic over time may be compared to reference data previously obtained from the same subject, e.g. reference data obtained prior to the surgery on from a point earlier in the surgery. Divergence between the data sets may be indicative of a change in the microcirculation of the subject. Thus, the steps of comparing the test and reference data and determining whether or not they diverge (or correspond) may be performed using mathematical, or statistical techniques, and generally this will be implemented by software (i.e. it will be performed using a computer). Statistical or mathematical methods for performing such a comparison and determination of correspondence are well known and widely available in the art. In other embodiments correspondence (or divergence) may be assessed or estimated visually by the skilled person.

In more specific embodiments the method may involve an alarm or indicator, in particular an automated alarm or indicator, occurring when change in the microcirculation of the subject (as indicated by a characteristic of blood flow in the minor peripheral vasculature) passes a certain threshold value, e.g. a value which may be indicative or predictive of microvasculature dysfunction or a significant risk thereof.

In accordance with these aspects of the invention the characteristic of blood flow may be monitored in any blood vessel, or vessels, in the minor peripheral vasculature of the subject having a flow rate sufficient to be detectable in the pulse-Doppler response signals.

In certain embodiments the blood vessel, or vessels, are those at a site on a limb (e.g. arm, shoulder, leg, hand (e.g. inside or back or between thumb and forefinger), foot, toe, finger, paw, wing, fin, tail), neck or head (e.g. ear, nose, tongue, cheek, scalp, forehead).

In other embodiments the characteristic of blood flow may be monitored in any blood vessel, or vessels, in the peripheral microvasculature of the subject having a flow rate sufficient to be detectable in the pulse-Doppler response signals.

It may be advantageous in certain embodiments to monitor the characteristic of blood flow in arterial microvasculature. In this regard the inventors have recognised that characteristics of blood flow in the arterial microvasculature (especially the peripheral arterial microvasculature), which is the vasculature slightly upstream of the capillary beds, can provide information on the characteristics of blood flow in the microcirculation (especially the peripheral microcirculation) more generally, and especially in the context of the microvascular dysfunction.

In any of these embodiments said vessels may be superficial vessels.

In a further aspect the invention provides a method for treating or preventing dysfunction of the microvasculature in a vertebrate animal subject, said method comprising
  transmitting ultrasound pulses into the subject from an ultrasound transducer that is applied to an external surface of the peripheral anatomy of the subject;
  receiving reflections of the ultrasound pulses at the ultrasound transducer from at least one region containing at least one blood vessel of the minor peripheral vasculature, preferably a plurality thereof;
  generating pulse-Doppler response signals from the reflections; and
  processing the pulse-Doppler response signals to determine a characteristic of blood flow in the minor peripheral vasculature of the subject;
  monitoring the characteristic of blood flow over time; and optionally
  establishing a profile of said characteristic over time;
  wherein the characteristic or the profile of said characteristic over time is indicative or predictive of dysfunction in the microvasculature or variation in said characteristic or a profile of said characteristic over time is indicative or predictive of dysfunction in the microvasculature or is indicative or predictive of a change in the dysfunction of the subject's microvasculature;
  diagnosing dysfunction of the microvasculature or determining the likelihood of dysfunction occurring in said subject or progressing in said subject and treating said subject with a clinical intervention suitable for treating or preventing dysfunction of the microvasculature or reducing the likelihood of dysfunction occurring.

Clinical intervention suitable for treating or preventing dysfunction of the microvasculature may include anti-diabetic, antihypertensive, cholesterol lowering and lipid lowering pharmaceutical treatments, angioplasty or bypass surgery and lifestyle changes (e.g. smoking cessation, calorie restricted diets and increased exercise).

The features described above in connection with the methods for monitoring or predicting the onset of and/or progression of dysfunction of the microvasculature and/or a response to treatment thereof apply mutatis mutandis to this aspect.

In a further aspect the invention provides a method of surgery in a vertebrate animal, said method comprising monitoring microcirculation in the subject by
  transmitting ultrasound pulses into the subject from an ultrasound transducer that is applied to an external surface of the peripheral anatomy of the subject;
  receiving reflections of the ultrasound pulses at the ultrasound transducer from at least one region containing at least one blood vessel of the minor peripheral vasculature, preferably a plurality thereof;

generating pulse-Doppler response signals from the reflections; and processing the pulse-Doppler response signals to determine a characteristic of blood flow in the minor peripheral vasculature of the subject;

monitoring the characteristic of blood flow over time; and optionally establishing a profile of said characteristic over time;

wherein variation in said characteristic or the profile of said characteristic over time is indicative or predictive of a change in the microcirculation of the subject.

In a further aspect the invention provides a method of post-surgical treatment in a vertebrate animal, said method comprising monitoring microcirculation in a subject recovering from surgery by transmitting ultrasound pulses into the subject from an ultrasound transducer that is applied to an external surface of the peripheral anatomy of the subject;

receiving reflections of the ultrasound pulses at the ultrasound transducer from at least one region containing at least one blood vessel of the minor peripheral vasculature, preferably a plurality thereof;

generating pulse-Doppler response signals from the reflections; and processing the pulse-Doppler response signals to determine a characteristic of blood flow in the minor peripheral vasculature of the subject;

monitoring the characteristic of blood flow over time; and optionally establishing a profile of said characteristic over time;

wherein variation in said characteristic or the profile of said characteristic over time is indicative or predictive of a change in the microcirculation of the subject The features described above in connection with the methods for monitoring microcirculation in a subject undergoing or recovering from surgery apply mutatis mutandis to this aspect.

In other aspects the dysfunction of interest may be considered minor vasculature dysfunction, e.g. as characterised by reduced or irregular blood flow in the minor vasculature. The above discussion with respect to microvasculature dysfunction applies mutatis mutandis to such aspects, but any reference to microvascular or the like should be replaced by minor vasculature or the like as appropriate in the context.

Features of other aspects disclosed herein may be features of embodiments of these aspects also.

In some embodiments of any of the aspects disclosed herein the ultrasound transducer may comprise a heater, such as an electrical heating element or filament, or an infrared light source. This can prevent vasoconstriction of blood vessels due to cold, and therefore provide more accurate or consistent measurements of the characteristic of blood flow.

From a further aspect, the invention provides a medical ultrasound transducer comprising:

an ultrasound transducer element for transmitting ultrasound signals into a region of tissue of a vertebrate animal subject; and a heater, distinct from the ultrasound transducer element, for heating said region of tissue.

Features of other aspects and embodiments may be combined with this aspect.

The ultrasound transducer may comprise a thermostat for maintaining a target temperature in, or adjacent, said region of tissue. The ultrasound transducer may comprise control circuitry for controlling the heater—e.g. based on signals from the thermostat. The ultrasound transducer may be configured to receive an electrical current and/or signal from a controller, e.g., over an electrical lead, which may be used to control the heater. The ultrasound transducer may be configured to send a signal from the thermostat to a controller.

In some embodiments of any of the aspects disclosed herein the ultrasound transducer may comprise a force sensor. The ultrasound transducer or a separate controller may comprise a detector configured to process signals from the force sensor to determine when a contact force between the ultrasound transducer and the subject exceeds a threshold level. This can be useful to prevent restricting blood flow due to excessive pressure from the ultrasound transducer, and therefore provide more accurate or consistent measurements of the characteristic of blood flow. Small vessels close to the skin are especially vulnerable to compression.

From a further aspect, the invention provides a medical ultrasound system comprising:

an ultrasound transducer comprising i) an ultrasound transducer element for transmitting ultrasound signals into a vertebrate animal subject, and ii) a force sensor for measuring a contact force between the ultrasound transducer and the subject;

a detector configured to detect when the contact force between the ultrasound transducer and the subject exceeds a threshold; and an alert subsystem configured to output an alert when the contact force between the ultrasound transducer and the subject exceeds a threshold.

Features of other aspects and embodiments may be combined with this aspect.

The force sensor may use any appropriate sensor technology. It may comprise conductive rubber or plastic with electrodes embedded in the rubber or plastic, or it may comprise a strain gauge or a piezoelectric sensor.

The detector may be part of a controller as described elsewhere herein, or it may be built into the ultrasound transducer—e.g., inside a housing of the ultrasound transducer.

The alert subsystem may be part of the ultrasound transducer. For example, the ultrasound transducer may conveniently comprise a light, a sounder, or other output for alerting the user when the contact force exceeds a threshold. Alternatively, the alert subsystem may be separate from the ultrasound transducer—e.g., comprising a software app on a user's smartphone that is configured to notify the user when the contact force is too high.

The various characteristics of blood flow which may be monitored in accordance with aspects of the invention may include Pulsatile index (PI), Resistivity Index (RI), velocity, Max velocity (Vmax), Mean velocity (Vmean) and the Velocity Time Integral (VTI) (velocity area-under the curve), end diastolic velocity, peak diastolic velocity. In certain embodiments these metrics may be combined with other circulatory metrics, e.g. blood pressure (arterial, venous, diastolic, systolic) to form an index or a derivatised metric in order to better resolves trends and patterns. Such indices are considered characteristics of blood flow which may be monitored in accordance with aspects of the invention. In the context of sepsis and infants it may be advantageous to measure blood flow velocity and blood pressure (e.g. arterial blood pressure) concurrently and monitor an index of blood pressure/velocity as the characteristic of blood flow in accordance with the invention.

Some or all of the characteristics of blood flow recited herein may exhibit periodic behaviour in accordance with the heartbeat of the subject and in accordance with respiration rate. In certain embodiments oscillations or periodic patterns in these basic characteristics, having frequencies that do not correlate with the subject's heart rate or respiration rate (i.e., that are higher or lower in frequency than the heart rate or respiration rate), may be the profile of said characteristic over time which is established and used as the basis for the methods for monitoring for or predicting the onset or progression of a disease or pathological condition and/or a response to treatment in accordance with aspects of the invention. The frequency of said oscillations may be, for example, 0.005-0.5 Hz, e.g. 0.008-0.5, 0.01-0.5, 0.015-0.5, 0.02-0.5, 0.025-0.5, 0.03-0.5, 0.035-0.5, 0.04-0.5, 0.045-0.5, 0.05-0.5, 0.055-0.5, 0.06-0.5, 0.065-0.5, 0.07-0.5, 0.075-0.5, 0.08-0.5, 0.085-0.5, 0.09-0.5, 0.095-0.5, 0.1-0.5, 0.2-0.5, 0.3-0.5, 0.4-0.5, 0.005-0.008, 0.005-0.01, 0.005-0.015, 0.005-0.02, 0.005-0.025, 0.005-0.03, 0.005-0.035, 0.005-0.04, 0.005-0.045, 0.005-0.05, 0.005-0.055, 0.005-0.06, 0.005-0.065, 0.005-0.07, 0.005-0.075, 0.005-0.08, 0.005-0.085, 0.005-0.09, 0.005-0.095, 0.005-0.1, 0.005-0.15, 0.005-0.2, 0.005-0.25, 0.005-0.3, 0.005-0.35, 0.005-0.4, or 0.005-0.45 Hz. Any and all ranges which may be derived from any of the range endpoints recited above are expressly contemplated. In infant subjects the frequency of interest may be around 0.08 Hz, e.g. 0.01 to 0.2, 0.02 to 0.18, 0.03-0.16, 0.04-0.14, 0.05-0.12, 0.06-0.1, or 0.07-0.09 Hz. Any and all ranges which may be derived from any of the range endpoints recited above are expressly contemplated. For adults the frequency of interest may be around 0.02, e.g. 0.005-0.1, 0.008-0.08, 0.01-0.06, 0.012-0.05, 0.014-0.04, 0.016-0.03, 0.018-0.025 or 0.019-0.022 Hz. Any and all ranges which may be derived from any of the range endpoints recited above are expressly contemplated.

These oscillations in blood flow are referred to in the art as flowmotion or flow oscillations and are believed to arise via the effects of vasomotion: the oscillation in tone of blood vessels. Vasomotion, or at least certain elements thereof, may follow physiological rhythms, and may vary in different vascular beds in healthy subjects. Local cellular mechanisms in the vessel wall and autonomic neural activity both contribute to the phenomenon. Organ metabolic needs may also influence vasomotion. In the brain, such oscillations may be associated with or arise from cerebral haemodynamic autoregulation. There is evidence that vasomotion is altered under pathological conditions, including circulatory failure, hypertension and diabetes mellitus, and in sick infants more generally. The oscillations in blood flow characteristics which may be used in accordance with the invention (e.g. those which are associated with or arise from vasomotion oscillations and/or cerebral haemodynamic autoregulation) may be determined from readings of the above mentioned characteristics over time by the Fourier transformation (e.g. Fast Fourier transformation) or complex demodulation of such readings. This is well described in the art. Inter alia, the frequency and/or amplitude of these oscillations may be determined and used as the characteristic of blood flow, or profile thereof, monitored in accordance with the invention. In certain embodiments such information, and/or the blood flow characteristics or profiles thereof per se, may be used together with blood pressure measurements, e.g. arterial blood pressure measurements.

In certain embodiments the characteristic of blood flow which may be monitored in accordance with aspects of the invention may be a secondary characteristic which arises during or following a dynamic physical procedure performed by the or on the subject. In these contexts variation in a primary characteristic of blood flow (e.g. Pulsatile index (PI), Resistivity Index (RI), velocity, Max velocity (Vmax), Mean velocity (Vmean), Velocity Time Interval (VTI), end diastolic velocity, peak diastolic velocity during or following the procedure compared to the primary characteristic in the subject prior to the procedure (e.g. the extent of variation upon commencement or the recovery of the primary characteristic to baseline) is monitored. Dynamic procedures may be devised by the skilled person without undue burden. Merely as examples dynamic tests may include in following: valsalva manoeuvre, forced respiration test, static handgrip exercise, cold pressor test, leg-rise test and passive elevated arm test. More specifically, the dynamic procedure may investigate maximal relative variations of PI (or any of the above variables) between measurement at rest (e.g. 30 sec), measurement with passive elevated arm (e.g. 30 sec) and measurement at rest (e.g. 30 sec). Time to return to baseline may also be measured. PI (or other variable) Normalisation-time: measurement of the PI (other variable) on the hand at rest, during leg-rise-test (e.g. 1, 2 or 5 minutes) and again at rest. Time to return to baseline is measured. Maximal relative variations of mean velocity between measurement at rest, measurement during leg-rise-test (e.g. 1, 2 or 5 minutes) and again at rest. Time to return to baseline may also be measured.

The subject may be any human or a non-human vertebrate, e.g. a non-human mammal, bird, amphibian, fish or reptile. In a preferred embodiment the subject is a mammalian subject. The animal may be a livestock or a domestic animal or an animal of commercial value, including laboratory animals or an animal in a zoo or game park. Representative animals therefore include dogs, cats, horses, pigs, sheep, goats and cows. Veterinary uses of aspects of the invention are thus covered. The subject may be viewed as a patient. Preferably the subject is a human.

In certain embodiments the subject is a human adolescent or adult and in such subjects the following blood vessels typically have the following lumen diameters: elastic arteries (greater than about 10 mm); muscular arteries (about 0.5 mm to about 10 mm); arterioles (about 30 µm to about 500 µm), metarterioles (about 15 µm to about 30 µm) capillaries (about 1 µm to about 15 µm); venules (about 15 µm to about 500 µm), small veins (about 0.5 mm to about 10 mm); large veins (greater than about 10 mm).

In a further aspect the clinical methods described above may comprise a further step of therapeutically treating said subject in a manner consistent with the assessment, diagnosis, prediction, prognosis made in order to alleviate, reduce, remedy or modify at least one symptom or characteristic of the disease/condition of interest (including the more specifically defined embodiments thereof) or to improve, mitigate, alleviate, reduce, remedy or modify the predicted clinical outcome or to accommodate the predicted clinical outcome, e.g. by providing palliative care. Such treatments may include administering a pharmaceutical composition, performing a surgical procedure, performing physiotherapy, and/or making lifestyle changes appropriate to treat the disease/condition of interest and/or alter or accommodate the predicted clinical outcome and/or adjusting the lifestyle of the subject in a manner appropriate to treat the disease/condition of interest or accommodate the predicted clinical outcome. In this regard, the invention can be considered to relate to methods for the therapeutic treatment of a disease/condition of interest (including the more specifically defined embodiments thereof) and for guiding and/or optimising such treatments.

"Treatment" when used in relation to a disease or medical condition in a subject in accordance with the invention is used broadly herein to include any intervention which has a therapeutic effect, i.e. any beneficial effect in relation to the disease or on the condition. Thus included are pharmaceutical and surgical interventions but also lifestyle changes and physiotherapies. Thus, not only included are interventions which eradicate or eliminate the disease or condition, but also which provide an improvement in the disease or condition of the subject. Thus included for example, is an improvement in any symptom or sign of the disease or condition, or in any clinically accepted indicator of the disease or condition. Treatments thus includes both curative and palliative therapies "Response to treatment" includes any observable therapeutic effect, i.e. any beneficial effect in relation to the infection or on the condition. Thus, not only included is eradication or elimination of disease/condition, but also an improvement in the disease/condition of the subject. Thus included for example, is an improvement in any symptom or sign of the disease or condition, or in any clinically accepted indicator of the disease/condition. A response to treatment might, conversely, be expressed in terms of the lack of an observable therapeutic effect or limited therapeutic effect.

"Prevention" as used herein refers to any prophylactic or preventative effect. It thus includes delaying, limiting, reducing or preventing the disease/condition or the onset of the disease/condition, or one or more symptoms or indications thereof, for example relative to the disease/condition or symptom or indication prior to the prophylactic treatment. Prophylaxis thus explicitly includes both absolute prevention of occurrence or development of the disease/condition, or symptom or indication thereof, and any delay in the onset or development of the disease/condition or symptom or indication thereof, or reduction or limitation of the development or progression of the disease/condition or symptom or indication thereof.

"Monitoring or predicting the onset or and/or progression of a disease or pathological condition" includes diagnostic and prognostic aspects. This may include concluding that a subject has a disease/condition and/or establishing the severity thereof. It may also include determining the likelihood (assessing the risk) of a disease/condition developing in a subject or progressing or the rate at which progression will take place.

Features of any aspect or embodiment described herein may, wherever appropriate, be applied to any other aspect or embodiment described herein. Where reference is made to different embodiments or sets of embodiments, it should be understood that these are not necessarily distinct but may overlap.

BRIEF DESCRIPTION OF THE DRAWINGS

Certain preferred embodiments of the invention will now be described, by way of example only, with reference to the accompanying drawings, in which.

DETAILED DESCRIPTION

Figure 1:
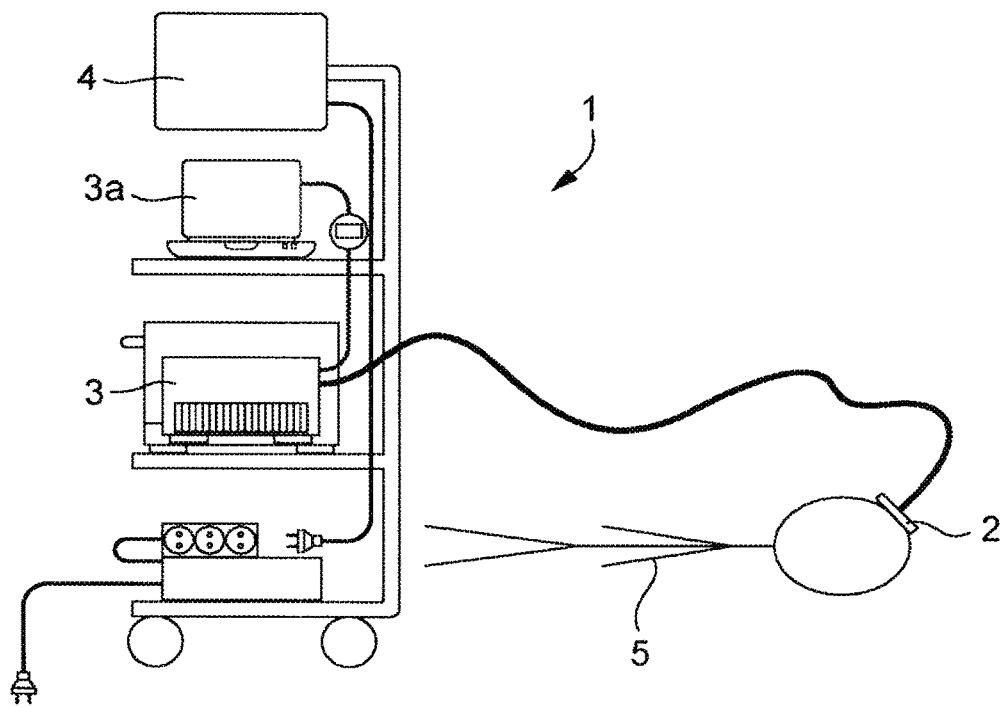
FIG. 1 is a diagram of an ultrasound monitoring system embodying the invention.

FIG. 1 shows a medical-ultrasound monitoring system 1, including an ultrasound transducer 2, a controller 3, an interaction terminal 3a, and a display device 4, for us in monitoring blood flow within a human or animal subject 5.

The ultrasound transducer 2 is connected to the controller 3 by a wire. The controller 3 is connected to the interaction terminal 3a and to the display device 4. The interaction terminal 3a may comprise a laptop computer and/or a control panel comprising a keyboard or trackball. The interaction terminal 3a may have its own display screen (e.g., where it is a laptop computer), however this is primarily for use by a researcher or administrator. In normal use, display output to a clinician will be shown on the display device 4, which may be an LCD monitor.

The transducer 2 contains a single piezoelectric transducer element. In use, the transducer 2 transmits a succession of ultrasonic plane-wave pulses and receives reflections of the waves, at the same transducer element, under the control of the controller 3. The transducer 2 can be fastened to a subject 5 by one or more straps, adhesive pads, clips, etc.

The transducer 2 can be fastened to a subject 5 by a clinician or technician and then left unattended for a period of minutes, hours or days, during which the monitoring system 1 monitors and records and/or analyses blood flow within the subject 5. The monitoring system 1 may output data such as a real-time plot of a blood flow curve from a particular region within the subject 5 on the display 4. It may also signal an alert if a predetermined criterion is met, such as if the blood flow drops rapidly. The alert may show on the display 4 (e.g., comprising a textual message or numerical value, or a flashing icon), or by another visual means (e.g., a strobe light), or audibly (e.g., from a siren or loudspeaker), or be sent to another device over a network connection, or a combination of these.

Various embodiments of the system 1 can, for example, be used to monitor cerebral circulation in a premature baby, or to monitor peripheral circulation after an operation, or for many other situations where changes in blood flow can provide a useful indication of the clinical condition of the subject 5.

Figure 2:
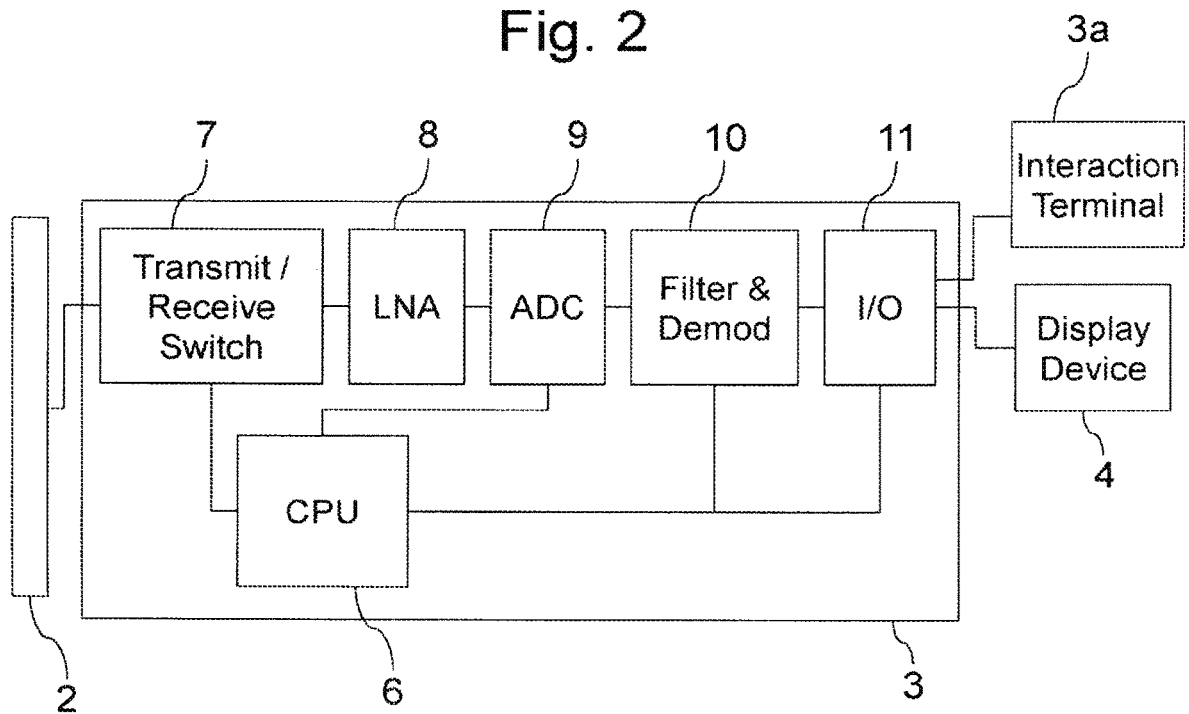
FIG. 2 is a schematic diagram of functional elements of the monitoring system.

FIG. 2 shows more details of the system 1. The controller 3 contains a central processing unit (CPU) 6. This CPU 6 may include one or more processor chips, microcontrollers, DSPs, FPGAs and/or other processing means. A transmit/receive switch unit 7 in the controller 3 is connected to the transducer 2. This switch unit 7 can switch between a transmitting mode and a receiving mode, under control of software executing on the central processing unit 6. The switch unit 7 passes electrical signals representing received ultrasonic reflections to a low-noise amplifier (LNA) 8 in the controller 3, which amplifies the received reflection signals. The LNA 8 outputs to an analogue-digital converter (ADC) 9 in the controller 3, which samples and digitises the received reflections from each pulse. The system 1 also includes memory (not shown) storing software instructions for execution by the CPU 6, and for storing data representing received data and the results of computations performed by the CPU 6.

In use, the transducer 2 can be controlled by the CPU 6 to transmit plane wave pulses (e.g., pulses one microsecond long) at a predetermined carrier frequency (e.g., 8 or 16 MHz) and at a predetermined pulse repetition rate (e.g., 10 kHz). The switch unit 7 switches between a transmitting mode and a receiving mode, at the repetition rate (e.g., 10 kHz), in order to receive echoes from each pulse at the transducer 2. The frequency spectrum of the received reflections will depend on the range of movement of tissue, relative to the transducer 2, in the regions within the subject 5 that are covered by the transmit and receive beams of the transducer 2. In contrast to conventional array-based beam-forming transducers, the single transducer element here gives a substantially cylindrical transmit beam, and a receive beam that is coincident with the transmit beam.

From the ADC, the sampled reflections (pulse-Doppler response signals) pass to a filter and complex demodulator unit 10 which bandpass filters and demodulates the digitised signals. The demodulated pulse-Doppler response signals are then sent to the CPU 6 for processing.

The CPU 6 may calculate measures related to the blood flow, and send data related to the blood flow to the display device 4 (which may be separate from the controller 3, or may be integral to it), via an input/output (I/O) unit 11, for displaying to a user. The CPU 6 may analyse blood flow at just one depth range, or at multiple different depth ranges simultaneously.

In an alternative embodiment, the demodulated pulse-Doppler response signals are passed directly to an external output device (which could be a mobile telephone or tablet computer, or a networked server) via the input/output (I/O) unit 11, and the external output device can analyse the response signals. The I/O unit 11 may comprise a wireless-communication unit, such as a Bluetooth™ radio. The external output device may store and/or display derived metrics from the response signals.

In some embodiments, the ultrasound transducer 2 may be integrated with the controller 3 in a common housing, rather than being connected by a wire. The controller 3 may then conveniently be very compact. It may be battery powered. In this way, the combined controller 3 and transducer 2 form a highly portable sensor unit. The sensor unit preferably transmits demodulated signals to a separate output device, for processing; this allows the controller 3 to have a relatively basic CPU 6, allowing it to be made at low cost.

The CPU 6 and/or an external output device may process the demodulated response signals to obtain values related to blood flow within the subject 5 using some of the techniques described below.

The interaction terminal 3*a* may be used by an operator to control the ultrasound transmission and processing, or to control the processing and display of information, or to configure alerts, or to perform any other actions. The terminal 3*a* may be a permanent part of the system 1, or it may be used only during a configuration or initialisation phase, and removed once the system 1 is in a monitoring phase.

Some embodiments may also dispense with the display 4, and instead output audible alerts (e.g., from a loudspeaker), or send data over a network connection to a central interface system, e.g., located at a nurses station remote from the subject 5.

Figure 3:
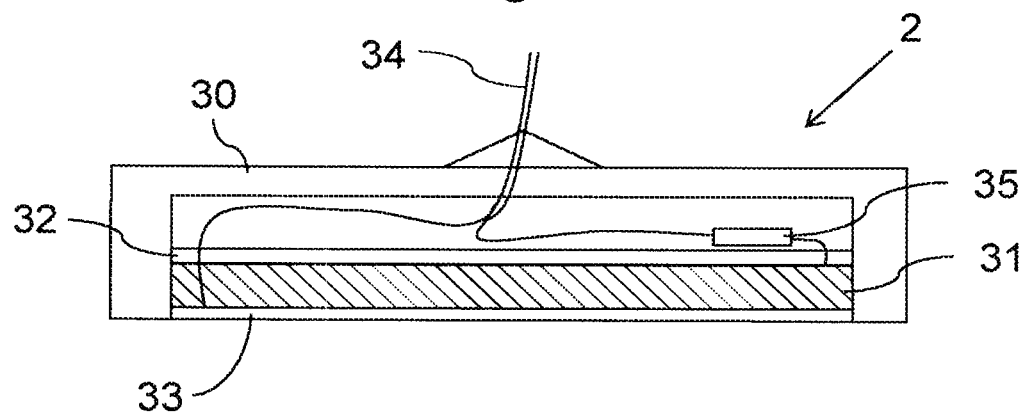
FIG. 3 is a schematic diagram of a first embodiment of an ultrasound transducer.

FIG. 3 shows the transducer 2 in more detail. A metal or plastic housing 30 contains a piezoelectric transducer element 31. The transducer element 31 may be a circular disc or may be rectangular, or any other appropriate shape. It may be a ceramic transducer, made of PZT (lead zirconate titanate) or a PZT-epoxy composite. Single crystal technology may be used. The transducer element 31 is mounted between a backing layer 32 and an acoustic-impedance matching layer 33. Wires 34 lead from the transducer 2 towards the monitoring system 1. The transducer 2 may include an electrical-impedance matching component 35 such as a helical coil. The transducer 2 is preferably wider than it is tall—e.g., approximately 10 mm in diameter, width or length, with the housing 30 being approximately 8 mm high (excluding any cable strain relief). This can reduce the chance of it being knocked when fastened to the subject 5.

Figure 4:
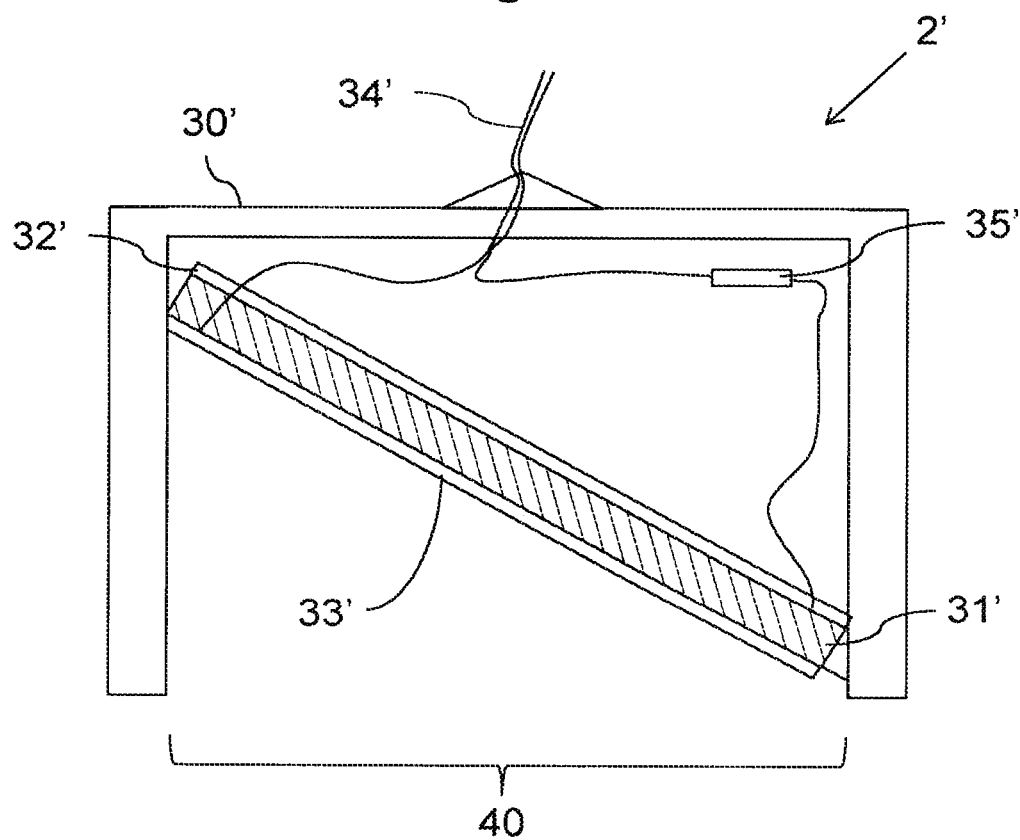
FIG. 4 is a schematic diagram of a second embodiment of an ultrasound transducer.

FIG. 4 shows a variant transducer 2', in which the primed reference numerals refer to corresponding features as the same-numbered labels in FIG. 3. The principal difference, compared with the transducer 2 of FIG. 3, is that the transducer element 31' is inclined, relative to the housing 30'. It may be inclined at any angle—e.g., 30 or 45 degrees from a planar window 40 defined by the base of the housing 30' (aligned with horizontal in the FIG. 4). Such a transducer 2' is useful for getting Doppler signals from blood vessels that are nearly parallel to the window 40, since the angle increases the component of motion perpendicular to the face of the transducer element 31'. In this example, the transducer element 31' is rectangular, 5 mm×16 mm, and the height of the housing 30' is 8 mm. However, any appropriate dimensions may be used.

In use, any void between the acoustic coupling layer 33 and the subject 5 will typically be filled with an acoustic gel, applied by the operator. The gel may, in some instances, be adhesive and may be sufficient to fasten the transducer 2, 2' to the subject 5. In other embodiments, a mechanical fastening is used.

Figure 5:
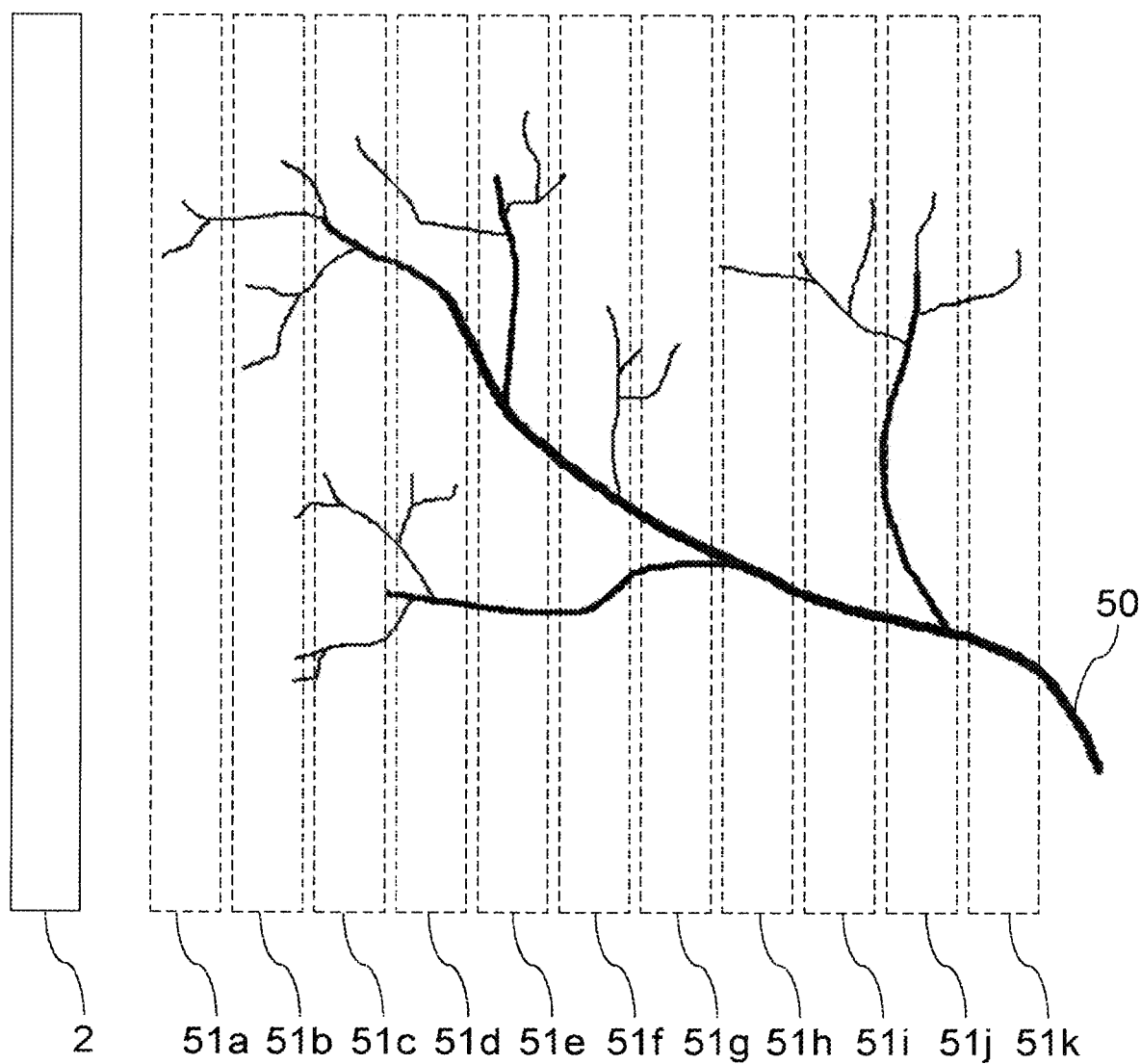
FIG. 5 is a simplified cross-section through a blood supply system and an ultrasound transducer.

FIG. 5 shows a branching blood vessel system 50 in cross section. The blood vessel system 50 may be a few millimetres or a few centimetres below the surface of the skin of the subject 5. The ultrasound transducer 2 at the left side of FIG. 5 is mechanically or adhesively fastened to the subject 5. It transmits plane wave pulses into the subject 5 in a substantially cylindrical beam (e.g., a circular cylinder or a rectangular cylinder, depending on the shape of the transducer element). The axis of the cylinder runs from left to right in FIG. 5. Returning reflections are sampled after each pulse. One sample is obtained for each of a set of cylindrical sample volumes 51*a*-51*k* in the subject 5, with the delay after the transmission of the pulse determining how far each sample volume 51*a*-51*k* is from the face of the transducer 2.

The transducer 2 is an unfocused transducer, without any acoustical lens. It has considerably larger dimensions than many prior-art focused transducers or array transducers—e.g. a circular disc with diameter 10 mm. It generates a uniform beam with substantially constant cross section in the depth direction—e.g. a cylindrical beam with diameter of approximately 10 mm, in the near field. The spatial sensitivity in receive is also substantially coincident with the transmit beam, so that the cross-sectional area of the sample volume will be much larger, compared with a traditional focused or beam-formed receive beam—approximately 10 mm again. This means that the system 1 can capture blood flow signals from a much larger area than a focused single-element transducer or a beam-forming array transducer does. This means that the probe location and orientation are less critical. A drawback with the broad beam compared to a focused beam, is that the signal from each individual blood cell becomes weaker. This introduces a limitation in the maximum depth that can be measured. Typically, range-gating will be used to limit response signals to regions that have a maximum distance from the transducer 2 that is in the same order of magnitude as a width of the transducer 2; for example, 0.5 cm to 4 cm deep.

Response samples from each pulse are collected, for each volume 51*a*-51*k*, and are filtered and complex demodulated by the demodulator unit 10 to give a respective baseband pulse-Doppler response signal for each volume 51*a*-51*k*.

By using a multi-gated Doppler technique, the response signal can be split into a large number of Doppler signals, each representing components of blood flow perpendicular to the ultrasound beam within a thin "slice" or volume 51*a*-51*k*. The thickness d of the slices is given by the length of the transmitted pulse: $d=N*\lambda/2$, where N is the number of periods in the transmitted pulse and λ is the ultrasound beam wavelength (e.g., 0.1-0.3 mm). Typical values for the thickness d are 0.15 mm to 1 mm (e.g., 0.5 mm). By frequency analysis of a series of the pulse-Doppler response signals from each volume 51a-51k (for example, by fast Fourier transform), a Doppler frequency spectrum is obtained, where the power density of each frequency component is given by the number of blood cells with a specific velocity component perpendicular to the transducer 2. A new Doppler frequency spectrum may be calculated every 5 milliseconds, for example.

The size of the spatial sensitivity region (receive beam width), b, in conventional focused ultrasound is given by $$b=D*\lambda/A=D/Nw,$$

where D is distance from the transducer, λ is the wavelength (e.g., 0.1-0.3 mm), A is the size (diameter) of the transducer, and Nw is the size of the transducer in #wavelengths. Typically, Nw=20-100 in conventional focused systems.

In the present system 1, however, the receive beam width is approximately equal to the diameter, A, of the transducer 2. This may therefore be fifty times larger (2,500 times larger in area) than the receive spot size of a typical convention system.

By using a transducer 2 with only one element, rather than an array, which would typically have 100-200 elements, it is not possible to steer the focus. Traditionally, such a single-element Doppler instrument would be designed with an elongate focus, which is obtained by using a high f-number, i.e. the probe diameter A is substantially less than the intended focal depth D. The beam width in the focal point will then be $D*\lambda/A$, where λ is the ultrasound beam wavelength. Typical values for a 10 MHz probe would be λ=0.15 mm, D=10 mm, A=3 mm, which would give a beam width of 0.45 mm. By instead using an unfocused, disc shaped transducer, without acoustical lens, having considerably larger dimensions than in the prior art (e.g. a circular disc with diameter 10 mm), the present system 1 has a uniform transmit beam, with constant cross section in the depth direction. The spatial sensitivity in receive will also be constant within the beam width, so that the cross sectional area of the sample volume will be much larger, compared to a focused beam.

For each volume 51a-51k, the blood flow is analysed in aggregate for all the blood vessels that pass through that volume. The distribution of velocities may, in some cases, allow signals from different vessels to be distinguished from each other within one volume (e.g., where there is some flow towards the transducer 2 and some flow away from the transducer 2). However, in general, unlike conventional Doppler flow analysis, where a single vessel is identified by an operator in a B-mode image, and the transmit and/or receive focus is then placed just on that vessel, for Doppler processing, in the present system 1, there is no two- or three-dimensional imaging and no focusing of a transmit or receive beam on a particular vessel.

Figure 6:
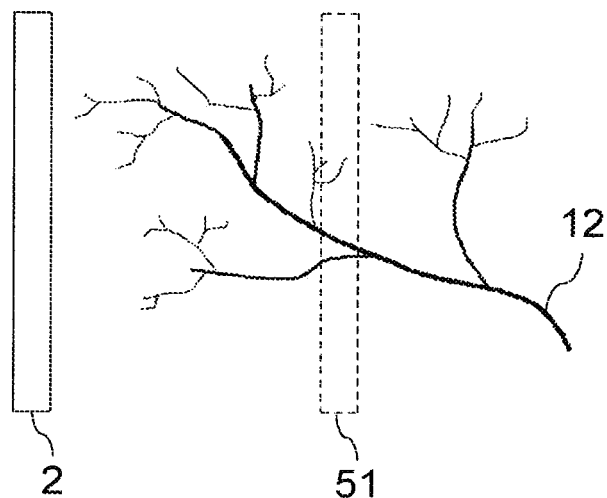
FIG. 6 is a simplified cross-section with the ultrasound transducer in a first orientation.

FIG. 6 shows the transducer 2 in a first orientation, with an exemplary volume 51 (typically a shallow cylinder or cuboid) intersecting the blood vessel system 50. In the case, a strong Doppler-shifted signal will be detected from the two branching arterioles that pass through the volume 51 substantially perpendicular to the face of the transducer 2.

Figure 7:
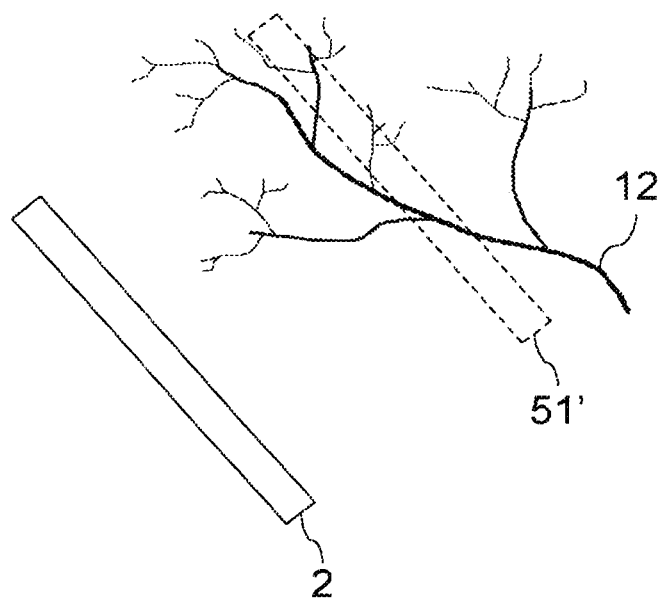
FIG. 7 is a simplified cross-section with the ultrasound transducer in a second orientation.

FIG. 7 shows the transducer 2 in a second orientation, with a different exemplary volume 51' intersecting the blood vessel system 50 at a different angle. The same major vessels (which account for the majority of the blood flow) are intersected in the first and second orientations. The steeper angle means that the Doppler shifts will be of lower amounts, but the larger length of the main vessels within the volume 51' mean that a stronger signal may be received. Where it is desired to monitor vessels that are nearly parallel to the front window of the transducer, a transducer 2' with an inclined element 31', as shown in FIG. 4, may be preferable.

Figure 8:
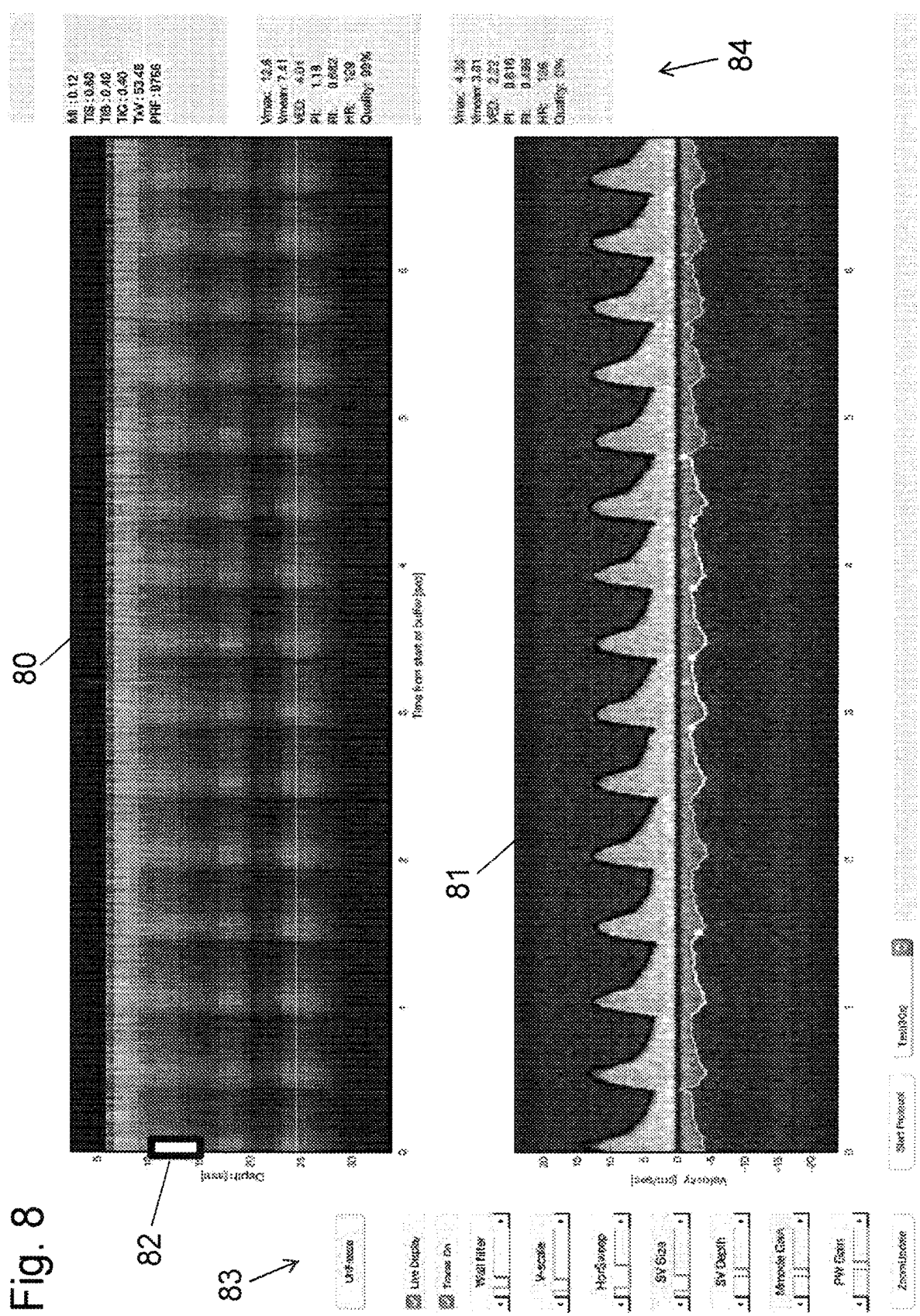
FIG. 8 is a first screenshot of a display output from the ultrasound scanning system showing detailed information of neonatal cerebral circulation at a first depth.

FIG. 8 is a screenshot of a graphical output that can be displayed on the display screen 4, showing the results of processing, by the CPU 6, of the Doppler response signals.

Figure 9:
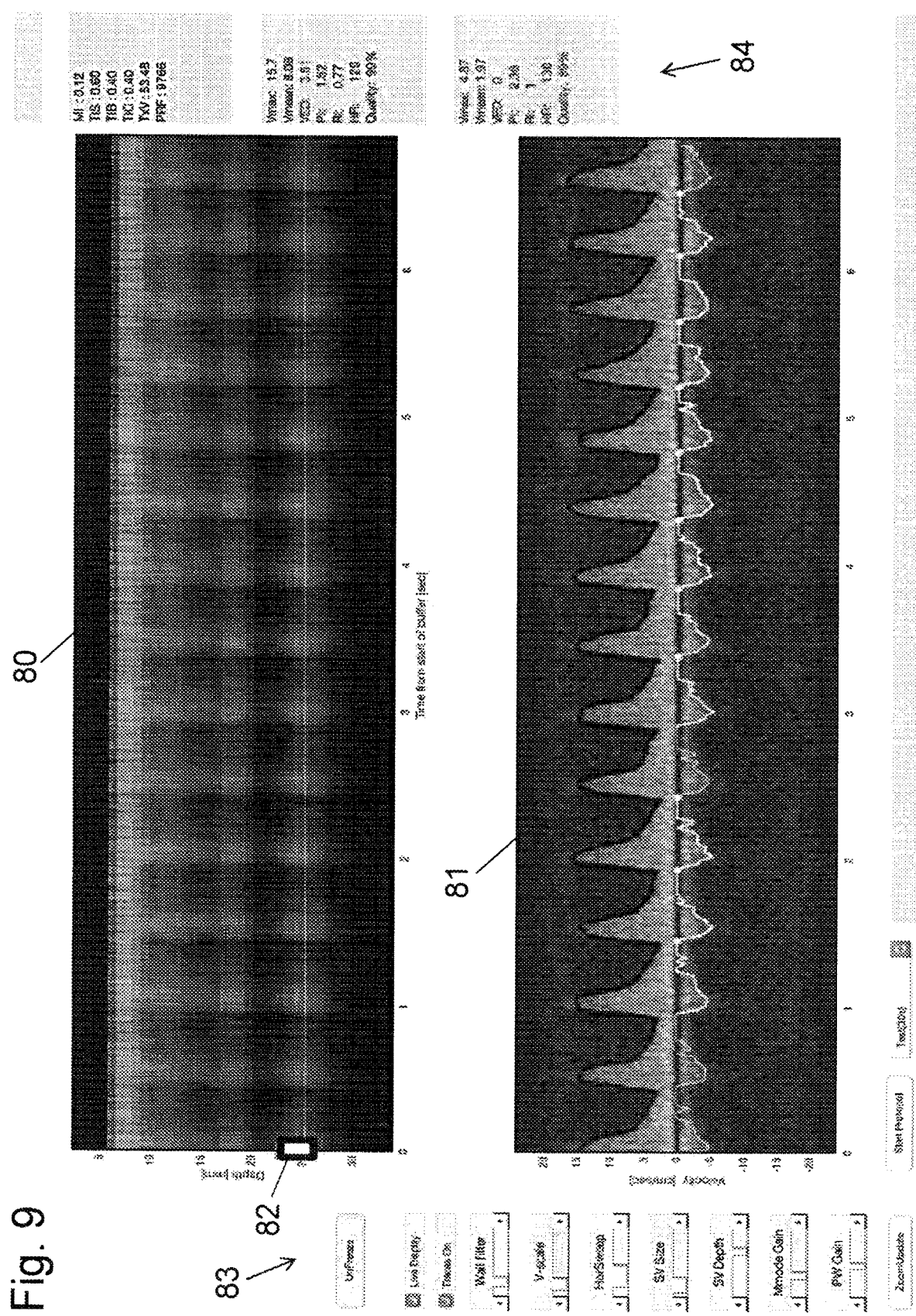
FIG. 9 is a second screenshot of a display output from the ultrasound scanning system showing detailed information of neonatal cerebral circulation at a second depth.

The data in FIGS. 8 and 9 relate to the cerebral circulation of a baby. However, the same user-interface may equally be used when monitoring other types of patient and other blood vessels, such as when monitoring adult peripheral circulation.

An upper rectangle 80 contains a plot of the power-weighted mean frequency, at different depths, over time. The vertical axis represents depth from the front of the transducer 2, here ranging from 0 mm to 35 mm. The horizontal axis represents time from the start of a receive buffer, and, in this example, ranges from 0 to 7 seconds. The plot is updated at regular intervals. Each pixel represents a depth range (corresponding to a particular sample volume 51a-51k as shown in FIG. 5) over a unit of time. In the original output, each pixel is shaded in red, blue or white, where red indicates that all of the Doppler response signal (after appropriate filtering) at that depth range was positively shifted, indicating flow towards the transducer 2; blue indicates that all of the Doppler response signal (after appropriate filtering) was negatively shifted, indicating flow away from the transducer 2; and white indicates both positive and negative frequency shifts, indicating that the region contains at least one vessel portion carrying blood towards the transducer and at least one other vessel portion carrying blood away from the transducer. In the period shown in FIG. 8, the original colour output is broadly orange, with variation between lighter and darker shades of orange. It will be appreciated that the Doppler response signal may first be filtered to remove contributions from stationary or near-stationary tissue (clutter filtering), using standard techniques. The intensity of each pixel represents a power-weighted mean frequency at the respective depth range and time period; this may be calculated from a Fourier transform of the response signals, or, more efficiently, by using autocorrelation to calculate the first moment of the power spectrum. Black therefore represents zero flow (any movement is under the noise floor).

The upper rectangle 80 effectively presents a one-dimensional "image" of the blood flow at different depths from the transducer 2, over time. This allows an operator who understands the anatomy of the subject 5 to position the transducer 2 so that one or more vessels of interest are within the transmit and receive beam, and to verify visually from the plot that proper alignment has been achieved.

A lower rectangle 81 contains a velocity spectrum, which shows velocity, here ranging from −25 cm/sec to +25 cm/sec, against time, here ranging from 0 to 7 seconds. The grayscale intensity at each pixel represents the signal strength in the respective velocity bin at the respective time interval. Positive and negative envelope traces are automatically calculated, based on a threshold minimum velocity-signal strength, and can be included on the plot, as shown by the upper (originally red) and lower (originally blue) lines, respectively, in FIG. 8. The velocity spectrum can be derived from the Fourier frequency spectrum, because frequency and velocity are linearly related by the Doppler equation: $\Delta f = 2 \cdot f_0 \cdot v \cdot \cos(\theta)/c$. where $\Delta f$ is Doppler shift frequency, $f_0$ is the ultrasound transmission frequency, v is the blood cell velocity, cos(θ) is the cosine of the angle between the ultrasound beam and the flow direction, and c is the speed of sound in soft tissue. It will be appreciated that "velocity", "frequency shift" and "frequency" (e.g., at baseband) can therefore be used interchangeably, and the use of one of these terms herein should be seen, wherever appropriate, as also extending to an equivalent expression using one of the other terms—e.g., a reference to a "velocity spectrum" also encompasses a "frequency spectrum".

The velocity data in the lower rectangle 81 is generated from the Doppler response signals at a particular depth range. This depth range may be specified by an operator or may be identified automatically by the system 1 (e.g., based on an automated comparison of respective quality values, as described below, for respective depths from a set of depths).

In FIG. 8, the operator has move and sized a rectangular selection marker 82 on the upper rectangle 80 to provide an input to the system 1 of the range of interest for the velocity plot in the lower rectangle 81. The size and location of the selection marker 82 can be adjusted by the operator. In this example, it indicates a depth range of 10 mm to 15 mm.

To the right of the screenshot, a panel 84 provides values of Vmax, Vmean, VED, PI, RI, HR and a Quality value, independently for the positive frequency spectrum and the negative frequency spectrum in the range of interest. Each of these values is a characteristic of blood flow in the region of interest. These values are calculated for every valid heartbeat in the seven-second time buffer of the velocity plot. The CPU 6 first generates the envelope traces (applying a threshold to identify velocity signals that have a strength are above a minimum floor), representing the spatial-maximum of velocity, in each direction, over the depth range of interest in each time period (e.g., every 5 milliseconds). It then identifies rising edges by applying a gradient threshold to the envelope traces over a minimum time period. These provide candidate heartbeats. The CPU 6 then compares successive heartbeats by autocorrelation of the envelope signals and generates a percentage quality value for each heartbeat based on how similar it is to the preceding heartbeat. This quality value may be derived from the height of a peak in the autocorrelation, or in any other appropriate way. Candidate heartbeats below a threshold quality are excluded from the calculations. The values of Vmax, Vmean, VED, PI, RI, HR and Quality are then calculated for each valid heartbeat and are then averaged over the seven-second time buffer, using only those heartbeats that meet the quality threshold. Vmax is the maximum trace velocity over the valid heartbeats. Vmean is the mean trace velocity over time. VED is the end diastolic trace velocity, averaged over the valid heartbeats. PI is the pulsatility index. RI is the resistance index. HR is the heart rate in beats/minute. The Quality measure is a percentage value which is an average of the individual heartbeat Quality values over all of the valid heartbeats in the seven-second time buffer.

Of course, other durations of time buffer may be used—e.g., anywhere between 5-60 seconds, and other derived values may be displayed, including first or second order statistics of any of the parameters detailed above.

The lower velocity plot 81 in FIG. 8 shows a strong signal flowing towards the transducer 2, from one or more arteries, and a weaker venous signal from blood flowing away from the transducer 2. This is consistent with the generally orange shade in the original colour upper depth plot 80 at the depth range of interest, formed of a mix of red pixels (flow only towards the transducer 2) and some white pixels (flow in both directions).

This ability to distinguish flow in both directions, in the upper plot 80, from zero flow may be especially useful to the clinician. By contrast, conventional colour Doppler plots are based on the mean velocity, averaged over all frequency shifts, positive and negative. Such a mean velocity value cannot discriminate between bidirectional flow, and zero or low flow. This is not normally a problem in conventional Doppler scans, because the receive beam is focused on a single vessel. However, in the context of the broad, unfocused receive beam of the present system 1, which will typically capture signals from multiple vessels, the display methodology described here is extremely valuable.

FIG. 9 shows the same data in the upper plot 80, but here the operator has set the rectangular selection marker 82 deeper and to a smaller range—approximately 23-26 mm. The velocity plot 81 shows that the vessels at this depth exhibit a similar heartbeat cycle to those in FIG. 8, but with a higher Vmax systolic velocity and a lower VED end diastolic velocity.

The controller 3 may be configured to test calculated values (e.g., a succession of Vmax values) against an alert criterion. It may do this repeatedly at intervals. It may signal an alert if, for example, Vmax falls below a preset threshold and/or falls or rises faster than a preset gradient. In some embodiments, a detailed display similar to that of FIG. 8 need not be provided, and instead a simpler alert system may be provided.

In some embodiments, the controller 3 calculates a Fourier transform of Vmax (e.g., by fast Fourier transform) to identify different frequency components in Vmax. It may monitor one or more frequency components or ranges outside the normal heartbeat. It may signal an alert if such a frequency component satisfies an alert condition, such as diminishing in intensity below a preset level or faster than a preset rate.

Figure 10:
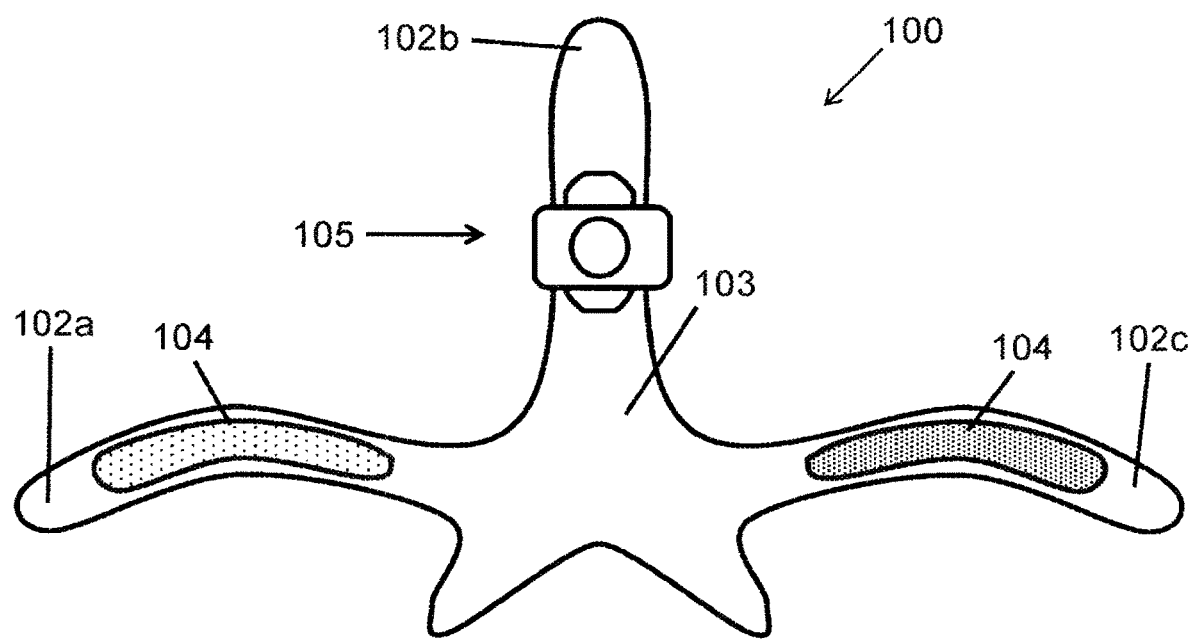
FIG. 10 is a schematic diagram of a first fastener for an infant's head, embodying the invention.

FIG. 10 shows a first head mounting arrangement 100 for securing an ultrasound transducer, similar or identical to the transducer 2 of FIG. 3, around the head 109 of a baby. The head mounting arrangement 100 is shown from the front perspective. The face of the arrangement 100 shown in FIG. 10 contacts the head 109 of the baby.

The arrangement 100 has three flexible fabric straps 102a, 102b, and 102c which extend from a central fabric section 103. Two side straps 102a and 102c have adhesive or hook-and-loop strips 104 adhered to them. In order to secure the strap in position on the head 109 of a baby, the central portion 103 is placed against the rear of the baby's head 109. The first side strap 102a is then wrapped across the front of the baby's forehead, the central strap 102b is bought forward over the top of the baby's head, the second side strap 102c is then wrapped across the baby's forehead, over the first side strap 102a so that the second side strap 102c adheres to the adhesive or hook-and-loop portion 104 of first side strap 102a. The two side straps 102a, 102c hold the central strap 102b in position by friction. The head mounting arrangement 1 may be arranged so that any excess length of the end of the central strap 102b, which would otherwise obscure the baby's face when in use, can be fastened to the outward facing side of the second side strap 102c.

Figure 11:
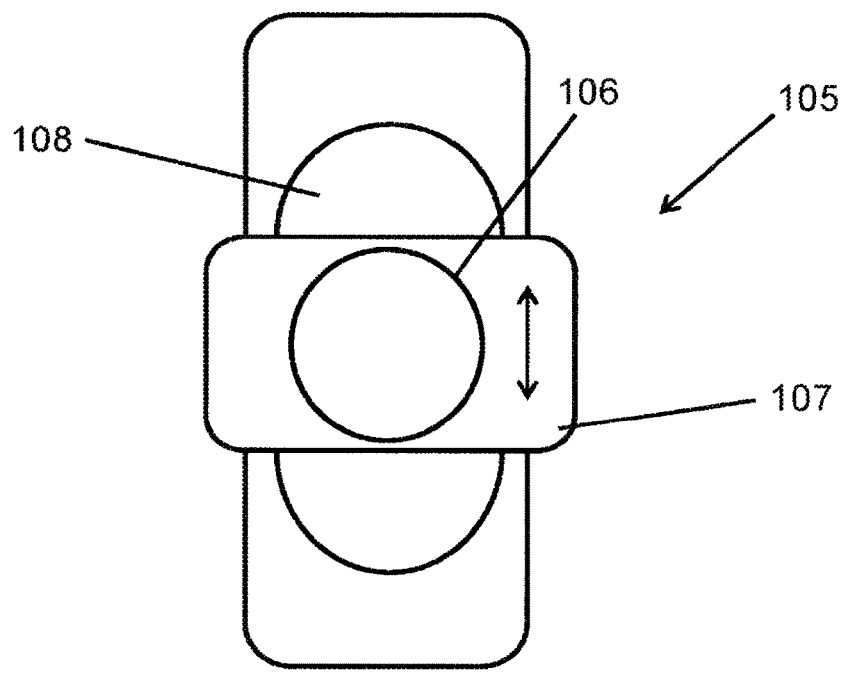
FIG. 11 is a schematic diagram showing a close-up of part of the first fastener.

The central strap 102b includes a sliding portion 105, shown in more detail in FIG. 11. The sliding portion 105 includes a plastic, cylindrical mount 106 for receiving a disc-shaped ultrasound transducer as a friction fit within the mount 107. The straps 102a, 102b, 102c are sized and arranged so that the mount 106 can hold the ultrasound transducer 2 in position over the baby's anterior fontanelle. The mount 106 is attached to a slider 107 which is attached across a cut-away section 108 of the central strap 102b, such that the slider 107, and with it the mount 106, are able to move in the direction shown by the arrow in FIG. 11. This movement of the mount anteriorly and posteriorly when the arrangement 100 is secured to the head 109 of a baby, allows the mount 106 to be more accurately positioned over the fontanelle.

Figure 12:
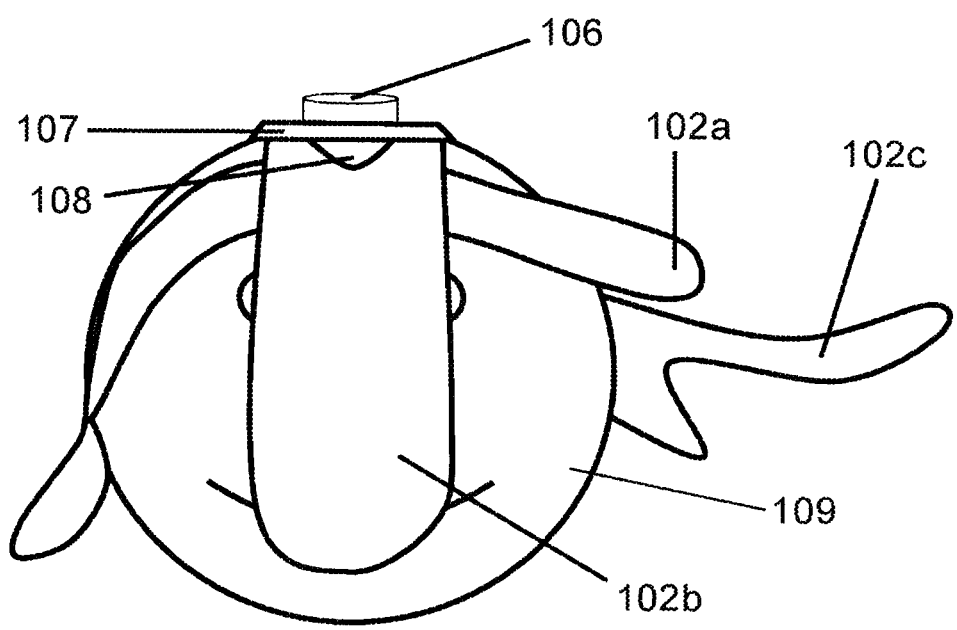
FIG. 12 is a schematic diagram showing the first fastener being applied to an infant's head.

FIG. 12 shows the head mounting arrangement 100 in position on a baby's head 109, part way through the process of securing it to the baby's head 109. FIG. 12 shows the first side strap 102a and the central strap 102b in their secured position, prior to the second side strap 102c being wrapped around the baby's head 109 and adhered to the first side strap 102a, thus securing the straps in place. The mount 106 and the slider 107 are positioned approximately over the anterior fontanelle, and a fine anterior-posterior adjustment can then be made by adjusting the slide 107. Once the mount 106 is in place, ultrasound gel can be applied to the baby's scalp, and the transducer 2 can be pushed into place in the mount 106.

Figure 13:
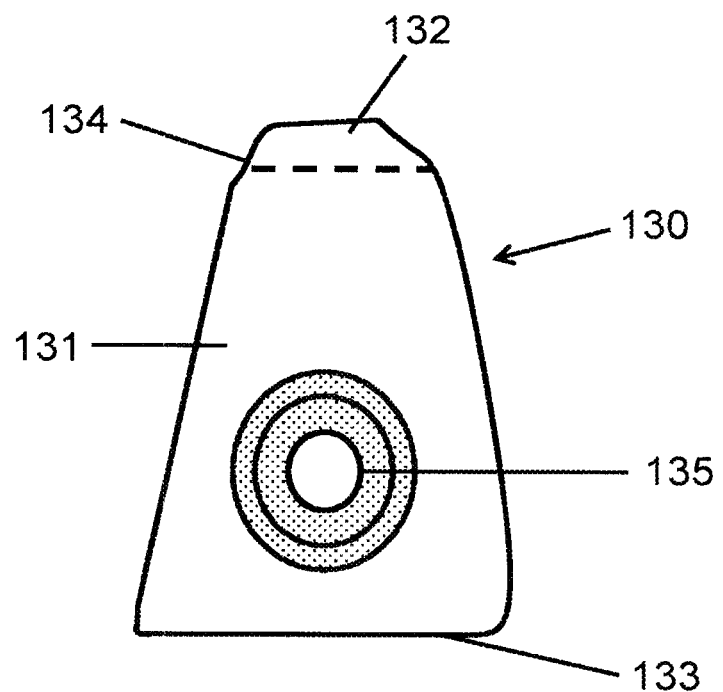
FIG. 13 is a schematic diagram of a second fastener for an infant's head, embodying the invention.
Figure 14:
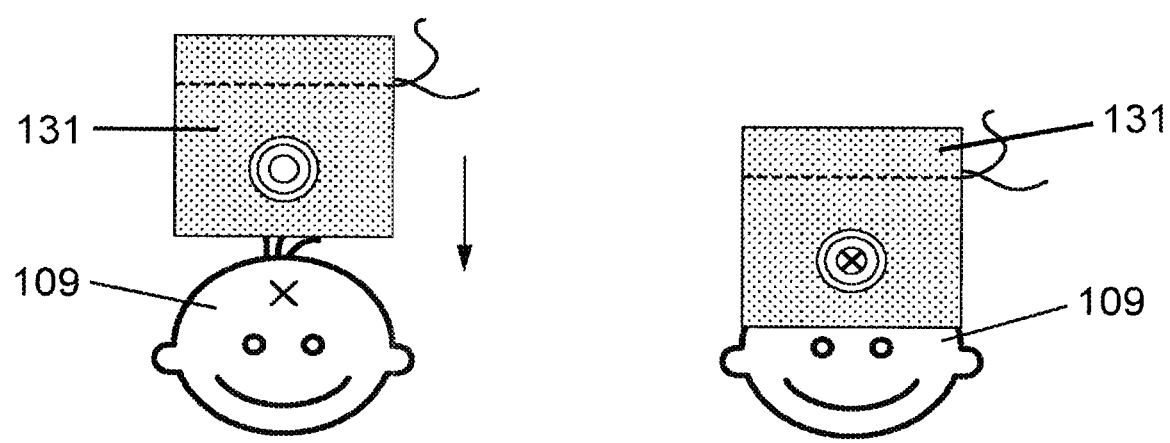
FIG. 14 is a schematic sequence showing how the second fastener is applied to an infant's head.

FIG. 13 shows a second embodiment of a head mounting arrangement 130. This head mounting arrangement 130 comprises a tube 131 of elasticated stocking material, having a distal end 132 and a proximal end 133. The distal end 133 could be open or could be stitched closed, or, as shown here, may be closable by a draw string 134. The tube 131, when not tensioned, has a circumference smaller than the typical circumference of a premature baby's head 109. In this way, the open proximal end 133 of the tube can be stretched and placed over the top portion of a baby's head 109, as shown in FIG. 14, and the tube 131 will stay in place by providing a friction fit against the baby's scalp due to the tension in the tube 131. The drawstring 134 can be pulled to keep spare material of the tube 131 gathered together to prevent snagging of the excess material.

This second head mounting arrangement 130 again includes a plastic mount 135, suitable for mounting the ultrasound transducer 2. The mount 135 is attached to the elasticated tube 131 by a fixing portion 136. This fixing portion 136 may be an annular piece of fabric which overlaps a planar base of the mount 135 and is stitched to the tube 131 so as to sandwich the base of the mount 135 between the fixing portion 136 and the tube 131.

The position of the mount 135 can be adjusted so that it is over the anterior fontanelle, or even over the posterior fontanelle or a suture, of the head 109 of the baby by a clinician sliding the elasticated material of the tube 131 against the infant's scalp. The use of elasticated material allows the mount 135 to be positioned with great versatility on the head 109 of the baby.

Figure 15:
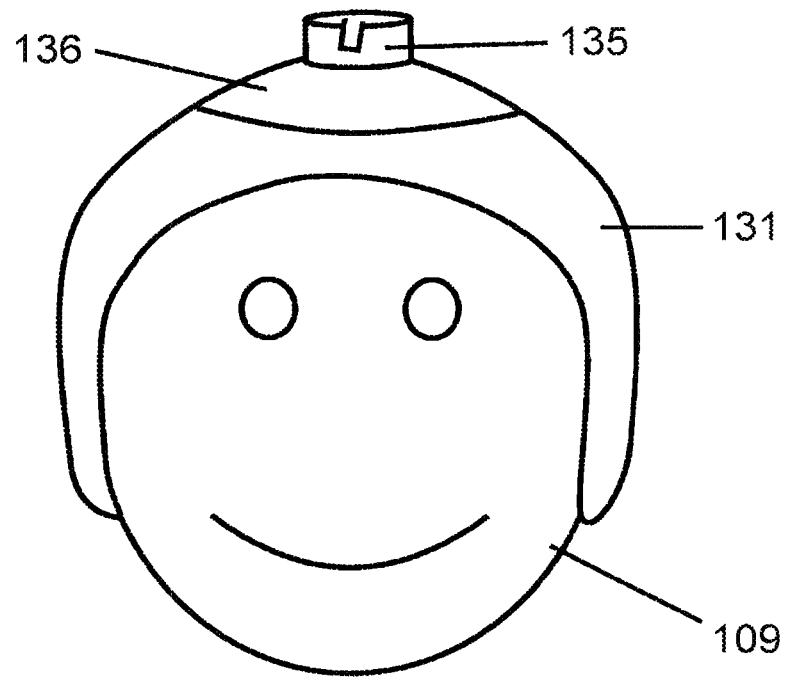
FIG. 15 is a schematic diagram of the second fastener in place on an infant's head.
Figure 16:
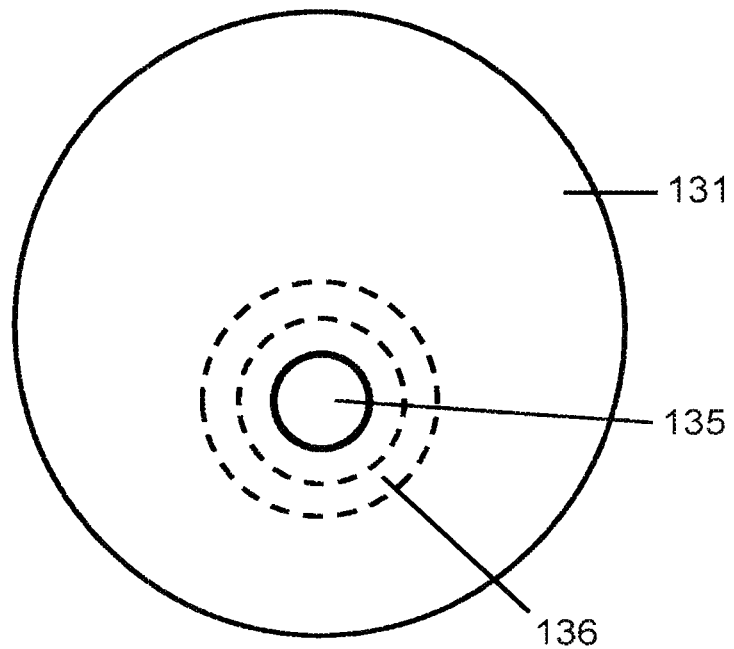
FIG. 16 is a top view of the second fastener for an infant's head.

FIGS. 15 and 16 provide front and top views, respectively, of the second head mounting arrangement 130 positioned so that the mount 135 is located over the anterior fontanelle of the baby's head 109. As before, ultrasound gel can be applied to the skin, through the mount 135, once the mount 135 is in place on the infant's skull, and then a single-element ultrasound transducer 2 can be clipped into the mount 135.

As can be seen in FIG. 15, the plastic mount 135 has an upstanding circular cylindrical portion, which can receive the transducer 2. Vertical cuts in the cylindrical portion may help it to yield when the transducer is inserted, while still providing sufficient friction to hold the transducer in place once it has been received. In some embodiments, this upstanding portion may be a spherical segment, rather than a circular cylinder, so as to provide a socket in which the angle of the disc-shaped transducer 2 can be adjusted. The transducer 2 may have complementary curved outer faces to facilitate this movement.

An operator may look at a display such as that shown in FIG. 8 while moving the transducer 2 into an optimal position, and may position a selection marker 82 to select a desired depth range—for example, the depth range containing the strongest arterial signal.

Figure 17:
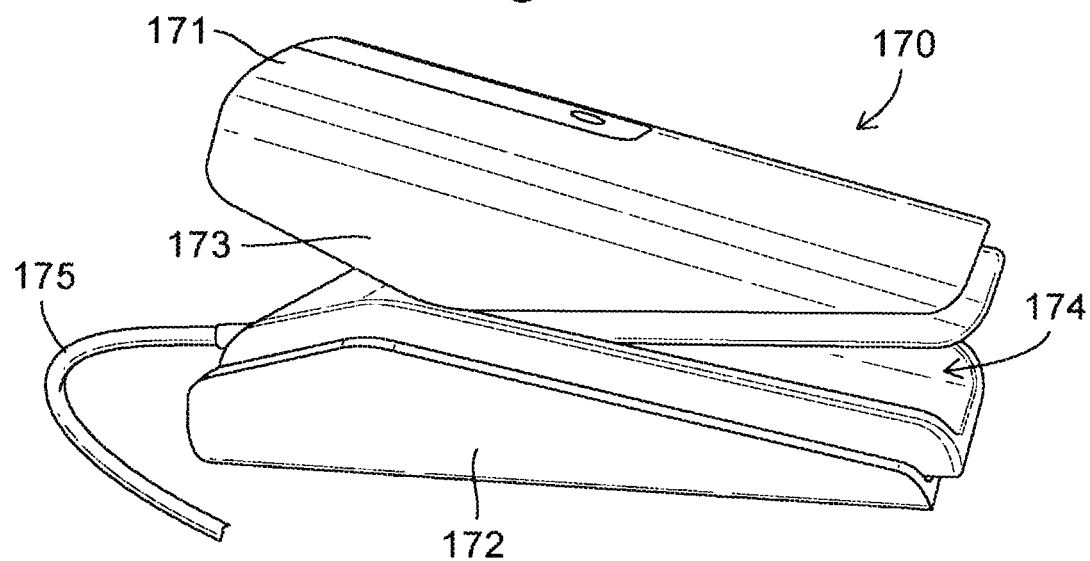
FIG. 17 is a schematic diagram of a fastener for a patient's digit, embodying the invention, not applied to a patient.

FIG. 17 shows a digit clip fastener 170 for attaching an ultrasound transducer, similar to the transducer 2 of FIG. 3 (albeit potentially minus the housing 30) to a digit—i.e., a finger or toe—of a human or animal subject. This can be useful for monitoring purely the microcirculation, since the fingers and toes contain only minor arteries.

The clip fastener 170 comprises an upper jaw 171 and a lower jaw 172, connected by a sprung hinge 173. The upper and lower jaws 171, 172 define a proximal opening 174 which is urged shut by the sprung hinge 173. An electrical lead 175 extends from the clip fastener 170 for connecting the clip fastener 170 to a controller 3.

Figure 18:
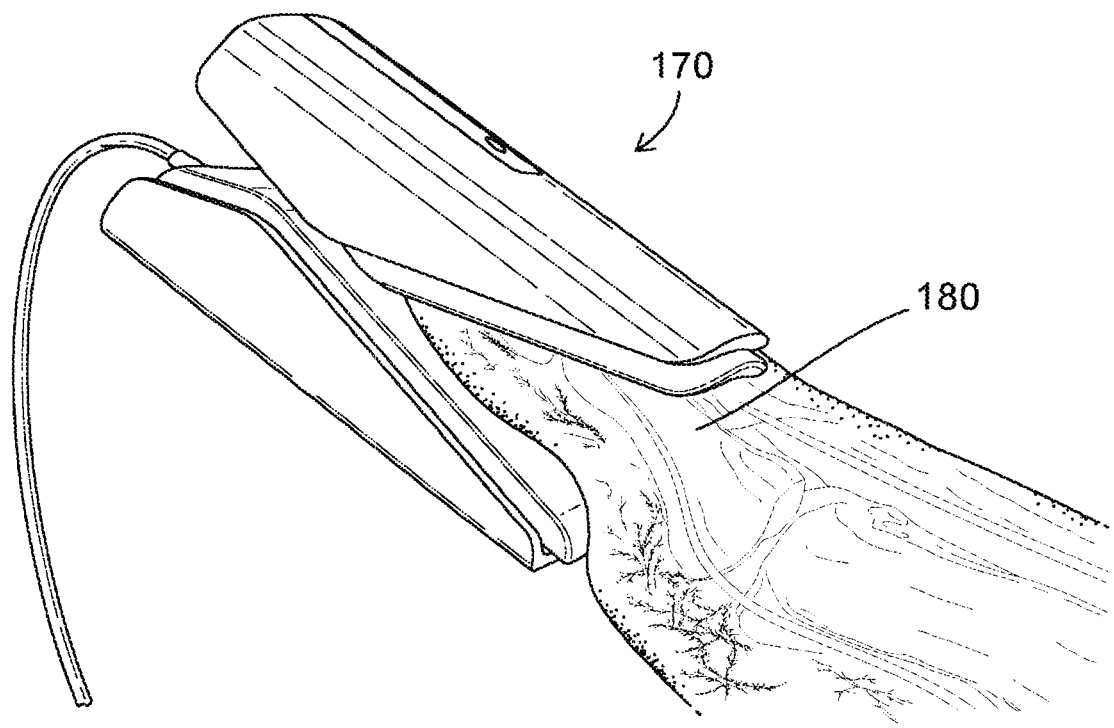
FIG. 18 is a schematic diagram of the fastener for a patient's digit, applied to a patient's big toe.

FIG. 18 shows the clip fastener 170 in position on a big toe 180 of a human subject's right foot.

Figure 19:
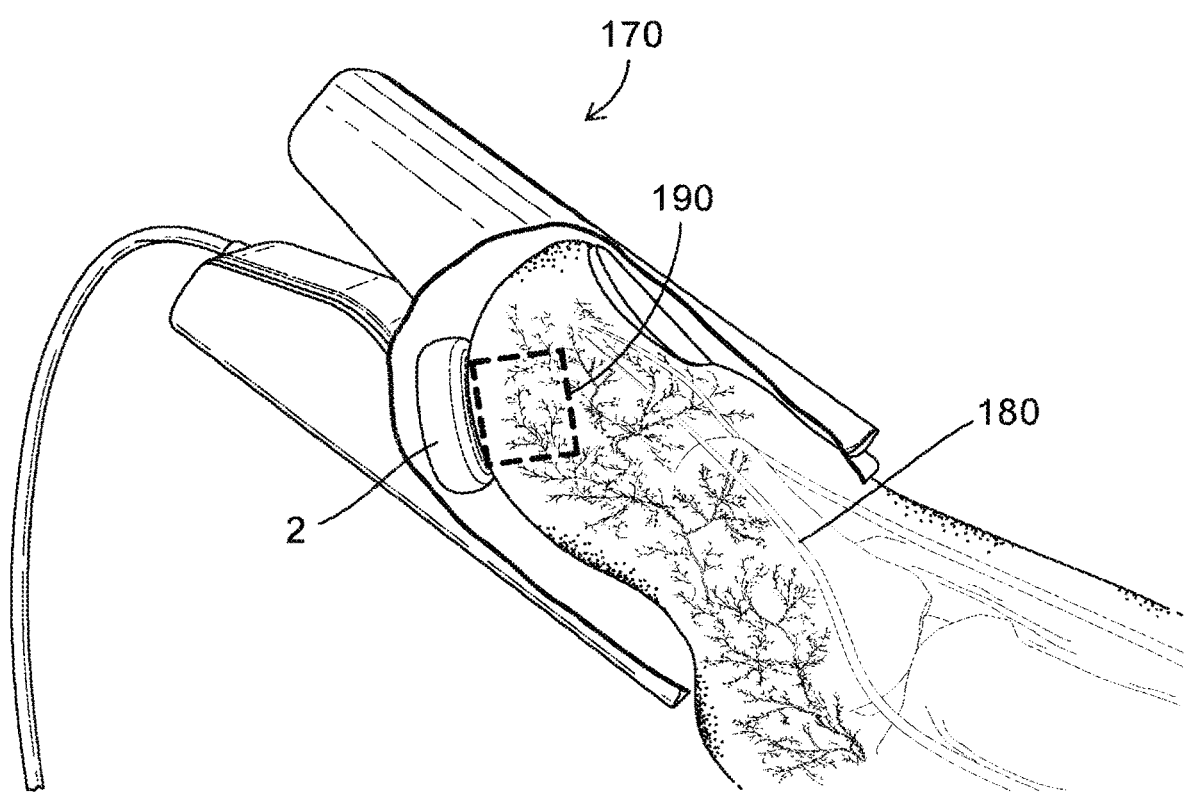
FIG. 19 is a ghosted diagram of the fastener applied to the patient's big toe.

FIG. 19 shows the position of a single-element ultrasound transducer 2 inside the lower jaw 172 of the clip fastener 170. The transducer 2 is positioned so as to contact the skin of a digit inserted in the clip fastener 170, and the system 1 can control the ultrasound transmission and reception so as to monitor blood flow within part or all of a cylindrical region 190 in front of the transducer 2.

The sprung hinge 173 is preferably designed to apply sufficient pressure to keep the clip fastener 170 from becoming easily dislodged, but not so much pressure that the microvessels are constricted.

In some embodiments, the clip fastener 170 may have a force sensor (not shown) within the upper or lower jaw 171, 172 which measures a contact force between the jaw 171, 172 and the digit. This may allow an operator to adjust the tension in the sprung hinge 173 to an optimal level.

In some embodiments, the clip fastener 170 has an electrical heating element (not shown) within the lower jaw 172, adjacent the ultrasound transducer 2. It may also have a thermometer for measuring temperature adjacent the digit. Signals may be sent over the lead 175 to and from the controller 3 for controlling the heating element so as to maintain a temperature within a desired range so as to avoid temperature-induced vasoconstriction in the digit.

FIGS. 20 to 29 relate to an experimental set-up of a transducer system embodying the invention, and results obtained therefrom. The results compare the performance of various different piezoelectric materials that may be used in the piezoelectric transducer element of the system. As explained below, hard PZT materials—especially Pz24— have been found to be particularly effective, although other ceramic and/or polymer and/or composite piezoelectric materials may nevertheless be used in some embodiments.

The transducers that were tested are suitable for use in a system shown in FIGS. 1 & 2. However, for characterising the transducer 200 performance, experimental set-ups, such as the pulse-echo set-up shown in FIG. 20, were used.

Fabricated transducers 200 were characterized by electrical impedance measurements, acoustic beam profile measurements and acoustic pulse-echo measurements. Electrical impedance was measured in air and in water using a network analyzer (Rohde & Schwarz ZVL, Munich, Germany).

Figure 20:
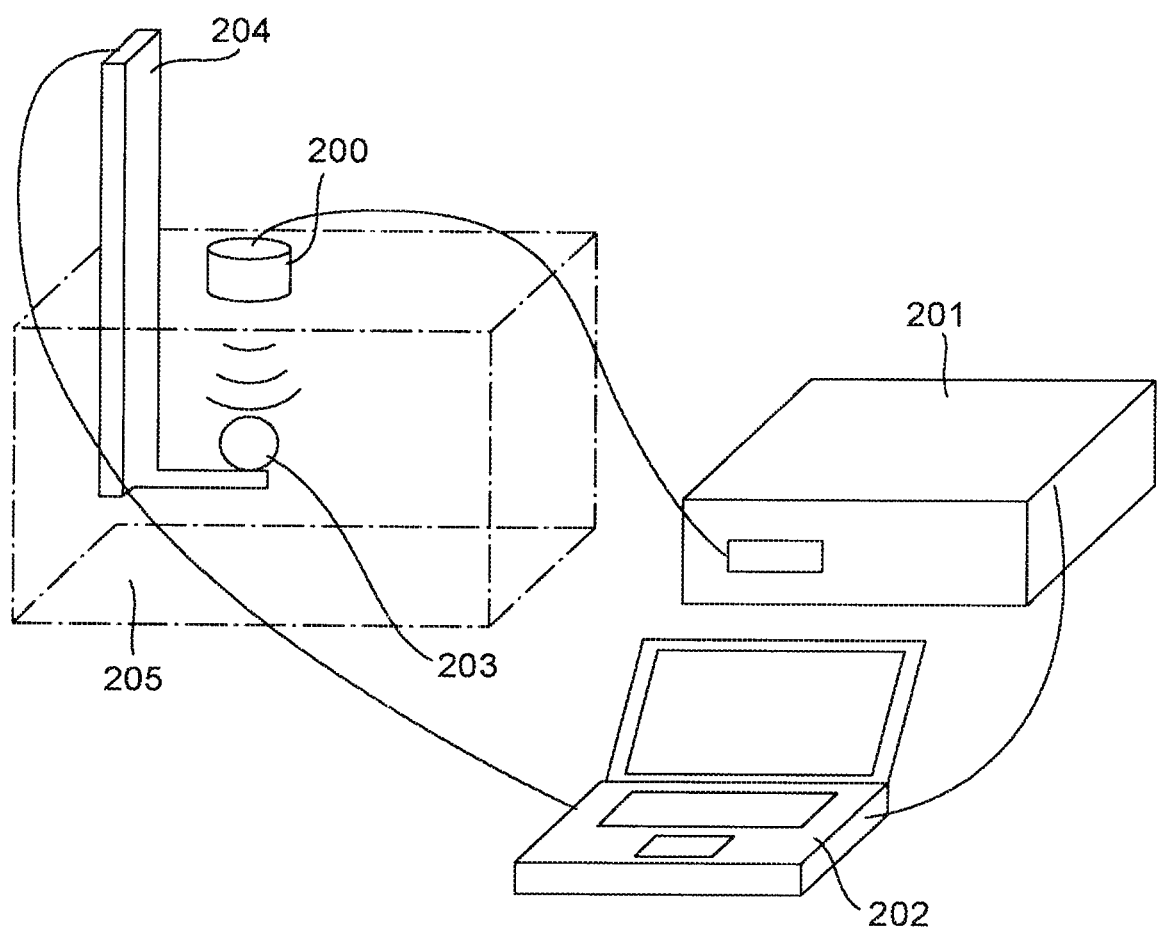
FIG. 20 is a schematic diagram of a text set-up used to characterise different ultrasound transducer materials for transducers for use in systems embodying the invention.

Two-way sensitivity of the transducers was investigated in a pulse-echo set-up of FIG. 20. A single-element transducer 200 was connected to a controller 201 (a Manus EIM-A produced by Aurotech Ultrasound AS, Tydal, Norway). A computer 202 is connected to the scanner using an Ethernet network cable. The transducer 200 was directed towards an 18 mm diameter stainless steel sphere 203 positioned for maximal reflection, 157 mm from the transducer 200. The controller/scanner 201 was used to drive the transducer 200, and acquire the received echoes. Received pulses were transferred to the computer 202, to be stored and analyzed in Matlab.

Using another set-up (not shown), beam profiles were also measured, in an Onda AIMS III measurement tank (Onda Corp. Sunnyvale, CA), controlled by Onda AIMS Soniq 5.2 software. The transducers 200 were driven by a Panametrics 5052PR Pulser Receiver (Olympus Corp. Waltham, MA). The resulting sound beams were scanned laterally at a fixed distance, using an Onda HGL-0200 hydrophone with an AG-2010 Preamplifier, calibrated in the frequency range 1 to 20 MHZ. The output was digitized at 250 MSa/s in a Picoscope PS5244A analog to digital converter (Pico Technology. St Neots, UK), and digitized pulses transferred to a computer to be stored and analyzed in Matlab.

Three common piezoelectric materials were studied for use in pulsed wave Doppler ultrasound embodying the invention, where high sensitivity is required, while bandwidth is less important. A large transducer aperture, 80 mm$^2$, results in a low electrical impedance, making the transducers challenging to drive with conventional electronics and cables. Air-backed transducers with electrical tuning circuitry and cable assembly were made using the piezoelectric materials Pz24, Pz27, and Pz29. Pz24 is a hard PZT, with dielectric constant of 240, the other materials are soft PZT with dielectric constants around 1000. It was found that the transducer made with Pz24 gave 2 dB better two-way sensitivity compared to those made with the other PZT-variants. The improved performance is explained by the higher electrical impedance from using Pz24.

Doppler measurements are a common diagnostic ultrasound technique used to detect blood flow or muscle movement. Echoes scattered by the red blood cells carry information about the velocity of the blood. These echoes are weak, so the transducer should have a high sensitivity, while a large bandwidth and short pulse length are less important. The study described in the following paragraph compares a variety of possible single element ultrasound transducers optimized for high sensitivity and demonstrates the particular suitability of Pz24.

Three different piezoelectric materials were tested, Pz29, Pz27 and Pz24 (Meggitt A/S, Kvistgaard, Denmark). Soft piezoelectrics, e.g. Pz29 and Pz27, having large dielectric constant $\varepsilon_r$, are commonly used in medical ultrasound applications. However, for a single-element Doppler transducer having a large aperture area, embodying the present invention, the resulting high capacitance and low impedance may be hard to drive electrically, especially through a long, thin cable. Hence, for this particular application, a hard piezoelectric with lower $\varepsilon_r$, e.g. Pz24, might be preferred.

All transducers in the study were designed for an 8 MHz centre frequency. The transducer designs were optimised for high sensitivity with less requirements to the bandwidth, so a solution with one acoustic matching layer in front and air backing was chosen. The matching layer thickness was set to be a quarter of the wavelength in the matching layer material. Two different geometries were investigated, one rectangular and one circular. The active element of the rectangular transducers was 16 mm by 5 mm, while that of the circular transducers was 10 mm diameter, giving equal active aperture areas.

Piezoelectric materials with high coupling coefficients were selected to achieve high sensitivity. Conventional soft PZT materials, Pz27 and Pz29 were chosen due to their frequent use in medical ultrasound transducers. However, for a 8 MHz centre frequency the surface area 80 mm$^2$ is large. This gives a low electrical impedance, which making the active elements hard to drive. To investigate the effect of this, a "hard" PZT material, Pz24, with low dielectric constant, was also tested. A list of the central material properties is given in the following table.

| Property | Unit | Pz24 | Pz27 | Pz29 |
|---|---|---|---|---|
| Electromechanical coupling coeff. $k_t$ | (—) | 0.508 | 0.469 | 0.524 |
| Piezoelectric constant $d_{33}$ | pC/N | 149 | 425 | 574 |
| Clamped dielectric constant $\epsilon_{33,r}^S/\epsilon_0$ | (—) | 239 | 914 | 1220 |
| Dielectric Loss tan$\delta$ | (—) | 0.002 | 0.017 | 0.016 |
| Density | kg/m$^3$ | 7700 | 7700 | 7460 |
| Longitudinal wave velocity | m/s | 4851 | 4331 | 4498 |
| Characteristic acoustic impedance | MRayl | 37.35 | 33.35 | 33.56 |

An electrical tuning network was implemented to match the electrical impedance to 50Ω. The one-dimensional Mason model was used to design models for encapsulation of the transducers.

The piezoelectric plates and discs came polarized in the thickness direction and had silver painted electrodes. A matching layer of Eccosorb MF112 (Laird N. V. Geel, BE) was lapped down to the desired thickness. The matching layer was made larger than the piezoelectric, to act as support when mounting the transducer in the housing. This allows the piezoelectric element to be air-backed and have unclamped edges.

After lapping, the matching layer was covered with a tape-mask, sputtered with a seed layer of chrome to promote adhesion, before sputtering on a conductive layer of gold. The PZT was bonded to the sputtered matching layer using epoxy (Scotch-Weld Epoxy Adhesive DP460, 3M, Maplewood, MN). Conductive silver epoxy was used to connect wires to the electrode on the back of the PZT and to the gold sputtered on the matching layer. Silver epoxy was chosen to allow easy assembly and avoid localized heating from a soldering iron, which could cause de-poling.

Figure 21:
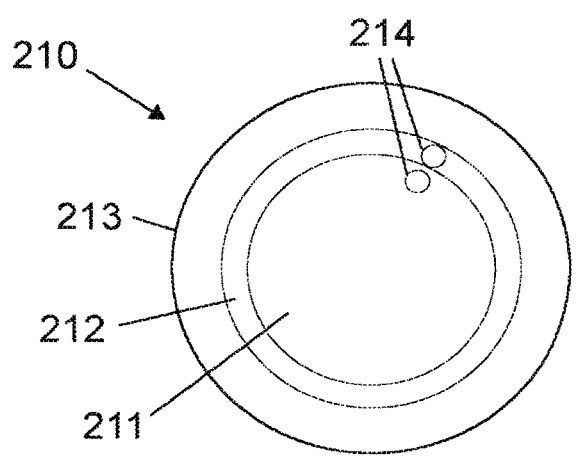
FIG. 21 is a plan-view schematic diagram of a circular ultrasound transducer element for use with embodiments of the invention.

FIG. 21 shows a circular transducer 210 having an active piezoelectric element 213 of 10 mm diameter and a matching layer which has a sputtered surface 212 and an unsputtered surface 213. Wires were bonded using silver epoxy at two bonding points 214.

Figure 22:
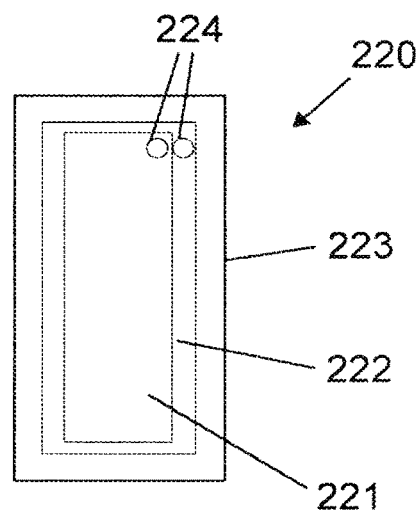
FIG. 22 is a plan-view schematic diagram of a rectangular ultrasound transducer element for use with embodiments of the invention.

FIG. 22 shows a rectangular transducer 220 having a 5 mm×16 mm rectangular active piezoelectric element 223 and a matching layer which has a sputtered surface 222 and an unsputtered surface 223. Wires were bonded using silver epoxy at two bonding points 224.

A stereolithographic 3D-printer was used to print the models designed in SolidWorks.

Figure 24A:
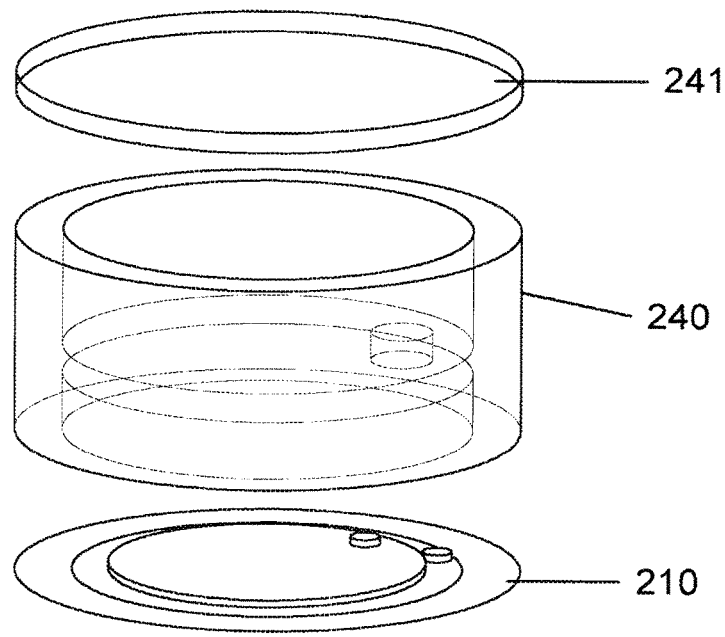
FIG. 24A is an exploded ghosted projection view of an ultrasound transducer for use with embodiments of the invention.
Figure 24B:
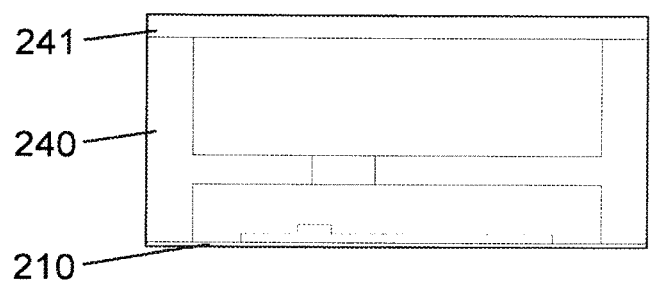
FIG. 24B is a vertical cross-sectional view of the ultrasound transducer.
Figure 24C:
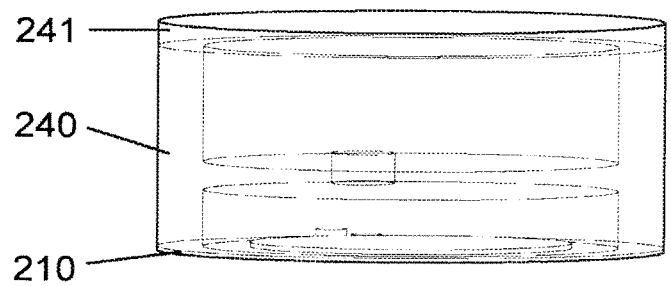
FIG. 24C is a ghosted side view of the ultrasound transducer.

FIGS. 24A, 24B, 24C show the completed transducer stack from various views. The stack, including the circular transducer 210, was assembled in a bottom compartment of a main housing 240, with tuning electronics located in an upper compartment of the main housing 240. A flat disc 241 was put on the top to seal the upper compartment after assembly.

The transducers were electrically matched to 50Ω, by adding a parallel inductor and a transformer, and the housed transducers were electrically shielded to reduce pick-up of environmental noise. This was achieved by sputtering a layer of chrome and then gold, covering the whole transducer assembly. The finished transducer was connected to a tri-axial cable, where the two inner conductors were interconnected with the piezoelectric, and the outer conductor was connected to the shielding of the transducer housing.

Figure 23:
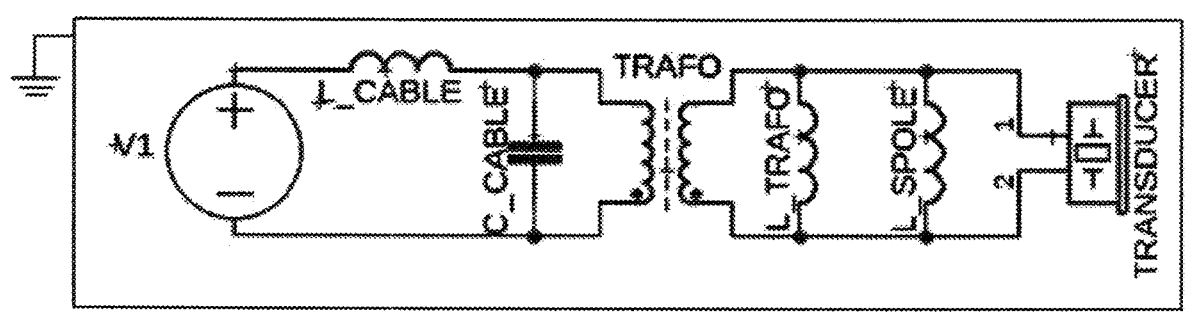
FIG. 23 is a circuit diagram of tuning circuitry in an ultrasound transducer for use with embodiments of the invention.

FIG. 23 is a circuit diagram of the shielded transducer with tuning components and cable. The LC circuit represents the cable. The whole diagram is enclosed in a Faraday cage, consisting of the outer shield of the tri-axial cable and the chrome-gold enclosing the transducer housing.

For the study, five transducers were fabricated and characterized. Three were made with a rectangular aperture, two using Pz27 and one with Pz29, and two with a circular aperture, one with Pz29 and one with Pz24.

Figure 25:
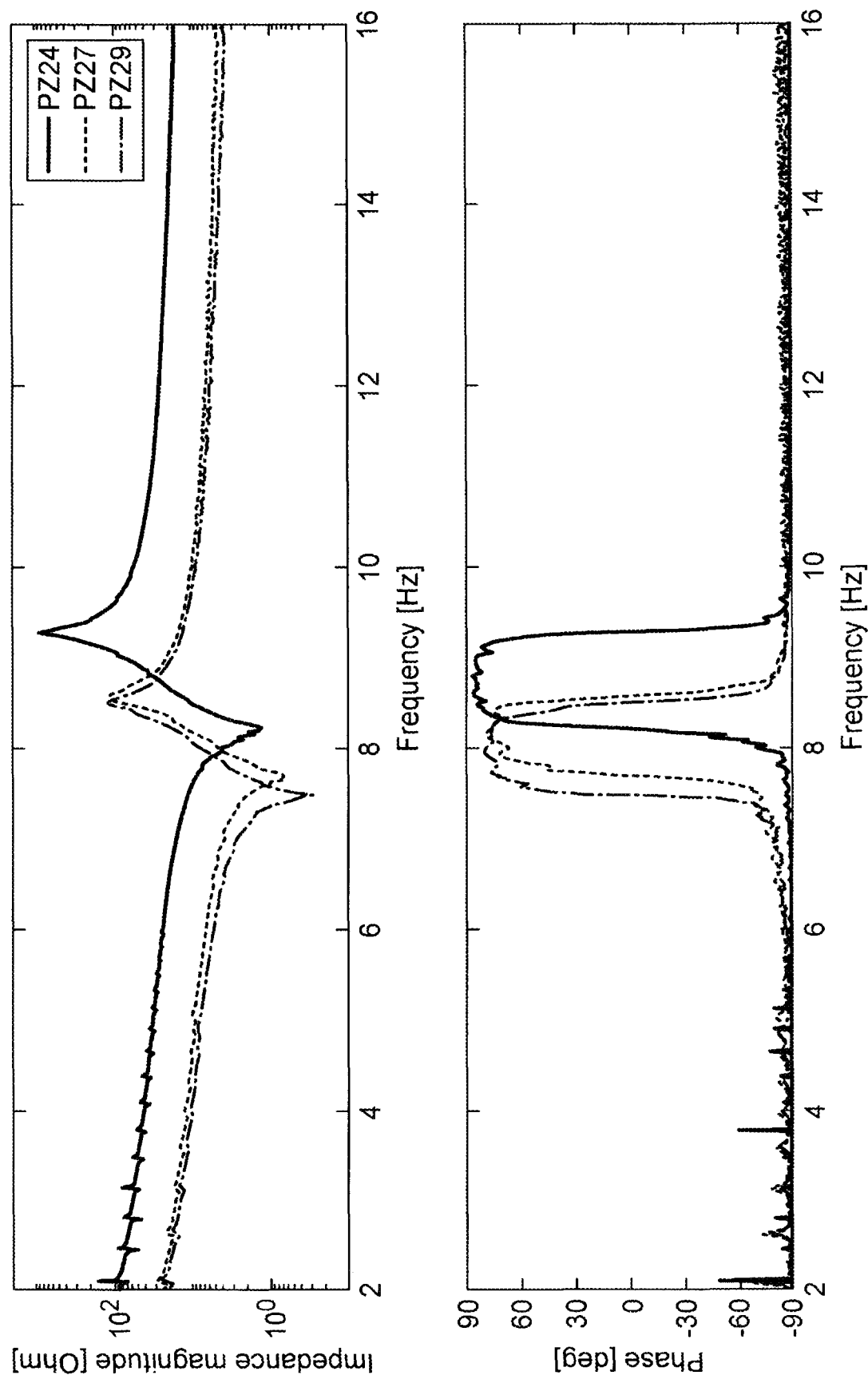
FIG. 25 shows two horizontally-aligned plots of measured electrical impedance (magnitude and phase against frequency) of three piezoelectric materials.

FIG. 25 shows the measured electrical impedance of the three piezoelectric materials, without matching layers, measured in air. The Pz24 sample is circular, while the Pz27 and Pz29 samples are rectangular. The surface area of the three elements are close to equal, and therefore comparable. Note the higher impedance in the Pz24 sample.

Figure 26:
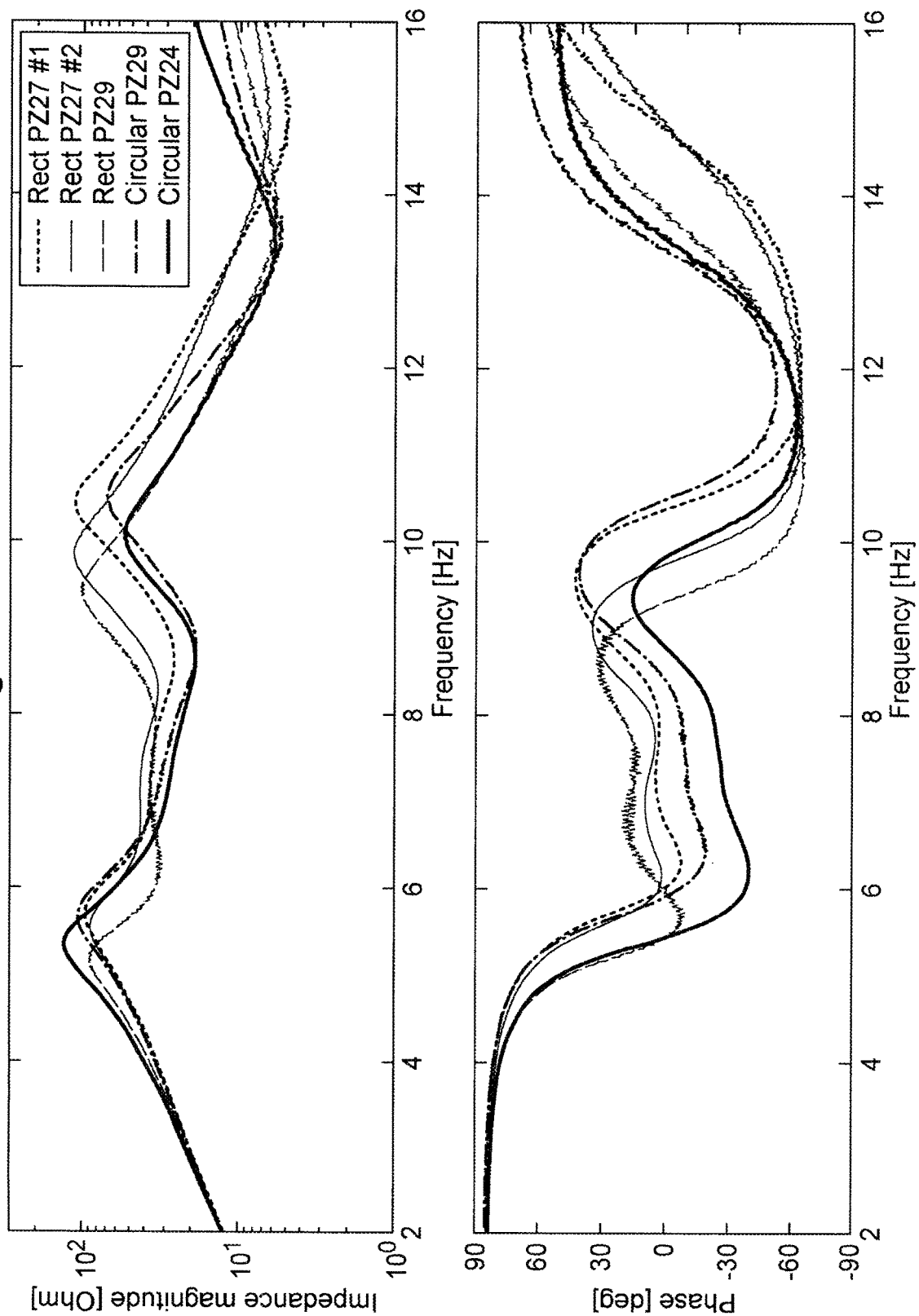
FIG. 26 shows two horizontally-aligned plots of measured electrical impedance (magnitude and phase against frequency) of three piezoelectric materials within respective completed transducer assemblies.

FIG. 26 shows the measured electrical impedances of the finished transducer assemblies, including tuning circuitry and a cable, measured in water. These transducers have a single acoustic matching layer, are electrical tuned to 50Ω, and have similar cable lengths.

Figure 27:
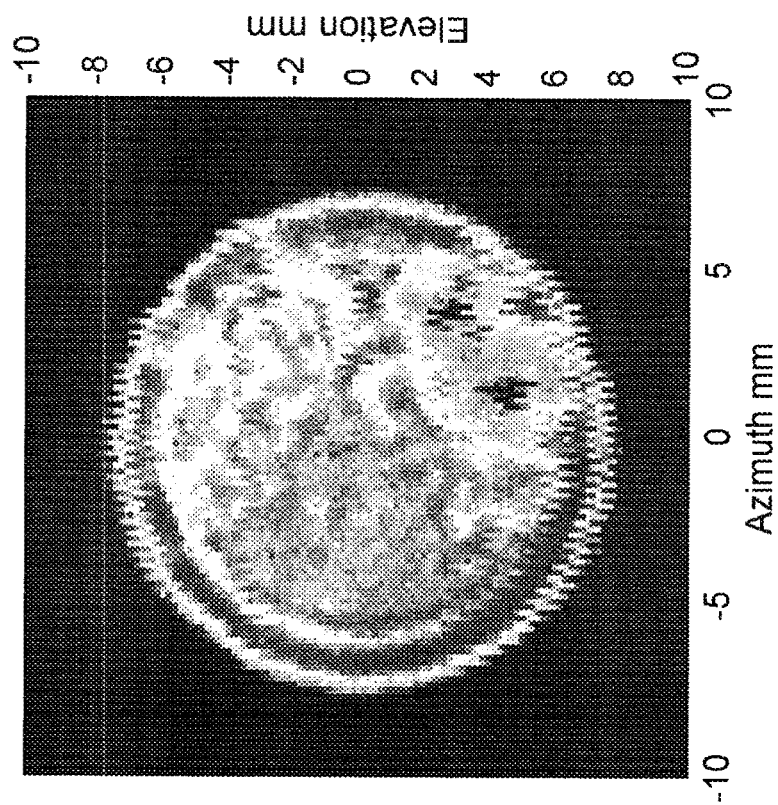
FIG. 27 shows beam profiles of two different transducers.
Figure 27:
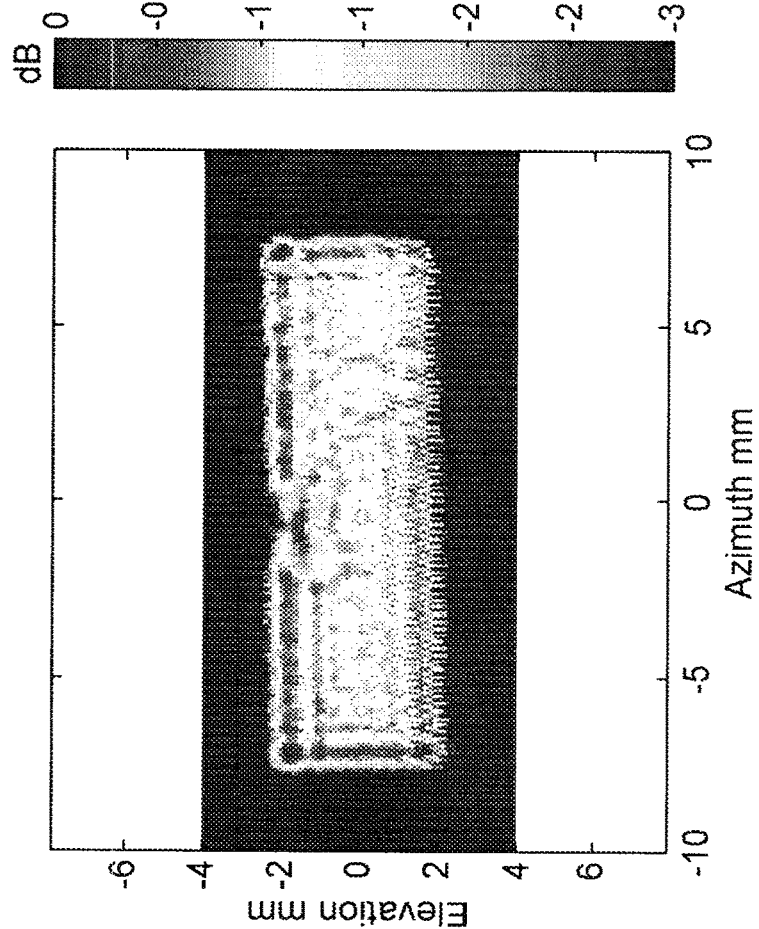

FIG. 27 shows the beam profiles of two transducers. The left panel is for the Pz27 transducer having a rectangular aperture made from, while the right panel is for the Pz29 transducer having a circular aperture. All were measured at 3 mm distance from the transducer surface, with 100 μm lateral resolution.

The pulse echo measurement set-up of FIG. 20 was used to compare the sensitivities of the transducers. The envelope of the received signals was acquired after around 210 μs, corresponding to 157 mm distance between the transducer and reflector.

Figure 28:
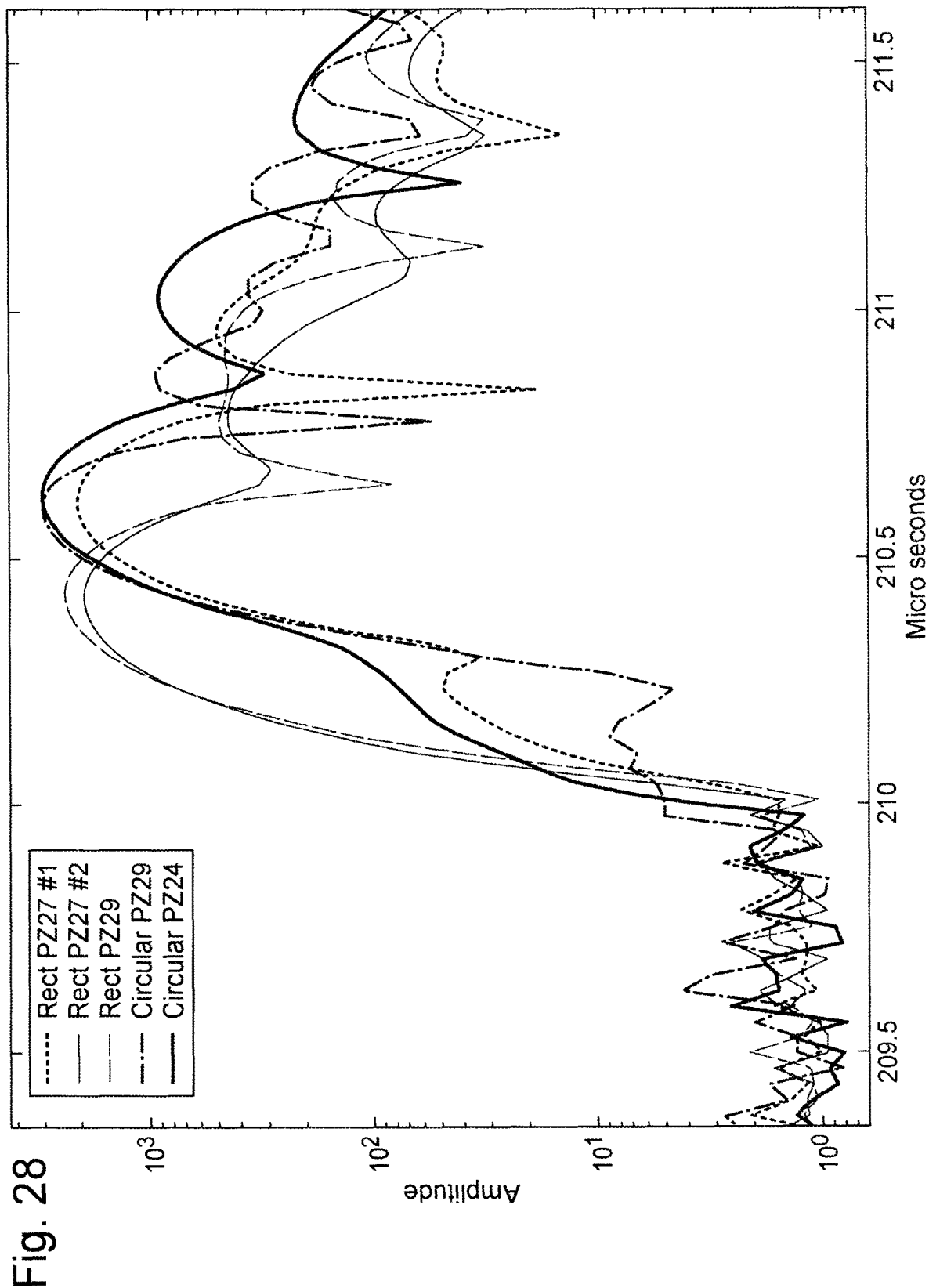
FIG. 28 is a plot of amplitude against time for envelopes of received echoes with five different transducers.

FIG. 28 shows the envelopes of the received echoes.

Figure 29:
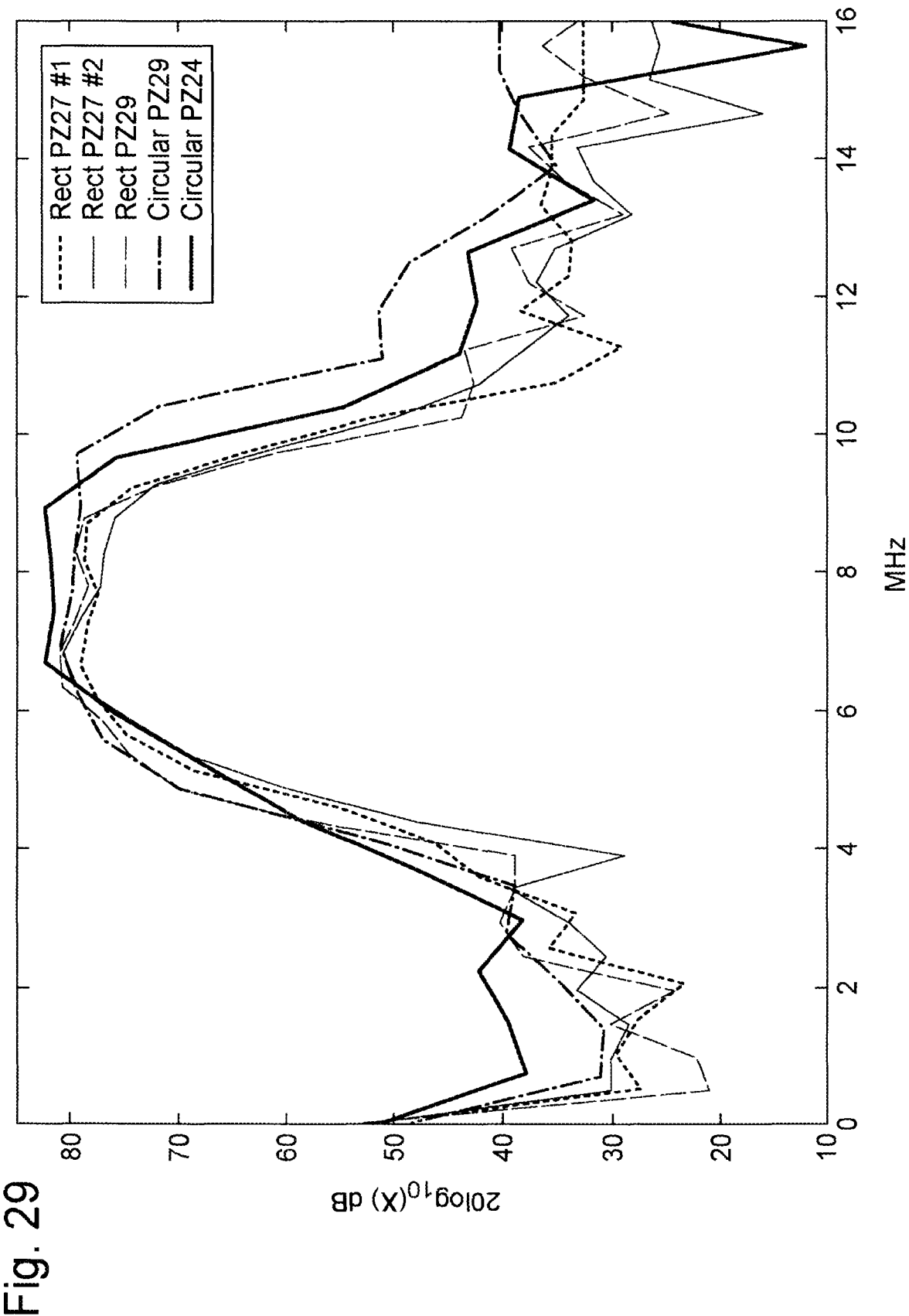
FIG. 29 is a plot of power against frequency for received echoes with the five different transducers.

FIG. 29 shows corresponding power spectra.

The envelope verifies that the distance between transducer and reflector was the same, and gives an indication of the signal to noise ratio.

For all the studied transducers, the relatively large surface area of the aperture (compared with elements used in conventional array-based transducers) results in a low impedance, which may make the transducers difficult to drive. It was predicted that the 'hard' Pz24 material, with its low dielectric constant, would be easier to drive. This is seen in the electrical impedance results in FIG. 25. However, after tuning with transformers, the finished transducers show similar electrical impedances. The slightly lower phase of the two circular transducers in the resonance region may be explained by imprecise thickness of the matching layer, or by the tuning components.

After tuning, the impedance magnitude at 8 MHz was between 20 and 40Ω and the phase within ±25 degrees, for all transducers, when measured in water. For all transducers, tuning circuitry was able to move the impedance into a region suitable for conventional driving electronics. However, this tuning has to be placed at the transducer end of the cable, thereby increasing its size and weight, which may not always be acceptable. The impedance measurement on the Pz24 transducer demonstrate how this material can be chosen to achieve a higher impedance, avoiding a tuning transformer.

The beam profiles in FIG. 27 show small regions with reduced radiated energy. This corresponds to the positions 214, 224 where wires were connected to the back-electrode of the PZT using silver epoxy. This absorbed some energy, causing a 3 dB reduction in transmitted energy. This result demonstrates that the influence of the wire connection is not negligible, a careful application of silver epoxy is important to minimize the influence on the transducer vibrations, while ensuring a secure connection.

From FIG. 28, it can be seen that the peak of the transducers named "Rect PZ27 #2" and "Rect PZ29" have a slight offset compared to the others. This is explained by a small inaccuracy in the positioning of the measurement setup, and does not influence the results.

When comparing the spectra in FIG. 29, it can be seen that the two transducers with rectangular aperture made with Pz27 are not identical. The transducer "Rect PZ27 #2" has an uneven top with its peak at 6.8 MHz, while the transducer "Rect PZ27 #1" has a flatter top. The difference at 8 MHz is 1 dB, and may be explained by process variations, e.g. inaccuracies in thicknesses of the matching and bonding layers. The third rectangular transducer "Rect PZ29" displays the same uneven top as the transducer "Rect PZ27 #2", and has 0.6 dB higher sensitivity than "Rect PZ27 #1". This can be explained by the higher coupling coefficient, $k_t$, of the Pz29 material.

Of the transducers with a circular aperture, the transducer made with Pz24 yielded a 2 dB-improved sensitivity over the transducer made with Pz29. The lower permittivity of Pz24 gives a higher electrical impedance, which for this large element area makes it easier to drive.

The transducers made with a circular aperture have an overall higher sensitivity than the rectangular transducers, due to the different beam pattern from the two geometries. Overall, the transducers performed well, with signal strength 75 to 85 dB above the recorded noise level. The −3 dB bandwidth for the transducers was found to between 30% and 40%, which is suitable for the pulsed wave Doppler application they were targeted at.

In summary transducers made from three different piezoelectric materials were studied. The transducers were targeted at pulsed Doppler applications, embodying the invention, where high sensitivity may typically be required, while the bandwidth requirement may be less important. The resulting large aperture area causes a low impedance, which is challenging for the driving electronics.

Two conventional soft PZT materials with high coupling coefficients, Pz27 and Pz29, were compared to a hard PZT, Pz24, with low dielectric constant. The results show that using the hard Pz24 makes it feasible to increase the sensitivity by 3 to 5 dB compared to the other materials and/or to dispense with tuning circuitry, thereby resulting in a lower manufacturing cost for the transducers.

CLINICAL EXAMPLES

Figure 30A:
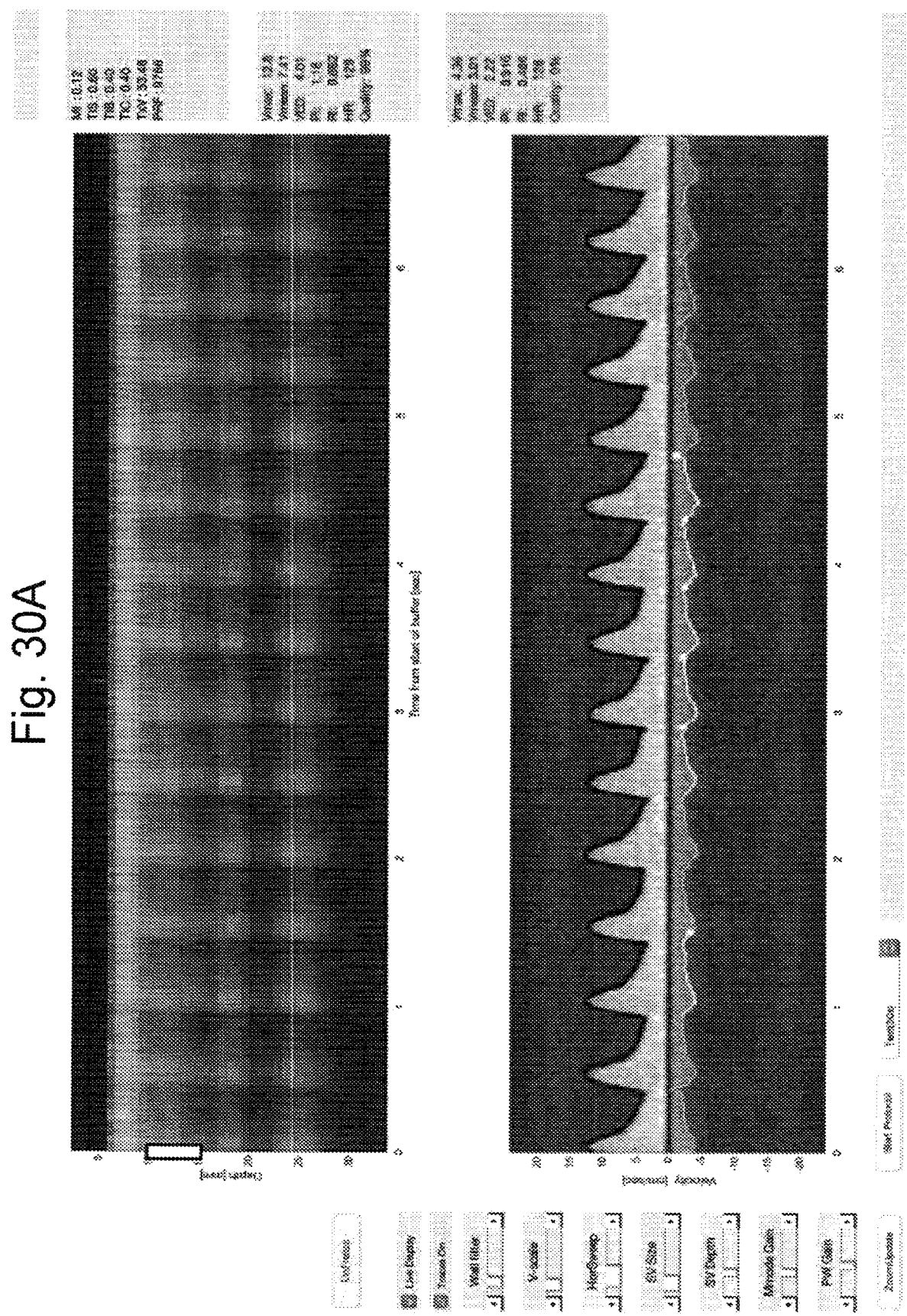
FIGS. 30*a*-30*c* are screenshots of a display output from an ultrasound scanning system embodying the invention showing blood flow traces from vessels at three respective depth ranges in the brain of a human infant.
Figure 30B:
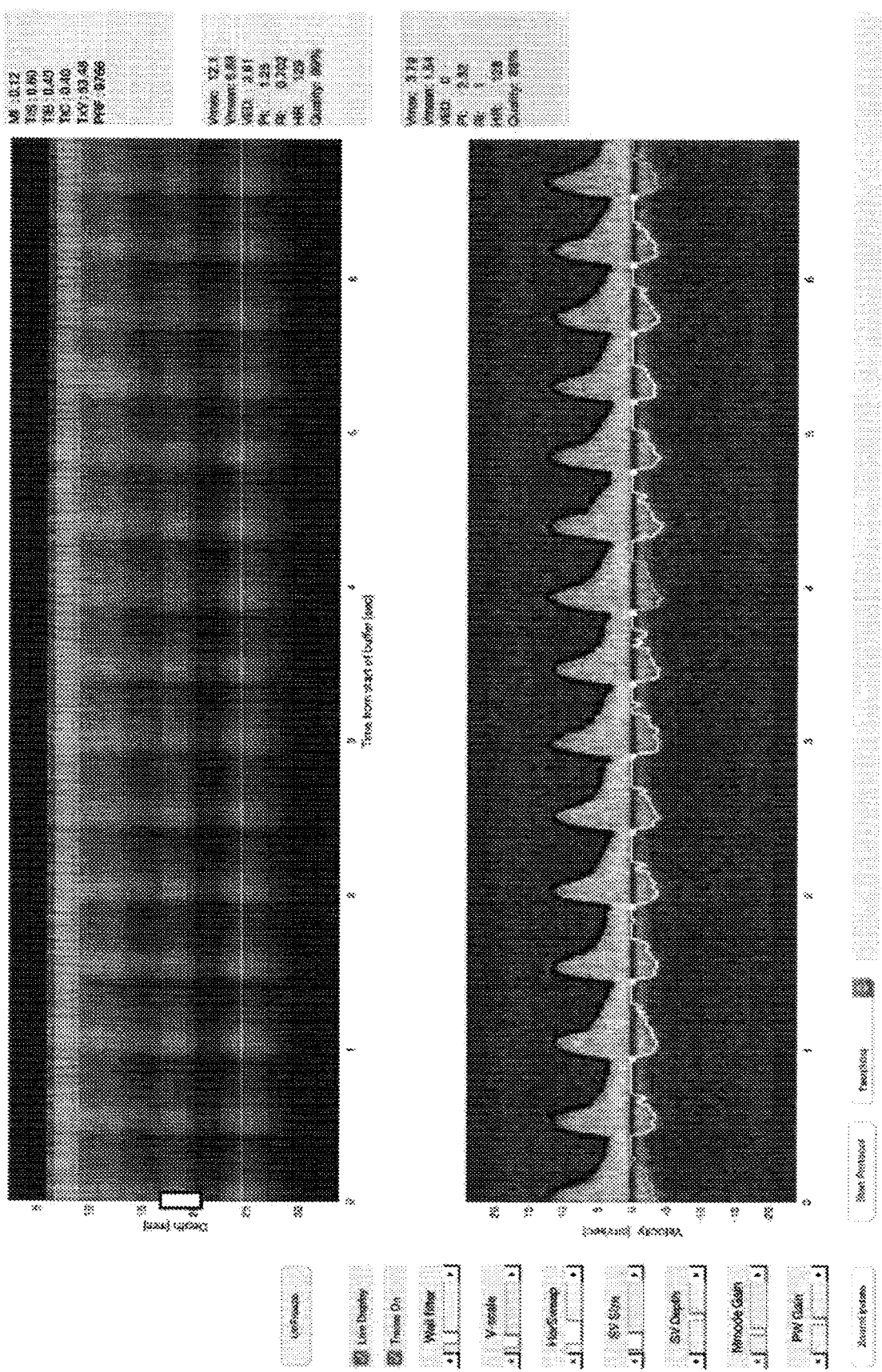
Figure 30C:
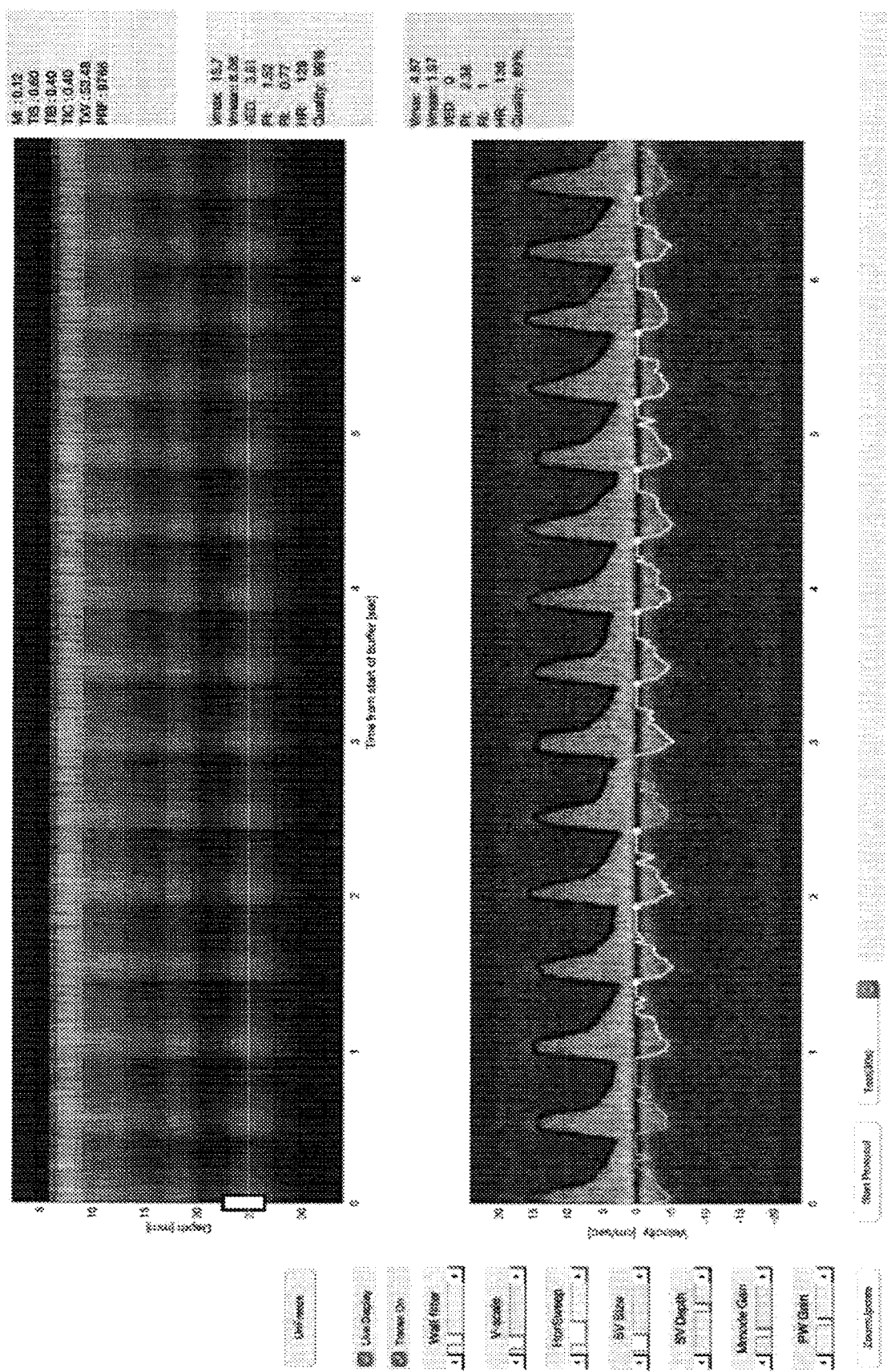

Example 1-Continual Analysis of Cerebral Blood Flow in Neonatal Preterm Humans with Unfocused Doppler Ultrasound The test subject was an infant of gestational age 32, birth weight: 1830 gram receiving no respiratory support. Ultrasound apparatus as described herein was used to obtain continuous measurements from the cerebral circulation via the anterior fontanelle for 7 seconds with 10 second pauses in between. FIGS. 30a, 30b and 30c show the same recording, but present Doppler curves from different depth ranges (represented by white rectangle). In FIG. 30a, the Doppler curve was obtained from a depth of 10-15 mm. In FIG. 30b, the Doppler curve was obtained from a depth of around 20 mm. In FIG. 30c, the Doppler curve was obtained from a depth of around 25 mm. Safety measurements were visualized continuously for each recording (right upper corner of FIGS. 30a-c).

Figure 31:
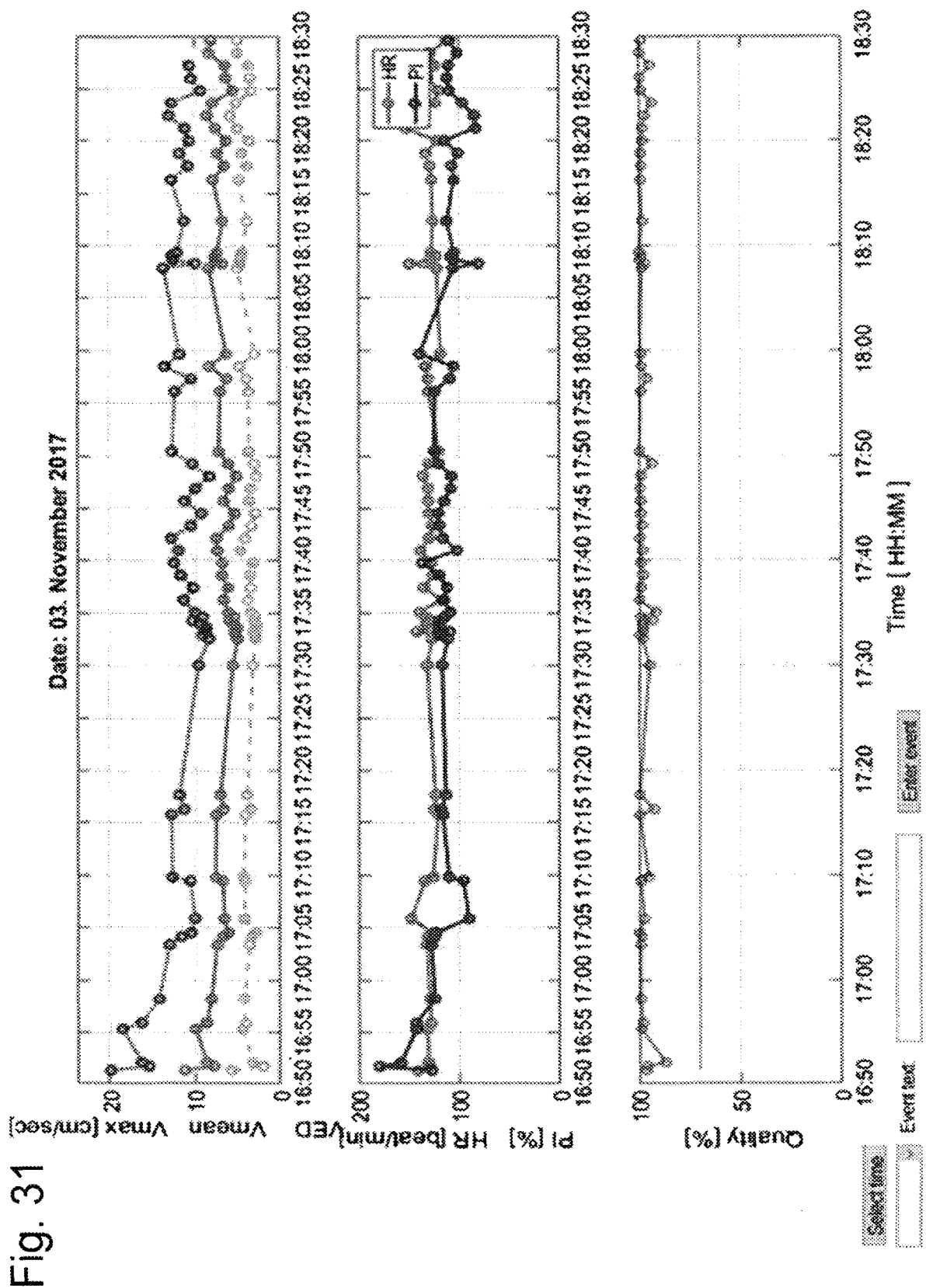
FIG. 31 shows graphs of cerebral Vmax, Vmean, VED, heart rate, pulsatile index (PI) and a Quality measure over time for a specific human subject.
Figure 32A:
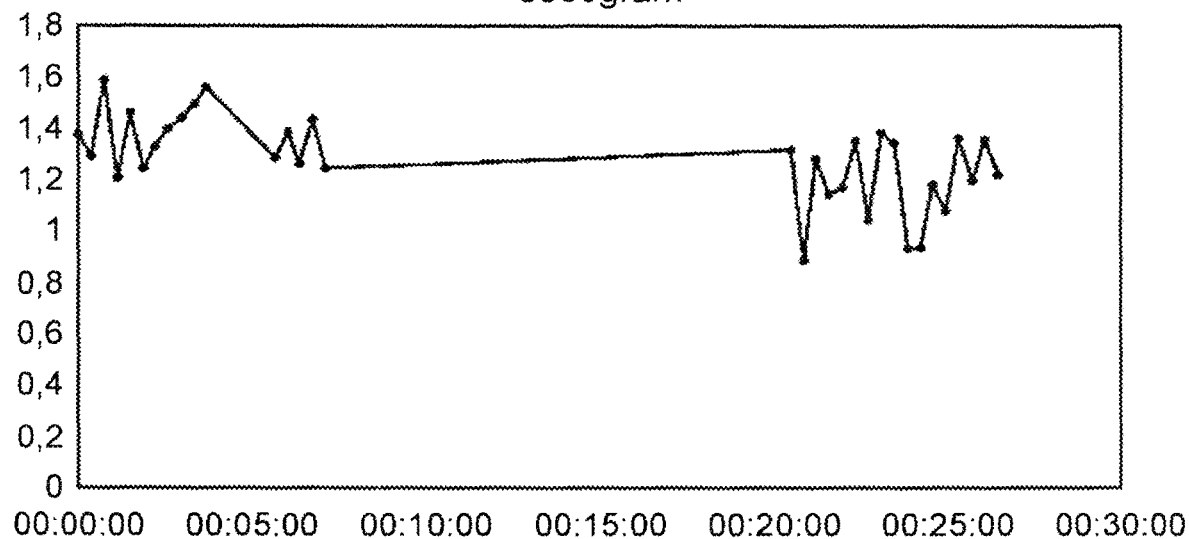
FIGS. 32a-32h are graphs of cerebral PI over a 30 minute time period in different respective patients.
Figure 32B:
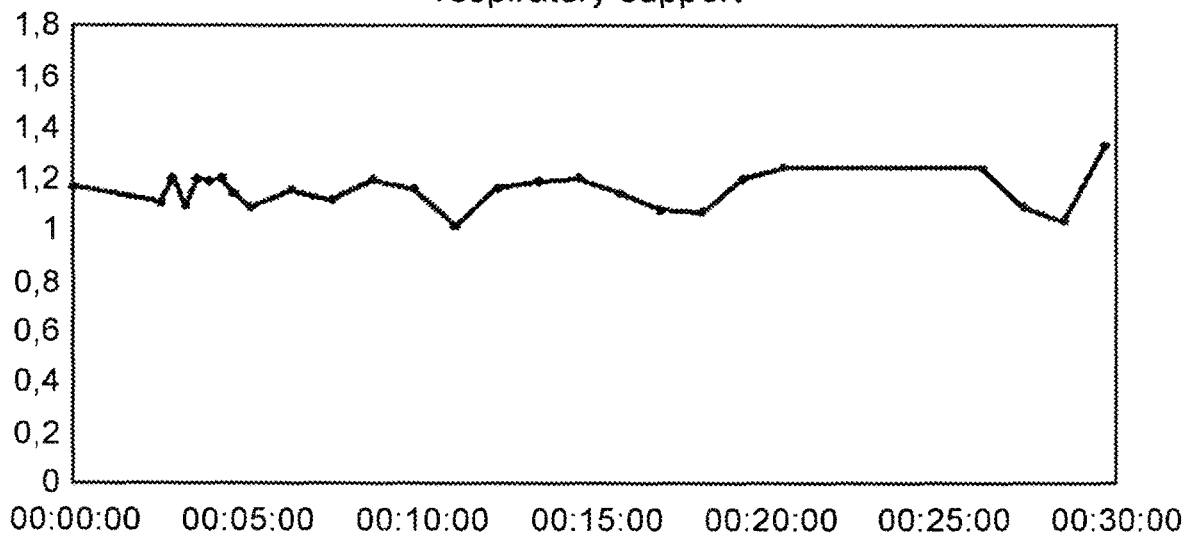
Figure 32C:
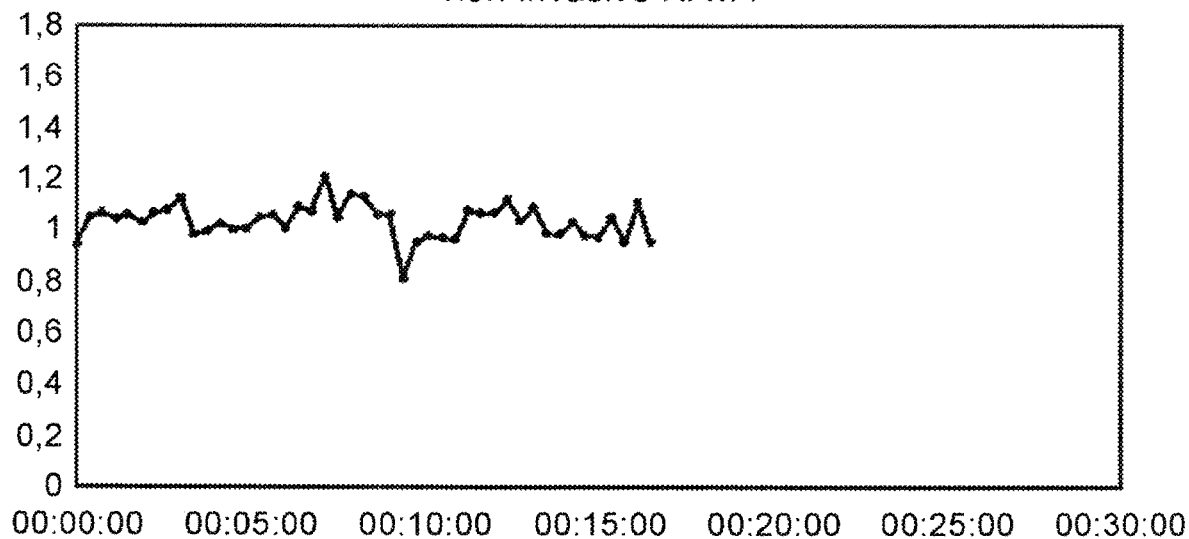
Figure 32D:
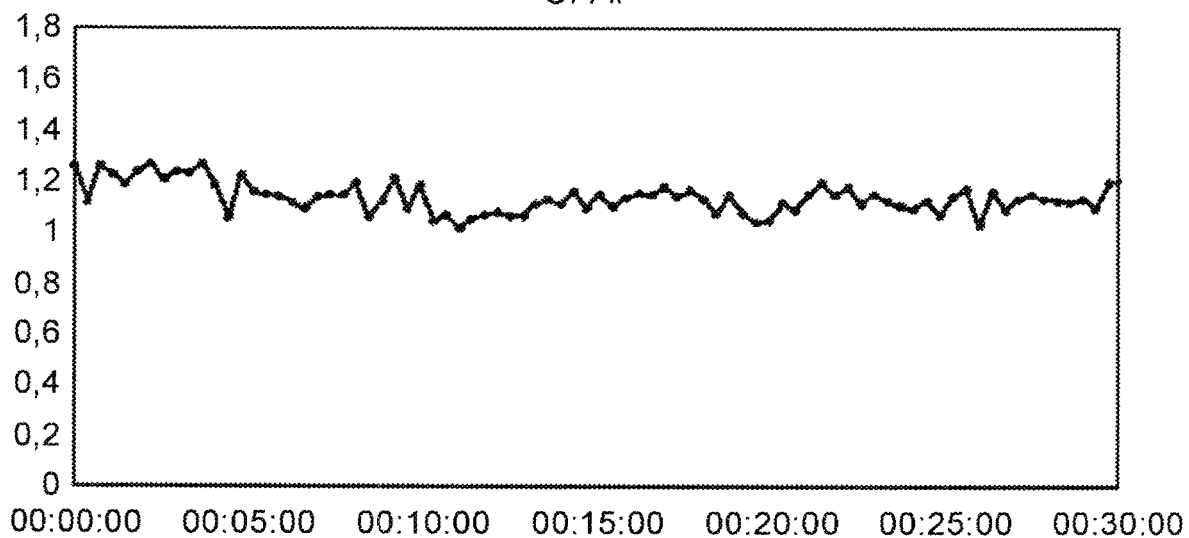
Figure 32E:
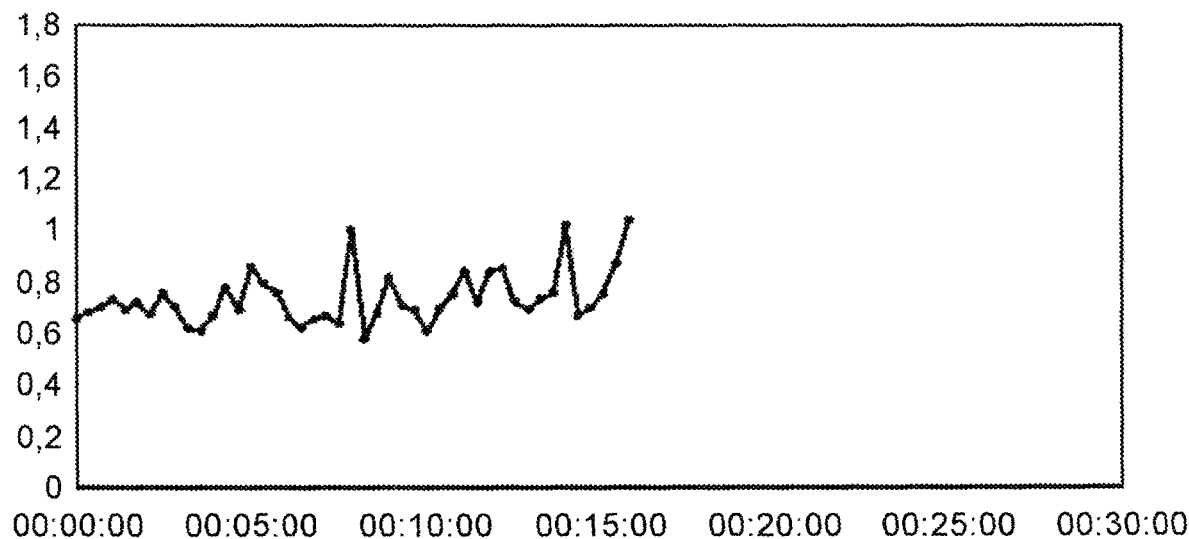
Figure 32F:
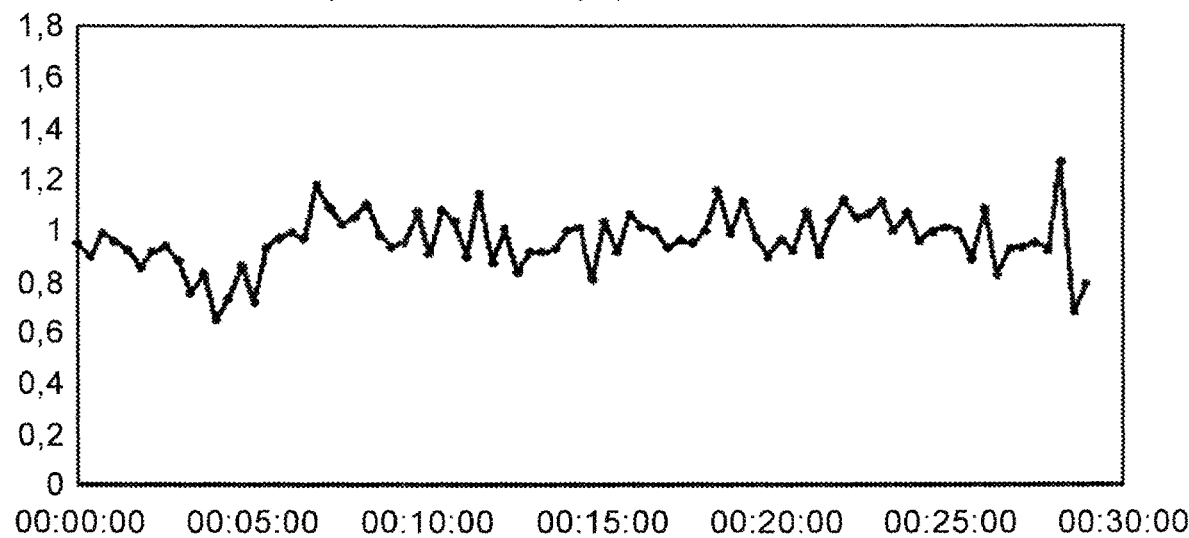
Figure 32G:
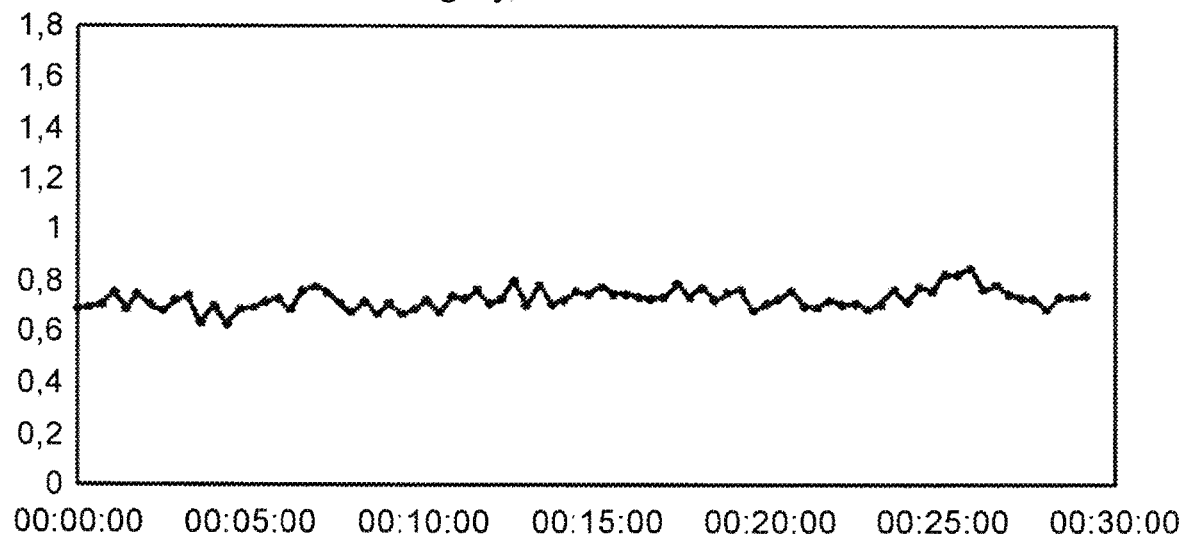
Figure 32H:
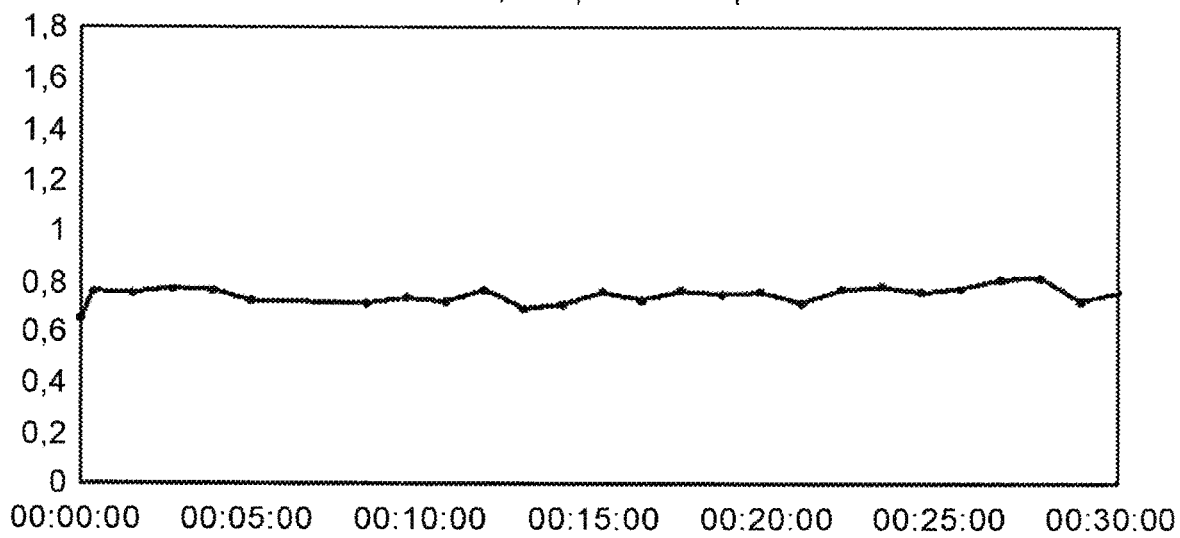

A trend curve was visualized based on multiple recordings as represented in FIG. 30 (FIG. 31). Each small circle represents one 7 second recording. Some recordings of 7 seconds had a 10 s pause between readings and some had a pause of 1 min. The upper chart shows traces of velocity measurements (maximum velocity, mean velocity and lowest velocity (end diastolic velocity VED)). The middle chart shows traces of heart rate and pulsatility index (which is a measure of vascular resistance). The lower chart shows the quality of the measurements, which in this case is close to 100% on every recording. FIG. 31 shows that reproducible readings of high quality may be obtained and would be capable of forming the basis of reproducible assessment of cerebral circulation in infant subjects. The infant was sleeping during the recordings and consequently the parameters where stable.

Example 2-Continual Monitoring of Cerebral Blood Flow in Neonatal Humans with Unfocused Doppler Ultrasound-Comparison with Conventional Ultrasound

BACKGROUND

There is a strong need for continuous cerebral circulation monitoring in neonatal care, because brain injury due to low or variable blood flow frequently complicates prematurity and critical illnesses in neonates. NeoDoppler is a novel, non-invasive method based on unfocused Doppler ultrasound (as described herein) which is designed to monitor cerebral blood flow continuously. By recording and analysing the cerebral circulation over time in different depths of the brain simultaneously, the timing of medical interventions can be optimised. The NeoDoppler probe is operator independent and can be gently fixed to the fontanel by a specially designed housing.

Objective

In this feasibility study, the general quality of the NeoDoppler measurements and the fluctuations of cerebral blood flow in neonates over time were investigated. Comparison with different protocols for cerebral blood flow monitoring was also made. The method was validated by comparing snap shot measurements of cerebral blood flow velocities (CBFV) obtained with NeoDoppler with measurements performed by conventional ultrasound.

Design/Method

Infants born at different gestational ages (GA) with a variety of diagnosis on admission to the Neonatal Care Unit (NICU) were included prospectively. The NeoDoppler probe was attached to the anterior fontanelle for a duration of three to four hours, and maximum velocity (Vmax), end diastolic velocity (ED), mean velocity (Vmean), pulsatility index (PI) and resistance index (RI) were recorded over time. Two different recording protocols were used: seven and 30 seconds of Doppler recordings, followed by breaks of ten and 30 seconds, respectively, followed by the next Doppler recording interval. The conventional ultrasound was performed using pulsed wave Doppler identifying one vessel at the corresponding depth as the NeoDoppler. The sample volume was placed exactly over this Results Ten infants, GA ranging from 24+6 to 40+2 weeks, and birth weights ranging from 615 to 4340 gram, were included. Clinical diagnosis ranged from extreme to moderate prematurity, gastroschisis and sepsis. The NeoDoppler curves were in general of high quality, and the method was shown to be able to provide cerebral blood flow data over time. FIG. 32 shows variation of PI over time in seven patients with the two different NeoDoppler protocols. The data were collected from recordings were the data quality were >90%, defined by the analysis system based on the quality of the Doppler curves. TI values are set to always be below 0.7.

The mean PI measured by conventional ultrasound shows good correlation with NeoDoppler after initial calibration and improvements of Doppler tracings. Examples of these paired measurements are shown in FIG. 37.

Conclusion

This feasibility study indicates that NeoDoppler can provide reliable and continuous data of high quality on cerebral blood flow in neonates at different gestational ages and with different clinical diagnoses. The data correlates well with data obtained via conventional ultrasound. However, measurements made with standard ultrasound at different depths have to be done sequentially, whereas with NeoDoppler measurements from different depths can be done at exactly the same time. By optimising medical interventions based on NeoDoppler, fluctuations in cerebral blood flow and hypoperfusion may be avoided during a very sensitive period of brain development.

Example 3-Analysis of Microvascular Circulatory Changes

Background

Microvascular physiological responses or endothelial functions as vaso-constriction or -dilatation and vasomotion, are well studied in healthy as well as in diabetic subjects. A range of non-invasive methods has been developed and is shown to adequately assess vasomotor responses. There are a number of potential devices and techniques that are in use to evaluate microcirculatory function, i.e. transcutaneous oxygen tension (TcPO), skin pulp blood flow (i.e. laser Doppler fluxometry), iontophoresis or capillaroscopy. These techniques, as of today, need further development to optimally cover their clinical purposes due to lack of standardization and official guidelines which results in large differences in methodology and reduces reproducibility and comparability between studies performed.

The present study was performed to compare and validate a novel flat unfocused ultrasound probe in accordance with at least some aspects of the invention (Earlybird) against already well-known clinical and laboratorial applicable devices intended for the analysis of microcirculatory changes, i.e. radial artery Doppler, laser Doppler fluxmetry and photoplethysmography. The device consists of one acoustic element. Over the whole area of the acoustic element the device can measure blood flow velocities in the small arteries feeding the arterioles and the arterioles themselves at depths ranging from 0.2 to 4.0 cm. The blood flow velocity was measured at the skin pulp and evaluates the microcirculation function in that vicinity. The probe is easy to use, more stable, user independent and cheaper to produce than already existing devices. It is therefore interesting to evaluate the flat unfocused ultrasound probe against already well-known devices designed for the analysis of microcirculatory changes due to different physiologic stimuli in healthy individuals.

Design/Method

In this study a novel flat unfocused ultrasound probe (Earlybird) was evaluated. Earlybird consists of three main parts: transducer, scanner and user interface. The transducer converts an electric signal burst into acoustic energy, which is transmitted into the patient, reflected and collected by the transducer. The pulse is ten wavelengths at the nominal frequency 7.8 MHZ, and it is transmitted at a rate of 8 kHz. The circular, single-element transducer (probe) is manufactured by Imasonic SAS (France). The material exposed to the patient is an epoxy resin, which is USP class VI approved. Between the probe and skin is a hydrogel standoff, with a thickness of three millimeter (HydroAid, Kikgel, Poland). The probe simultaneously records signals from 2 mm to 40 mm depth in slices perpendicular to the skin surface. This makes it possible to detect blood flow in all layers from skin to bone simultaneously. The probe is connected to an ultrasound scanner (generic OEM Manus EIM-A produced by Aurotech Ultrasound AS, Tydal, Norway). A computer is connected to the scanner using an Ethernet network cable, and is used as user interface and display. The data collected is showed in real time as a Doppler spectrum (Matlab, Mathworks, Massachusetts, U.S.A), stored to a disk and enabled for later re-examination. The ultrasound probe is not yet CE-marked but approved by Norwegian health authorities to be tested at volunteered patients and healthy individuals.

Ten healthy volunteers, six males, median age 39 years (range 18-64) participated in the test of the probe. Median BodyMassIndex (BMI) 23.5 (range 20.3-30.3). Two of the test persons use antihistamines (desloratidin 5 mg or cetirizinhydroklorid 10 mg). One person has a minor form of thalassemia without any complications. Prior to the examination, six persons had drunk coffee and two had drunk tea.

All tests were performed in one session and took place in a study room with a room temperature between 23-26° Celsius. Lightning was dimmed. The participants were comfortably clothed. The measurements were done with the test persons in supine position in a bed with the head slightly elevated. The bed was draped with a warming blanket. The test persons achieved a normo-temperature-state.

A well-equipped vascular physiological laboratory was used. Several simultaneous recordings were performed. A standard three diverted ECG and mean arterial blood flow velocity ($cm \cdot sec^{-1}$) in the right radial artery (except in one person were the left radial artery was used) was recorded with a 10 MHz pulsed Doppler probe (SD-50; GE Vingmed Ultrasound, Horten, Norway). Continuous blood pressure was recorded as finger arterial pressure recordings by a photoplethysmographic volume-clamp method (Finometer; FMS Finapres Medical Systems BV, Amsterdam, The Netherlands). Skin pulp blood flow was measured with laser Doppler fluxmetry (LDF; Periflux PF 4000; Perimed AB, Jarfalla, Sweden) and with photoplethysmography (PPG; STR Teknikk, strteknikk.no, Aalesund, Norway). Respiration motion was recorded by nostril temperature sensors detecting in- and out-flow (STR Teknikk, strteknikk.no Aalesund, Norway). Heart rate was derived from the ECG. All data were assessed simultaneously and recorded at 1000 Hz in LabChart (ADINSTRUMENTS, Dunedin, New Zealand).

Each subject successively recorded a five minutes baseline and four different test protocols, each protocol repeated twice; (1) forced respiration, (2) static handgrip exercise, (3) valsalva manoeuvre and (4) cold pressor test. Between each protocol a sufficient pause was held for the subject to recover completely. The baseline recording was performed while the subject was resting at comfortable bed in a quiet room for five minutes.

1: While executing the forced respiration test the subjects inhaled or exhaled on the command of an instructor. The test started with 30 seconds of rest with normal breathing, followed by a cycle of 60 seconds with forced respiration with sequences of 4 seconds of inhalation and 4 seconds of exhalation. At the end the subject was asked to breath normally for an additional 30 seconds.
2: Before starting the static handgrip exercise the subjects were familiarized with the equipment. A test of maximum contraction on the handgrip dynamometer was performed and the highest produced forced was noted. The subjects were able to visually control the force and were instructed to hold a 50% of their maximum force during the test period. The static handgrip exercise recording consisted of 30 seconds of rest, 60 seconds of 50% of maximum produced force, followed by 30 seconds of rest.
3: The valsalva test started with 30 seconds of normal breathing. The subjects then followed a total cycle of 60 seconds containing of two sequences of 15 seconds of valsalva manoeuvre and 15 seconds of rest. The valsalva maneuver was performed as a maximal expiratory effort maintained against closed airways. Intrathoracic pressure was not measured during the exercise. The protocol ended with 30 seconds of normal breathing.
4: The cold pressor test was performed by immersing the left hand in ice-water for the scheduled time. The test started with recording of 30 seconds of rest with the left hand by the side of the test person. The left hand, contralateral to the hand equipped with the recording equipment, was then lowered into a combination of ice and water for 60 seconds, followed by 30 seconds of recording while the hand was left to rest in room temperature.

Figure 33A:
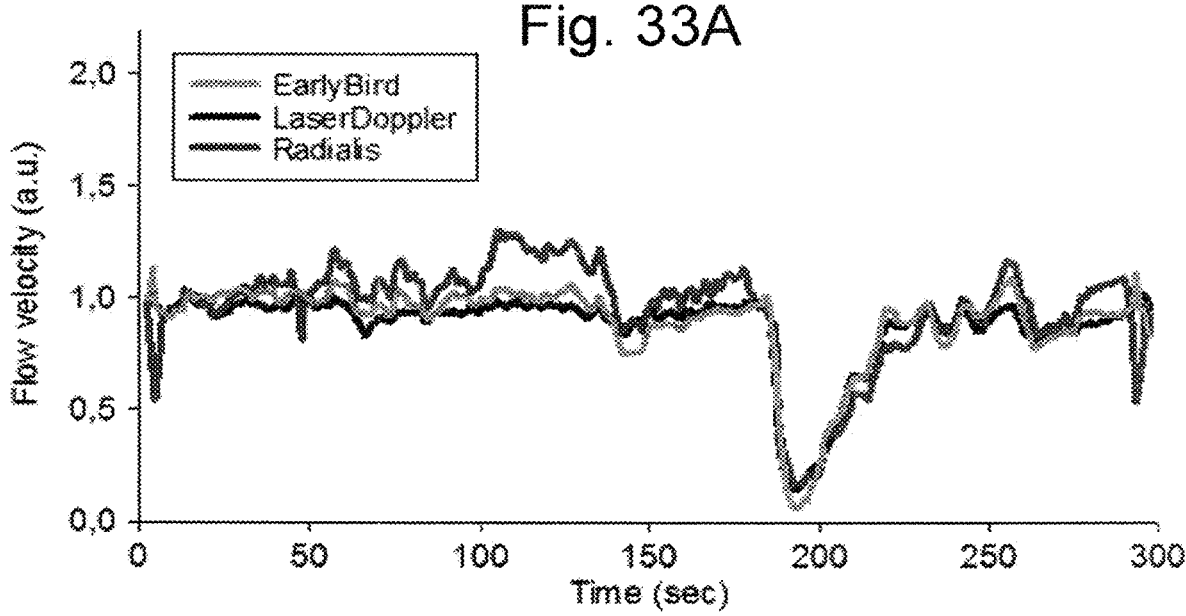
FIGS. 33a and 33b are graphs of flow velocity in the radial artery of a test subject taken every 5 minutes using laser Doppler fluxometry, pulse-Doppler and unfocussed ultrasound Doppler recordings and the correlation between the laser Doppler fluxometry and unfocussed ultrasound Doppler recordings.
Figure 33B:
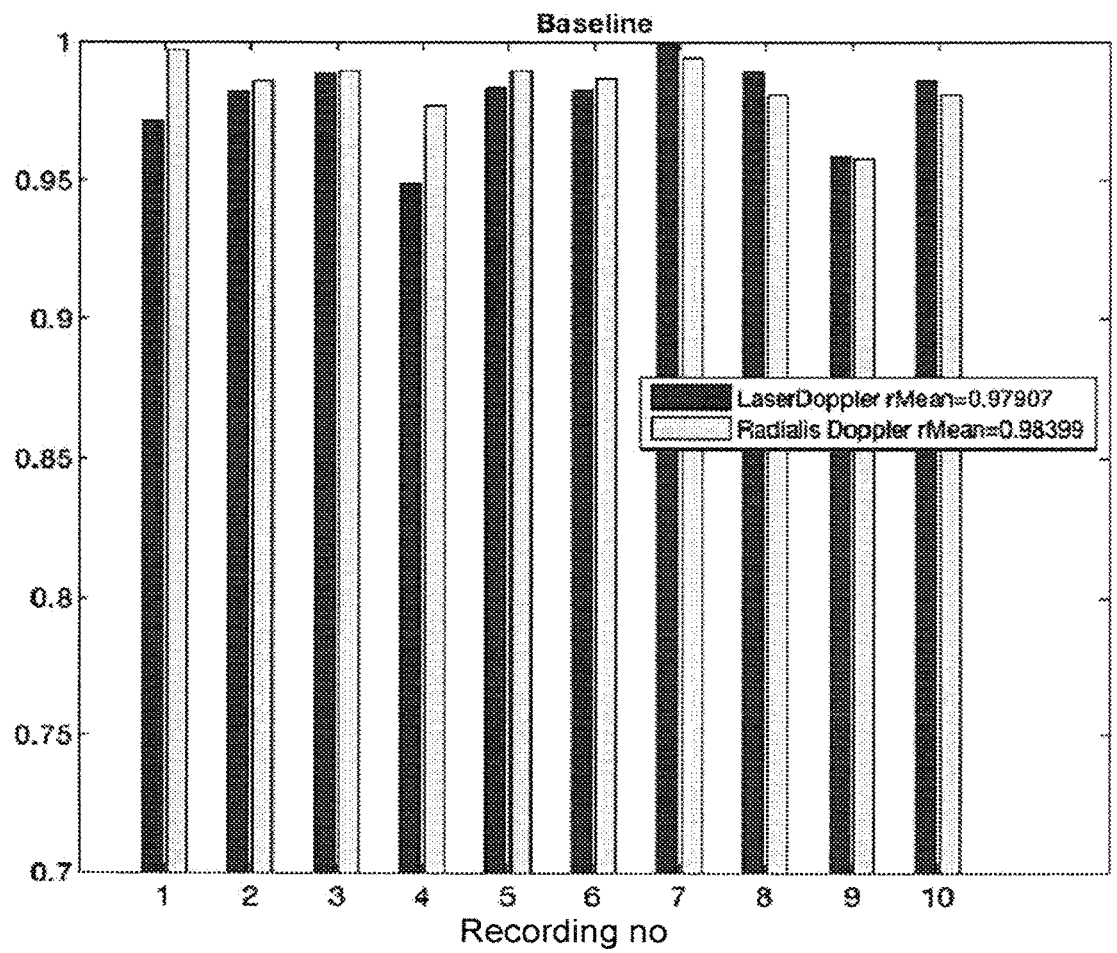
Figure 34:
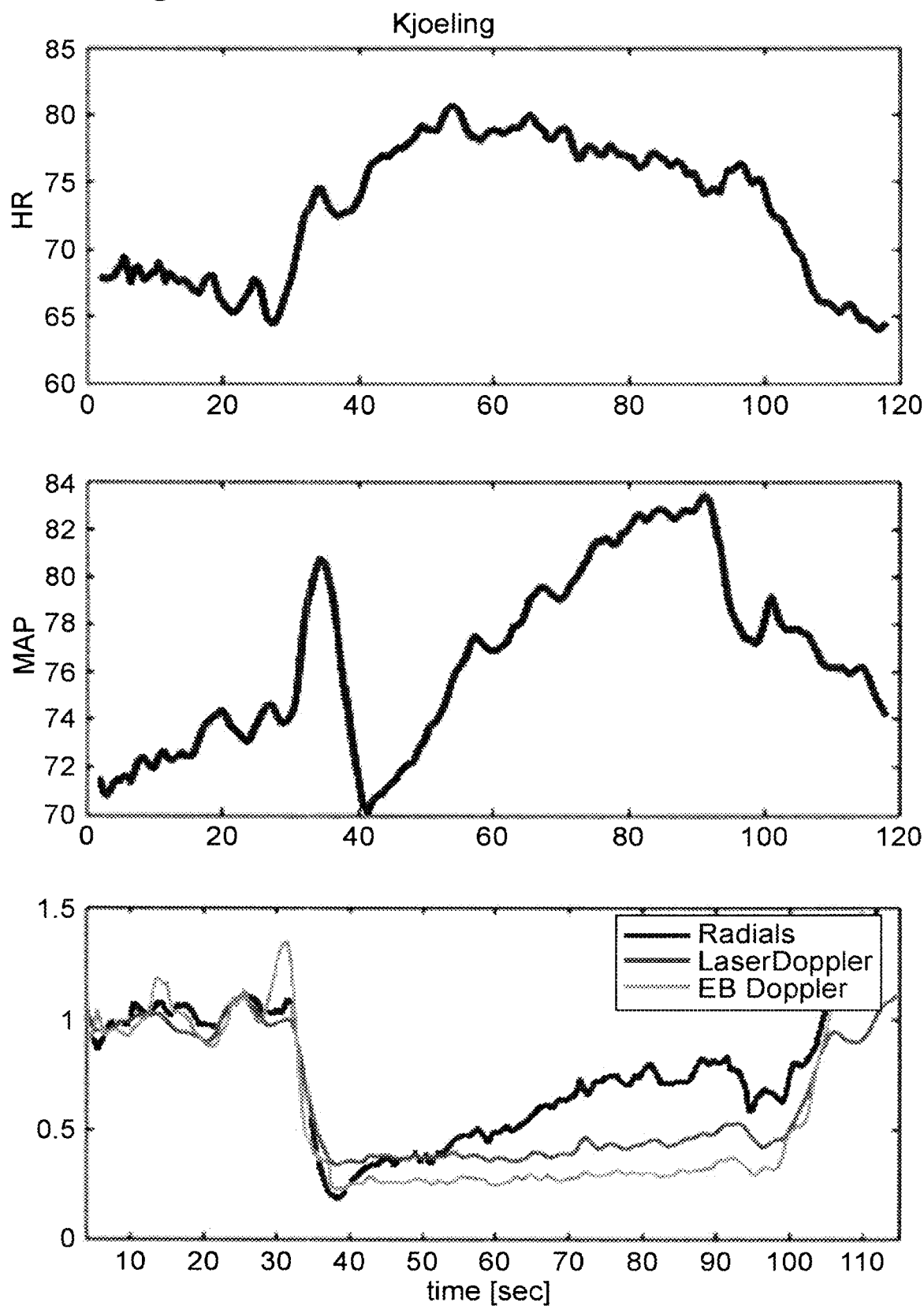
FIG. 34 shows Dresponse curves for HR, MAP, Doppler flow of the radial artery, skin pulp blood flow measured with laser Doppler fluxometry and unfocussed ultrasound Doppler upon cold induction test.

All data recordings from Labchart were combined and synchronized with the Doppler flow curves from the novel unfocused ultrasound probe (Earlybird) recorded in MatLab. The mean values for all of the test subjects were pooled. The data were normalized. Curves were then plotted in SigmaPlot version 13.0. Correlation between the different curves were calculated for each recording, Results Baseline readings of flow velocity in the radial artery were taken every 5 minutes using each technique (Earlybird, laserDoppler fluxometry and pulse-Doppler recordings). An example of baseline recordings from subject 7 is shown in FIG. 33a. Correlation was 0.97 (range 0.9-1.0) (FIG. 33b). FIG. 34 shows response curves upon cold induction test (HR, MAP, Doppler flow of the radial artery, skin pulp blood flow measured with laser Doppler fluxometry and EarlyBird Doppler).

As can be seen, the novel flat unfocused probe (EarlyBird) is capable of detecting vasomotion and vasomotor response upon different physiological stimuli at least as well as other comparable devices.

Example 4-Analysis of Blood Flow in the Peripheral Circulation of Subjects with Sepsis

BACKGROUND

When sepsis is suspected, as a complication in a patient with assumed infection and blood-stream-infection (BSI), the sepsis diagnosis is based on clinical and biochemical observations occurring relatively late during sepsis development. It is however recognised that the earlier diagnosis of sepsis can be made, the earlier intervention may be started, and this leads to a greater likelihood of a successful outcome.

The Sepcease-Doppler is based on the same unfocused ultrasound technology and principles as described for EarlyBird above and may be applied to any patient admitted to the health care system, to examine micro-circulatory blood flow patterns. Its primary purpose is to distinguish pathologic blood flow patterns in case of sepsis, from normal microcirculatory conditions in case of less grave infections, thereby providing a means to differentiate sepsis patients early in the progression of the condition. Likewise, it may be used to track a sepsis patient's response to treatment.

The apparatus is small and lightweight. It may be fastened by rubber band and an ultrasound-transparent adhesive pad, e.g. to the inside or the back of the hand of a patient, where we easily find small arteries and pre-capillary arterioles regulating microcirculation of the hand. In this area the measurements will not be disturbed by blood flow velocities of larger arteries. Its light weight and miniaturized size does not disturb the patient more than any medium-sized bandage around the hand. The typical in-hospital setting is examination of the patient at the emergency room, at the ward or in any high dependency unit (HDU) or the intensive care unit (ICU).

Design/Method

Ten healthy volunteers with no cardiovascular disease and aged between 18 and 40 years were recruited. All blood flow measurements were conducted during rest, in supine position, and the following parameters were all within normal range: respiratory rate, systemic blood pressure, blood oxygen saturation.

Blood flow velocities and blood flow patterns were analysed with apparatus in accordance with the invention from the smallest available arteries/arterioles at the tip of the second finger or the thumb, and then from gradually larger arteries at the wrist, elbow, cheek. It was clear that all samples from larger arteries, i.e. proximal of the wrist, were dominated by high velocities, clearly not originating from pre-capillary vessels of the microcirculation.

4 patients with septic shock were recruited. Blood flow velocities and blood flow patterns were analysed with apparatus in accordance with the invention from the smallest available arteries/arterioles at the tip of the second finger or the thumb. General clinical like data was also recorded (respiratory rate, systemic blood pressure, blood oxygen saturation).

Results

Figure 35:
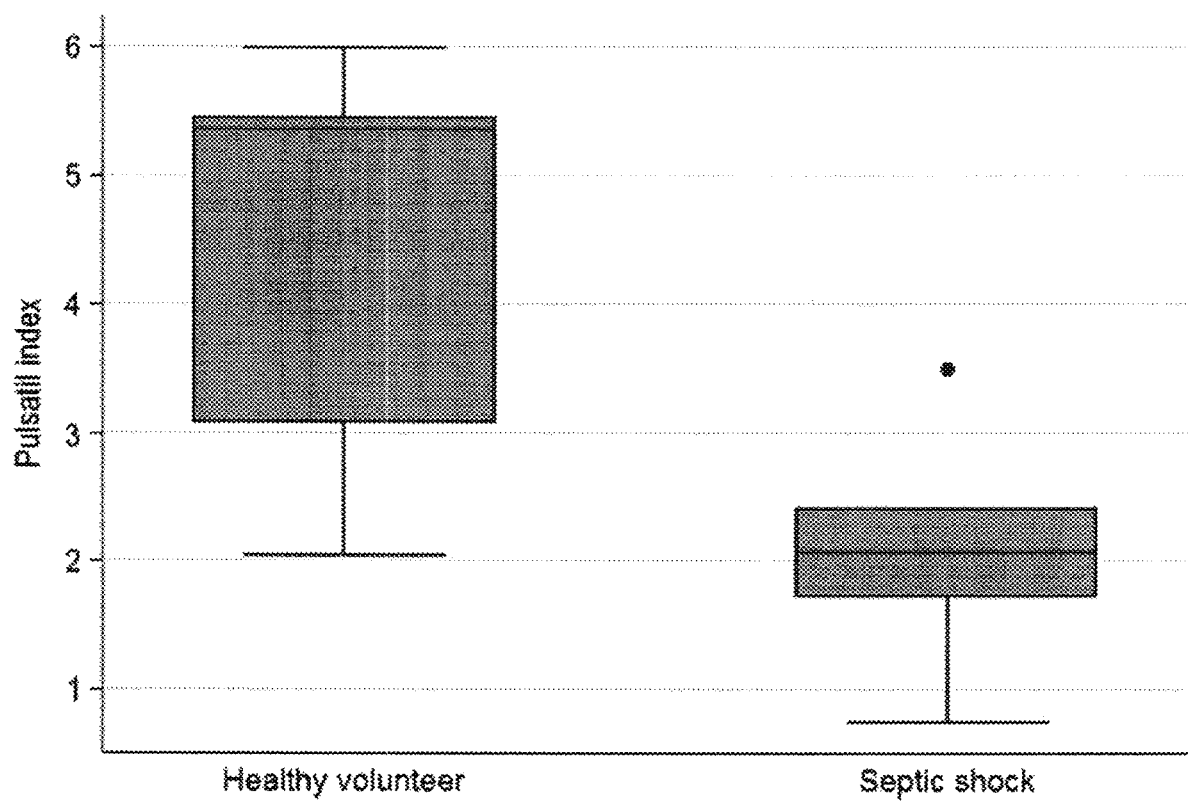
FIG. 35 shows PI from the smallest available arteries/arterioles at the tip of the second finger or the thumb in patients in septic shock and healthy patients.

As shown in FIG. 35 the patients with sepsis are significantly different from the healthy subjects.

Discussion

Sepcease is capable of distinguishing patients with sepsis from healthy subjects at least by differences in PI measurements from finger tips. Patients admitted to the emergency unit with suspected serious infection will be monitored with Sepcease in accordance with at least some aspects of the invention and will then be followed up at the ward or the ICU/HDU, to confirm that Sepcease is an accurate predictor of sepsis and to identify how early Sepcease is able to distinguish patients developing sepsis from those which are not.

Figure 36:
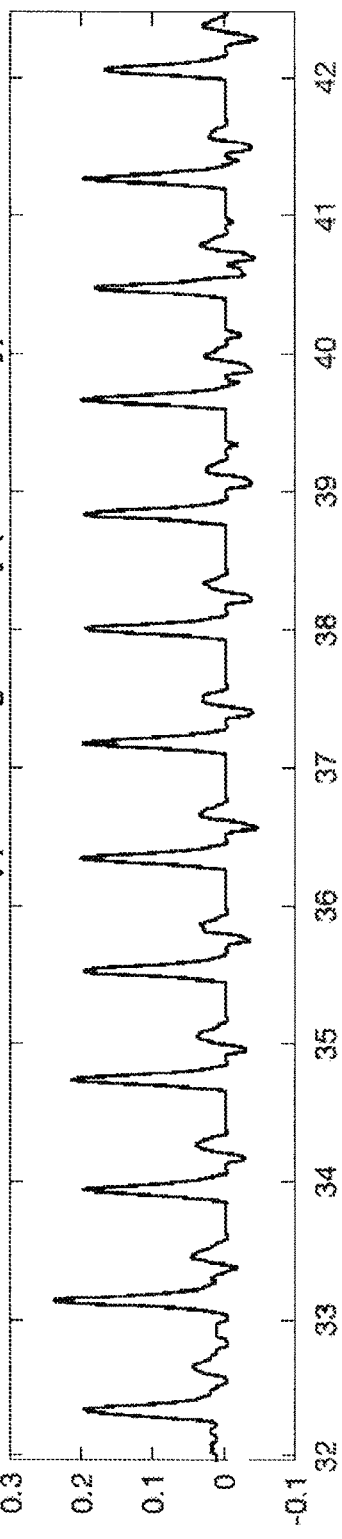
FIG. 36 shows peripheral blood flow during constriction of the arterioles in the fingers of patients undergoing a cold pressor test recorded with 3 different techniques: 1) conventional Doppler measuring blood flow in the radial artery in the lower arm; 2) unfocused Doppler ultrasound in accordance with the invention measuring flow in arterioles and small arteries feeding the arterioles of the finger from at least 2 mm depth; and 3) laserDoppler measuring microcirculation in a thin layer of the skin within 2 mm of the surface.
Figure 36:
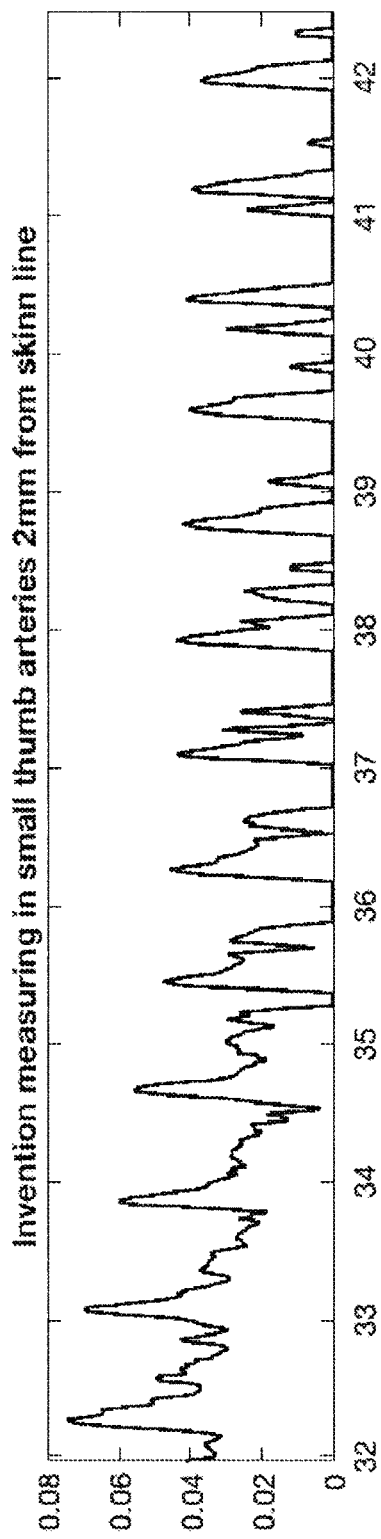
Figure 36:
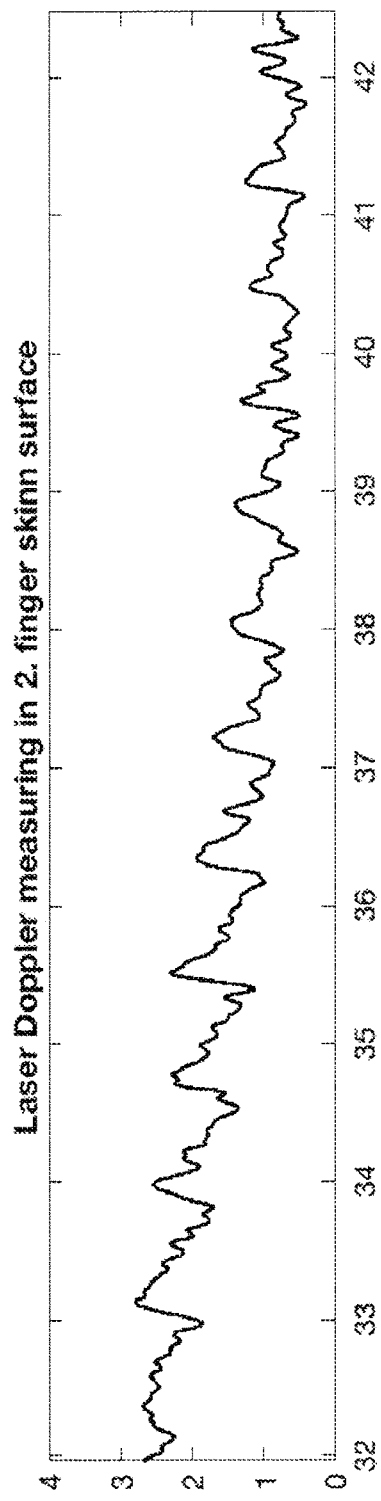
Figure 37A:
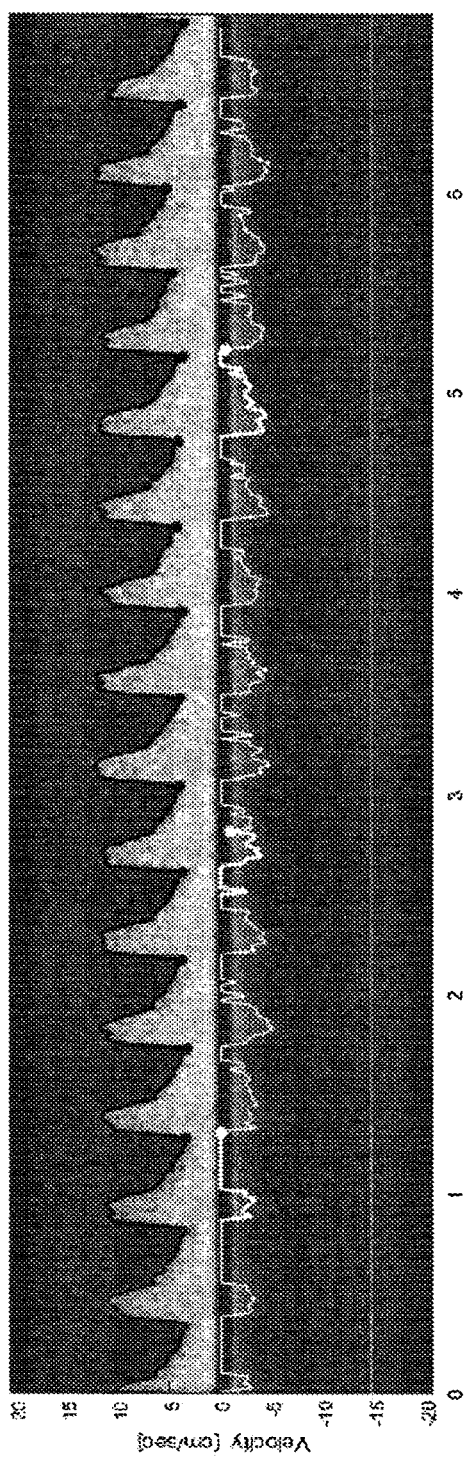
FIG. 37 shows Doppler traces from the brain of a human infant using ultrasound in accordance with the invention (37a and 37c) and conventional, pulse wave Doppler ultrasound (37b and 37d) at 15 mm (37a and 37b) and 10 mm (37c and 37d).
Figure 37B:
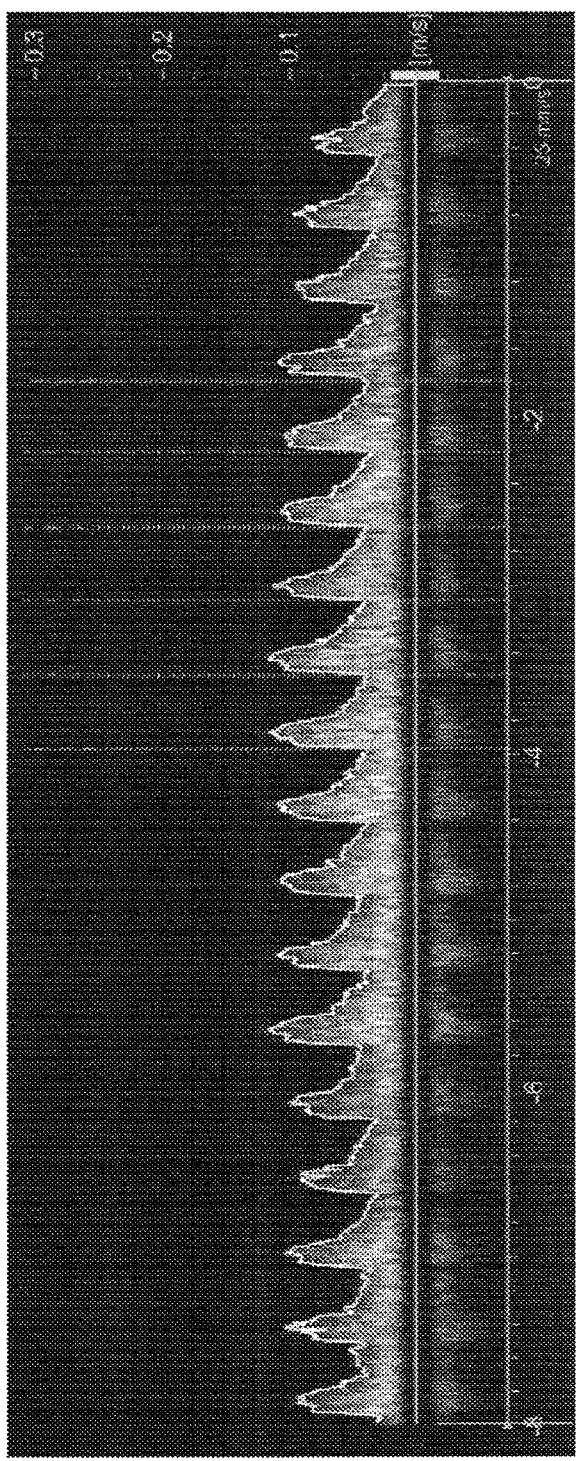
Figure 37C:
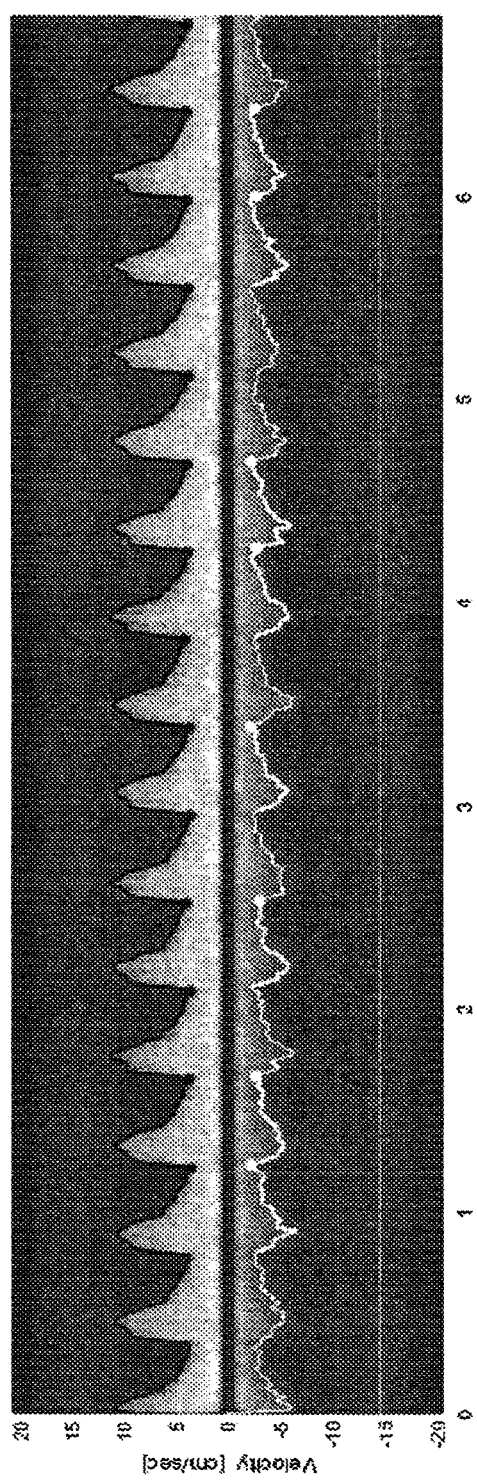
Figure 37D:
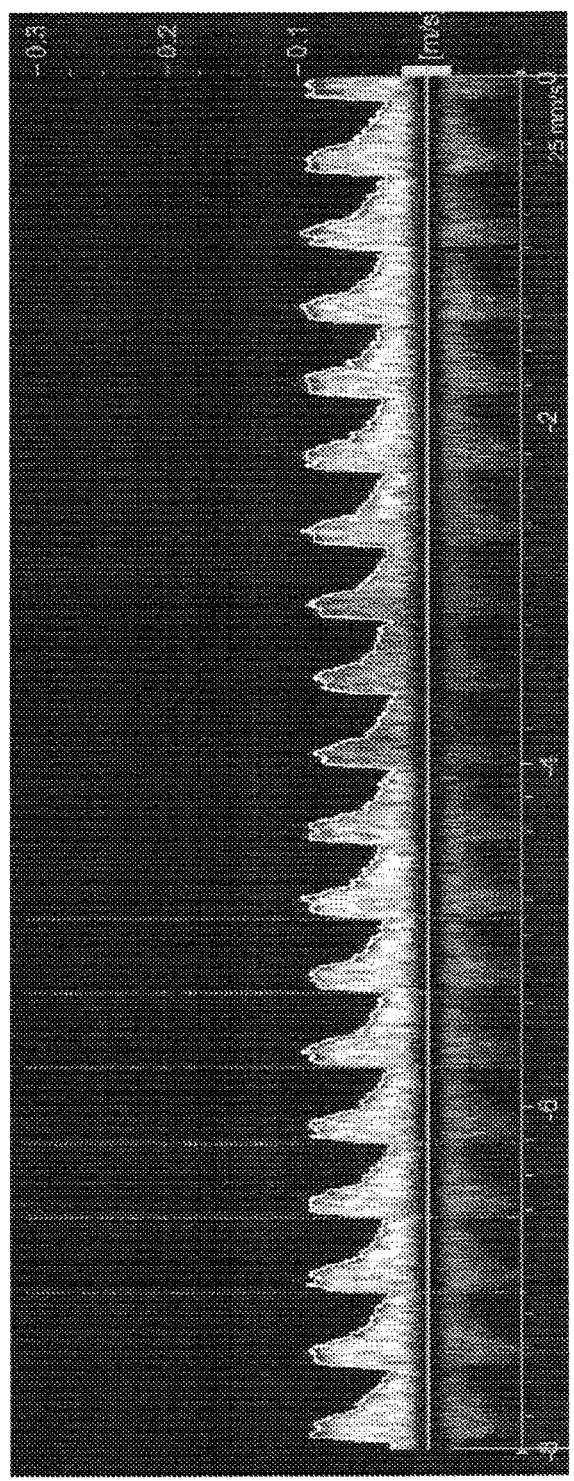
Figure 38A:
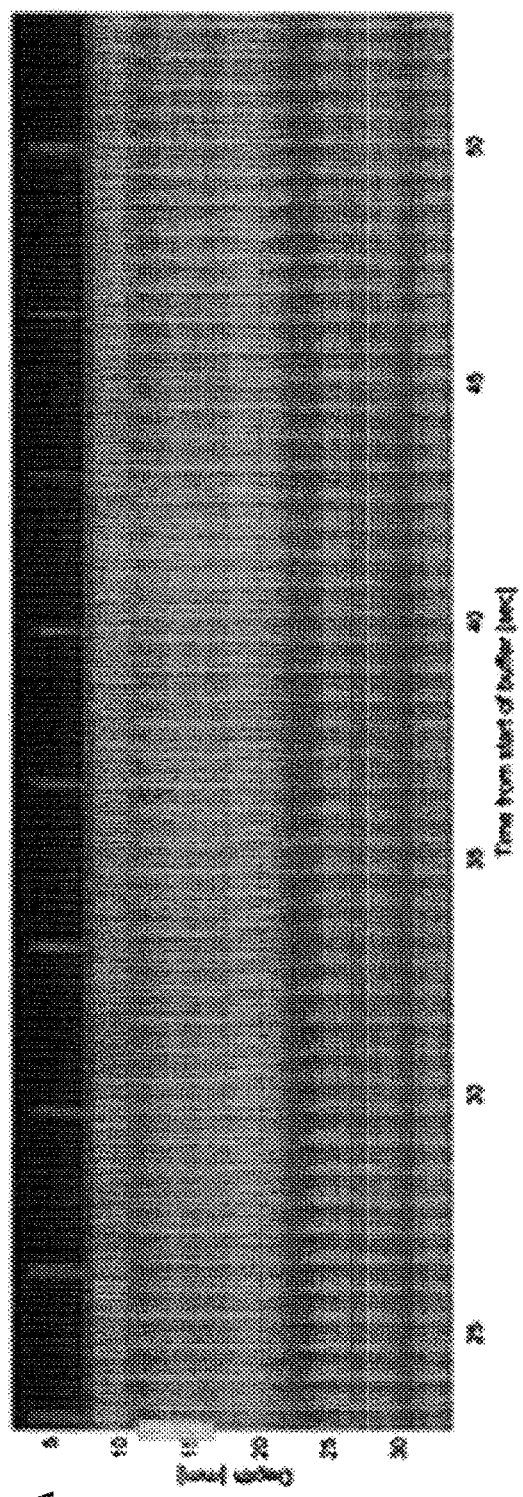
FIG. 38 shows screenshots of a display output from an unfocused ultrasound scanning system embodying the invention showing combined Doppler signals obtained from a range of depths (approx. 5-35 mm) (A) and simultaneous velocity traces obtained from different sub-ranges within that range (B-F) from the brain of a haemodynamically stable infant patient with asphyxia during rewarming following hypothermic therapy. The velocity traces at all selected sub-ranges show low frequency flow oscillations.
Figure 38B:
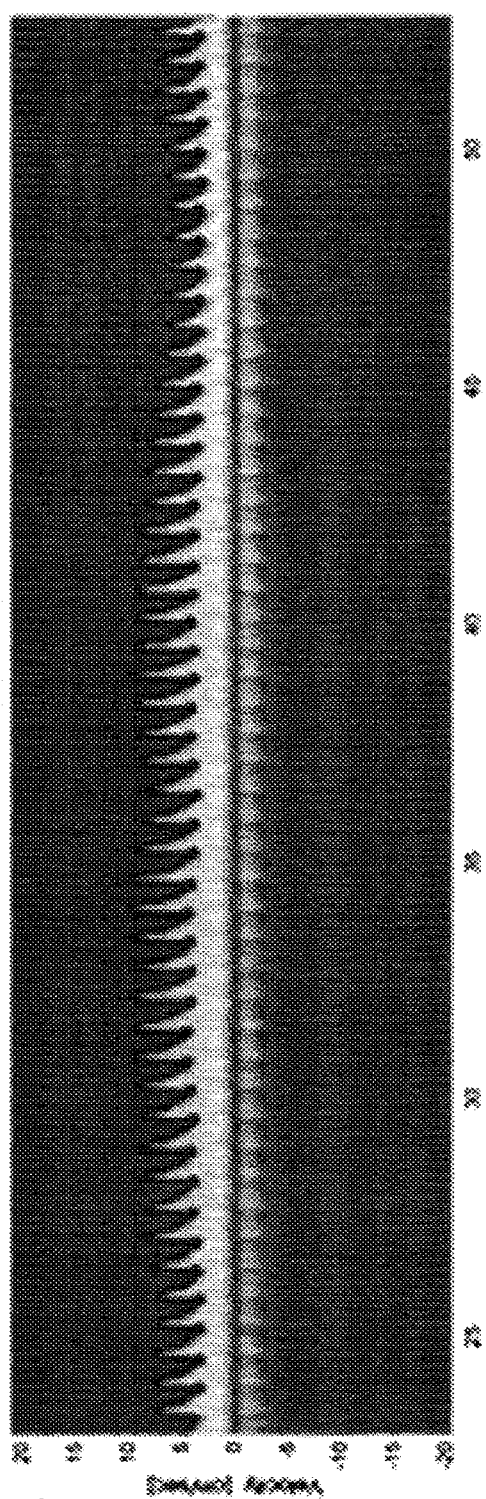
Figure 38E:
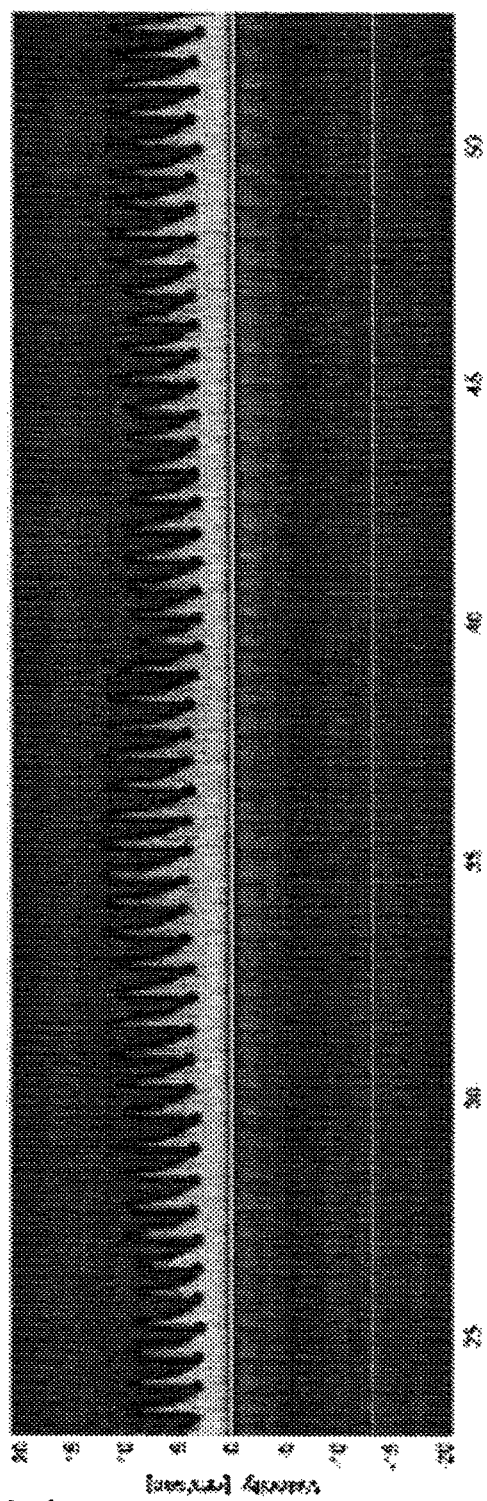
Figure 38F:
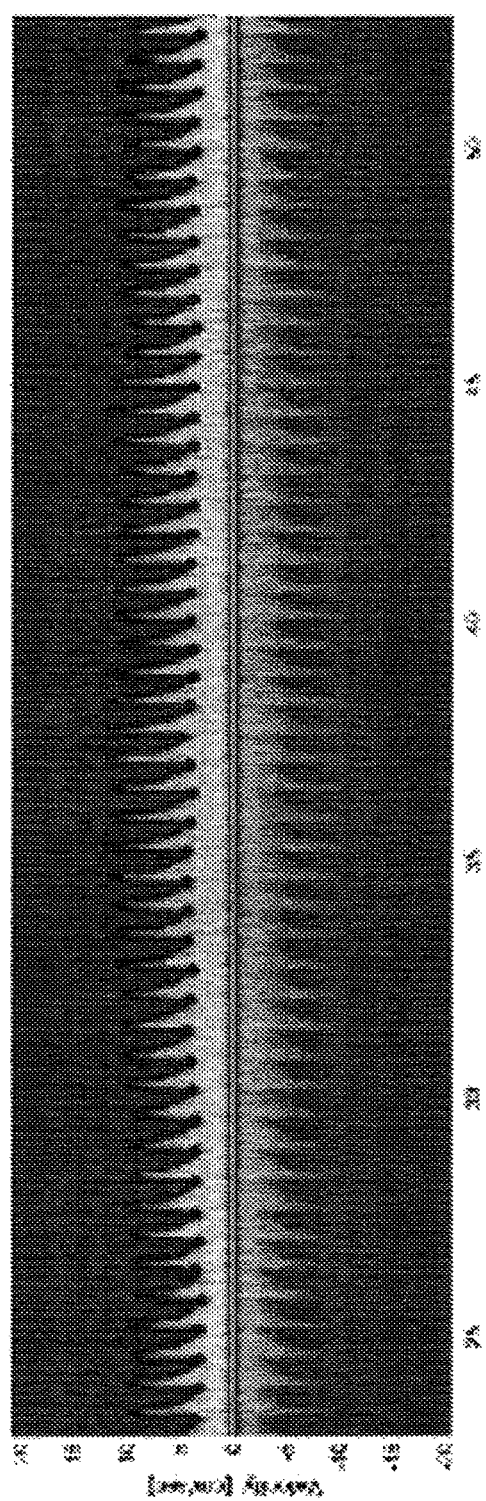

Example 5-Analysis of Blood Flow in the Peripheral Circulation of Healthy Subjects Undergoing Cold Pressor Test-Comparison of Analytical Techniques The monitoring of blood flow in the small arteries feeding the microcirculation using unfocused Doppler ultrasound in accordance with at least some aspects of the invention provides useful blood flow characteristics of the microcirculation which are not seen with conventional techniques (FIG. 36).

In this example, peripheral blood flow during constriction of the arterioles in the fingers of patients undergoing a cold pressor test (as described in Example 3) were recorded with 3 different techniques: 1) conventional Doppler measuring blood flow in the radial artery in the lower arm; 2) unfocused Doppler ultrasound in accordance with the invention measuring flow in arterioles and small arteries feeding the arterioles (arterial microcirculation) of the finger from at least 2 mm depth; and 3) laserDoppler measuring microcirculation in a thin layer of the skin within 2 mm of the surface.

Results are shown in FIG. 36. Reduction in flow is evident for all three measurements, however, the mid panel (unfocused Doppler) shows a characteristic change in waveform occurring from timepoint 35 sec (initiation of cold pressor), indicating an oscillatory collapse in the tone of the arterioles. Thus the invention provides greater and more useful information on the characteristics of microcirculation in response to stimulus.

Example 6-Continual Analysis of Cerebral Blood Flow in Neonatal Humans with Unfocused Doppler Ultrasound Ultrasound apparatus as described herein was used to obtain continuous pulse Doppler measurements from the cerebral circulation of test subjects via the anterior fontanelle. FIGS. 38-44, 49 and 50 show sample recordings from each subject.

FIG. 38 shows results from a patient (gestational age—41+6; birth weight—4270 g; medication-clonidine, dopamine, gentamycin and penicillin) with asphyxia during rewarming following hypothermic therapy. Patient was monitored over 6 hours with rising temperature from 33.3-36.2° C. This patient was circulatory stable, with stable blood pressure.

Arterial blood flow velocity was monitored at a variety of depth ranges simultaneously. At all depths analysed stable low frequency oscillations in blood flow velocity were observed.

This result suggests that the ultrasound system of the invention has advantages over conventional Doppler monitoring techniques because it means that it may be possible for clinically useful readings to be obtained from a comparatively wide range of target regions (i.e. any region containing one or more of various central cerebral blood vessels) rather than requiring a specific vessel to be accurately located and analysed. This in turn may mean that the ultrasound system of the invention may be used by operators which are not as highly trained as those required to operate conventional Doppler ultrasound and/or makes the system of the invention more amenable to automation.

Figure 39A:
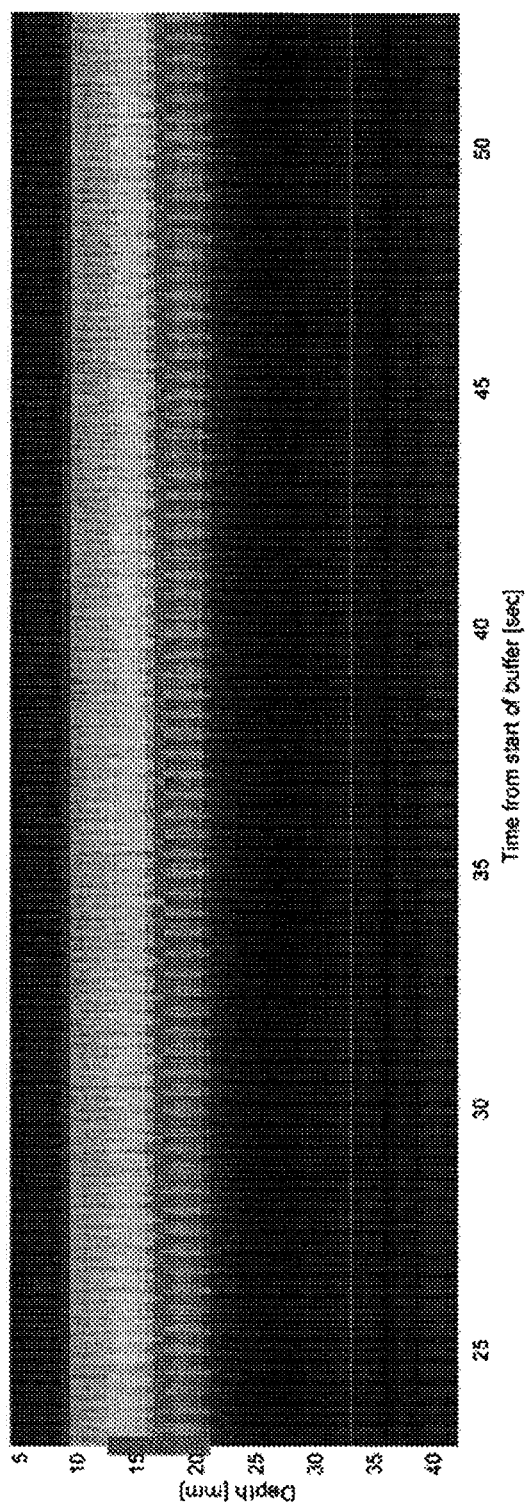
FIG. 39 shows screenshots of a display output from an unfocused ultrasound scanning system embodying the invention showing combined Doppler signals obtained from a range of depths (approx. 5-40 mm) including venous flow at approx. 12-16 mm (light grey) and arterial flow at approx. 16-21 mm (dark grey) (A) and a velocity trace from signals obtained from a depth range of approx. 12-21 mm (B) from the brain of a haemodynamically unstable infant patient with asphyxia during rewarming following hypothermic therapy. The arterial velocity trace shows no evidence of low frequency flow oscillations. In the original colour traces venous flow was shown in blue and arterial flow was shown in red.
Figure 39B:
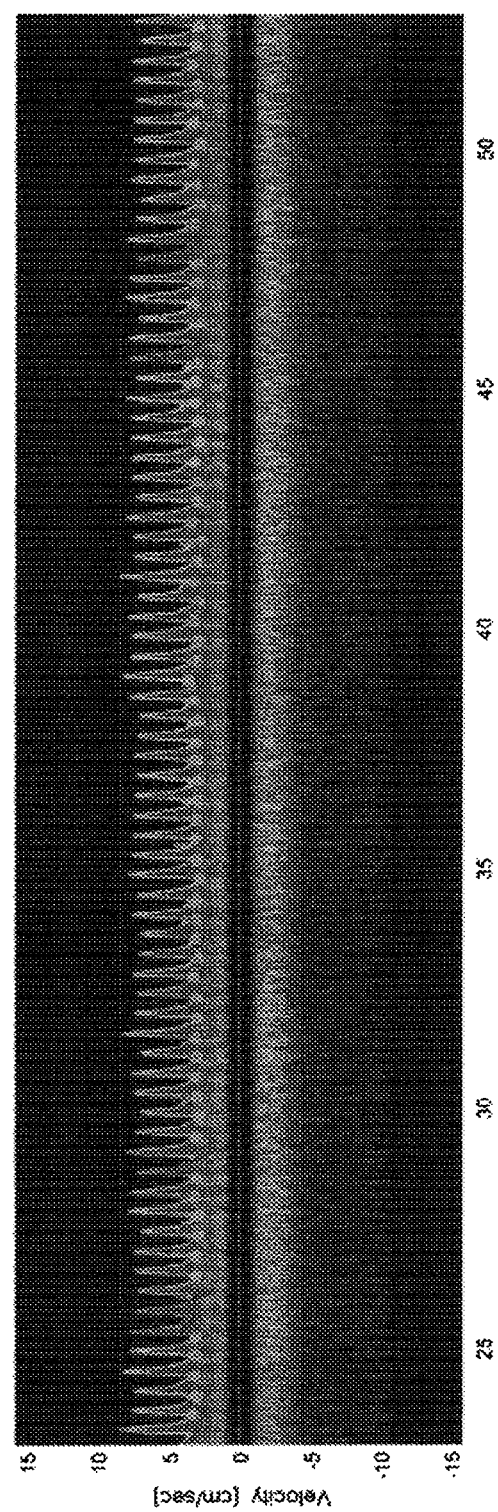

FIG. 39 shows results from a patient (gestational age—42+1; birth weight—4185 g; medication—antibiotics, fentanyl, clonidine, dopamine) with asphyxia during hypothermic therapy. This patient was haemodynamically unstable with low blood pressure (mean arterial pressure—21 mmHg).

Both venous and arterial blood flow velocity was monitored concurrently. Nearly no low frequency oscillations in the arterial flow were observed.

As can been seen the medically stable subject showed pronounced low frequency oscillations in arterial flow velocity over the course of the recordings. In contrast, the velocity profile of the critically ill subject is consistent over the course of the recording.

Figure 40A:
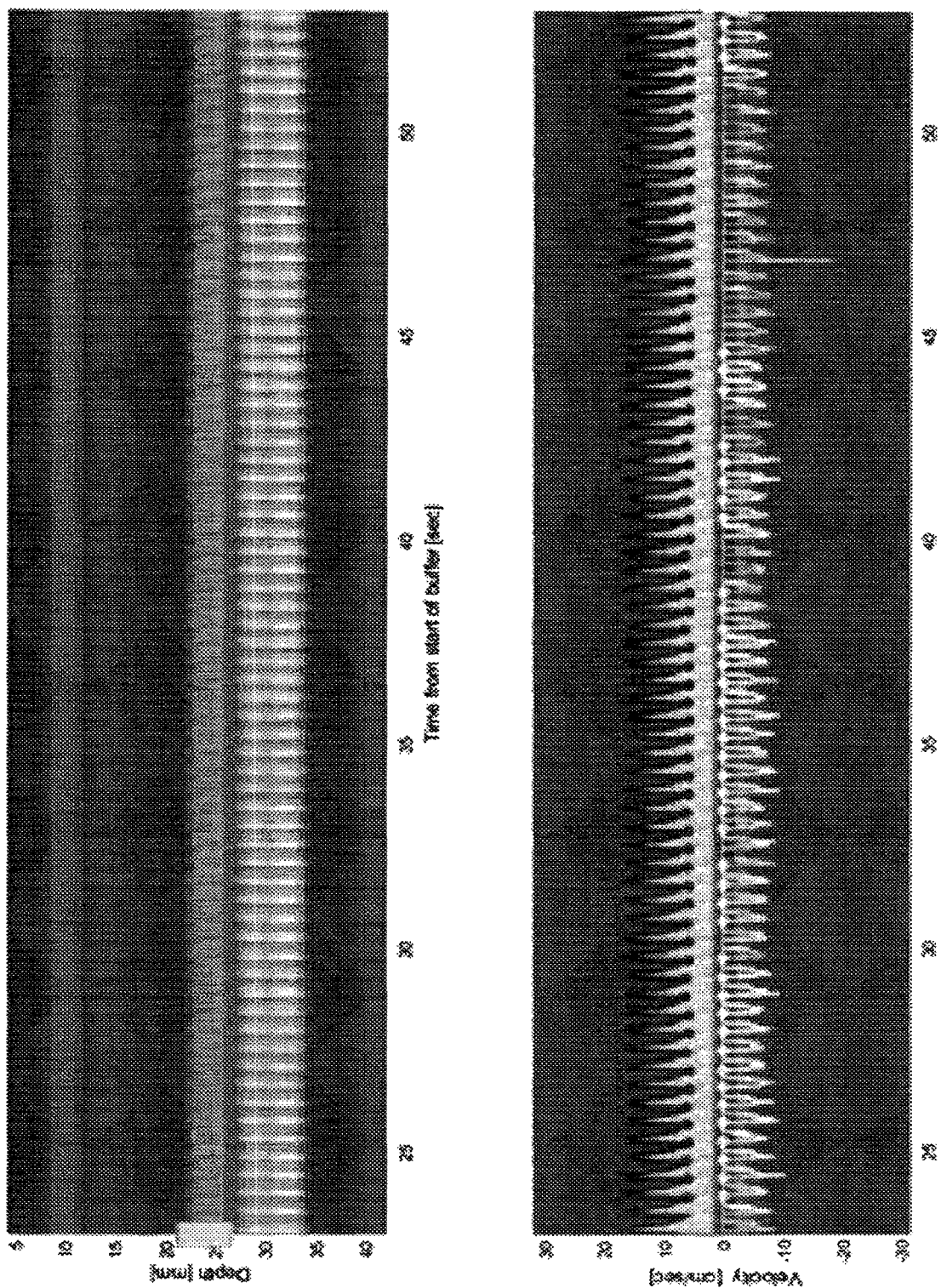
FIG. 40 shows screenshots of a display output from an unfocused ultrasound scanning system embodying the invention showing combined Doppler signals obtained from a range of depths (5-40 mm) and a velocity trace from signals obtained from a depth range of approx. 22-26 mm from the brain of a haemodynamically very unstable premature infant patient with E. coli sepsis (A); a graphical representation of the positive flow velocity trace (B); and the results of a Fourier transformation of the positive velocity trace (C). Fourier transformation revealed the patient's heart beat as the only significant frequency component in the flow velocity trace.

FIG. 40 shows results from a premature neonatal patient (gestational age-35+1; postmenstrual age-35+3; birth weight—2895 g; medication-antibiotics, dopamine) with *E. coli* sepsis and very unstable circulation after surgery for gastrochisis.

Fourier transformation revealed the patient's heart beat (135 bpm) as the only significant frequency component in the arterial flow velocity trace.

Figure 41A:
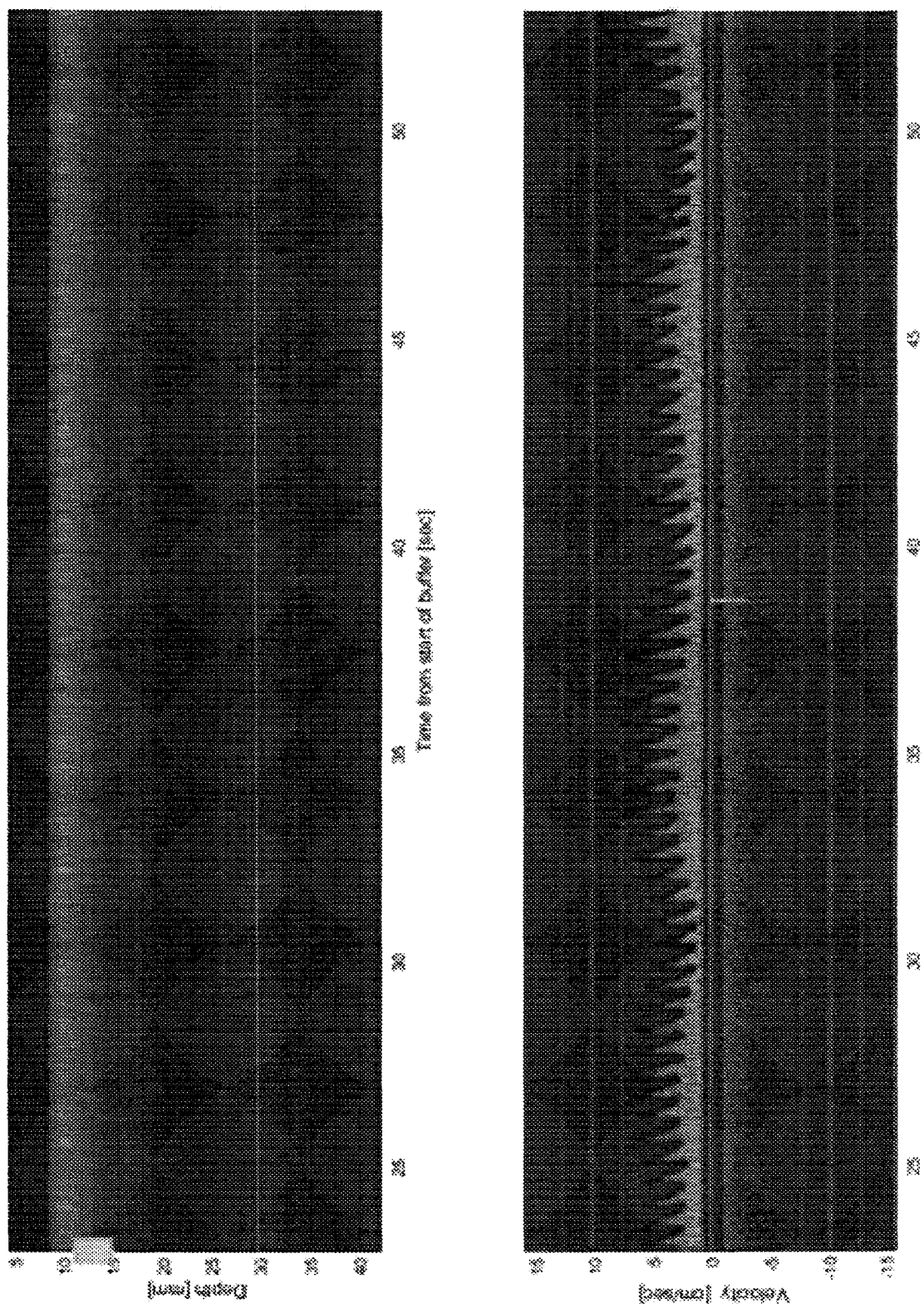
FIG. 41 shows screenshots of a display output from an unfocused ultrasound scanning system embodying the invention showing combined Doppler signals obtained from a range of depths (approx. 5-40 mm) and a velocity trace from signals obtained from a depth range of approx. 12-15 mm from the brain of a haemodynamically stable full term infant patient with infection but not sepsis 12 hrs after initiation of antibiotic therapy (A); a graphical representation of the positive flow velocity trace (B); and the results of a Fourier transformation of the positive velocity trace (C). Fourier transformation revealed a frequency component representing the patient's heart beat and one other frequency component in the flow velocity trace at around 5 bpm which possibly represents normal (healthy) cerebral blood flow oscillations of a brain with intact cerebral haemodynamic autoregulation.
Figure 41B:
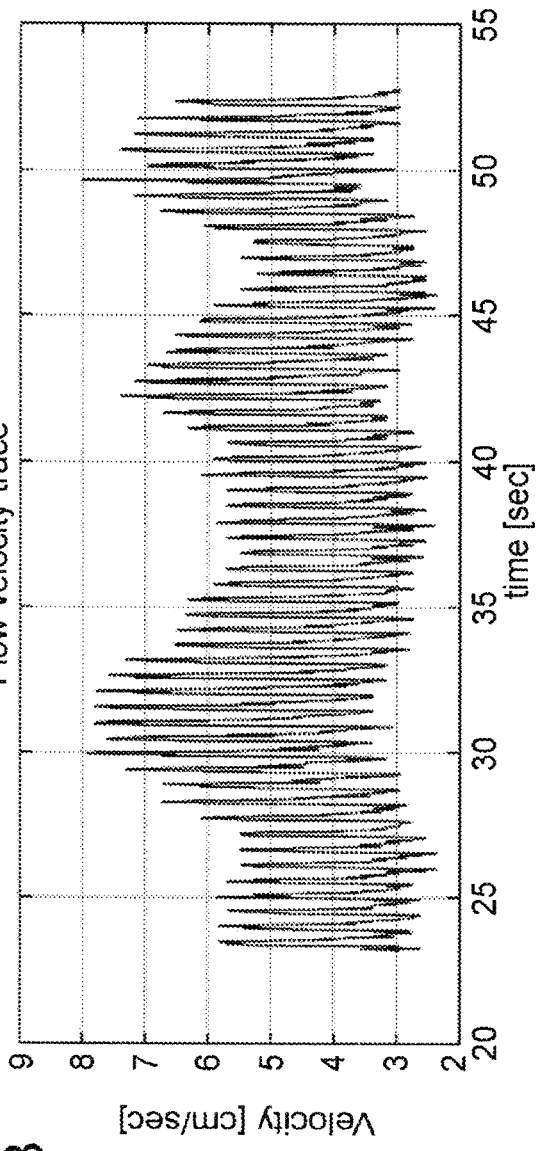
Figure 41C:
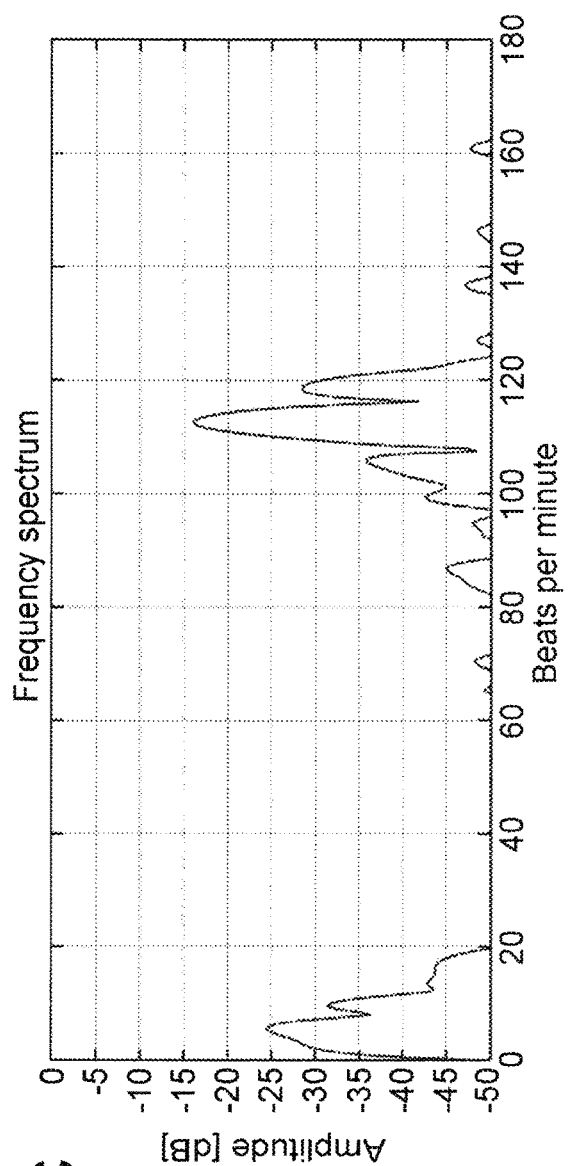
Figure 42E:
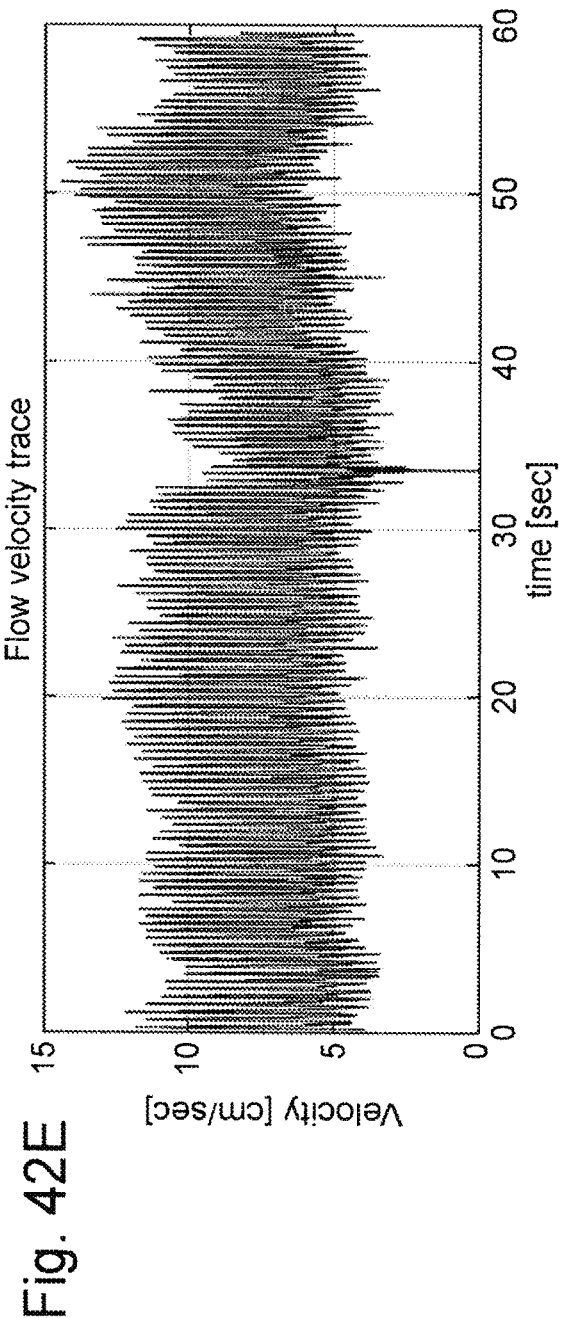
FIG. 42 shows a graphical representations of 4 separate blood flow velocity traces obtained via an unfocused ultrasound scanning system embodying the invention from the brain of a healthy infant (A, C, E and G); and the results of a Fourier transformations of the velocity traces (B, D, F and H, respectively). Fourier transformation revealed a frequency component representing the subject's heart beat at around 140 bpm and further significant frequency components in the flow velocity trace at around 2-5 bpm.
Figure 42F:
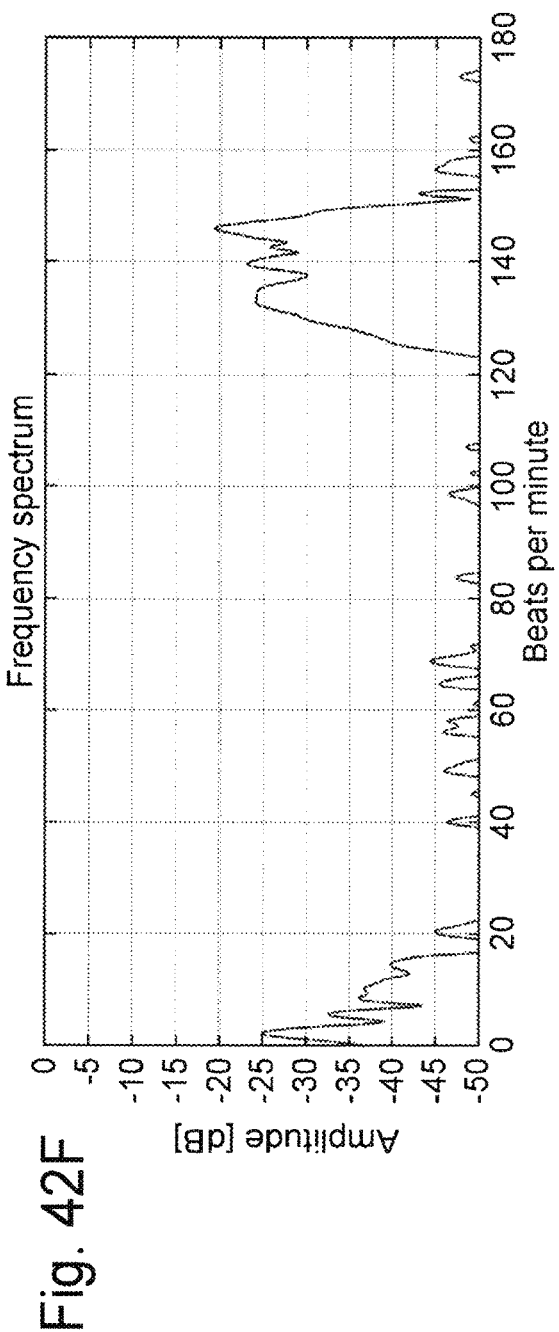
Figure 42G:
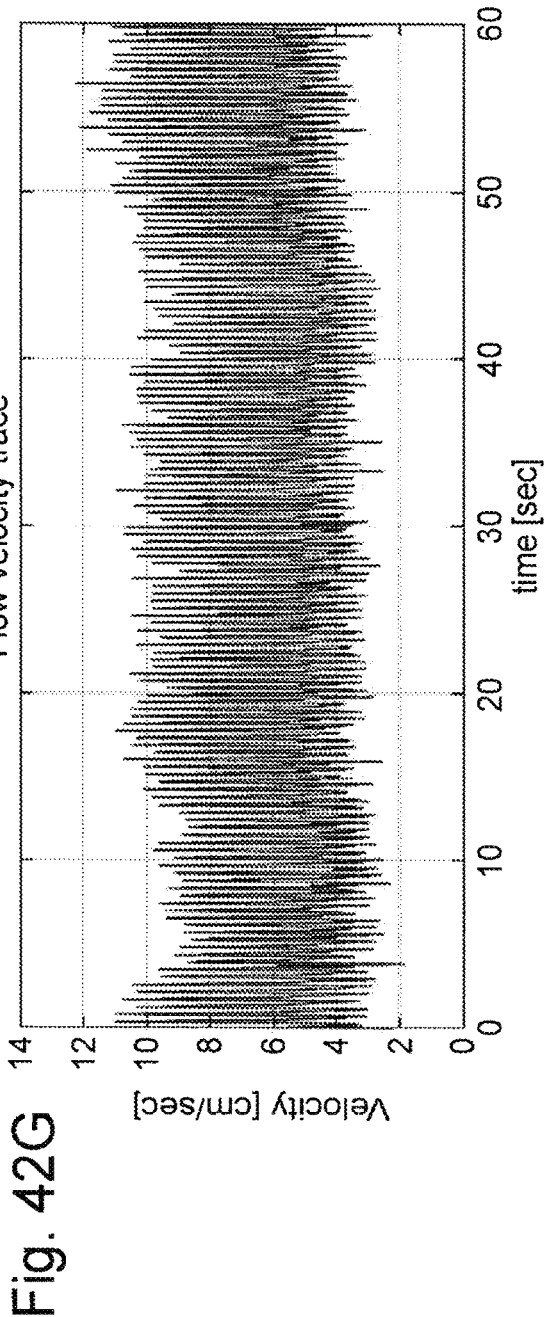
Figure 42H:
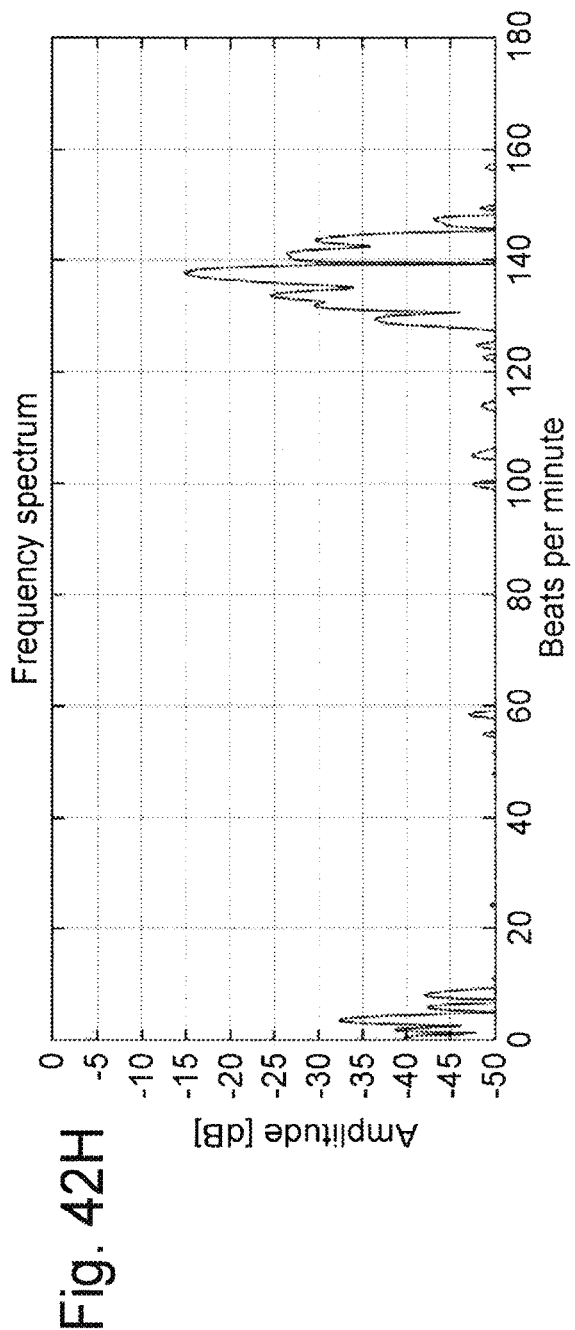
Figure 43A:
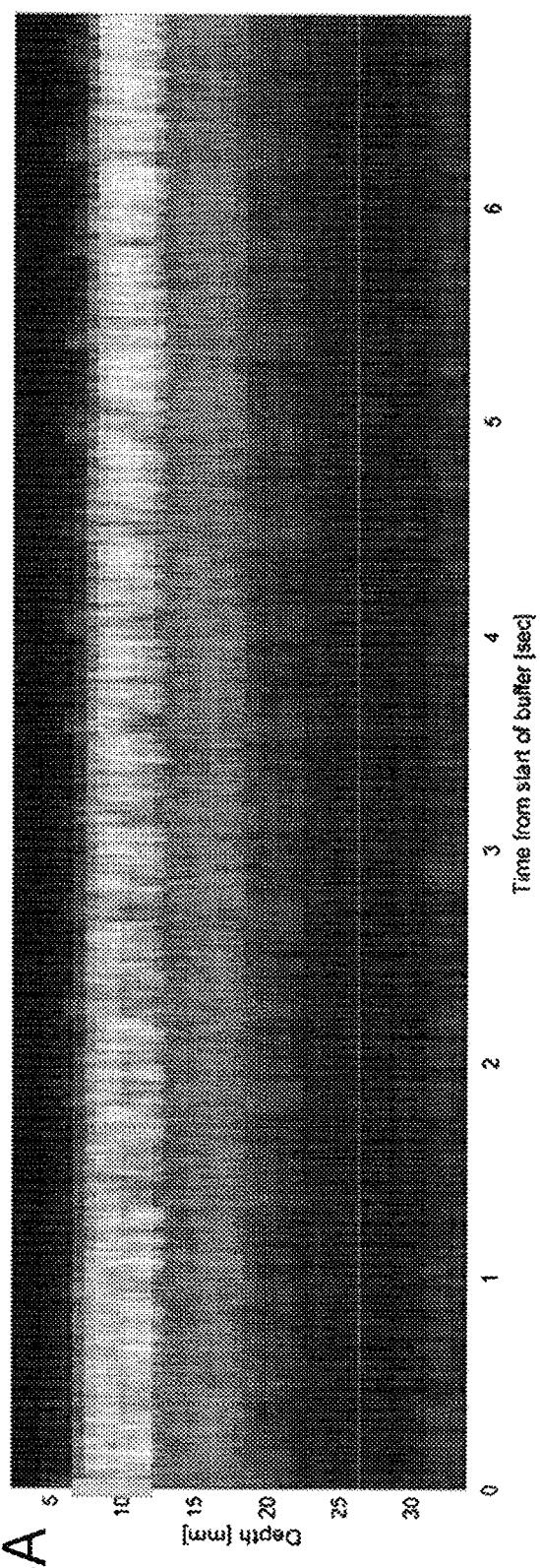
FIG. 43 shows screenshots of a display output from an unfocused ultrasound scanning system embodying the invention showing combined Doppler signals obtained from a range of depths (approx. 5-35 mm) (A, C and E) and velocity traces obtained from different sub-ranges within that range (B (approx. 7-12 mm), D (approx. 10-12 mm) and F (approx. 5-10 mm)) from the brain of a haemodynamically stable infant patient with pneumothorax. The venous flow velocity traces (the negative velocity traces) at all selected depths show steady flow patterns.
Figure 43B:
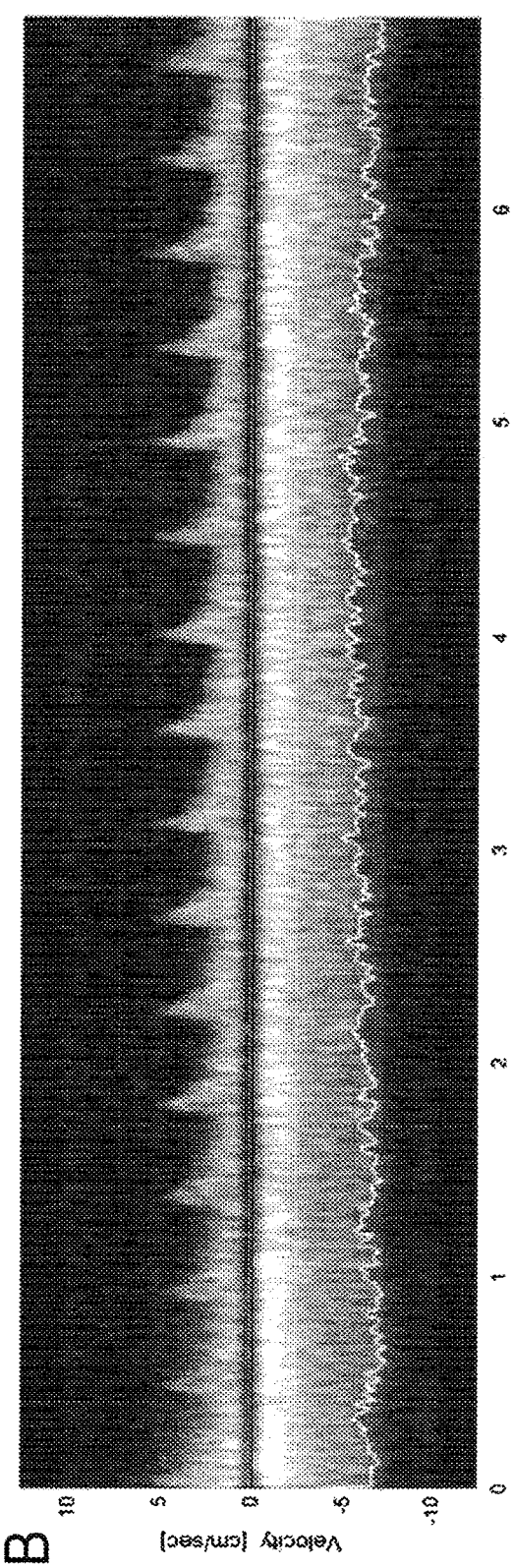
Figure 43C:
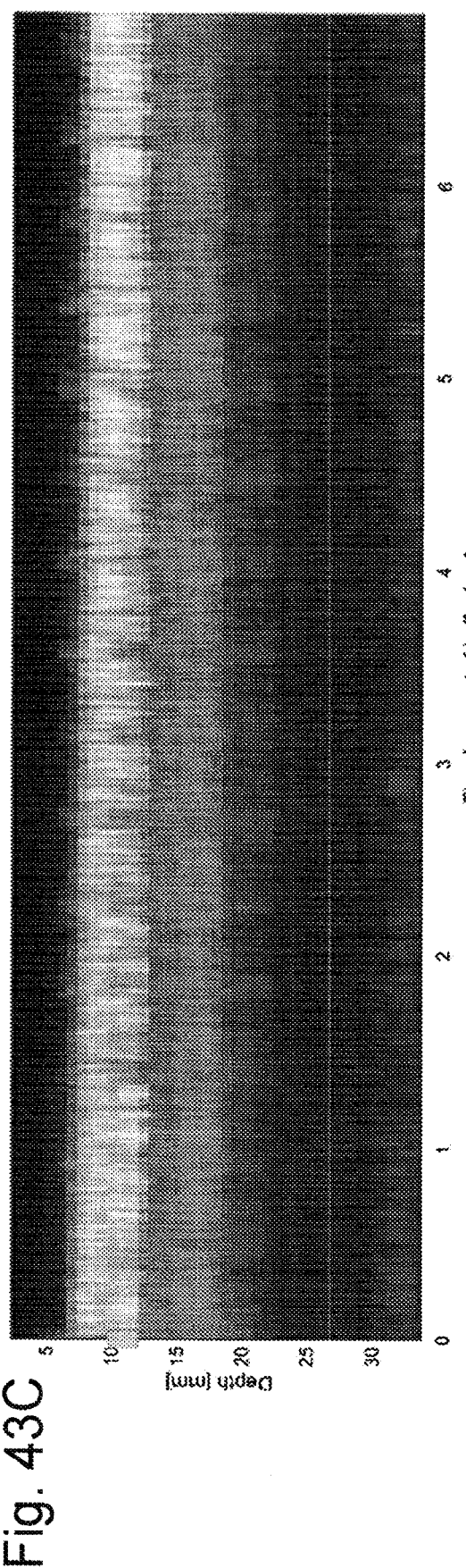
Figure 43D:
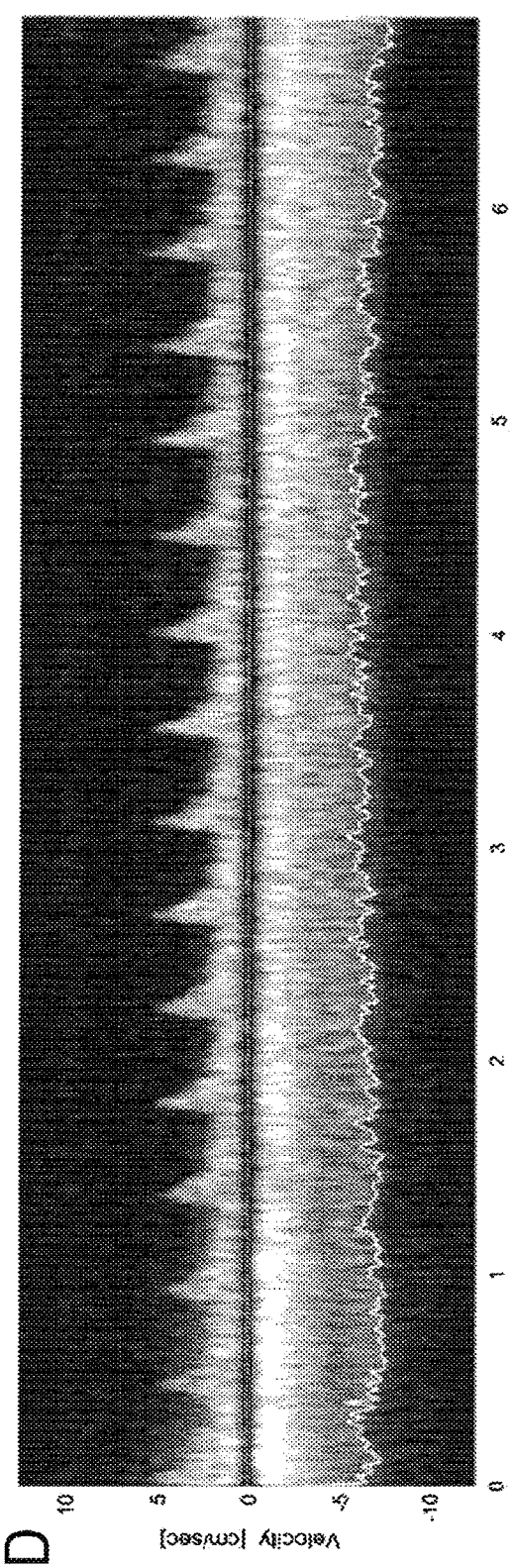
Figure 43E:
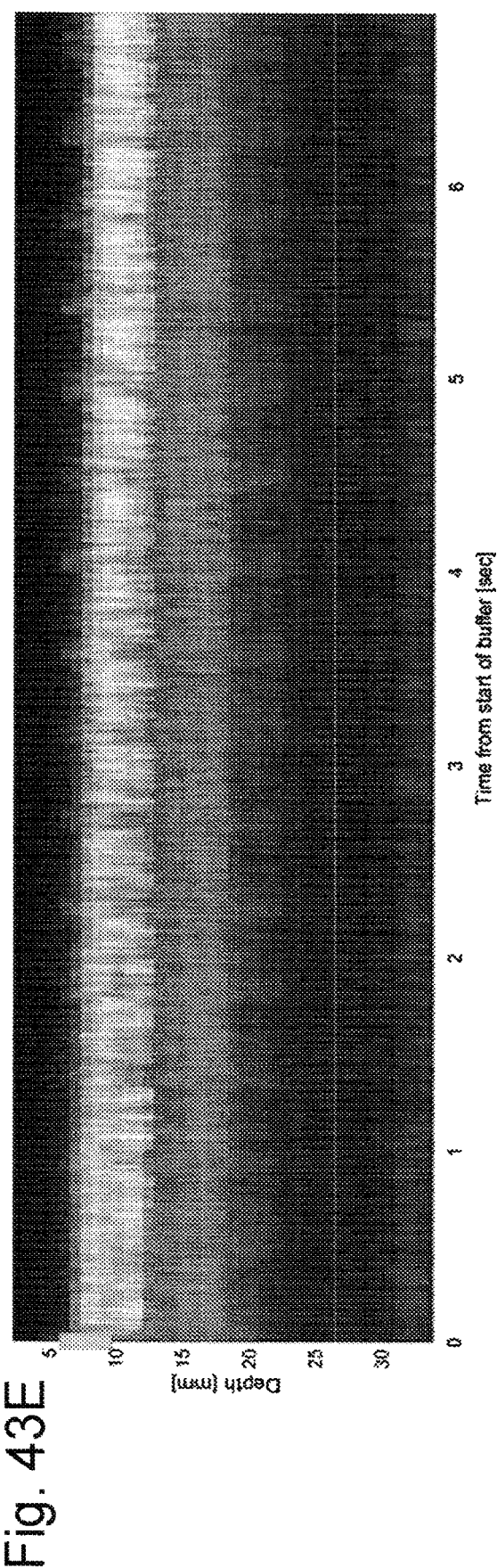
Figure 43F:
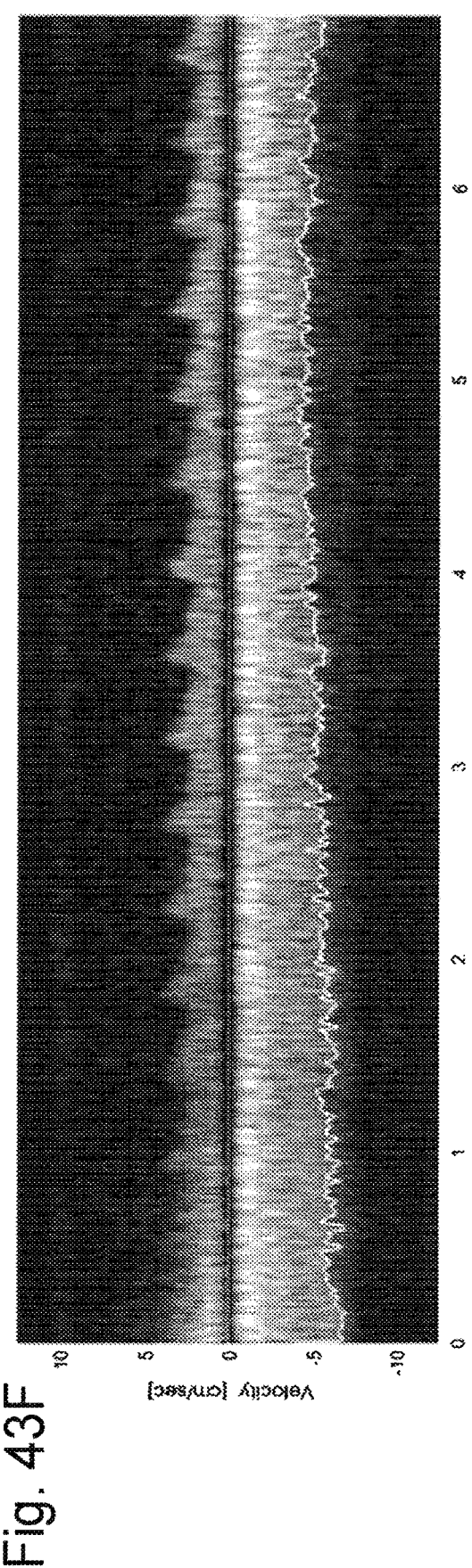

FIG. 41 shows results from a full term infant patient (gestational age-41+0; postmenstrual age—41+1; birth weight—4090 g; medication-antibiotics; CRP 96) with infection but not sepsis 12 hrs after initiation of antibiotic therapy. This patient was haemodynamically stable. Subject was asleep during recording.

Fourier transformation revealed the patient's heart beat (around 110 bpm) and also another significant frequency component in the arterial flow velocity trace at around 5 bpm.

FIG. 42 shows results from 4 separate investigations in a healthy infant subject. Fourier transformation revealed the subject's heart beat was around 140 bpm and the presence of further significant frequency component in the arterial flow velocity trace at around 2-5 bpm.

These results show that low frequency oscillations in arterial blood flow velocities at about 0.08 Hz as measured by an unfocused ultrasound system of the invention and revealed by Fourier transformation of the velocity readings can represent a marker of health in an infant subject. It is believed that such oscillations are associated with, or at least a marker of, functional cerebral haemodynamic autoregulation. In critically ill infant subjects, for instance those with or developing brain injury or sepsis, this autoregulation has become dysfunctional leading to, or because of, the breakdown in haemodynamic stability in such patients. Thus, in the critically ill haemodynamically unstable patients from which the results reported in FIGS. 39 and 40 were obtained, such oscillations were absent, but in the haemodynamically stable patients from which the results reported in FIGS. 38 and 41 were obtained, this marker was present. Importantly, this marker is capable of distinguishing subjects with an infection which is under control (FIG. 41) from subjects with sepsis. This marker may be referred to as the cerebral haemodynamic autoregulation index. (HDAR-index). Thus an unfocused ultrasound system of the invention is capable of monitoring this marker and this allows a subject's general health to be estimated or monitored over time or, more specifically, a subject's haemodynamic status may be estimated or monitored over time. This may allow a clinician to monitor or predict the onset or progression of a disease or pathological condition and/or a response to treatment.

Thus, by monitoring such blood characteristics, alone or together with other circulatory parameters (e.g. arterial blood pressure) a patient's sepsis status may be estimated at any time and any change therein may be detected rapidly. It is believed that such changes in blood flow characteristics measured by the unfocused Doppler ultrasound system of the invention would be detectable before outward signs of deterioration or improvement would be observed using conventional techniques and equipment.

FIG. 43 shows results from a full term infant patient (gestational age—40+2) with pneumothorax. This patient was haemodynamically stable and was not on respiratory support during recording. Venous blood flow velocity was monitored at a variety of depth ranges. At all depths analysed steady blood flow velocity was observed.

Figure 44A:
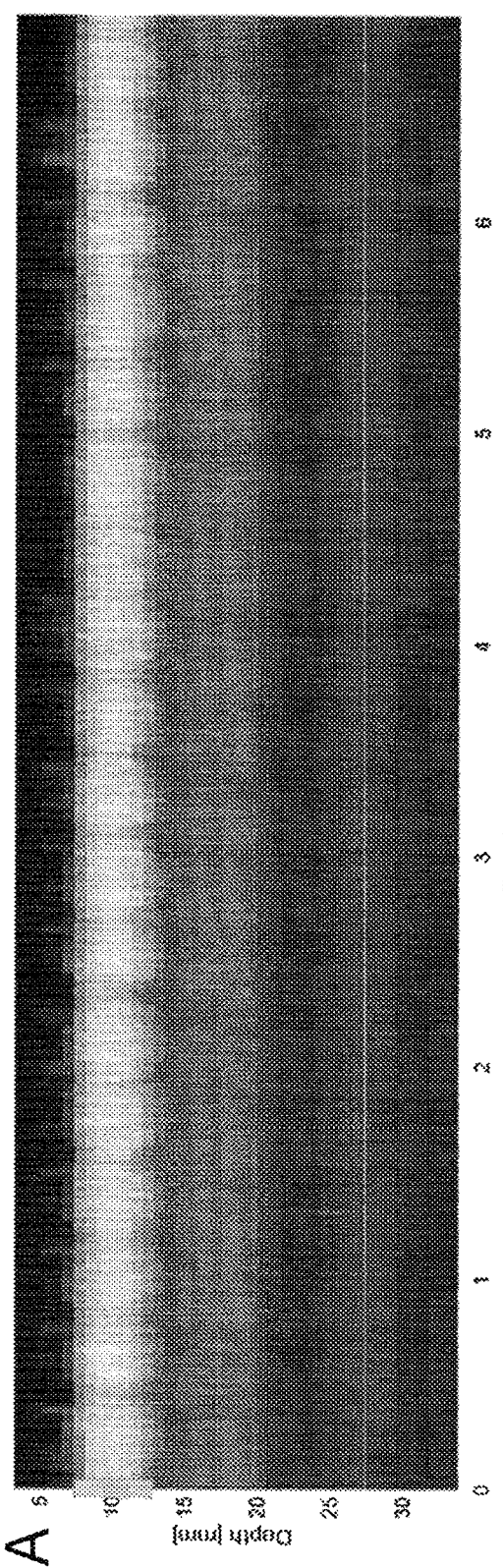
FIG. 44 shows screenshots of a display output from an unfocused ultrasound scanning system embodying the invention showing combined Doppler signals obtained from a range of depths (approx. 5-35 mm) (A and C) and velocity traces obtained from different sub-ranges within that range (B (approx. 7-12 mm) and D (approx. 14-17 mm)) from the brain of an intubated infant patient one respiratory support one day following surgery to correct gastroschisis. The venous flow velocity traces (the negative velocity traces) at both selected depths show fluctuating venous flow patterns, which may indicate increased risk of intracerebral haemorrhage.
Figure 44B:
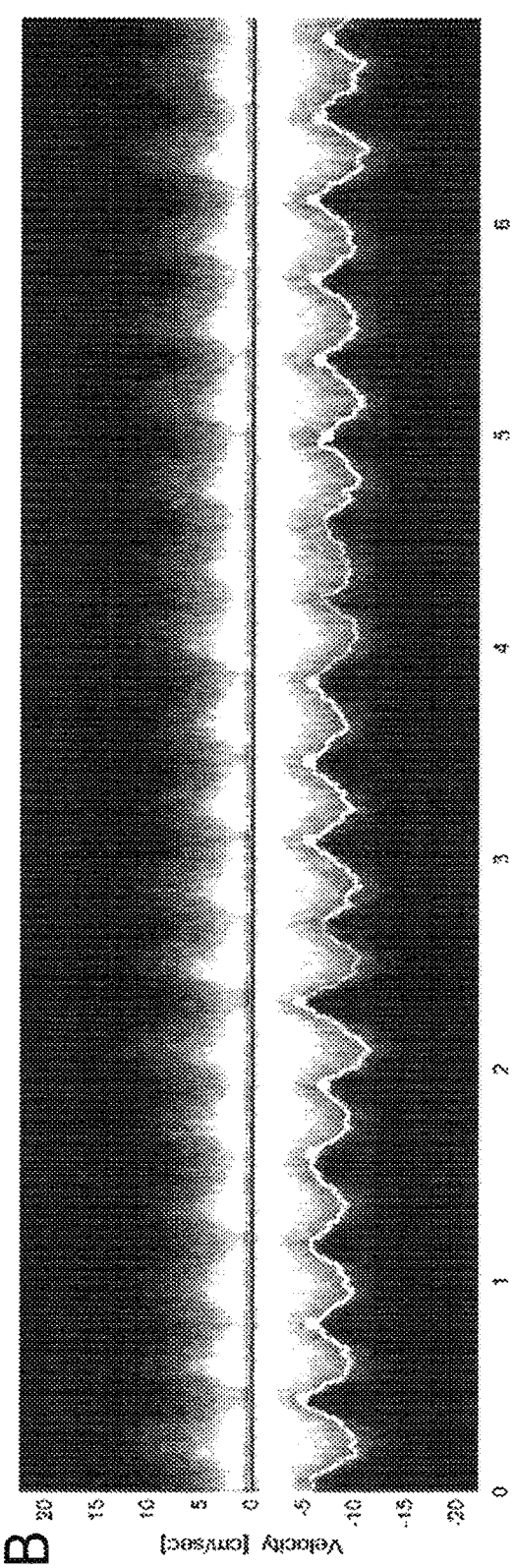
Figure 45A:
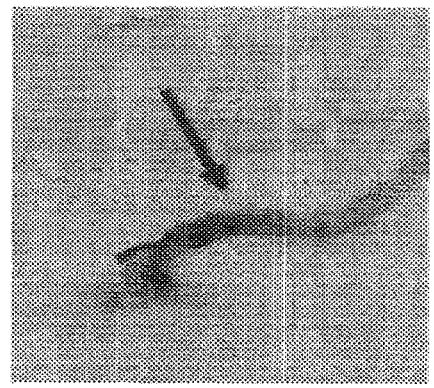
FIG. 45 shows angiogram/CT scans of the iliac artery of a patient presenting with claudication (microvasculature dysfunction) and screenshots of a display output from an unfocused ultrasound scanning system embodying the invention showing blood flow velocity traces from the minor vasculature of the pulp of the patient's big toe before angioplasty (A and D; stenosis highlighted by arrow) after angioplasty of a first stenosis in the iliac artery (B and E), before angioplasty of a second stenosis in the iliac artery (C; stenosis highlighted by arrow), and after angioplasty of the second stenosis (F). Blood flow velocity in the minor vasculature of the toe increases following each surgical intervention indicating the surgical intervention has improved microvascular dysfunction in this patient.
Figure 45B:
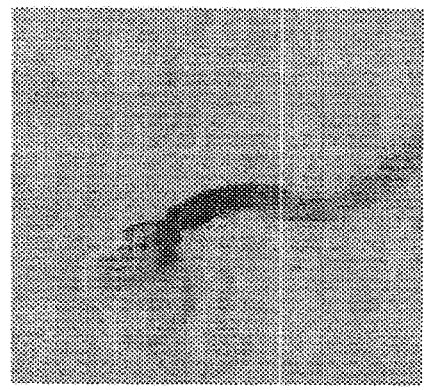
Figure 45C:
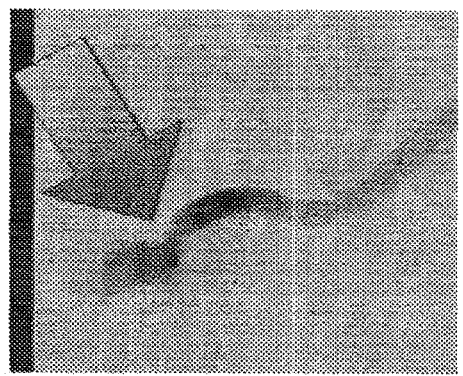
Figure 45D:
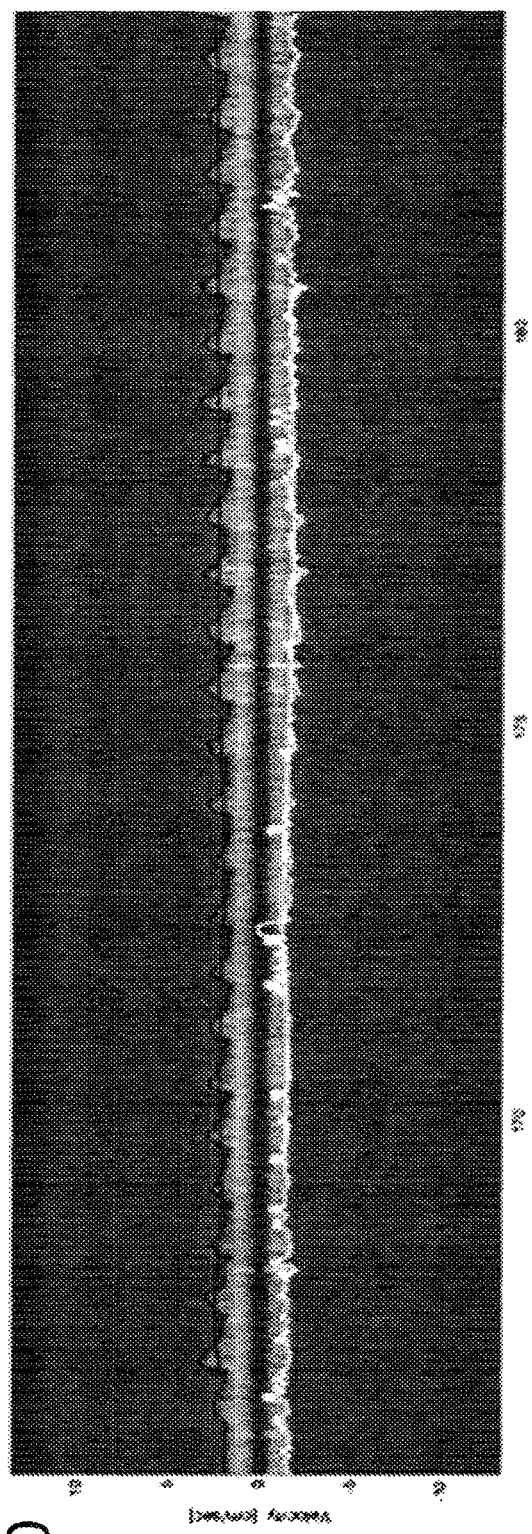
Figure 45E:
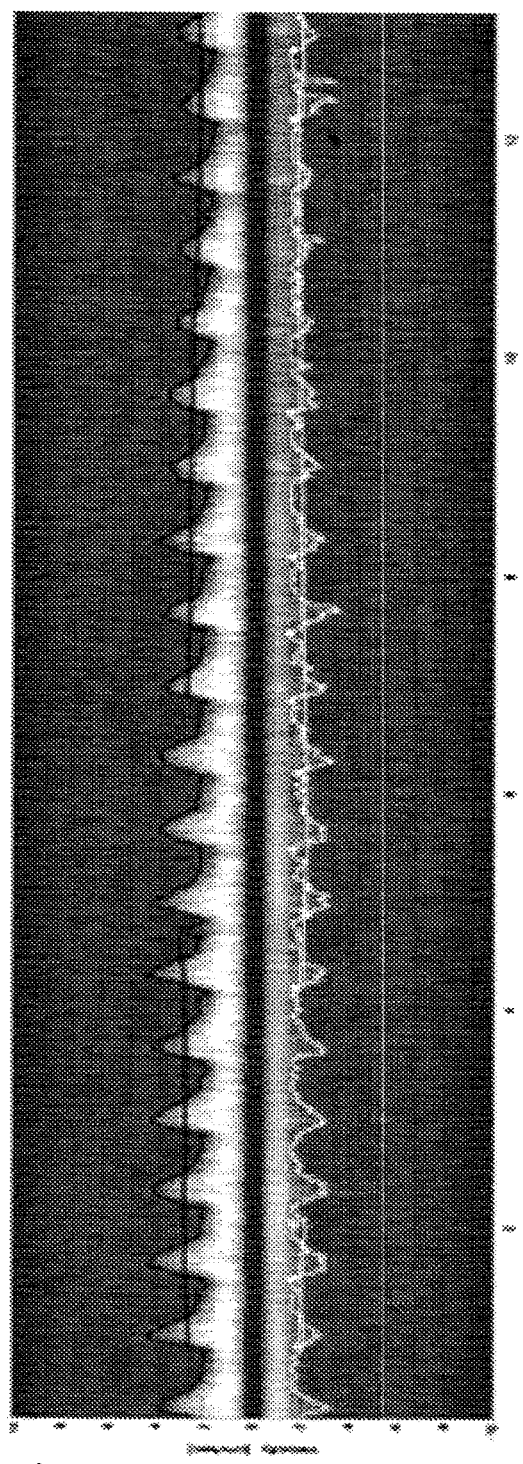
Figure 45F:
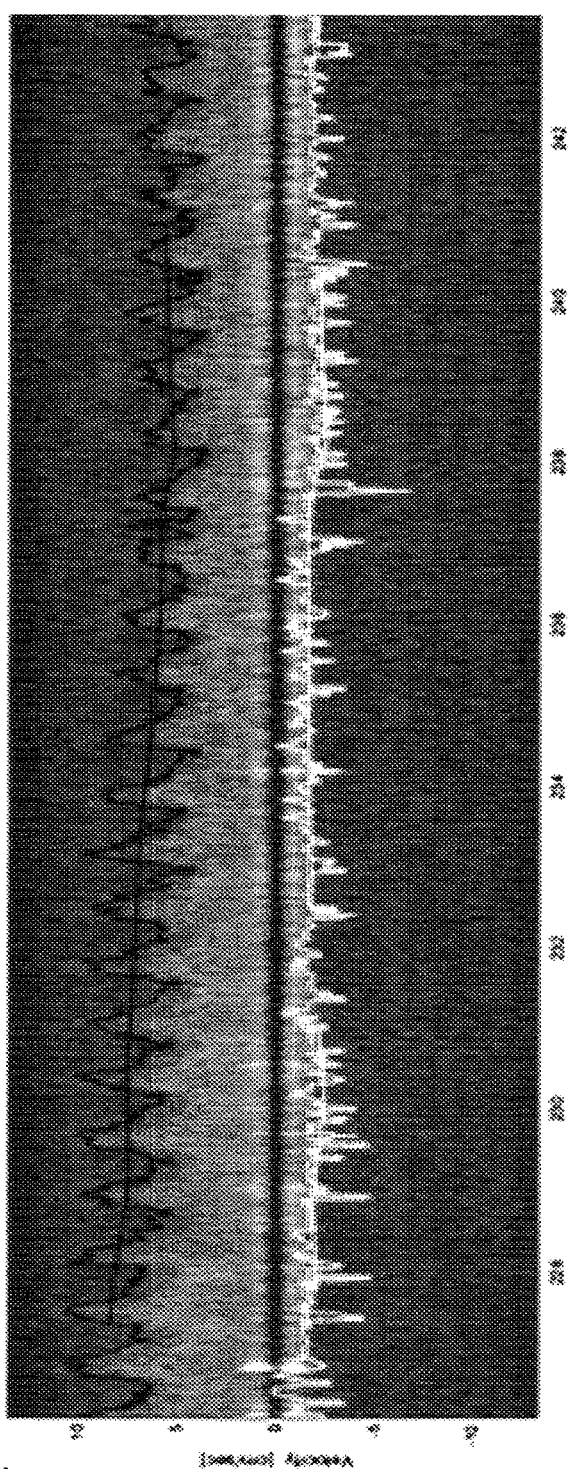

In contrast to FIG. 43, FIG. 44 shows results from a premature neonatal patient (gestational age—36+0; birth weight—2400 g; medication—ampicillin, gentamicin and paracetamol) on respiratory support after surgery for gastrochisis. Venous blood flow velocity was monitored at two different depth ranges. At each depth analysed venous blood flow velocity was fluctuating. This is a known risk factor for intraventricular haemorrhage.

These results show that monitoring cerebral venous blood flow in infants with an unfocused ultrasound system of the invention can detect potentially pathological flow patterns. This may allow a clinician to monitor or predict the onset or progression of a disease or pathological condition and/or a response to treatment.

Figure 49C:
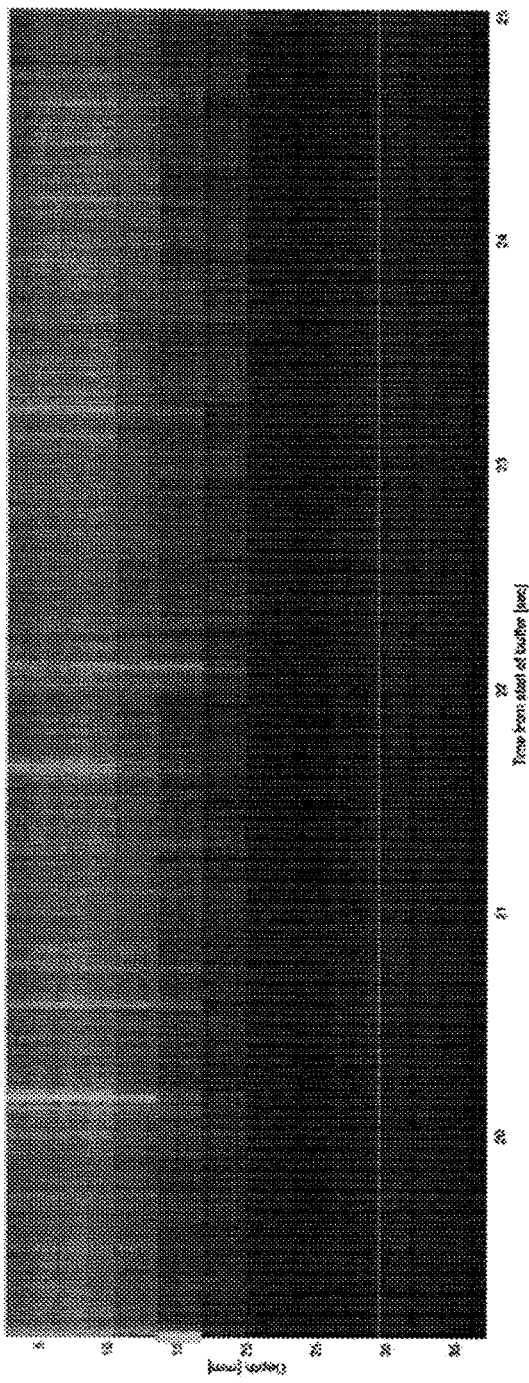
FIG. 49 shows screenshots of a display output from an unfocused ultrasound scanning system embodying the invention showing combined Doppler signals obtained from a range of depths (approx. 3-35 mm) (A and C) and velocity traces obtained from sub-ranges within that range (B and D) from the brain of a premature infant at age 1 day (ductus arteriosus not hemodynamically significant, normal diastolic forward flow, PI 0.919) (A and B) and age 19 days (ductus arteriosus hemodynamically significant (moderate); diastolic flow reduced/nearly missing; PI 1.99) (B and C).
Figure 49D:
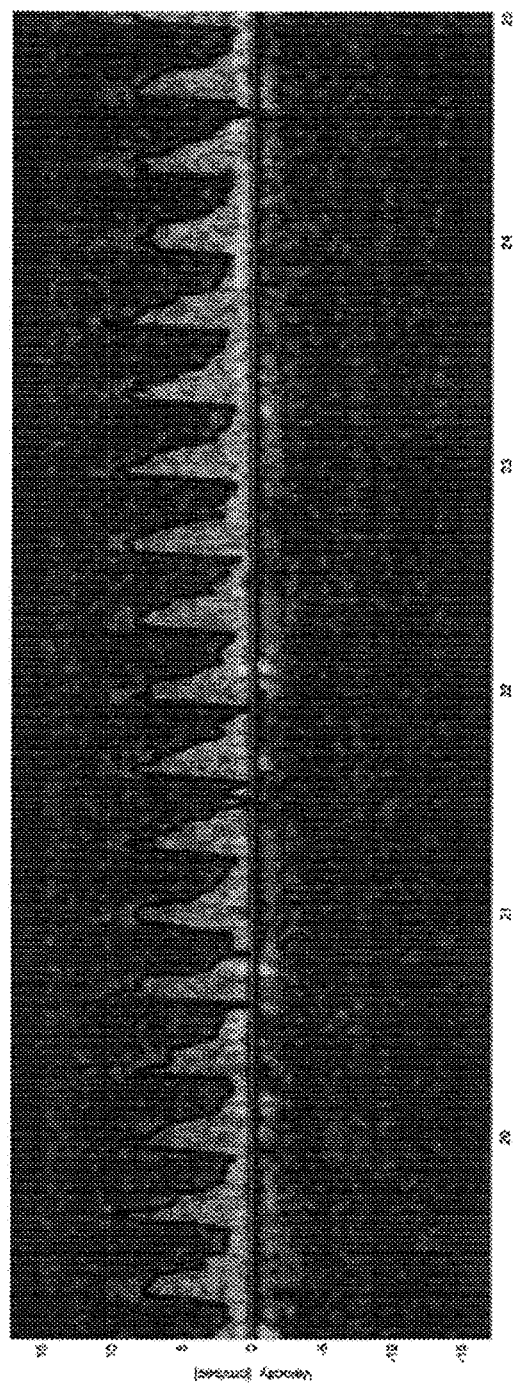

FIG. 49 shows results from a premature infant (gestational age—29; birth weight—905 g) which developed hemodynamically significant (moderate) ductus arteriosus potentially requiring clinical intervention. FIG. 49 (B) shows that at 1 day old arterial blood flow velocity profiles displayed normal diastolic forward flow. A PI of 0.919 was calculated from these readings. This indicated that the ductus arteriosus was not hemodynamically significant and intervention for this complication was not required at that time. However, FIG. 49 (D) shows that at 19 days old diastolic flow was reduced/nearly missing and PI had risen 1.99. This indicated that the ductus arteriosus was now moderately hemodynamically significant and intervention for this complication (e.g. prostaglandin inhibitors) should be considered.

This study shows that measuring arterial blood flow velocity and/or PI over time with an unfocused ultrasound system of the invention can help a clinician detect when a patent ductus arteriosus is increasing in significance and in this way the ideal timing of treatment (e.g. prostaglandin inhibitors) can be provided.

Figure 50:
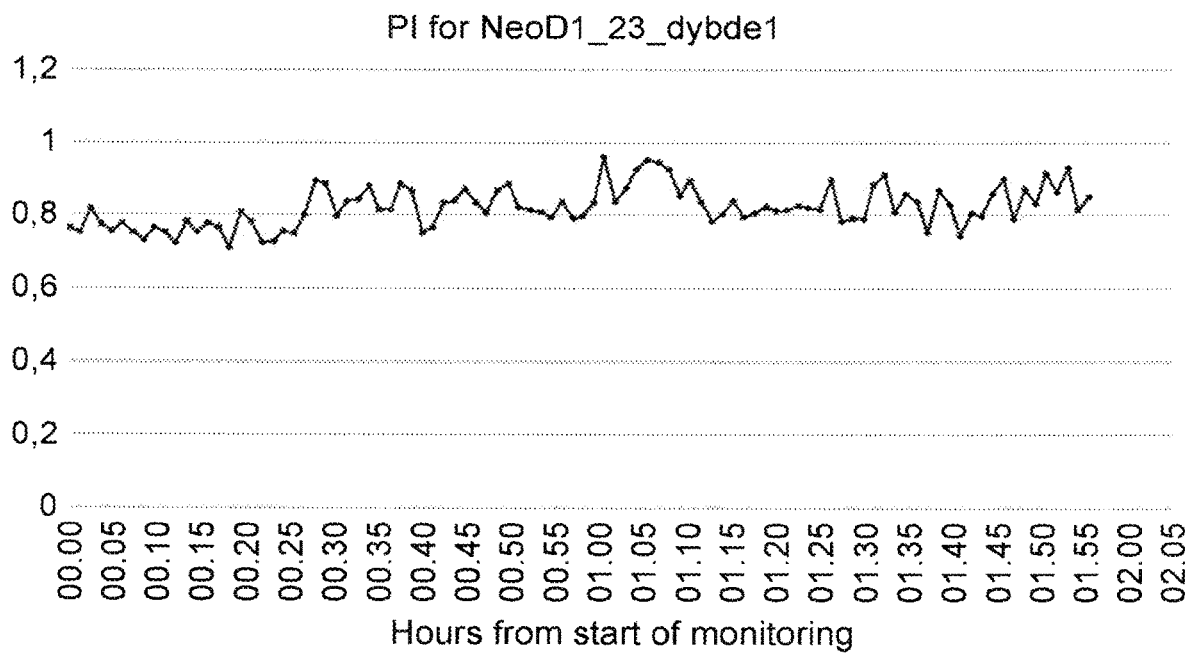
FIG. 50 shows graphical representations of PI values over time from two depths (1.5-2 cm (upper graph) and 2.5-3.1 cm (lower graph)) of the brain of a clinically stable premature infant using an unfocused ultrasound scanning system embodying the invention. Measurements were taken simultaneously.
Figure 50:
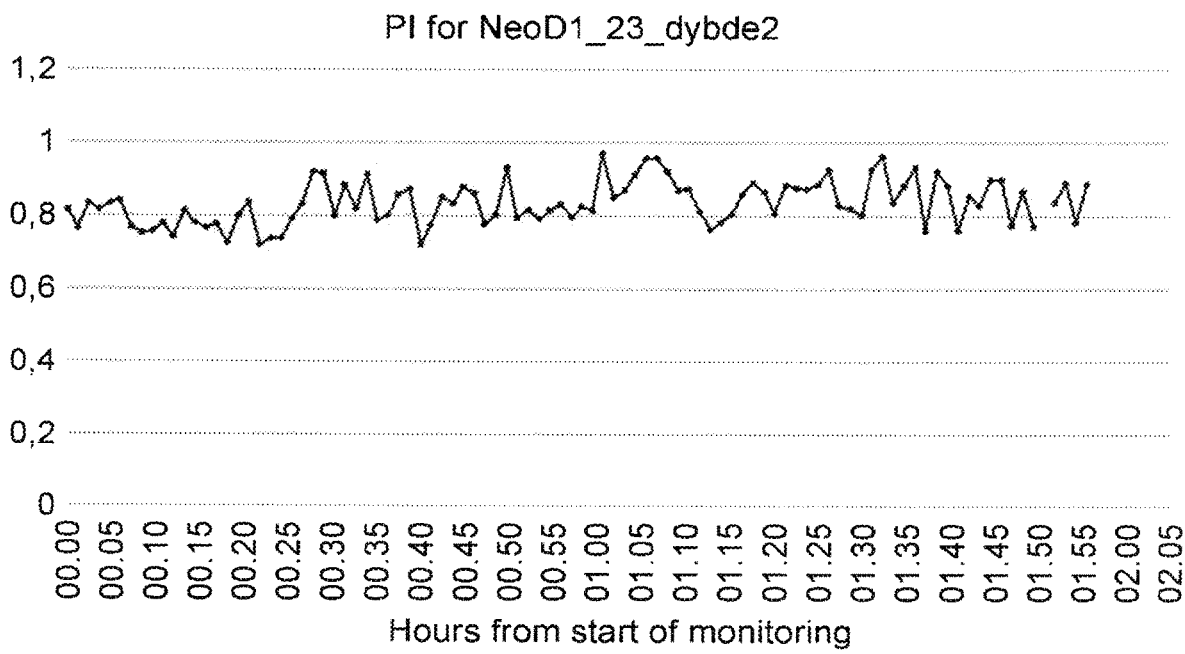

FIG. 50 shows results from clinically stable premature infant (gestational age—34+5; birth weight—2021 g; no medication or respiratory support). Simultaneous monitoring of arterial blood flow at two different depths showed that PI measurements and their profiles were consistent thus indicating that the invention may be practiced at different depths and consistent results obtained. This result suggests that the ultrasound system of the invention has advantages over conventional Doppler monitoring techniques because it means that it may be possible for clinically useful readings to be obtained from a comparatively wide range of target regions (i.e. any region containing one or more of various central cerebral blood vessels) rather than requiring a specific vessel to be accurately located and analysed. This in turn may mean that the ultrasound system of the invention may be used by operators which are not as highly trained as those required to operate conventional Doppler ultrasound and/or makes the system of the invention more amenable to automation.

Example 7-Analysis of Blood Flow in the Peripheral Circulation of Subjects with Microvascular Dysfunction Undergoing Surgical Intervention Patient 1

This patient was a 65 year old male presenting with claudication, i.e. microvasculature dysfunction in the lower limbs arising from stenosis in an upstream blood vessel. As shown in FIG. 45 (D) the velocity of the pulsatile (arterial) blood flow in the minor vasculature of the pulp of the patient's big toe, as measured by an ultrasound system of the invention, was modest providing further evidence of microvasculature dysfunction in the lower limbs. As shown in FIG. 45 (A) angiogram/CT scans of the iliac artery of the patient revealed a stenosis. Angioplasty of that stenosis resulted in significantly increased arterial blood flow in the minor vasculature of the big toe, but flow velocity as measured by an ultrasound system of the invention was still considered low and remained indicative of continued microvasculature dysfunction. This led to further analysis of the angiogram and the detection of a further suspected stenosis. Angioplasty at this location resulted in a more than doubling of the arterial blood flow in the minor vasculature of the big toe. Under conventional protocols it is likely that this second stenosis would have been identified only after the patient was assessed following the conclusion of the first surgery, thus requiring a second surgical intervention at another time. The present invention therefore prevented the risks and costs of a second surgical intervention in this patient.

This study shows how an ultrasound system of the present invention may be used to monitor peripheral microcirculation in a vertebrate animal subject undergoing or recovering from surgery and guide treatment. It also shows how an ultrasound system of the present invention may be used to detect and monitor microvascular dysfunction more generally.

Patient 2

Figure 46A:
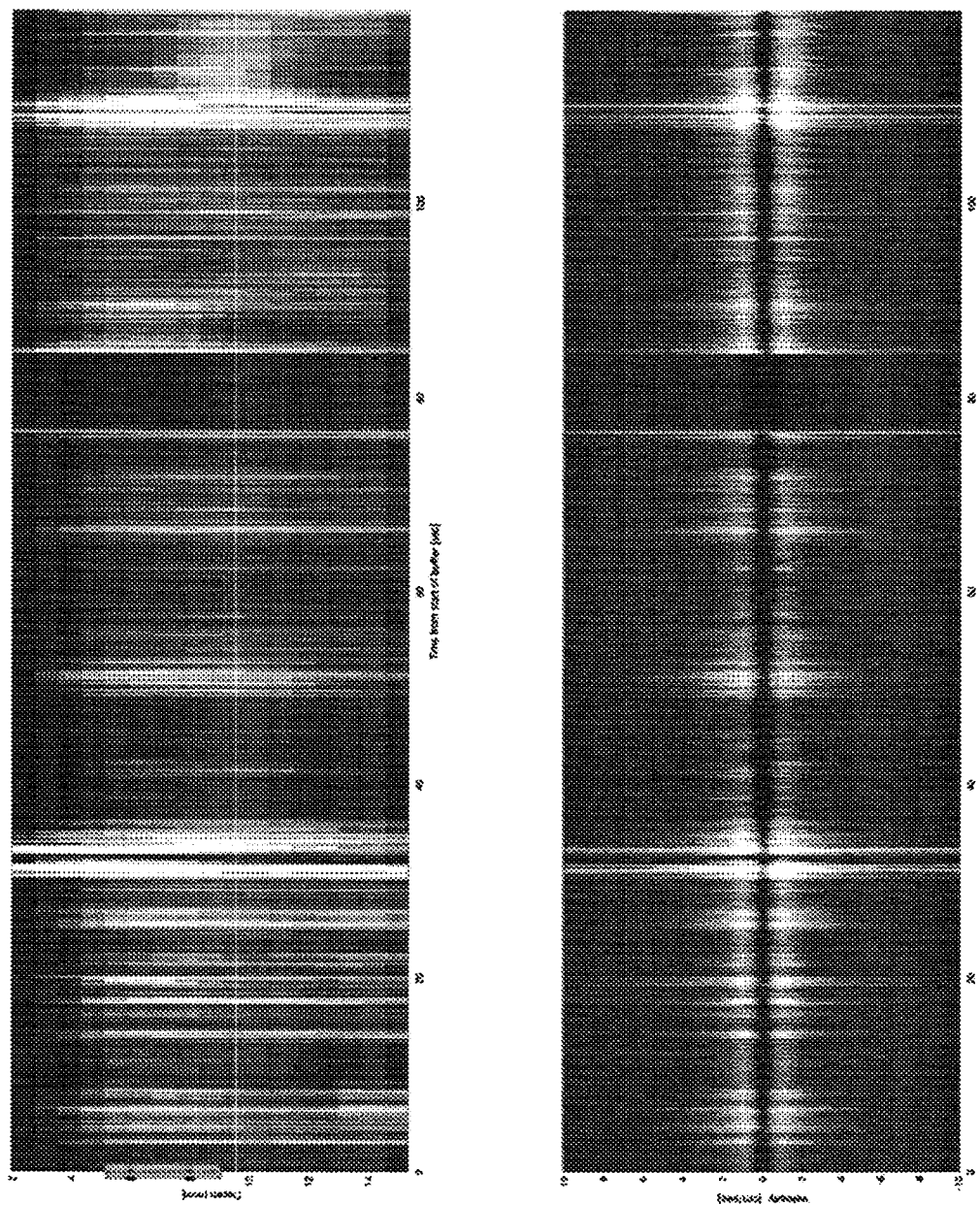
FIG. 46 shows angiogram/CT scans of the thigh and leg arteries of a patient with diabetes and an associated foot ulcer (microvascular dysfunction) and screenshots of a display output from an unfocused ultrasound scanning system embodying the invention showing combined Doppler signals obtained from a range of depths (approx. 2-15 mm) and velocity traces obtained from different sub-ranges within that range in the minor vasculature of the pulp of the patient's big toe before angioplasty (A) and after angioplasty (B). It was not possible to obtain stable blood flow readings from the minor vasculature of the patient prior to angioplasty (i.e. state of microvascular dysfunction) but, in contrast, robust and stable readings were seen following angioplasty (i.e. following normalisation of microvascular dysfunction).
Figure 46A:
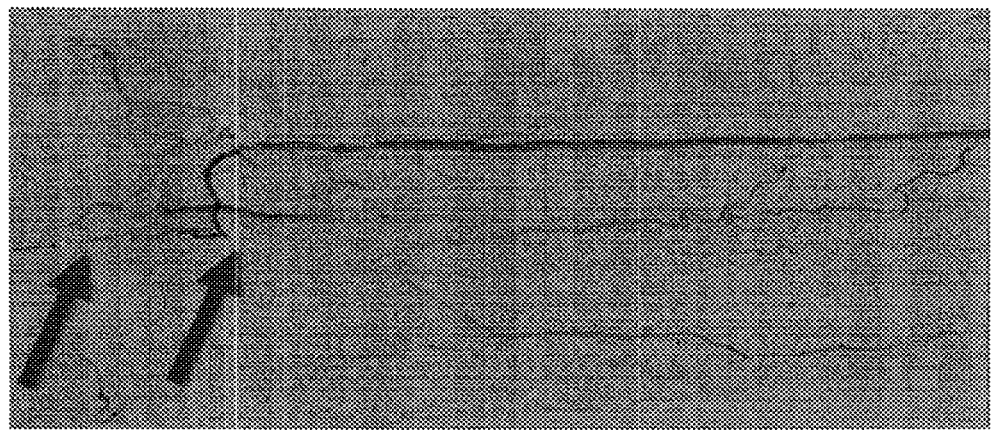

This patient was an 80 year old male with diabetes and associated renal failure and foot ulcer, i.e. evidence of microvascular dysfunction. As shown in FIG. 46 (A) angiogram/CT scans of the thigh and leg arteries revealed multiple significant occlusions (arrows). As shown in FIG. 46 (B), following angioplasty these occlusions were rectified. FIG. 46 further shows that using an ultrasound system in accordance with the invention arterial blood flow readings from the minor vasculature of the patient (pulp of the big toe) were highly unstable prior to angioplasty (i.e. state of microvascular dysfunction) but, in contrast, robust and stable readings in arterial flow were seen following angioplasty (i.e. following normalisation of microvascular dysfunction).

This study shows how an ultrasound system of the present invention may be used to detect microvascular dysfunction by determining blood flow characteristics in peripheral minor vasculature (unstable readings) and monitor that dysfunction (stabilisation of readings following treatment to rectify that dysfunction). This study also shows how an ultrasound system of the present invention may be used to monitor peripheral microcirculation in a vertebrate animal subject undergoing or recovering from surgery.

Patient 3

This patient was an 80 year old female presenting with claudication, i.e. microvasculature dysfunction in the lower limbs arising from stenosis in an upstream blood vessel. Angiogram/CT scans of the iliac artery of the patient revealed a stenosis. An ultrasound system of the invention was used to measure blood flow velocity in the arteria *dorsalis* pedis before, during and after angioplasty of the stenosis. Arterial blood flow velocity in the arteria *dorsalis* pedis was significantly increased following the procedure indicting successful revascularisation and reduction in microvascular dysfunction (data not shown).

This study shows how an ultrasound system of the present invention may be used to monitor peripheral microcirculation in a vertebrate animal subject undergoing or recovering from surgery. It also shows how an ultrasound system of the present invention may be used to detect and monitor microvascular dysfunction more generally.

Example 8-Analysis of Blood Flow Parameters in the Peripheral Circulation of Subjects with Sepsis or Septic Shock Design/Method 2 patients with sepsis/septic shock and undergoing ICU care following surgical complications were recruited and repeatedly examined during the first days at the ICU. Examinations were performed during the acute critical phase through to stabilization and as such these patients served as their own controls. Blood flow measurements using an unfocused ultrasound system embodying the invention were typically performed at the dorsum of the wrist, at the base of the wrist-thumb joint, or the thenar eminence for four minutes, with simultaneously recordings of laser-doppler skin blood perfusion at the nearby underarm skin and continuously invasive arterial blood pressure measurement.

Results—Patient 1

Male, 70 years old, presented with acute ruptured aortic aneurysm successfully stabilized following emergency surgery, but intestinal perforation lead to abdominal sepsis with septic shock. After several days a secondary complication of insufficient intestinal blood flow arose which was rectified by surgery. Patient finally stabilized and was discharged to home. Blood pressure, unfocused ultrasound and laser Doppler recordings was performed during septic shock and stabilization as shown in FIG. 47.

On the day following surgery Patient 1 was in septic shock but was showing outward signs of improvement. As shown in FIG. 47(A) fluctuations in arterial blood pressure (ART), ultrasound measured blood flow velocity (vNeg) and peripheral resistance (Rp) at 15/min (0.25 Hz) are observed (light grey/blue arrows). These fluctuations are caused by the mechanical ventilator which was running at a respiratory rate (RR) of 15/min. In addition, fluctuations at approximately 1/min (0.017 Hz; dark grey arrows) were observed most distinctly in the Rp trace, but also in the ultrasound measured blood flow velocity trace. It is believed that these oscillations are caused by spontaneous vasomotions.

Figure 47B:
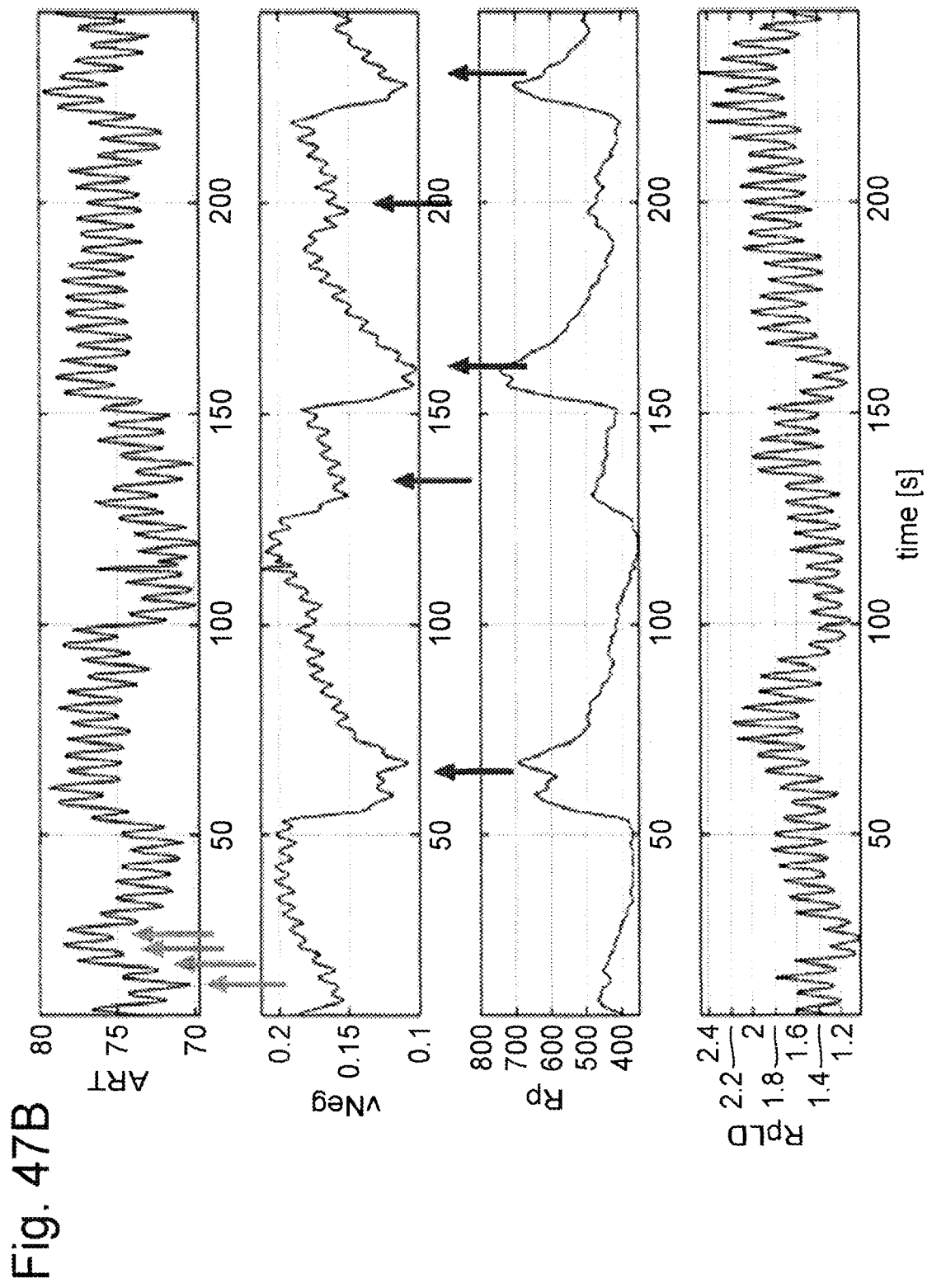
FIG. 47 shows graphical representations of mean arterial blood pressure at the left distal radial artery (ART; mmHg), blood flow velocity as measured by an unfocused ultrasound scanning system embodying the invention at the dorsum of the wrist, the wrist-thumb joint or the thenar eminence (vNeg; cm/second), peripheral vascular resistance (Rp, ART/vNeg) and peripheral vascular resistance (RpLD, ART/laser Doppler blood flow velocity) in a patient suffering from septic shock following surgery at (A) surgery+1 day, septic shock improving; (B) septic shock improving; (C) surgery+9 days, septic shock worsening, ischaemic gut, secondary surgery on day 8; (D) original surgery+10 days, septic shock improving after secondary surgery on day 8. Light grey arrows (mechanical ventilation respiratory rate); dark grey arrows (low frequency vasomotor oscillations).

As shown in FIG. 47(B), after further outward improvement in the Patient's septic shock condition, the oscillations in the vNeg and Rp traces at approximately 0.017 Hz (dark grey arrows) became more distinct.

Figure 47C:
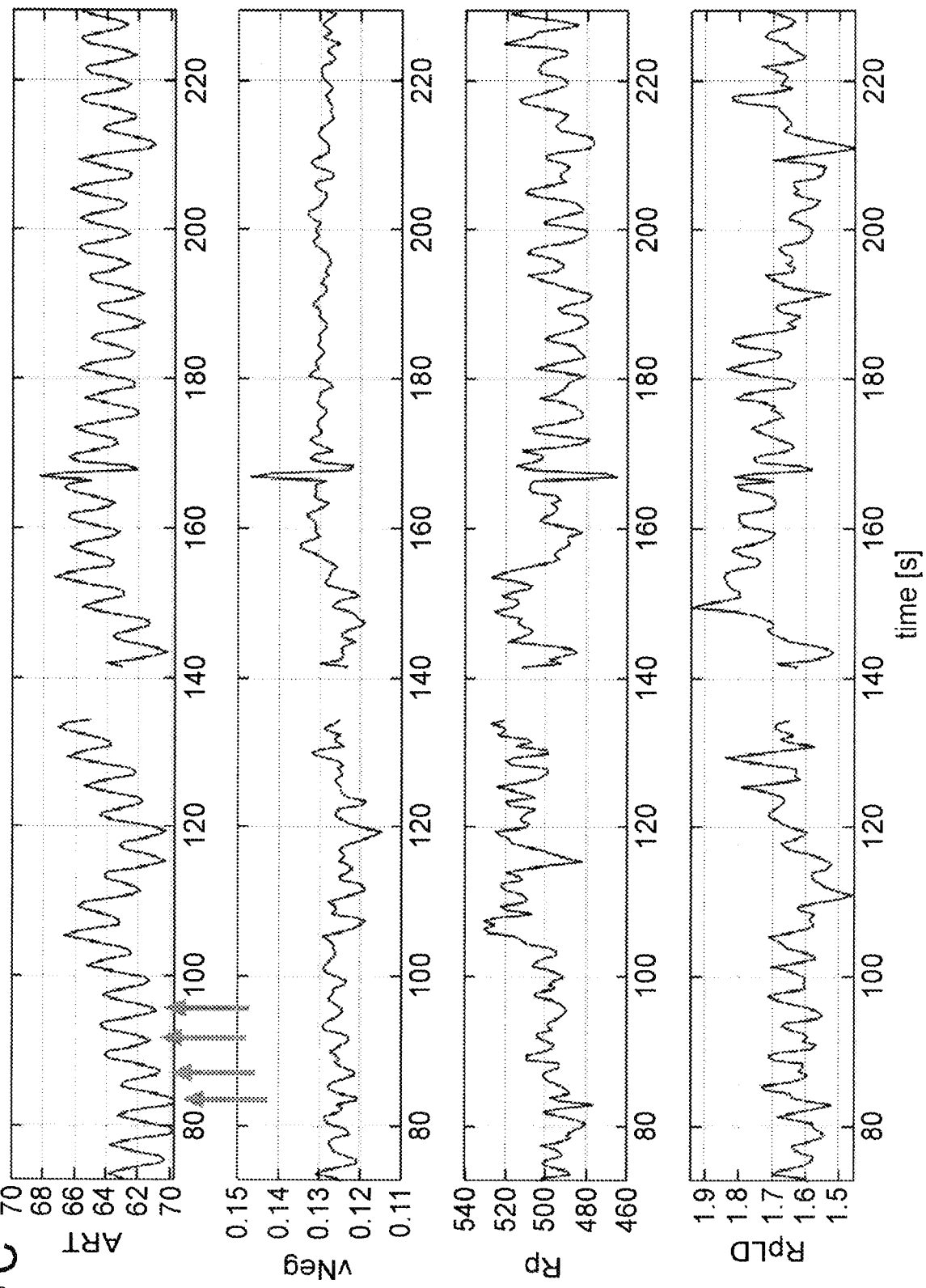
Figure 47D:
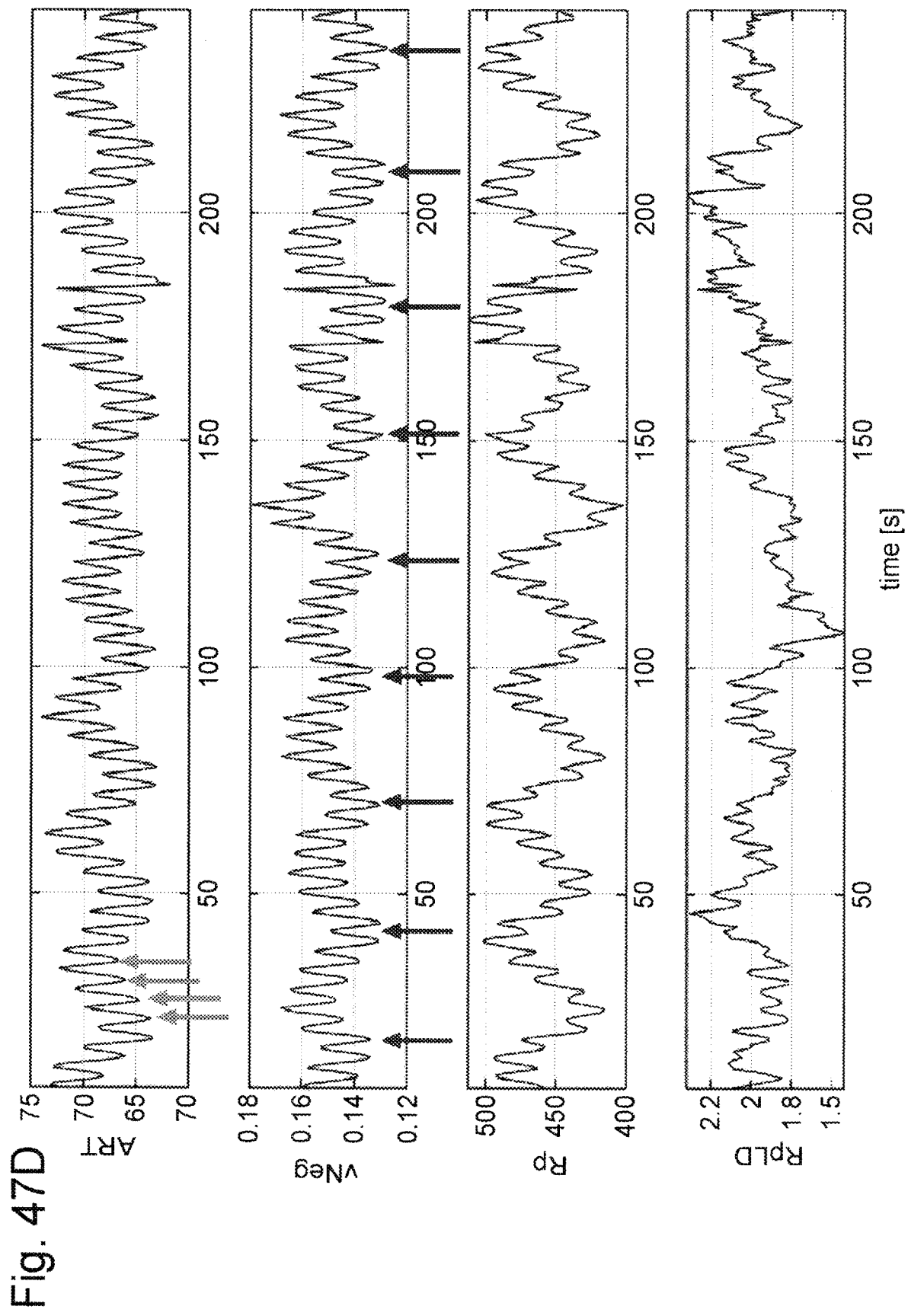
Figure 48A:
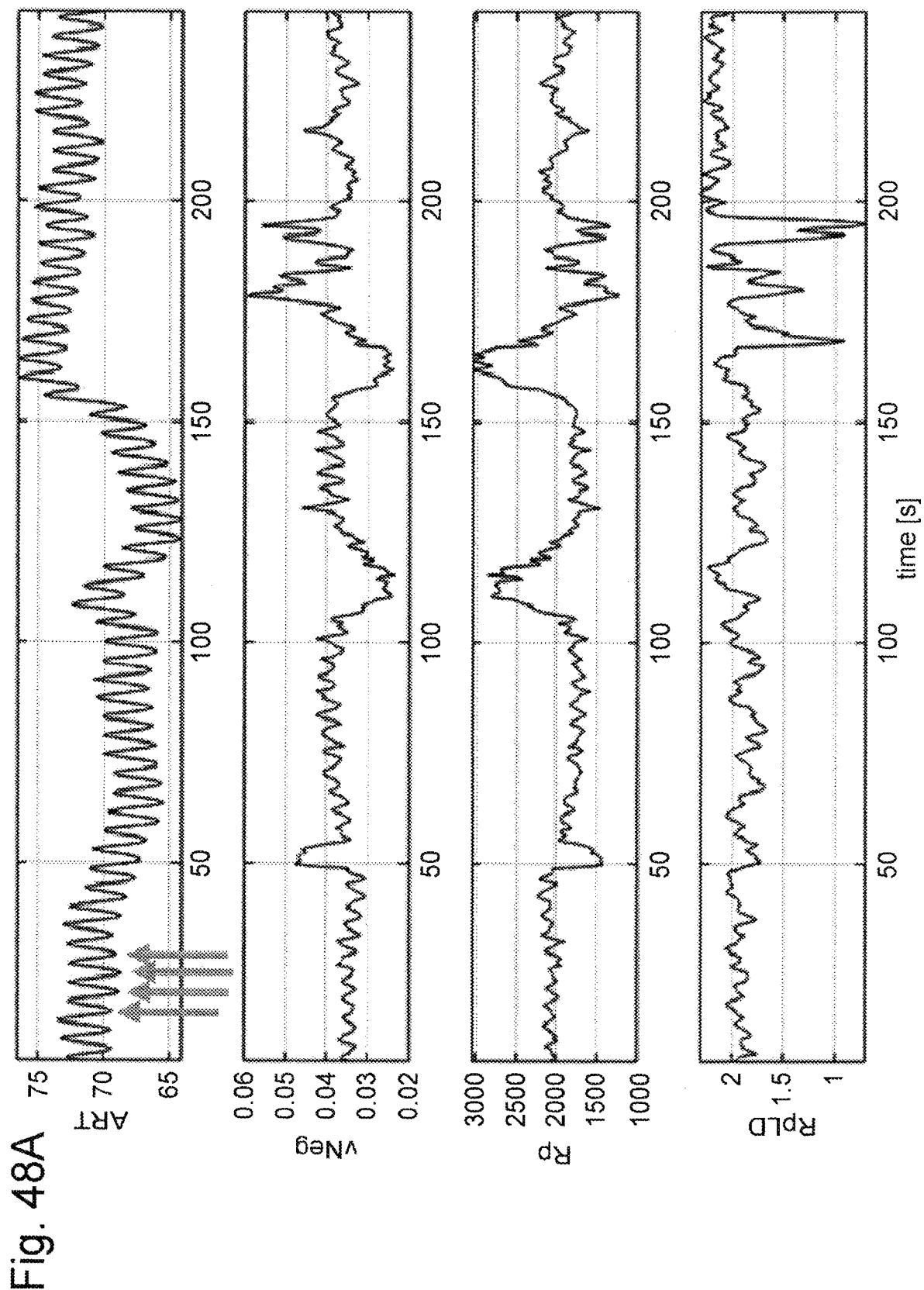
FIG. 48 shows graphical representations of mean arterial blood pressure at the left distal radial artery (ART; mmHg), blood flow velocity as measured by an unfocused ultrasound scanning system embodying the invention at the dorsum of the wrist, the wrist-thumb joint or the thenar eminence (vNeg; cm/second), peripheral vascular resistance (Rp, ART/vNeg) and peripheral vascular resistance (RpLD, ART/laser Doppler blood flow velocity) in a patient suffering from sepsis following iatrogenic perforation of the small intestine during surgery at (A) day 1 shortly after surgery, sepsis pronounced patient close to haemodynamic instability; (B) later on day 1, sepsis improving; (C) day 2, sepsis improving; (D) day 5, sepsis further improving Light grey arrows (mechanical ventilation respiratory rate); dark grey arrows (low frequency vasomotor oscillations).
Figure 48B:
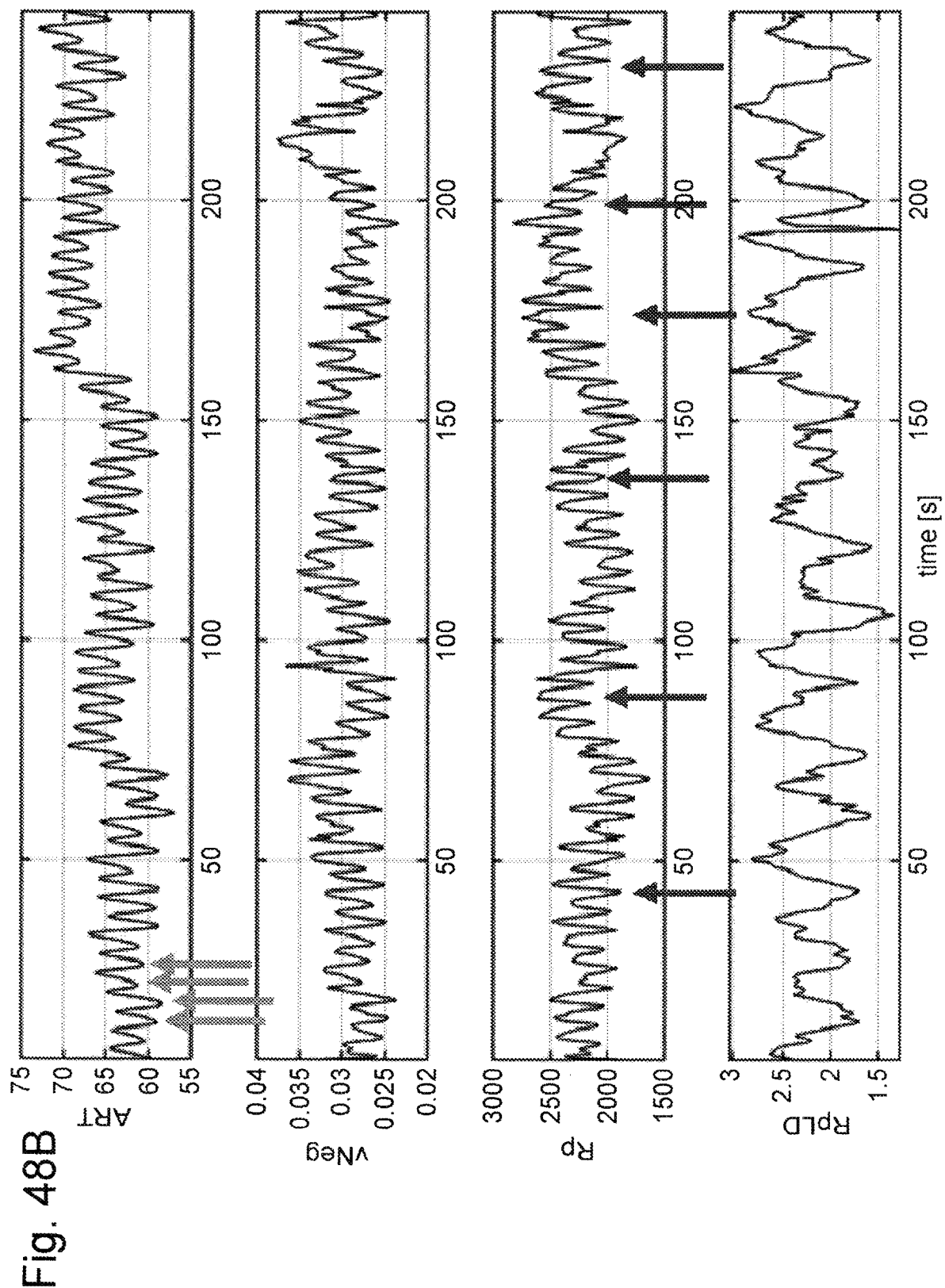
Figure 48C:
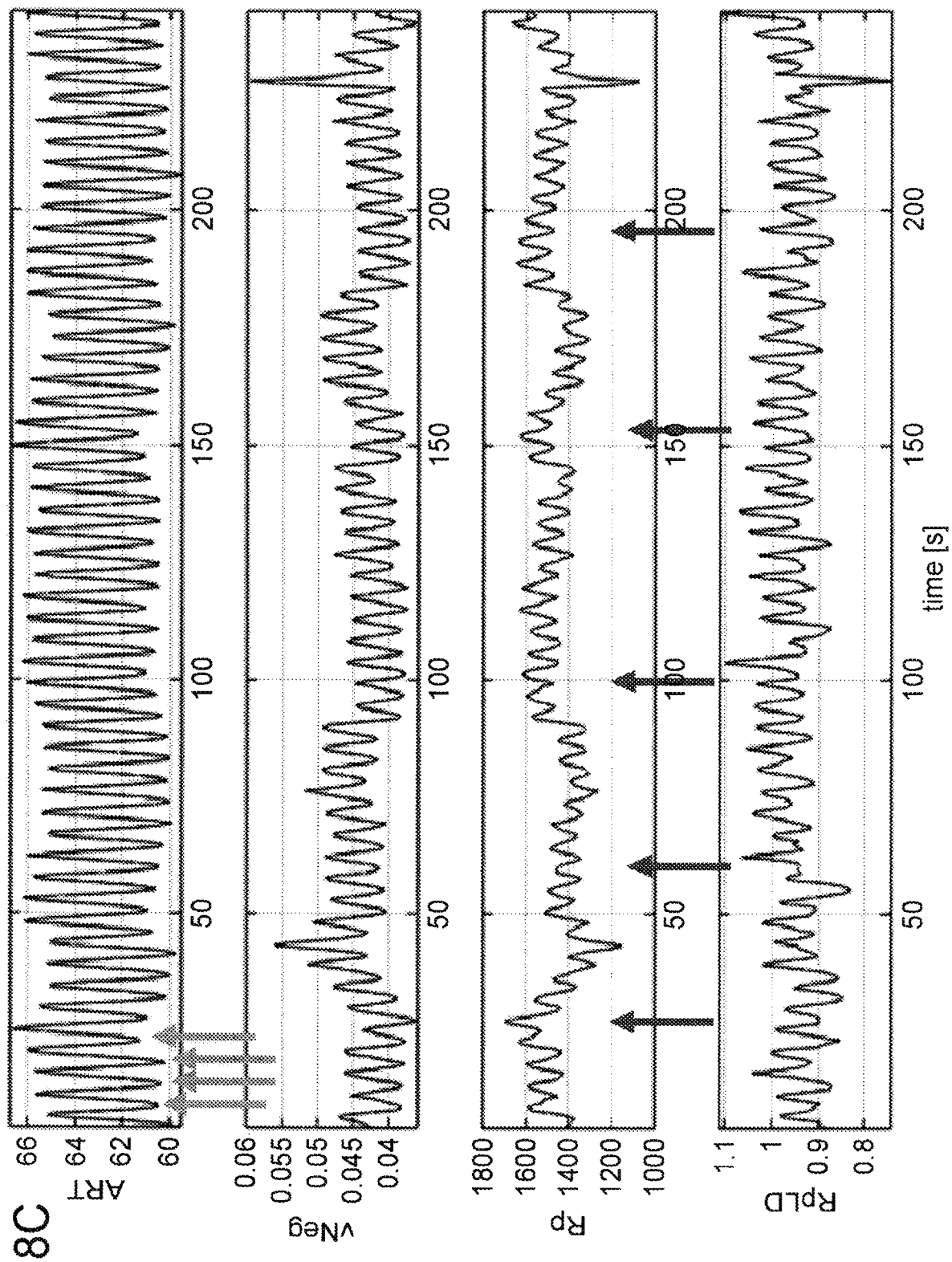
Figure 48D:
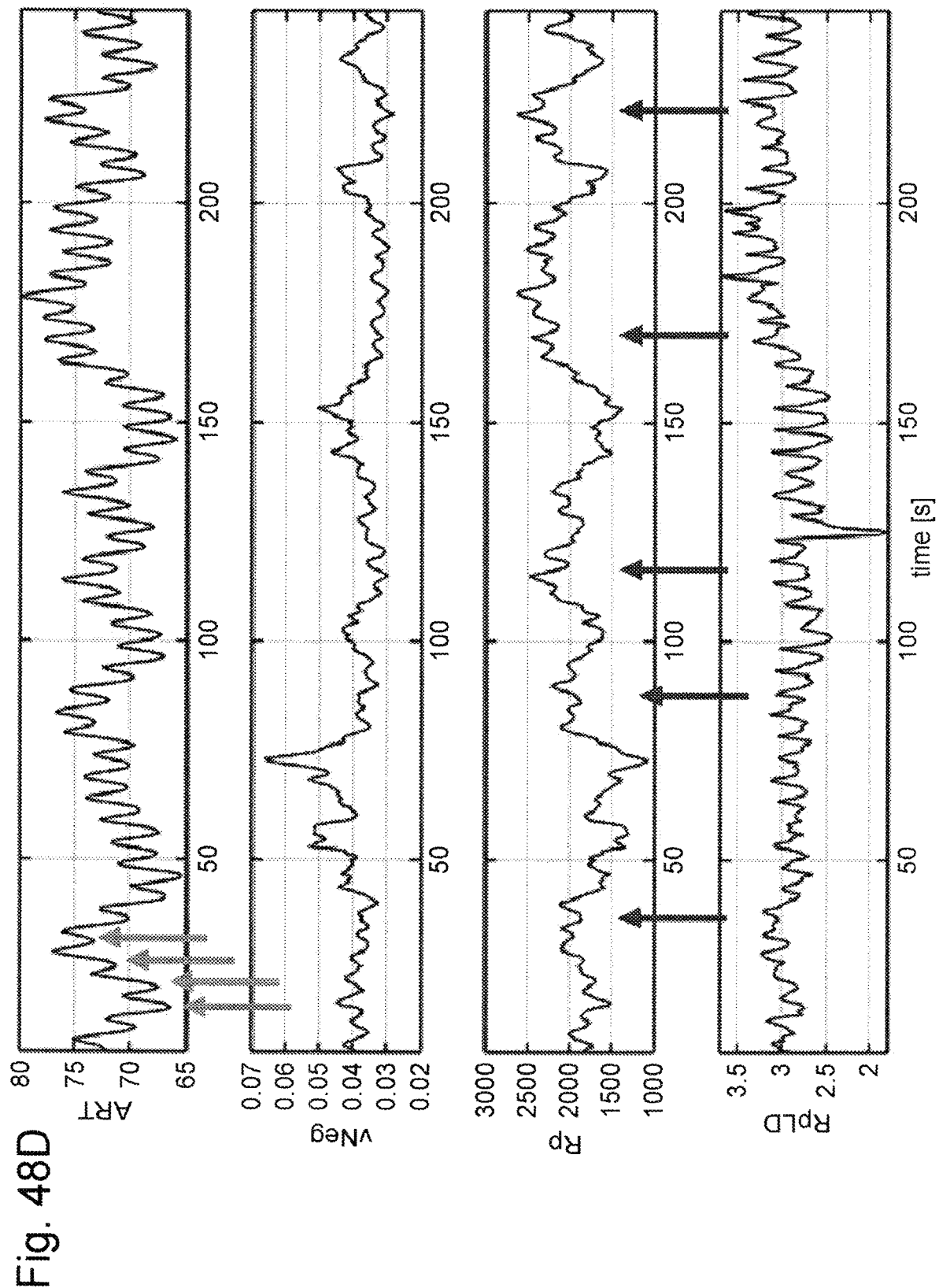

By day 8 the Patient's condition had deteriorated and he had required surgery to correct an ischaemic gut. On day 9 his septic shock status was critical and deteriorating and he was becoming haemodynamically unstable. As shown in FIG. 47(C) the fluctuations in the various parameters at 0.25 Hz (light grey arrows) corresponding to the mechanical ventilator respiratory rate (RR) of 15/min remained but the 0.017 Hz oscillations were absent.

By day 10 the Patient's septic shock status was improving once again and the Patient was considered haemodynamically stable. At this time the oscillations in the vNeg and Rp traces at approximately 0.017-0.025 Hz (dark grey arrows) became more distinct.

Results—Patient 2

Male, 70 years old, presented with iatrogenic perforation of the small intestine during planned procedure. Surgical and antibiotic therapy were needed. Abdominal sepsis was most pronounced at ICU day one, the day of surgery, and slowly improved during the following five days.

As shown in FIG. 48 (A), on day 1, shortly after surgery, with sepsis pronounced and the Patient showing haemodynamic instability, fluctuations in arterial blood pressure (ART), ultrasound measured blood flow velocity (vNeg) and peripheral resistance at 14/min (0.23 Hz) are observed (light grey/blue arrows). These fluctuations are caused by the mechanical ventilator which was running at a respiratory rate (RR) of 14/min. No other significant oscillations were readily discernible.

Later on day 1 and on day 2, with sepsis improving and the Patient becoming haemodynamically stable; fluctuations at approximately 1/min (0.017 Hz; dark grey arrows) were observed in addition to those caused by ventilation. This was most distinct in the Rp trace, but also in the ultrasound measured blood flow velocity trace. It is believed that these oscillations are caused by spontaneous vasomotions. The same patterns were also seen on day 5, with sepsis further improving. In this case, the strength of the 0.017 Hz oscillations did not vary as greatly as in Patient 1, but this is thought to be because Patient 2 did not ever become as critically ill as Patient 1.

Discussion

It can be seen from this study that oscillations in blood flow characteristics, e.g. blood flow velocity, as measured by the unfocused Doppler ultrasound system of the invention, which are lower in frequency than respiration rate or heart rate (e.g. at 0.015-0.03 Hz) are indicative of haemodynamic instability and in particular the severity of sepsis/septic shock. Thus, by monitoring such blood characteristics, alone or together with other circulatory parameters (e.g. arterial blood pressure) a patient's sepsis status may be estimated at any time and any change therein may be detected rapidly. It is believed that such changes in blood flow characteristics measured by the unfocused Doppler ultrasound system of the invention would be detectable before outward signs of deterioration or improvement would be observed using conventional techniques and equipment.

Figure 51:
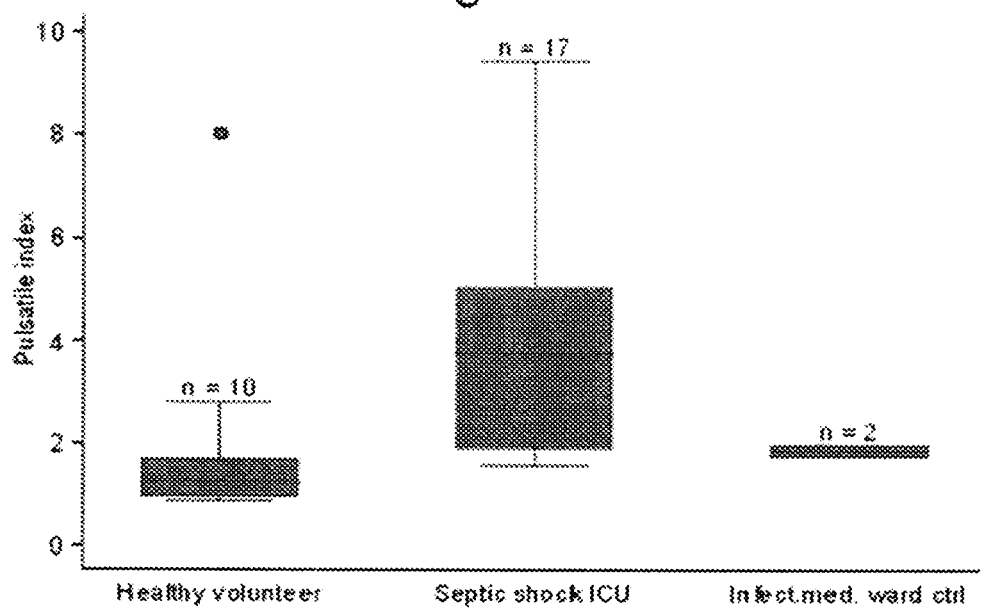
FIG. 51 shows a graphical representation of Pulsatile Index (PI) measurements from distal arm, wrist or hand of septic shock patients during a clinical phase of relatively unstable circulation within the first 24 hours of ICU stay as, compared with corresponding measurements in healthy controls and in patients on the same ward with infection but not septic shock.
Figure 52:
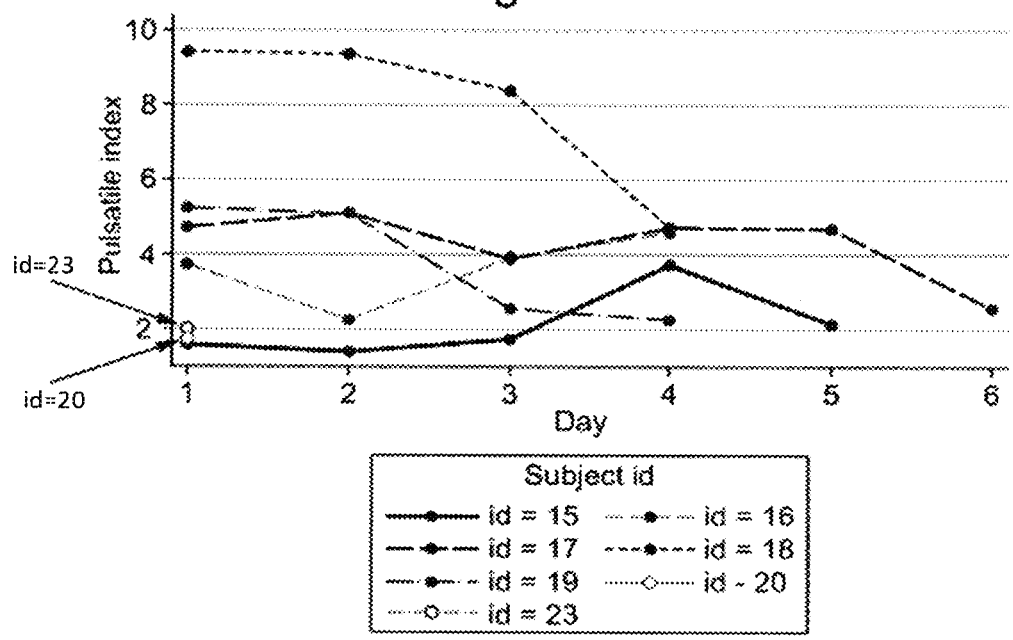
FIG. 52 shows a graphical representation of consecutive Pulsatile Index (PI) measurements from distal arm, wrist or hand of 5 septic shock patients over days 4-10 of their ICU stay as compared to 2 control patients on the same ward (infection but not septic shock; marked by arrows, id 20 and 23).

Example 9-Analysis of Blood Flow Parameters in the Peripheral Circulation of Subjects with Septic Shock Patients with septic shock were recruited in the ICU during a clinical phase of relatively unstable circulation. Blood flow velocity was measured over the course of their ICU stay by an unfocused Doppler ultrasound system of the invention at the distal arm, wrist or hand and PI calculated therefrom. The same measurements were taken in healthy controls and control patients on the same ward (infection but not septic shock). All patients undergoing treatment showed clinical signs recovery over the course of the experiment and ultimately were discharged from the ICU FIG. 51 shows that patients with septic shock have PI values which are higher than in healthy controls and also higher than in patients with an infection but which are not in septic shock. FIG. 52 also shows that patients with septic shock generally have PI values which are higher than in healthy controls when critically ill and that as these patients undergo treatment and recover, PI values decrease to control levels.

The invention claimed is:

1. A method for monitoring a characteristic of blood flow in a vertebrate animal subject, wherein the characteristic of blood flow relates to the velocity of the blood flow and/or wherein the characteristic of blood flow relates to the total blood flow within a region within the subject, the method comprising:
    transmitting unfocussed plane-wave ultrasound pulses into the subject from a single-element ultrasound transducer that is fastened to the subject;
    receiving reflections of the ultrasound pulses at the single-element ultrasound transducer;
    generating a time series of pulse-Doppler response signals from the received reflections;
    selecting a depth or depth range at which to monitor the characteristic of blood flow within the subject;
    identifying a time-series of one or more heartbeats from the pulse-Doppler response signals from the selected depth or depth range;
    evaluating a quality metric for each of the identified one or more heartbeats from the selected depth or depth range, by comparing data associated with successive heartbeats by autocorrelation, to determine a respective quality value associated with each of the identified one or more heartbeats, wherein the quality value associated with each heartbeat depends on a similarity of data derived from the pulse-Doppler response signals for the respective heartbeat, to data derived from the pulse-Doppler response signals for a preceding heartbeat and wherein a higher value of the quality metric indicates a higher confidence that a heartbeat has been identified correctly;
    determining a set of valid heartbeats consisting of heartbeats for which the respective quality value exceeds a threshold level;
    processing the pulse-Doppler response signals from the selected depth or depth range over a time window to determine values of the characteristic of blood flow within the subject, over time, at the selected depth or depth range for the set of valid heartbeats, comprising excluding from the time window periods of time covering pulse-Doppler response signals for which the identified heartbeats are determined as having a quality value below the threshold level, so as to evaluate the characteristic of blood flow only over those heartbeats for which the associated quality value exceeds the threshold level; and
    detecting when one or more of the determined values of the characteristic of blood flow, for the set of valid heartbeats, satisfies a predetermined alert criterion, and, in response, signalling an audible or visual alert.

2. The method of claim 1, further comprising processing each pulse-Doppler response signal from the selected depth or depth range to determine, from the respective pulse-Doppler response signal, a respective sequence of spatial-maximum velocity values over time for blood flowing through a respective region at the selected depths or depth ranges, wherein the sequences comprise spatial-maximum velocity values for common time periods across the selected depth or depth ranges.

3. The method of claim 1, wherein selecting the depth or depth range comprises receiving, from a human operator, an input identifying the depth or depth range.

4. The method of claim 1, wherein selecting the depth or depth range comprises a controller automatically selecting the depth or depth range at which to determine the characteristic of blood flow.

5. The method of claim 1, wherein the single-element ultrasound transducer is fastened to a skull of the subject, the method comprising transmitting the unfocussed plane-wave ultrasound pulses through a suture or a fontanelle of the skull of the subject.

6. The method of claim 1, comprising: monitoring the characteristic of blood flow in a neonate or a preterm baby, or in a post-operative patient; or monitoring cerebral circulation; or monitoring microcirculation; or monitoring for sudden blood loss in an emergency setting.

7. The method of claim 1, wherein comparing data associated with successive heartbeats by autocorrelation comprises comparing successive heartbeats by autocorrelation of the envelope signals.

8. A system for monitoring a characteristic of blood flow in a vertebrate animal subject, wherein the characteristic of blood flow relates to the velocity of the blood flow and/or wherein the characteristic of blood flow relates to the total blood flow within a region within the subject, the system comprising:
   a single-element ultrasound transducer for fastening to the subject;
   a controller,
wherein the controller is configured to:
   control the single-element ultrasound transducer to transmit unfocussed plane-wave ultrasound pulses into the subject;
   sample reflections of the ultrasound pulses received at the single-element ultrasound transducer;
   generate a time-series of pulse-Doppler response signals from the received reflections;
   determine a selection of a tissue depth or depth range at which to monitor the characteristic of blood flow within the subject;
   identify a time-series of one or more heartbeats from the pulse-Doppler response signals from the selected depth or depth range;
   evaluate a quality metric for each of the identified one or more heartbeats from the selected depth or depth range, by comparing data associated with successive heartbeats by autocorrelation, to determine a respective quality value associated with each of the identified one or more heartbeats, wherein the quality value associated with each heartbeat depends on a similarity of data derived from the pulse-Doppler response signals for the respective heartbeat, to data derived from the pulse-Doppler response signals for a preceding heartbeat and wherein a higher value of the quality metric indicates a higher confidence that a heartbeat has been identified correctly;
   determine a set of valid heartbeats consisting of heartbeats for which the respective quality value exceeds a threshold level; and
   process the pulse-Doppler response signals from the selected depth or depth range over a time window to determine values of the characteristic of blood flow within the subject, over time, at the selected depth or depth range only over the set of valid heartbeats, comprising excluding from the time window periods of time covering pulse-Doppler response signals for which the identified heartbeats are determined as having a quality value below the threshold level, so as to evaluate the characteristic of blood flow only over those heartbeats for which the associated quality value exceeds the threshold level; and
   wherein the controller is further configured to detect when one or more of the determined values of the characteristic of blood flow, for the set of valid heartbeats, satisfies a predetermined alert criterion, and, in response, to signal an audible or visual alert.

9. The system of claim 8, further comprising a fastener or an adhesive layer for fastening the single-element ultrasound transducer to the subject.

10. The system of claim 8, wherein the controller is configured to use an autocorrelation operation to identify heartbeats from the pulse-Doppler response signals.

11. The system of claim 8, further comprising a display device, wherein the controller is further configured to display values of the characteristic of blood flow on the display device.

12. The system of claim 8, wherein the controller is configured to receive, from a human operator, an input identifying the selected depth or depth range.

13. The system of claim 8, wherein the controller is configured to automatically select the depth or depth range at which to determine the characteristic of blood flow.

14. The system of claim 8, wherein the ultrasound transducer has a planar transmitting face having a width that is at least 10 mm.

15. The system of claim 8, wherein the characteristic of blood flow is any of: a spatial-maximum velocity; a time-average of a spatial-maximum velocity; a peak systolic velocity; an end diastolic velocity; a pulsatile index; or a resistive index.

16. The system of claim 8, wherein the characteristic of blood flow is time-averaged over the set of valid heartbeats.

17. The system of claim 8, wherein the controller is further configured to detect displacement of the single-element transducer, relative to the subject, from the pulse-Doppler response signals.

* * * * *